(12) United States Patent
Mackenzie et al.

(10) Patent No.: US 10,100,056 B2
(45) Date of Patent: Oct. 16, 2018

(54) SHIP1 MODULATORS AND METHODS RELATED THERETO

(71) Applicant: Aquinox Pharmaceuticals (Canada) Inc., Vancouver (CA)

(72) Inventors: Lloyd F. Mackenzie, North Vancouver (CA); Curtis Harwig, Vancouver (CA); David Bogucki, Surrey (CA); Jeffery R. Raymond, Vancouver (CA); Jeremy D. Pettigrew, Burnaby (CA)

(73) Assignee: Aquinox Pharmaceuticals (Canada) Inc., Vancouver (CA)

( * ) Notice: Subject to any disclaimer, the term of this patent is extended or adjusted under 35 U.S.C. 154(b) by 0 days.

(21) Appl. No.: 14/772,737

(22) PCT Filed: Feb. 27, 2014

(86) PCT No.: PCT/US2014/019125
§ 371 (c)(1),
(2) Date: Sep. 3, 2015

(87) PCT Pub. No.: WO2014/143561
PCT Pub. Date: Sep. 18, 2014

(65) Prior Publication Data
US 2016/0083387 A1    Mar. 24, 2016
US 2017/0253596 A2    Sep. 7, 2017

Related U.S. Application Data

(60) Provisional application No. 61/785,860, filed on Mar. 14, 2013.

(51) Int. Cl.
| | | |
|---|---|---|
| C07D 473/34 | (2006.01) |
| C07D 207/335 | (2006.01) |
| C07D 207/06 | (2006.01) |
| C07D 213/38 | (2006.01) |
| C07D 231/12 | (2006.01) |

(Continued)

(52) U.S. Cl.
CPC .......... *C07D 473/34* (2013.01); *C07C 215/42* (2013.01); *C07C 225/10* (2013.01); *C07C 233/23* (2013.01); *C07C 233/74* (2013.01); *C07C 255/31* (2013.01); *C07C 275/24* (2013.01); *C07C 279/08* (2013.01); *C07C 311/04* (2013.01); *C07D 207/06* (2013.01); *C07D 207/335* (2013.01); *C07D 209/08* (2013.01); *C07D 213/38* (2013.01); *C07D 213/64* (2013.01); *C07D 231/12* (2013.01); *C07D 233/60* (2013.01); *C07D 239/34* (2013.01); *C07D 241/18* (2013.01);
(Continued)

(58) Field of Classification Search
CPC .. C07D 473/34; C07D 207/06; C07D 207/08; C07D 207/335; C07D 207/416; C07D 209/08; C07D 213/04; C07D 213/30; C07D 213/36; C07D 213/38; C07D 213/64; C07D 213/81; C07D 213/82; C07D 295/096; C07D 231/12; C07D 233/60; C07D 233/72; C07D 235/06; C07D 39/34; C07D 241/18; C07D 249/08; C07D 307/68; C07D 317/46; C07D 317/58; C07D 239/34
See application file for complete search history.

(56) References Cited

U.S. PATENT DOCUMENTS 3,682,983 A   8/1972 Prezewowsky et al.
3,869,467 A   3/1975 Guthrie et al.
(Continued)

FOREIGN PATENT DOCUMENTS

DE   1 084 718    7/1960
GB   1291644      10/1972
(Continued)

OTHER PUBLICATIONS

Kubinyi, (3D QSAR in Drug Design: Ligand-Protein Interactions and Molecular Similarity, vol. 2-3, Springer, 1998, 800 pages), pp. 243-244 provided.

(Continued)

*Primary Examiner* — Rebecca L Anderson
(74) *Attorney, Agent, or Firm* — Seed IP Law Group LLP

(57) ABSTRACT

Compounds of formula (I): where $R^1$, $R^2$, $R^3$, $R^{4a}$, $R^{4b}$, $R^5$, $R^6$ and $R^7$ are defined herein, or stereoisomers or pharmaceutically acceptable salts thereof, are described herein. Such compounds have activity as SHIP1 modulators, and thus may be used to treat any of a variety of diseases, disorders or conditions that would benefit from SHIP1 modulation. Compositions comprising a compound of formula (I) in combination with a pharmaceutically acceptable carrier or diluent are also disclosed, as are methods of SHIP1 modulation by administration of such compounds to an animal in need thereof.

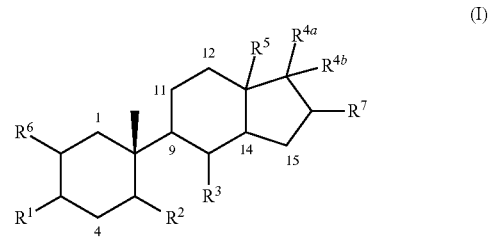

7 Claims, No Drawings

(51) Int. Cl.
| | |
|---|---|
| C07D 249/08 | (2006.01) |
| C07D 233/60 | (2006.01) |
| C07D 209/08 | (2006.01) |
| C07D 317/46 | (2006.01) |
| C07D 295/096 | (2006.01) |
| C07D 213/64 | (2006.01) |
| C07D 239/34 | (2006.01) |
| C07D 241/18 | (2006.01) |
| C07C 279/08 | (2006.01) |
| C07C 215/42 | (2006.01) |
| C07C 233/23 | (2006.01) |
| C07C 311/04 | (2006.01) |
| C07C 225/10 | (2006.01) |
| C07C 233/74 | (2006.01) |
| C07C 255/31 | (2006.01) |
| C07C 275/24 | (2006.01) |

(52) U.S. Cl.
CPC ....... C07D 249/08 (2013.01); C07D 295/096 (2013.01); C07D 317/46 (2013.01)

(56) References Cited

U.S. PATENT DOCUMENTS

| | | |
|---|---|---|
| 3,962,275 A | 6/1976 | Guthrie et al. |
| 5,686,621 A | 11/1997 | Clark et al. |
| 6,046,185 A | 4/2000 | Burgoyne et al. |
| 6,635,629 B2 | 10/2003 | Raymond et al. |
| 6,696,580 B2 | 2/2004 | Burgoyne et al. |
| 6,982,329 B2 | 1/2006 | Burgoyne et al. |
| 7,601,874 B2 | 10/2009 | Raymond et al. |
| 7,999,010 B2 | 8/2011 | Raymond et al. |
| 8,084,503 B2 | 12/2011 | Raymond et al. |
| 8,673,975 B2 | 3/2014 | Raymond et al. |
| 2001/0010293 A1 | 8/2001 | Ishida et al. |
| 2014/0371252 A1 | 12/2014 | Raymond et al. |
| 2016/0376222 A1 | 12/2016 | Mackenzie et al. |
| 2017/0204048 A1 | 7/2017 | Harwig et al. |
| 2017/0362250 A1 | 12/2017 | Mackenzie et al. |

FOREIGN PATENT DOCUMENTS

| | | |
|---|---|---|
| JP | 1-290624 A | 11/1989 |
| JP | 5-221901 A | 8/1993 |
| JP | 5-221924 A | 8/1993 |
| WO | WO 93/13124 A1 | 7/1993 |
| WO | WO 94/14833 A2 | 7/1994 |
| WO | WO 95/01960 A1 | 1/1995 |
| WO | WO 96/11939 A1 | 4/1996 |
| WO | WO 03/033517 A1 | 4/2003 |
| WO | WO 2004/035601 A1 | 4/2004 |
| WO | WO 2004/092100 A1 | 10/2004 |
| WO | WO 2007/147251 A1 | 12/2007 |
| WO | WO 2007/147252 A1 | 12/2007 |
| WO | WO 2011/069118 A1 | 6/2011 |
| WO | WO 2014/143561 A1 | 9/2014 |
| WO | WO 2014/158654 A1 | 10/2014 |
| WO | WO 2016/210146 A1 | 12/2016 |
| WO | WO 2017/127753 A1 | 7/2017 |

OTHER PUBLICATIONS

Wermuth, The Practice of Medicinal Chemistry, 2nd ed. (2003), 768 pages, Chapters 9-10 provided.
U.S. Appl. No. 14/772,731, filed Sep. 4, 2015, Mackenzie et al.
Ahmad et al., "The Baeyer-Villiger Oxidation of 5α-Cholestane-3,6-Dione," *Acta Chim. Acad. Sci. Hung.* 106(2): 111-113, 1981.
Barber et al., "PI3Kγ inhibition blocks glomerulonephritis and extends lifespan in a mouse model of systemic lupus," *Nature Medicine* 11(9): 933-935, Sep. 2005.
Buckingham et al., "6-Phenylazocholestane derivatives: Reassignment of the Structures of Products from Phenylhydrazine and Ozonised Cholesterol Derivatives," *J. Chem. Soc. (C)* 18: 1703-1706, 1967.
Camps et al., "Blockade of PI3Kγ suppresses joint inflammation and damage in mouse models of rheumatoid arthritis," *Nature Medicine* 11(9): 936-943, Sep. 2005.
Clinton et al., "Steroidal[3,2-c]pyrazoles. II. Androstanes, 19-Norandrostanes and their Unsaturated Analogs," *Journal of the American Chemical Society* 83: 1478-1491, Mar. 20, 1961.
Coggeshall et al., "How do inhibitory phosphatases work?," *Molecular Immunology* 39: 521-529, 2002.
Cookson et al., "Photochemical Rearrangement of α-Hydroxyketones to Lactones," *J. Chem. Soc. (C)*: 2494-2500, 1968.
Damen et al., "The 145-kDa protein induced to associate with Shc by multiple cytokines is an inositol tetraphosphate and phosphatidylinositol 3,4,5-trisphosphate 5-phosphatase," *Proc. Natl. Acad. Sci. USA* 93: 1689-1693, Feb. 1996.
Dauben et al., "Stereocontrolled Synthesis of Steroidal Side Chains," *J. Am. Chem. Soc.* 103: 237-238, 1981.
Deane et al., "Phosphoinositide 3-Kinase: Diverse Roles in Immune Cell Activation," *Annu. Rev. Immunol.* 22: 563-598, 2004.
Fan et al., "A dual PI3 kinase/mTOR inhibitor reveals emergent efficacy in glioma," *Cancer Cell* 9: 341-349, May 2006.
Fukuda et al., "Alteration of phosphatidylinositol 3-kinase cascade in the multilobulated nuclear formation of adult T cell leukemia/lymphoma (ATLL)," *PNAS* 102(42): 15213-15218, Oct. 18, 2005.
Gallou et al., "Practical Synthesis of Unsymmetrical Ureas from Isopropenyl Carbamates," *J. Org. Chem* 70: 6960-6963, 2005.
Goclik et al., "Pelorol from the Tropical Marine Sponge *Dactylospongia elegans*," *J. Nat. Prod.* 63: 1150-1152, 2000.
Gumulka et al, "Oxidative Cleavage of the Double Bond of 7-Dehydrocholesterol Acetate Peroxide," *Polish Journal of Chemistry* 57(4/5/6): 403-411, 1983.
Kaspar et al., "Steroid Binding to the Cytosolic Estrogen Receptor From Rat Uterus. Influence of the Orientation of Substituents in the 17-Position of the 8β- and 8α-Series," *J. steroid Biochem.* 23(3): 259-265, 1985.
Halpern et al., "On the Nature of the Chemical Mediators Involved in Anaphylactic Reactions in Mice," *Brit. J. Pharmacol.* 20: 389-398, 1963.
Hazen et al., "SHIP is required for a functional hematopoietic stem cell niche," *Blood* 113(13): 2924-2933, Mar. 26, 2009.
Helgason et al., "A Dual Role for Src Homology 2 Domain-containing Inositol-5-Phosphatase (SHIP) in Immunity: Aberrant Development and Enhanced Function of B Lymphocytes in SHIP$^{-/-}$ Mice," *J. Exp. Med.* 191(5): 781-794, Mar. 6, 2000.
Helgason et al., "Targeted disruption of *SHIP* leads to hemopoietic perturbations, lung pathology, and a shortened life span," *Genes & Development* 12: 1610-1620, 1998.
Hennessy et al., "Exploiting the PI3K/AKT Pathway for Cancer Drug Discovery," *Nature Reviews: Drug Discovery* 4: 988-1004, Dec. 2005.
Kalesnikoff et al., "The role of SHIP in cytokine-induced signaling," *Rev. Physiol. Biochem. Pharmacol.* 149: 87-103, 2003.
Knight et al., "A Pharmacological Map of the PI3-K Family Defines a Role for p110α in Insulin Signaling," *Cell* 125: 733-747, May 19, 2006.
Kwak et al., "Sesquiterpene Quinols/Quinones from the Micronesian Sponge *Petrosaspongia metachromia*," *J. Nat. Prod.* 63: 1153-1156, 2000.
Lettré et al., "Mehrwertige Alkohole aus Sterinen und Sterinderivaten. IV. 7.8-seco-Derivate des Cholestanols," *Justus Liebigs Annalen Der Chemie* 697: 217-221, 1966.
Liang et al., "Quantification of change in phosphorylation of BCR-ABL kinase and its substrates in response to Imatinib treatment in human chronic myelogenous leukemia cells," *Proteomics* 6: 4554-4564, 2006.
Luo et al., "Mutation Analysis of SHIP Gene in Acute Leukemia," *Journal of Experimental Hematology* 12(4): 420-426, 2004.
Madaio et al., "Minor 5,6-Secosterols From the Marine Sponge *Hippospongia communis*. Isolation and Synthesis of (7Z,22E,24R)-24-Methyl-5,6-Secocholesta-7,22-Diene-3β,5β,6-Triol," *Journal of Natural Products* 53(3): 565-572, May-Jun. 1990.

(56) References Cited

OTHER PUBLICATIONS

Manson et al., "Steroidal Heterocycles. VII. Androstano[2,3-d]isoxazoles and Related Compounds," *J. Med. Chem.* 6(1): 1-9, Jan. 18, 1963.
Mincione et al., Synthesis via Organoiron Complexes of 9-(4-Keto-1-Methylcyclohex-2-enyl)-8-Keto-des-AB-Ergost-22,23-ene; A Useful Chiral Intermediate in Steroid Synthesis, *Heterocycles* 23(7): 1607-1610, 1985.
Ong et al., "Small-molecule agonists of SHIP1 inhibit the phosphoinositide 3-kinase pathway in hematopoietic cells," *Blood* 110(6): 1942-1949, Sep. 15, 2007.
Ovary et al., "Passive Cutaneous Anaphylaxis in the Mouse," *J. Immunol.* 81: 355-357, 1958.
Reichstein et al., "Über Bestandteile der Nebennierenrinde und verwandte Stoffe—Allo-pregnan-diol-(3, 17)-Derivate der 17($\beta$)-Reihe. Weiterer Beweis für die Zugehörigkeit der Substanzen P und K zur 17($\beta$)-Reihe," *Helv. Chim. Acta* 22(III): 728-741, 1939.
Rodewald et al., "Secosteroids. I. Synthesis of vic-Diols in B-Secocholestane Group," *Journal Prakt. Chem.* 330(5): 775-881, 1988.
Rodewald et al., "Selective Esterification of Hydroxyl Groups in Methyl Ester of 3$\beta$,8$\alpha$-Dihydroxy-7,8-Secocholestan-7-oic Acid," *Roczniki Chemii Ann. Soc. Chim. Polonorum* 51(4): 809-814, 1977.
Rohrschneider et al., "Structure, function, and biology of SHIP proteins," *Genes & Development* 14: 505-520, 2000.
Simon, "Using Isoform-Specific Inhibitors to Target Lipid Kinases," *Cell* 125: 647-649, May 19, 2006.
Sly et al., "SHIP, SHIP2, and PTEN activities are regulated in vivo by modulation of their protein levels: SHIP is up-regulated in macrophages and mast cells by lipopolysaccharide," *Experimental Hematology* 31: 1170-1181, 2003.
Sly et al., "LPS-Induced Upregulation of SHIP is Essential for Endotoxin Tolerance," *Immunity* 21: 227-239, Aug. 2004.
Speckamp et al., "6-Thiasteroids A Novel Stereoselective Preparation of 6-Heterosteroids," *Tetrahedron Letters* 38: 3405-3408, 1974.
Suginome et al., "Photoinduced Transformations. 77. A Four-Step Substitution of a Carbonyl Group of Steroidal Ketones by an Oxygen Atom. A New Method for the Synthesis of Cyclic Ethers," *Journal of Organic Chemistry* 50(14): 2489-2494, 1985.
Vanderwinden et al., "Differences in signaling pathways and expression level of the phosphoinositide phosphatase SHIP1 between two oncogenic mutants of the receptor tyrosine kinase KIT," *Cellular Signalling* 18: 661-669, 2006.
Vivanco et al., "The Phosphatidylinositol 3-Kinase-AKT Pathway in Human Cancer," *Nature Reviews: Cancer* 2: 489-501, Jul. 2002.
Vonakis et al., "Src homology 2 domain-containing inositol 5' phosphatase is negatively associated with histamine release to human recombinant histamine-releasing factor in human basophils," *J. Allergy Clin. Immunol.* 108: 822-831, 2001.
Westmijze et al., "Ag(I)-Assisted Hydrolysis of Mestranol Methanesulfonate Into Epimestranol," *Tetrahedron Letters* 21: 2665-2666, Apr. 15, 1980.
Winter et al., "Carrageenin-Induced Edema in Hind Paw of the Rat as an Assay for Antiinflammatory Drugs," *Proc. Soc. Exp. Biol. Med.* 111: 544-547, 1962.
Workman et al., "Drugging the PI3 kinome," *Nature Biotechnology* 24(7): 794-796, Jul. 2006.
Yang et al., "Synthesis of Pelorol and Analogues: Activators of the Inositol 5-Phosphatase SHIP," *Organic Letters* 7(6): 1073-1076, 2005.
Beilstein Database, Beilstein Registry No. 3061562, 1968, 1 page.
Beilstein Database, Beilstein Registry No. 3102039, 1967, 1 page.
Chemical Abstracts Database, Accession No. 82:73301, 1974, 2 pages.
Chemical Abstracts Database, Accession No. 101:192278, 1983, 2 pages.
Chemical Abstracts Database, Accession No. 112:211000, Nov. 1989, 2 pages.
Chemical Abstracts Database, Accession No. 120:77523, Aug. 1993, 3 pages.
Chemical Abstracts Online, Accession No. 1959:17427, 1959, 2 pages.
Chemical Abstracts Online, Accession No. 1967:46521, 1966, 2 pages.
Chemical Abstracts Online, Accession No. 2013:381943, 2013, 2 pages.
International Preliminary Report on Patentability, dated Oct. 21, 2005, for International Application No. PCT/CA2004/000566, 8 pages.
International Preliminary Report on Patentability, dated Sep. 15, 2015, for International Application No. PCT/US2014/019125, 8 pages.
International Preliminary Report on Patentability, dated Sep. 15, 2015, for International Application No. PCT/US2014/019126, 11 pages.
Altomare et al., "*SIR97*: a new tool for crystal structure determination and refinement," *J. Appl. Cryst.* 32: 115-119, 1999.
Feuer et al., "The Reduction of Oximes, Oxime Ethers, and Oxime Esters with Diborane. A Novel Synthesis of Amines," *The Journal of Organic Chemistry* 34(6): 1817-1821, Jun. 1969.
Hara, "Azasteroid. IV. Synthesis of B-Azacholane Derivative," Chemical Abstracts Online, Accession No. 1959:17427, 1959. See also *Yakugaku Zasshi* 78(9): 1030-1033, Sep. 1958.
Ibers et al., "Dispersion corrections and crystal structure refinements," *Acta Cryst.* 17: 781-782, 1964.
Lettré and Werner, "Polyols from steroids and steroid derivatives. IV. 7,8-Seco-derivatives of cholestanols," Chemical Abstracts Online, Accession No. 1967:46521, 1967. See Also *Justus Liebigs Annalen Der Chemie* 697: 217-221, 1966.
Ley et al., "Microencapsulation of Osmium Tetroxide in Polyurea," *Organic Letters* 5(2): 185-187, 2003.
MacRae et al., "*Mercury CSD* 2.0—new features for the visualization and investigation of crystal structures," *J. Appl. Cryst.* 41: 466-470, 2008.
Mirjafary et al., "Oxime ethers as versatile precursors in organic synthesis: a review," *RSC Adv.* 5: 79361-79384, 2015.
Nicolaou et al., "An Expedient Procedure for the Oxidative Cleavage of Olefinic Bonds with PhI(OAc)$_2$, NMO, and Catalytic OsO$_4$," *Org. Lett.* 12(7): 1552-1555, Apr. 2, 2010.
Savitzky et al., "Smoothing and Differentiation of Data by Simplified Least Squares Procedures," *Analytical Chemistry* 36(8): 1627-1639, Jul. 1964.
Seto et al., "Epimerization at C-5 of brassinolide with sodium methoxide and the biological activity of 5-epi-brassinolide in the rice lamina inclination test," *J. Chem. Soc., Perkin Trans.* 1: 3355-3358, 1998.
Stenton et al., "Characterization of AQX-1125, a small-molecule SHIP1 activator Part 1. Effects on inflammatory cell activation and chemotaxis in vitro and pharmacokinetic characterization in vivo," *British Journal of Pharmacology* 168: 1506-1518, 2013.
Xing et al., "Gold(I)-Catalyzed Oxidative Cleavage of a C—C Double Bond in Water," *Organic Letters* 8(4): 693-696, 2006
Yang et al., "Ruthenium-Catalyzed Oxidative Cleavage of Olefins to Aldehydes," *J Org. Chem.* 66: 4814-4818, 2001.
Yong et al., "Synthesis of CD-ring modified 1$\alpha$,25-dihydroxy vitamin D analogues: Five-membered D-ring analogues," *Bioorganic & Medicinal Chemistry Letters* 7(7): 923-928, 1997.
International Search Report, dated Sep. 6, 2016, for PCTAN PCT/US2016/039040, 6 pages.
Written Opinion of the International Searching Authority, dated Sep. 6, 2016, for PCTAN PCT/US2016/039040, 9 pages.
International Search Report, dated Mar. 13, 2017, for PCTAN PCT/US2017/014446, 5 pages.
Written Opinion of the International Searching Authority, dated Mar. 13, 2017, for PCTAN PCT/US2017/014446, 7 pages.
Habermacher et al., "Prostatitis/Chronic Pelvic Pain Syndrome," *Annu. Rev. Med.* 57: 195-206, 2006.
Krieger et al., "NIH Consensus Definition and Classification of Prostatitis," *JAMA* 281(3): 236-237, Jul. 21, 1999.
Leaker et al., "The effects of the novel SHIP1 activator AQX-1125 on allergen-induced responses in mild-to-moderate asthma," *Clinical & Experimental Allergy* 44: 1146-1153, 2014.

(56) References Cited

OTHER PUBLICATIONS

Nickel et al., "Category III Chronic Prostatitis/Chronic Pelvic Pain Syndrome: Insights from the National Institutes of Health Chronic Prostatitis Collaborative Research Network Studies," *Curr Urol. Rep.* 9(4): 320-327, 2008.

Nickel et al., "A Phase II Study of the Efficacy and Safety of the Novel Oral SHIP1 Activator AQX-1125 in Subjects with Moderate to Severe Interstitial Cystitis/Bladder Pain Syndrome," *The Journal of Urology* 196: 747-754, Sep. 2016.

Radhakrishnan et al., "Development and characterization of a novel animal model of prostate inflammation-induced chronic pelvic pain," *Inflammopharmacology* 17: 23-28, 2009.

Tu et al., "Painful urological syndromes: Overview of the diagnosis and treatment of painful bladder syndrome/interstitial cystitis and chronic non-bacterial prostatitis/chronic pelvic pain syndrome (CPPS)," *Doul. et Analq.* 20: 154-166, 2007.

Vykhovanets et al., "Experimental rodent models of prostatitis: limitations and potential," *Prostate Cancr and Prostatic Diseases* 10: 15-29, 2007.

International Search Report and Written Opinion, dated Dec. 11, 2017 for PCTAN PCT/US2017/053554, 14 pages.

SHIP1 MODULATORS AND METHODS RELATED THERETO

FIELD OF THE INVENTION

The present invention is generally directed to SHIP1 modulators, as well as to compositions and methods related to the same.

BACKGROUND OF THE INVENTION

In response to extracellular signals, phosphoinositide 3-kinase (PI3K) becomes activated and phosphorylates phosphatidylinositol-4,5-bisphosphate (PI-4,5-$P_2$) within the plasma membrane to generate phosphatidylinositol-3,4,5-trisphosphate ($PIP_3$). $PIP_3$ then initiates a cascade of downstream signaling pathways by interacting with pleckstrin homology (PH) domain-containing proteins, such as protein kinase B (PKB, also known as Akt), that regulate cellular activation, function, proliferation and/or survival, depending on the cell type and stimulus (Deane et al., *Annu Rev Immunol* 22, 563-598, 2004). Cellular levels of $PIP_3$ are normally tightly regulated by PI3K, the 5' inositol phosphatases SHIP1 (SH2 domain-containing inositol phosphatase), SHIP2, and by the 3' inositol phosphatase PTEN. SHIP1 and SHIP2 dephosphorylate $PIP_3$ to phosphatidylinositol-3,4-bisphosphate (PI-3,4-$P_2$), whereas PTEN dephosphorylates $PIP_3$ to PI-4,5-$P_2$ (Sly et al., *Exp Hematol* 31, 1170-1181, 2003; Vivanco et al., *Nat Rev Cancer* 2, 489-501, 2002). Of these three, SHIP1 is unique in that its expression is restricted primarily to immune and hematopoietic cells (Sly et al., *Exp Hematol* 31, 1170-1181, 2003; Damen et al., *Proc Natl Acad Sci USA* 93, 1689-1693, 1996).

SHIP1's role in immune cell homeostasis is shown both by the myeloproliferative syndrome observed in SHIP1$^{-/-}$ mice, as well as the hypersensitivity of SHIP1$^{-/-}$ mice and cells to immune stimulation (Helgason et al., *Genes Dev* 12, 1610-1620, 1998; Sly et al., *Immunity* 21, 227-239, 2004). SHIP1 has been shown to mediate signaling from the inhibitory FcγRIIB receptor (Coggeshall et al., *Mol Immunol* 39, 521-529, 2002), and is important in terminating signal transduction from activating immune/hematopoietic cell receptor systems (Kalesnikoff et al., *Rev Physiol Biochem Pharmacol* 149, 87-103, 2003).

Diminished SHIP1 activity or expression has been observed in human inflammatory diseases (Vonakis et al., *J Allergy Clin Immunol* 108, 822-831, 2001) and hematopoietic malignancies (Liang et al., *Proteomics* 6, 4554-4564, 2006; Fukuda et al., *Proc Natl Acad Sci USA* 102, 15213-15218, 2005; Luo et al., *Zhongguo Shi Yan Xue Ye Xue Za Zhi* 12, 420-426, 2004; Vanderwinden et al., *Cell Signal* 18, 661-669, 2006; Ong, C. J. et al., *Blood* (2007), Vol. 110, No. 6, pp. 1942-1949).

Because dysregulated activation of the PI3K pathway contributes to inflammatory/immune disorders and cancer, intense efforts have been invested into the development of inhibitors of PI3K itself, as well as downstream protein kinases (Workman et al., *Nat Biotechnol* 24, 794-796, 2006; Simon, *Cell* 125, 647-649, 2006; Hennessy et al., *Nat Rev Drug Discov* 4, 988-1004, 2005; Knight et al., *Cell* 125, 733-747, 2006; Ong, C. J. et al., *Blood* (2007), Vol. 110, No. 6, pp. 1942-1949). The precedent for discovery and biologic efficacy of kinase inhibitors is well established, and a number of promising new PI3K isoform-specific inhibitors have recently been developed and used in mouse models of inflammatory disease (Camps et al., *Nat Med* 11, 936-943, 2005; Barber et al., *Nat Med* 11, 933-935, 2005) and glioma (Fan et al., *Cancer Cell* 9, 341-349, 2006) with minimal toxicities. However, because of the dynamic interplay between phosphatases and kinases in regulating biologic processes, inositol phosphatase activators represent a complementary, alternative approach to reduce cellular $PIP_3$ levels. Of the phosphoinositol phosphatases that degrade $PIP_3$, SHIP1 is a particularly ideal target for development of therapeutics for treating immune and hemopoietic disorders because its hematopoietic-restricted expression (Hazen A L, et al. 113, 2924-33, 2009; Rohrschneider L R, Fuller J F, Wolf I, Liu Y, Lucas D M. Structure, function, and biology of SHIP proteins. *Genes Dev.* 14:505-20, 2000) would limit the effects of a specific SHIP1 agonist to target cells.

To date, a number of small molecule SHIP1 modulators have been disclosed, including sesquiterpene compounds such as pelorol. Pelorol is a natural product isolated from the topical marine sponge *Dactylospongia elegans* (Kwak et al., *J Nat Prod* 63, 1153-1156, 2000; Goclik et al., *J Nat Prod* 63, 1150-1152, 2000). Other reported SHIP1 modulators include the compounds set forth in PCT Published Patent Application Nos. WO 2003/033517, WO 2004/035601, WO 2004/092100 (or U.S. Pat. No. 7,601,874), WO 2007/147251, WO 2007/147252 and WO 2011/069118.

While significant strides have been made in this field, there remains a need for effective small molecule SHIP1 modulators. There is also a need for pharmaceutical compositions containing such compounds, as well as for methods relating to the use thereof to treat disorders or conditions that would benefit from SHIP1 modulation. The present invention fulfills these needs, and provides other related advantages.

SUMMARY OF THE INVENTION

The present invention is generally directed to compounds which are SHIP1 modulators and pharmaceutical compositions comprising the compounds and methods of using the compounds and the pharmaceutical compositions of the invention for the treatment of diseases, disorders or conditions that would benefit from SHIP1 modulation. As used herein, a SHIP1 modulator can serve as either an agonist or antagonist to SHIP1.

Accordingly, in one aspect, this invention is directed to compounds of formula (I):

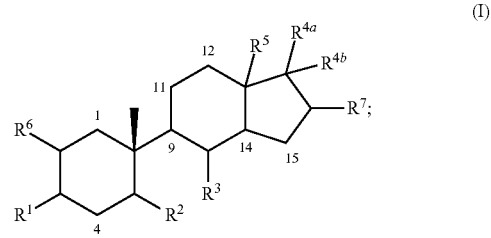

wherein:
C1, C4, C11 and C12 are each independently substituted with two hydrogens;
C9 is substituted with one hydrogen;
C14 is substituted with one hydrogen when $R^5$ is not a direct bond to C14;
C15 is substituted with two hydrogens when $R^7$ is not a direct bond to C15, and one hydrogen when $R^7$ is a direct bond to C15;
$R^1$ is —$R^8$—$OR^9$ or —$R^8$—$N(R^9)_2$;

$R^2$ is $-R^8-OR^9$, $-R^8-CN$, $-R^8-C(O)OR^9$, $-R^8-C(O)N(R^9)_2$, $-R^8-N(R^9)_2$, $-R^8-N(R^9)C(O)R^9$, optionally substituted heterocyclylalkyl or optionally substituted heteroarylalkyl;

$R^{4a}$ is hydrogen or alkyl, $R^{4b}$ is a direct bond to the carbon to which $R^7$ is attached, and $R^3$ is $-CH_2NH_2$ or $-CH_2N(H)C(O)(CH_2)_3CH_3$;

or $R^{4a}$ and $R^{4b}$ are each independently selected from hydrogen and alkyl and $R^3$ is $-CH_2OH$, $-CH_2NH_2$, $-CH_2N(H)CH_3$, $-CH_2N(CH_3)_2$, $-CH_2N(H)CH_2$-cyclopropyl, $-CH_2N(H)CH_2$-pyrrolyl, $-CH_2N(H)C(O)CH_3$, $-CH_2N(H)C(O)$-phenyl, $-CH_2N(H)S(O)_2CH_3$ or $-CH_2N(H)C(=NH)NH_2$;

or $R^{4a}$ and $R^{4b}$ together form methylene and $R^3$ is $-OH$, $-CH_2-OH$, $-CH_2-CH_2-OH$, $-CH_2-O-(3,5$-dimethoxy)benzyl, $-CH_2-O$-benzyl, $-CH_2-O-CH_2$-pyridinyl, $-C(O)OH$, $-CH_2-CN$, $-CH_2-C(O)NH_2$, $-CH_2-NH_2$, $-CH_2-CH_2-NH_2$, $-CH_2-N(H)-CN$, $-CH_2-N(H)-OCH_3$, $-CH_2-N(H)C(O)-(2$-methyl)phenyl, $-CH_2-N(H)C(O)-(3$-methyl)phenyl, $-CH_2-N(H)C(O)-(4$-fluoro)phenyl, $-CH_2-N(H)C(O)-(4$-methoxy)phenyl, $-CH_2-N(H)C(O)-(4$-methyl)phenyl, $-CH_2-N(H)C(O)-(4$-trifluoromethyl)phenyl, $-CH_2-N(H)C(O)-2$-pyridinyl, $-CH_2-N(H)C(O)-2$-pyrrolyl, $-CH_2-N(H)C(O)-3$-pyridinyl, $-CH_2-N(H)C(O)-4$-pyridinyl, $-CH_2-N(H)C(O)$-benzodioxolyl, $-CH_2-N(H)C(O)$-butyl, $-CH_2-N(H)C(O)CF_3$, $-CH_2-N(H)C(O)$-cyclohexyl, $-CH_2-N(H)C(O)$-cyclopropyl, $-CH_2-N(H)C(O)$-ethyl, $-CH_2-N(H)C(O)$-furanyl, $-CH_2-N(H)C(O)$-isopropyl, $-CH_2-N(H)C(O)$-naphthyl, $-CH_2-N(H)C(O)$-phenyl, $-CH_2-N(H)C(O)$-propyl, $-CH_2-N(H)C(O)$-pyrazinyl, $-CH_2-N(H)C(O)$-t-butyl, $-CH_2-CH_2-N(H)C(O)$benzodioxolyl, $-CH_2-N(H)CH_2-(2,2$-difluorobenzodioxolyl), $-CH_2-CH_2-N(4$-methoxybenzyl)$_2$, $-CH_2-CH_2-N(H)-(4$-methoxy)benzyl, $-CH_2-N(H)-(2$-fluoro-4-methoxy)benzyl, $-CH_2-N(H)-(2$-fluoro-4-methyl)benzyl, $-CH_2-N(H)-(2$-methoxy-4-fluoro)benzyl, $-CH_2-N(H)-(2$-methyl)benzyl, $-CH_2-N(H)-(2$-methyl-4-fluoro)benzyl, $-CH_2-N(H)-(3,5$-dimethoxy)benzyl, $-CH_2-N(H)-(3$-methyl)benzyl, $-CH_2-N(H)-(4$-fluoro)benzyl, $-CH_2-N(H)-(4$-methoxy)benzyl, $-CH_2-N(H)-(4$-methyl)benzyl, $-CH_2-N(H)-(4$-nitro)benzyl, $-CH_2-N(H)-(4$-trifluoromethyl)benzyl, $-CH_2-N(H)-(4$-benzoyl)benzyl, $-CH_2-N(H)CH_2$-benzimidazolyl, $-CH_2-CH_2-N(H)CH_2$-benzodioxolyl, $-CH_2-N(H)CH_2CH_2-(4$-methoxy)phenyl, $-CH_2-N(H)CH_2$-pyridinyl, $-CH_2-N(H)C(O)N(H)$-benzyl, $-CH_2-N(H)C(O)N(H)$-ethyl, $-CH_2-N(H)C(O)N(H)$-phenyl, $-CH_2-N(H)C(S)N(H)CH_3$, $-CH_2$-benzimidazolyl, $-CH_2$-indolinyl, $-CH_2$-indolyl, $-CH_2$-purinyl, $-CH_2$-pyrazolyl, or $-CH_2$-triazolyl;

$R^5$ is alkyl or $R^5$ is a direct bond to C14;

$R^6$ is hydrogen;

$R^7$ is hydrogen, $-R^8-OR^9$ or a direct bond to C15, provided that when $R^7$ is a direct bond to C15, $R^{4b}$ is not a direct bond to the carbon to which $R^7$ is attached;

each $R^8$ is independently a direct bond or a straight or branched alkylene chain; and each $R^9$ is independently hydrogen, alkyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl or optionally substituted heteroarylalkyl;

or a stereoisomer, enantiomer or tautomer thereof or mixtures thereof;

or a pharmaceutically acceptable salt or solvate thereof.

In another aspect, this invention is directed to compositions comprising a pharmaceutically acceptable excipient, carrier and/or diluent and a compound of formula (I), or a stereoisomer, enantiomer or tautomer thereof or mixtures thereof; or a pharmaceutically acceptable salt or solvate thereof.

In another aspect, this invention is directed to a method for modulating SHIP1 activity in a mammal comprising administering an effective amount of a compound of formula (I), or a stereoisomer, enantiomer or tautomer thereof or mixtures thereof; or a pharmaceutically acceptable salt or solvate thereof, or a composition comprising a compound of formula (I), or a stereoisomer, enantiomer or tautomer thereof or mixtures thereof; or a pharmaceutically acceptable salt or solvate thereof, to the mammal in need thereof.

In another aspect, this invention is directed to methods for treating a disease, disorder or condition in a mammal comprising administering an effective amount of a compound of formula (I), or a stereoisomer, enantiomer or tautomer thereof or mixtures thereof; or a pharmaceutically acceptable salt or solvate thereof, as set forth above, to the mammal in need thereof, where the disease, disorder or condition is an autoimmune disease, disorder or condition, an inflammatory disease, disorder or condition, or a neoplastic or cell proliferative disease, disorder or condition.

In another aspect, this invention is directed to methods of treating a disease, disorder or condition in a mammal comprising administering an effective amount of a compound of formula (I), or a stereoisomer, enantiomer or tautomer thereof or mixtures thereof; or a pharmaceutically acceptable salt or solvate thereof, typically in the form of a composition, to the mammal in need thereof. Methods of this invention include administering an effective amount of a compound of formula (I), or a stereoisomer, enantiomer or tautomer thereof or mixtures thereof; or a pharmaceutically acceptable salt or solvate thereof, to the mammal in need thereof (such as a human).

In another aspect, this invention is directed to methods of preparing compounds of formula (I), or stereoisomers, enantiomers or tautomers thereof or mixtures thereof; or pharmaceutically acceptable salts or solvates thereof.

These aspects and embodiments thereof are described in more detail below. To this end, various references are set forth herein which describe in more detail certain background information, procedures, compounds and/or compositions, and are each hereby incorporated by reference in their entirety.

DETAILED DESCRIPTION OF THE INVENTION

Definitions

As used in the specification and appended claims, unless specified to the contrary, the following terms have the meaning indicated:

"Oxo" refers to $=O$.

"Cyano" refers to $-CN$.

"Nitro" refers to $-NO_2$.

"Hydroxy" refers to $-OH$.

"Alkyl" refers to a straight or branched hydrocarbon chain radical consisting solely of carbon and hydrogen atoms, containing no unsaturation, having from one to twelve carbon atoms, preferably one to eight carbon atoms, more preferably one to six carbon atoms, and which is attached to the rest of the molecule by a single bond, e.g., methyl, ethyl, n-propyl, 1-methylethyl (iso-propyl), n-butyl, n-pentyl, 1,1-dimethylethyl (t-butyl), 3-methylhexyl, 2-methylhexyl, and the like. When specifically stated in the specification, an alkyl group may be optionally substituted by one of the following groups: alkyl, halo, haloalkyl, cyano, nitro, aryl, cycloalkyl, heterocyclyl, heteroaryl, oxo, trimethylsilanyl, —OR$^{20}$, —OC(O)—R$^{20}$, —N(R$^{20}$)$_2$, —C(O)R$^{20}$, —C(O)OR$^{20}$, —C(O)N(R$^{20}$)$_2$, —N(R$^{20}$)C(O)OR$^{22}$, —N(R$^{20}$)C(O)R$^{22}$, —N(R$^{20}$)S(O)$_p$R$^{22}$ (where p is 1 to 2), —S(O)$_p$OR$^{22}$ (where p is 1 to 2), —S(O)$_t$R$^{22}$ (where t is 0 to 2), and —S(O)$_p$N(R$^{20}$)$_2$ (where p is 1 to 2) where each R$^{20}$ is independently hydrogen, alkyl, haloalkyl, cycloalkyl, cycloalkylalkyl, aryl, aralkyl, heterocyclyl, heterocyclylalkyl, heteroaryl or heteroarylalkyl; and each R$^{22}$ is alkyl, haloalkyl, cycloalkyl, cycloalkylalkyl, aryl, aralkyl, heterocyclyl, heterocyclylalkyl, heteroaryl or heteroarylalkyl.

"Alkenyl" refers to a straight or branched hydrocarbon chain radical group consisting solely of carbon and hydrogen atoms, containing at least one double bond, having from two to twelve carbon atoms, preferably one to eight carbon atoms and which is attached to the rest of the molecule by a single bond, e.g., ethenyl, prop-1-enyl, but-1-enyl, pent-1-enyl, penta-1,4-dienyl, and the like. When specifically stated in the specification, an alkenyl group may be optionally substituted by one of the following groups: alkyl, halo, haloalkyl, cyano, nitro, aryl, cycloalkyl, heterocyclyl, heteroaryl, oxo, trimethylsilanyl, —OR$^{20}$, —OC(O)—R$^{20}$, —N(R$^{20}$)$_2$, —C(O)R$^{20}$, —C(O)OR$^{20}$, —C(O)N(R$^{20}$)$_2$, —N(R$^{20}$)C(O)OR$^{22}$, —N(R$^{20}$)C(O)R$^{22}$, —N(R$^{20}$)S(O)$_p$R$^{22}$ (where p is 1 to 2), —S(O)$_p$OR$^{22}$ (where p is 1 to 2), —S(O)$_t$R$^{22}$ (where t is 0 to 2), and —S(O)$_p$N(R$^{20}$)$_2$ (where p is 1 to 2) where each R$^{20}$ is independently hydrogen, alkyl, haloalkyl, cycloalkyl, cycloalkylalkyl, aryl, aralkyl, heterocyclyl, heterocyclylalkyl, heteroaryl or heteroarylalkyl; and each R$^{22}$ is alkyl, haloalkyl, cycloalkyl, cycloalkylalkyl, aryl, aralkyl, heterocyclyl, heterocyclylalkyl, heteroaryl or heteroarylalkyl.

"Alkoxy" refers to a radical of the formula —OR$_a$ where R$_a$ is an alkyl radical as defined above containing one to twelve carbon atoms. The alkyl part of the alkoxy radical may be optionally substituted as defined above for an alkyl radical "Alkylene" or "alkylene chain" refers to a straight or branched divalent hydrocarbon chain linking the rest of the molecule to a radical group or linking two parts of the molecule, consisting solely of carbon and hydrogen, containing no unsaturation and having from one to twelve carbon atoms, e.g., —CH$_2$—, —CH$_2$—CH$_2$—, —CH$_2$—CH$_2$—CH$_2$—, and the like. The alkylene chain is attached to the rest of the molecule through a single bond and to the radical group through a single bond or is attached to two parts of the molecule through a single bond at each point of attachment. When specifically stated in the specification, an alkylene chain may be optionally substituted by one of the following groups: alkyl, alkenyl, halo, cyano, nitro, aryl, cycloalkyl, heterocyclyl, heteroaryl, oxo, trimethylsilanyl, —OR$^{20}$, —OC(O)—R$^{20}$, —N(R$^{20}$)$_2$, —C(O)R$^{20}$, —C(O)OR$^{20}$, —C(O)N(R$^{20}$)$_2$, —N(R$^{20}$)C(O)OR$^{22}$, —N(R$^{20}$)C(O)R$^{22}$, —N(R$^{20}$)S(O)$_p$R$^{22}$ (where p is 1 to 2), —S(O)$_p$OR$^{22}$ (where p is 1 to 2), —S(O)$_t$R$^{22}$ (where t is 0 to 2), and —S(O)$_p$N(R$^{20}$)$_2$ (where p is 1 to 2) where each R$^{20}$ is independently hydrogen, alkyl, haloalkyl, cycloalkyl, cycloalkylalkyl, aryl, aralkyl, heterocyclyl, heterocyclylalkyl, heteroaryl or heteroarylalkyl; and each R$^{22}$ is alkyl, haloalkyl, cycloalkyl, cycloalkylalkyl, aryl, aralkyl, heterocyclyl, heterocyclylalkyl, heteroaryl or heteroarylalkyl.

"Alkylidene" refers to a straight or branched hydrocarbon radical group consisting solely of carbon and hydrogen, containing at least one double bond, having from one to seven carbon atoms, and that is attached to the rest of the molecule through a double bond, e.g., methylene, ethylidene, propylidene, and the like. When specifically stated in the specification, an alkylidene radical may be optionally substituted by one of the following groups: alkyl, halo, haloalkyl, cyano, nitro, aryl, cycloalkyl, heterocyclyl, heteroaryl, oxo, trimethylsilanyl, —OR$^{20}$, —OC(O)—R$^{20}$, —N(R$^{20}$)$_2$, —C(O)R$^{20}$, —C(O)OR$^{20}$, —C(O)N(R$^{20}$)$_2$, —N(R$^{20}$)C(O)OR$^{22}$, —N(R$^{20}$)C(O)R$^{22}$, —N(R$^{20}$)S(O)$_p$R$^{22}$ (where p is 1 to 2), —S(O)$_p$OR$^{22}$ (where p is 1 to 2), —S(O)$_t$R$^{22}$ (where t is 0 to 2), and —S(O)$_p$N(R$^{20}$)$_2$ (where p is 1 to 2) where each R$^{20}$ is independently hydrogen, alkyl, haloalkyl, cycloalkyl, cycloalkylalkyl, aryl, aralkyl, heterocyclyl, heterocyclylalkyl, heteroaryl or heteroarylalkyl; and each R$^{22}$ is alkyl, haloalkyl, cycloalkyl, cycloalkylalkyl, aryl, aralkyl, heterocyclyl, heterocyclylalkyl, heteroaryl or heteroarylalkyl.

"Aryl" refers to a hydrocarbon ring system radical comprising hydrogen, 6 to 18 carbon atoms and at least one aromatic ring. For purposes of this invention, the aryl radical may be a monocyclic, bicyclic, tricyclic or tetracyclic ring system, which may included fused or bridged ring systems. Aryl radicals include, but are not limited to, aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. When specifically stated in the specification, an aryl group may be optionally substituted by one or more substituents independently selected from the group consisting of alkyl, alkenyl, halo, haloalkyl, cyano, nitro, aryl, aralkyl, cycloalkyl, cycloalkylalkyl, heterocyclyl, heterocyclylalkyl, heteroaryl, heteroarylalkyl, —R$^{21}$—OR$^{20}$, —R$^{21}$—OC(O)—R$^{20}$, —R$^{21}$—N(R$^{20}$)$_2$, —R$^{21}$—C(O)R$^{20}$, —R$^{21}$—C(O)OR$^{20}$, —R$^{21}$—C(O)N(R$^{20}$)$_2$, —R$^{21}$—N(R$^{20}$)C(O)OR$^{22}$, —R$^{21}$—N(R$^{20}$)C(O)R$^{22}$, —R$^{21}$—N(R$^{20}$)S(O)$_p$R$^{22}$ (where p is 1 to 2), —R$^{21}$—N=C(OR$^{20}$)R$^{20}$, —R$^{21}$—S(O)$_p$OR$^{22}$ (where p is 1 to 2), —R$^{21}$—S(O)$_t$R$^{22}$ (where t is 0 to 2), and —R$^{21}$—S(O)$_p$N(R$^{20}$)$_2$ (where p is 1 to 2) where each R$^{20}$ is independently hydrogen, alkyl, haloalkyl, cycloalkyl, cycloalkylalkyl, aryl, aralkyl, heterocyclyl, heterocyclylalkyl, heteroaryl or heteroarylalkyl; each R$^{21}$ is independently a direct bond or a straight or branched alkylene chain; and each R$^{22}$ is alkyl, haloalkyl, cycloalkyl, cycloalkylalkyl, aryl, aralkyl, heterocyclyl, heterocyclylalkyl, heteroaryl or heteroarylalkyl.

"Aralkyl" refers to a radical of the formula —R$_b$—R$_c$ where R$_b$ is an alkylene chain as defined above and R$_c$ is one or more aryl radicals as defined above, for example, benzyl, diphenylmethyl and the like. When specifically stated in the specification, the alkylene chain part of the aralkyl radical may be optionally substituted as described above for an optionally substituted alkylene chain. When specifically stated in the specification, the aryl part of the aralkyl radical may be optionally substituted as described above for an optionally substituted aryl group.

"Cycloalkyl" refers to a stable non-aromatic monocyclic or polycyclic hydrocarbon radical consisting solely of carbon and hydrogen atoms, which may include fused or bridged ring systems, having from three to fifteen carbon atoms, preferably having from three to ten carbon atoms, and which is saturated or unsaturated and attached to the rest of the molecule by a single bond. Monocyclic radicals include, for example, cyclopropyl, cyclobutyl, cyclopentyl, cyclohexyl, cycloheptyl, and cyclooctyl. Polycyclic radicals include, for example, adamantyl, norbornyl, decalinyl, and the like. When specifically stated in the specification, a cycloalkyl group may be optionally substituted by one or more substituents independently selected from the group consisting of alkyl, halo, haloalkyl, cyano, nitro, oxo, aryl, aralkyl, cycloalkyl, cycloalkylalkyl, heterocyclyl, heterocyclylalkyl, heteroaryl, heteroarylalkyl, $-R^{21}-OR^{20}$, $-R^{21}-OC(O)-R^{20}$, $-R^{21}-N(R^{20})_2$, $-R^{21}-C(O)R^{20}$, $-R^{21}-C(O)OR^{20}$, $-R^{21}-C(O)N(R^{20})_2$, $-R^{21}-N(R^{20})C(O)OR^{22}$, $-R^{21}-N(R^{20})C(O)R^{22}$, $-R^{21}-N(R^{20})S(O)_p R^{22}$ (where p is 1 to 2), $-R^{21}-N=C(OR^{20})R^{20}$, $-R^{21}-S(O)_p OR^{22}$ (where p is 1 to 2), $-R^{21}-S(O)_t R^{22}$ (where t is 0 to 2), and $-R^{21}-S(O)_p N(R^{20})_2$ (where p is 1 to 2) where each $R^{20}$ is independently hydrogen, alkyl, haloalkyl, cycloalkyl, cycloalkylalkyl, aryl, aralkyl, heterocyclyl, heterocyclylalkyl, heteroaryl or heteroarylalkyl; each $R^{21}$ is independently a direct bond or a straight or branched alkylene chain; and each $R^{22}$ is alkyl, haloalkyl, cycloalkyl, cycloalkylalkyl, aryl, aralkyl, heterocyclyl, heterocyclylalkyl, heteroaryl or heteroarylalkyl.

"Cycloalkylalkyl" refers to a radical of the formula $-R_b R_g$ where $R_b$ is an alkylene chain as defined above and $R_g$ is a cycloalkyl radical as defined above. When specifically stated in the specification, the alkylene chain and/or the cycloalkyl radical may be optionally substituted as defined above for optionally substituted alkylene chain and optionally substituted cycloalkyl.

"Halo" refers to bromo, chloro, fluoro or iodo.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1-fluoromethyl-2-fluoroethyl, 3-bromo-2-fluoropropyl, 1-bromomethyl-2-bromoethyl, and the like. The alkyl part of the haloalkyl radical may be optionally substituted as defined above for an alkyl group.

"Haloalkylidene" refers an alkylidene radical, as defined above, that is substituted by one or more halo radicals, as defined above. When specifically stated in the specification, an alkylidene radical may be optionally substituted by one of the following groups: alkyl, haloalkyl, cyano, nitro, aryl, cycloalkyl, heterocyclyl, heteroaryl, oxo, trimethylsilanyl, $-OR^{20}$, $-OC(O)-R^{20}$, $-N(R^{20})_2$, $-C(O)R^{20}$, $-C(O)OR^{20}$, $-C(O)N(R^{20})_2$, $-N(R^{20})C(O)OR^{22}$, $-N(R^{20})C(O)R^{22}$, $-N(R^{20})S(O)_p R^{22}$ (where p is 1 to 2), $-S(O)_p OR^{22}$ (where p is 1 to 2), $-S(O)_t R^{22}$ (where t is 0 to 2), and $-S(O)_p N(R^{20})_2$ (where p is 1 to 2) where each $R^{20}$ is independently hydrogen, alkyl, haloalkyl, cycloalkyl, cycloalkylalkyl, aryl, aralkyl, heterocyclyl, heterocyclylalkyl, heteroaryl or heteroarylalkyl; and each $R^{22}$ is alkyl, haloalkyl, cycloalkyl, cycloalkylalkyl, aryl, aralkyl, heterocyclyl, heterocyclylalkyl, heteroaryl or heteroarylalkyl.

"Heterocyclyl" refers to a stable 3- to 18-membered non-aromatic ring radical which consists of two to twelve carbon atoms and from one to six heteroatoms selected from the group consisting of nitrogen, oxygen and sulfur. Unless stated otherwise specifically in the specification, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of such heterocyclyl radicals include, but are not limited to, dioxolanyl, dioxinyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, 1,2,4-thiadiazol-5(4H)-ylidene, tetrahydrofuryl, trioxanyl, trithianyl, triazinanyl, tetrahydropyranyl, thiomorpholinyl, thiamorpholinyl, 1-oxo-thiomorpholinyl, and 1,1-dioxo-thiomorpholinyl. When specifically stated in the specification, a heterocyclyl group may be optionally substituted by one or more substituents selected from the group consisting of alkyl, alkenyl, halo, haloalkyl, cyano, oxo, thioxo, nitro, aryl, aralkyl, cycloalkyl, cycloalkylalkyl, heterocyclyl, heterocyclylalkyl, heteroaryl, heteroarylalkyl, $-R^{21}-OR^{20}$, $-R^{21}-OC(O)-R^{20}$, $-R^{21}-N(R^{20})_2$, $-R^{21}-C(O)R^{20}$, $-R^{21}-C(O)OR^{20}$, $-R^{21}-C(O)N(R^{20})_2$, $-R^{21}-N(R^{20})C(O)OR^{22}$, $-R^{21}-N(R^{20})C(O)R^{22}$, $-R^{21}-N(R^{20})S(O)_p R^{22}$ (where p is 1 to 2), $-R^{21}-N=C(OR^{20})R^{20}$, $-R^{21}-S(O)_p OR^{22}$ (where p is 1 to 2), $-R^{21}-S(O)_t R^{22}$ (where t is 0 to 2), and $-R^{21}-S(O)_p N(R^{20})_2$ (where p is 1 to 2) where each $R^{20}$ is independently hydrogen, alkyl, alkenyl, haloalkyl, cycloalkyl, cycloalkylalkyl, aryl, aralkyl, heterocyclyl, heterocyclylalkyl, heteroaryl or heteroarylalkyl; each $R^{21}$ is independently a direct bond or a straight or branched alkylene chain; and each $R^{22}$ is alkyl, alkenyl, haloalkyl, cycloalkyl, cycloalkylalkyl, aryl, aralkyl, heterocyclyl, heterocyclylalkyl, heteroaryl or heteroarylalkyl.

"N-heterocyclyl" refers to a heterocyclyl radical as defined above containing at least one nitrogen. The point of attachment of the N-heterocyclyl to the rest of the molecule can be through a nitrogen atom or a carbon atom in the N-heterocyclyl. When specifically stated in the specification, an N-heterocyclyl radical may be optionally substituted as described above for an optionally substituted heterocyclyl radical.

"Heterocyclylalkyl" refers to a radical of the formula $-R_b R_h$ where $R_b$ is an alkylene chain as defined above and $R_h$ is a heterocyclyl radical as defined above, and if the heterocyclyl is a nitrogen-containing heterocyclyl, the heterocyclyl may be attached to the alkyl radical at the nitrogen atom. When specifically stated in the specification, the alkylene chain of the heterocyclylalkyl radical may be optionally substituted as defined above for an optionally substituted alkyene chain. When specifically stated in the specification, the heterocyclyl part of the heterocyclylalkyl radical may be optionally substituted as defined above for an optionally substituted heterocyclyl group.

"Heteroaryl" refers to a 5- to 14-membered ring system radical comprising hydrogen atoms, one to thirteen carbon atoms, one to six heteroatoms selected from the group consisting of nitrogen, oxygen and sulfur, and at least one aromatic ring. For purposes of this invention, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzo[d]imidazolyl, benzthiazolyl, benzindolyl, benzodioxolyl, benzofuranyl, benzooxazolyl, benzothiazolyl, benzo[d]isoxazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, benzoxazolinonyl, benzimidazolthionyl, carbazolyl, cinnolinyl, dibenzofuranyl, dibenzothiophenyl, furanyl, furanonyl, isothiazolyl, imidazo[1,2-a]pyridinyl, imidazo[1,2-a]pyrimidinyl, imidazo[1,2-a]pyrazinyl, imidazo[1,5-a]pyrazinyl, imidazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, pteridinonyl, purinyl, pyrrolyl, pyrazolyl, pyridinyl, pyridinonyl, pyrazinyl, pyrimidinyl, pryrimidinonyl, pyridazinyl, pyrido[2,3-d]pyrimidinonyl, pyrazolo[1,5-a]pyrimidinyl, quinazolinyl, quinazolinonyl, quinoxalinyl, quinoxalinonyl, quinolinyl, isoquinolinyl, tetrahydroquinolinyl, thiazolyl, thiadiazolyl, thieno[3,2-d]pyrimidin-4-onyl, thieno[2,3-d]pyrimidin-4-onyl, triazolyl, tetrazolyl, triazinyl, and thiophenyl (i.e. thienyl). When specifically stated in the specification, a heteroaryl group may be optionally substituted by one or more substituents selected from the group consisting of alkyl, alkenyl, halo, haloalkyl, cyano, oxo, thioxo, nitro, thioxo, aryl, aralkyl, cycloalkyl, cycloalkylalkyl, heterocyclyl, heterocyclylalkyl, heteroaryl, heteroarylalkyl, —R$^{21}$—OR$^{20}$, —R$^{21}$—OC(O)—R$^{20}$, —R$^{21}$—N(R$^{20}$)$_2$, —R$^{21}$—C(O)R$^{20}$, —R$^{21}$—C(O)OR$^{20}$, —R$^{21}$—C(O)N(R$^{20}$)$_2$, —R$^{21}$—N(R$^{20}$)C(O)OR$^{22}$, —R$^{21}$—N(R$^{20}$)C(O)R$^{22}$, —R$^{21}$—N(R$^{20}$)S(O)$_p$R$^{22}$ (where p is 1 to 2), —R$^{21}$—N=C(OR$^{20}$)R$^{20}$, —R$^{21}$—S(O)$_p$OR$^{22}$ (where p is 1 to 2), —R$^{21}$—S(O)$_t$R$^{22}$ (where t is 0 to 2), and —R$^{21}$—S(O)$_p$N(R$^{20}$)$_2$ (where p is 1 to 2) where each R$^{20}$ is independently hydrogen, alkyl, alkenyl, haloalkyl, cycloalkyl, cycloalkylalkyl, aryl, aralkyl, heterocyclyl, heterocyclylalkyl, heteroaryl or heteroarylalkyl; each R$^{21}$ is independently a direct bond or a straight or branched alkylene chain; and each R$^{22}$ is alkyl, alkenyl, haloalkyl, cycloalkyl, cycloalkylalkyl, aryl, aralkyl, heterocyclyl, heterocyclylalkyl, heteroaryl or heteroarylalkyl.

"N-heteroaryl" refers to a heteroaryl radical as defined above containing at least one nitrogen. The point of attachment of the N-heteroaryl to the rest of the molecule can be through a nitrogen atom or a carbon atom in the N-heteroaryl. When specifically stated in the specification, an N-heteroaryl radical may be optionally substituted as described above for an optionally substituted heteroaryl radical.

"Heteroarylalkyl" refers to a radical of the formula —R$_b$R$_i$ where R$_b$ is an alkylene chain as defined above and R$_i$ is a heteroaryl radical as defined above. When specifically stated in the specification, the heteroaryl part of the heteroarylalkyl radical may be optionally substituted as defined above for an optionally substituted heteroaryl group. When specifically stated in the specification, the alkylene chain part of the heteroarylalkyl radical may be optionally substituted as defined above for an optionally substituted alkylene chain.

"Prodrugs" is meant to indicate a compound that may be converted under physiological conditions or by solvolysis to a biologically active compound of the invention. Thus, the term "prodrug" refers to a metabolic precursor of a compound of the invention that is pharmaceutically acceptable. A prodrug may be inactive when administered to a subject in need thereof, but is converted in vivo to an active compound of the invention. Prodrugs are typically rapidly transformed in vivo to yield the parent compound of the invention, for example, by hydrolysis in blood. The prodrug compound often offers advantages of solubility, tissue compatibility or delayed release in a mammalian organism (see, Bundgard, H., *Design of Prodrugs* (1985), pp. 7-9, 21-24 (Elsevier, Amsterdam)). A discussion of prodrugs is provided in Higuchi, T., et al., "Pro-drugs as Novel Delivery Systems," A.C.S. Symposium Series, Vol. 14, and in Bioreversible Carriers in Drug Design, Ed. Edward B. Roche, American Pharmaceutical Association and Pergamon Press, 1987, both of which are incorporated in full by reference herein.

The term "prodrug" is also meant to include any covalently bonded carriers, which release the active compound of the invention in vivo when such prodrug is administered to a mammalian subject. Prodrugs of a compound of the invention may be prepared by modifying functional groups present in the compound of the invention in such a way that the modifications are cleaved, either in routine manipulation or in vivo, to the parent compound of the invention. Prodrugs include compounds of the invention wherein a hydroxy, amino or mercapto group is bonded to any group that, when the prodrug of the compound of the invention is administered to a mammalian subject, cleaves to form a free hydroxy, free amino or free mercapto group, respectively. Examples of prodrugs include, but are not limited to, acetate, formate and benzoate derivatives of alcohol or amide derivatives of amine functional groups in the compounds of the invention and the like. Further, in the case of a carboxylic acid (—C(O)OH), esters may be employed, such as methyl esters, ethyl esters, and the like.

"Stable compound" and "stable structure" are meant to indicate a compound that is sufficiently robust to survive isolation to a useful degree of purity from a reaction mixture, and formulation into an efficacious therapeutic agent.

"Mammal" includes humans and both domestic animals such as laboratory animals and household pets, (e.g., cats, dogs, swine, cattle, sheep, goats, horses, rabbits), and non-domestic animals such as wildlife and the like.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution ("unsubstituted"). When a functional group is described as "optionally substituted," and in turn, substitutents on the functional group are also "optionally substituted" and so on, for the purposes of this invention, such iterations are limited to five, preferably such iterations are limited to two.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor- 10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Often crystallizations produce a solvate of the compound of the invention. As used herein, the term "solvate" refers to an aggregate that comprises one or more molecules of a compound of the invention with one or more molecules of solvent. The solvent may be water, in which case the solvate may be a hydrate. Alternatively, the solvent may be an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. The compound of the invention may be true solvates, while in other cases, the compound of the invention may merely retain adventitious water or be a mixture of water plus some adventitious solvent. Furthermore, some of the crystalline forms of the compounds of formula (I) may exist as polymorphs, which are included in the present invention.

A "pharmaceutical composition" refers to a formulation of a compound of the invention and a medium generally accepted in the art for the delivery of the biologically active compound to mammals, e.g., humans. Such a medium includes all pharmaceutically acceptable carriers, diluents or excipients therefor.

"Therapeutically effective amount" refers to that amount of a compound of the invention which, when administered to a mammal, preferably a human, is sufficient to effect treatment, as defined below, of a disease or condition alleviated by the modulation of SHIP1 in the mammal, preferably a human. The amount of a compound of the invention which constitutes a "therapeutically effective amount" will vary depending on the compound, the condition and its severity, the manner of administration, and the age of the mammal to be treated, but can be determined routinely by one of ordinary skill in the art having regard to his own knowledge and to this disclosure.

"Treating" or "treatment" as used herein covers the treatment of the disease or condition of interest in a mammal, preferably a human, having the disease or condition of interest, and includes:

(a) preventing the disease or condition from occurring in a mammal, in particular, when such mammal is predisposed to the condition but has not yet been diagnosed as having it;

(b) inhibiting the disease or condition, i.e., arresting its development;

(c) relieving (or ameliorating) the disease or condition, i.e., causing regression of the disease or condition; or (d) relieving (or ameliorating) the symptoms resulting from the disease or condition, i.e., relieving inflammation without addressing the underlying disease or condition.

As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

The compounds of the invention, or their pharmaceutically acceptable salts, may contain one or more asymmetric centres and may thus give rise to enantiomers, diastereomers, and other stereoisomeric forms that may be defined, in terms of absolute stereochemistry, as (R)- or (S)- or, as (D)- or (L)- for amino acids. Compounds of formula (I) may also possess axial chirality which may result in atropisomers. The present invention is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallisation. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centres of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present invention contemplates various stereoisomers and mixtures thereof and includes enantiomers, which refers to two stereoisomers whose molecules are nonsuperimposeable mirror images of one another. See, for example, Smith, M. B. and J. March, *March's Advanced Organic Chemistry: Reactions, Mechanisms, and Structure,* 6th edition (Wiley, 2007), for a detailed description of the structure and properties of enantiomers and stereoisomers.

A "tautomer" refers to a proton shift from one atom of a molecule to another atom of the same molecule. The present invention includes tautomers of any said compounds.

The use of parentheses and brackets in substituent groups is used herein to conserve space. Accordingly, the use of parenthesis in a substituent group indicates that the group enclosed within the parentheses is attached directly to the atom preceding the parenthesis. For example, the following substituent group:

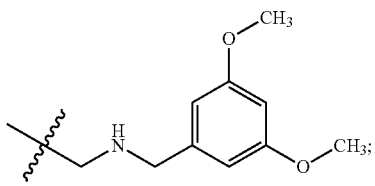 [SMILES: *CNCc1cc(OC)cc(OC)c1]

is represented herein as —$CH_2$—N(H)$CH_2$-(3,5-dimethoxy)phenyl.

The chemical naming protocol and structure diagrams used herein are a modified form of the I.U.P.A.C. nomenclature system, using ChemBioDraw Ultra Version 12.0 software program, wherein the compounds of the invention are named herein as derivatives of a central core structure. For complex chemical names employed herein, a substituent group is named before the group to which it attaches. For example, cyclopropylethyl comprises an ethyl backbone with cyclopropyl substituent. In chemical structure diagrams, all bonds are identified, except for some carbon atoms, which are assumed to be bonded to sufficient hydrogen atoms to complete the valency.

Certain carbons are identified by numerals in formula (I) of the compounds of the invention. For purposes herein, the carbon at numeral 1 in formula (I) is indicated herein as C1, and so forth. These numerals may or may not be the same as the locants in the compound names given herein.

Thus, for example, a compound of formula (I) wherein C1, C4, C11 and C12 are each independently substituted with two hydrogens, C9 is substituted with one hydrogen, C14 is substituted with one hydrogen, C15 is substituted with two hydrogens, $R^1$ is —OH, $R^2$ is —$CH_2$OH, $R^3$ is —$CH_2$—N(H)$CH_2$-(3,5-dimethoxy)phenyl, $R^{4a}$ and $R^{4b}$ together form methylene, $R^5$ is methyl, and $R^6$ and $R^7$ are each hydrogen, i.e., a compound of the following structure:

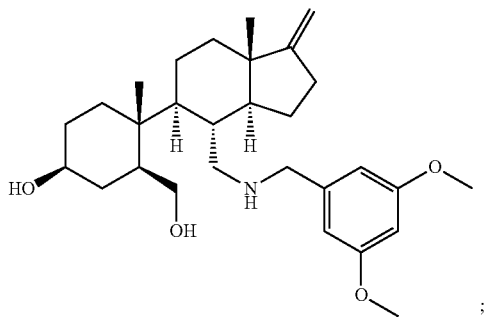 [SMILES: C=C1CC[C@H]2[C@H](CNCc3cc(OC)cc(OC)c3)[C@@H]([C@@]3(C)CC[C@H](O)C[C@@H]3CO)CC[C@]12C]

is named herein as (1S,3S,4R)-4-((3aS,4R,5S,7aS)-4-((3,5-dimethoxybenzylamino)methyl)-7a-methyl-1-methyleneoctahydro-1H-inden-5-yl)-3-(hydroxymethyl)-4-methylcyclohexanol.

EMBODIMENTS OF THE INVENTION

Of the various aspects of the invention set forth above in the Summary of the Invention, certain embodiments are preferred.

One preferred embodiment is a compound of formula (I), as described above in the Summary of the Invention, wherein C1, C4, C11 and C12 are each independently substituted with two hydrogens; C9 is substituted with one hydrogen; C14 is substituted with one hydrogen when $R^5$ is not a direct bond to C14; C15 is substituted with two hydrogens; $R^1$ is —$R^8$—$OR^9$ or —$R^8$—$N(R^9)_2$; $R^2$ is —$R^8$—$OR^9$, —$R^8$—CN, —$R^8$—C(O)$OR^9$, —$R^8$—C(O)N$(R^9)_2$, —$R^8$—$N(R^9)_2$, —$R^8$—$N(R^9)C(O)R^9$, optionally substituted heterocyclylalkyl or optionally substituted heteroarylalkyl; $R^{4a}$ is hydrogen or alkyl, $R^{4b}$ is a direct bond to the carbon to which $R^7$ is attached, and $R^3$ is —$CH_2NH_2$ or —$CH_2N(H)C(O)(CH_2)_3CH_3$; $R^5$ is alkyl or $R^5$ is a direct bond to C14; $R^6$ is hydrogen; $R^7$ is hydrogen or —$R^8$—$OR^9$; each $R^8$ is independently a direct bond or a straight or branched alkylene chain; and each $R^9$ is independently hydrogen, alkyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl or optionally substituted heteroarylalkyl.

Another embodiment is a compound of formula (I), as described above in the Summary of the Invention, wherein C1, C4, C11 and C12 are each independently substituted with two hydrogens; C9 is substituted with one hydrogen; C14 is substituted with one hydrogen; C15 is substituted with two hydrogens; $R^1$ is —$R^8$—$OR^9$; $R^2$ is —$R^8$—$OR^9$; $R^{4a}$ is hydrogen or alkyl, $R^{4b}$ is a direct bond to the carbon to which $R^7$ is attached, and $R^3$ is —$CH_2NH_2$ or —$CH_2N(H)C(O)(CH_2)_3CH_3$; $R^5$ is alkyl; $R^6$ is hydrogen; $R^7$ is hydrogen; each $R^8$ is independently a direct bond or a straight or branched alkylene chain; and each $R^9$ is independently hydrogen, alkyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl or optionally substituted heteroarylalkyl.

Another embodiment is a compound of formula (I), as described above in the Summary of the Invention, wherein C1, C4, C11 and C12 are each independently substituted with two hydrogens; C9 is substituted with one hydrogen; C14 is substituted with one hydrogen; C15 is substituted with two hydrogens; $R^1$ is —OH; $R^2$ is —$CH_2$—OH; $R^{4a}$ is hydrogen or methyl, $R^{4b}$ is a direct bond to the carbon to which $R^7$ is attached, and $R^3$ is —$CH_2NH_2$ or —$CH_2N(H)C(O)(CH_2)_3CH_3$; $R^5$ is methyl; $R^6$ is hydrogen; and $R^7$ is hydrogen.

Another embodiment is a compound of formula (I), as described above in the Summary of the Invention, selected from:
(1S,3S,4R)-4-((3aS,6S,7R,7aS)-7-(aminomethyl)-3,3a-dimethyl-3a,4,5,6,7,7a-hexahydro-1H-inden-6-yl)-3-(hydroxymethyl)-4-methylcyclohexanol; and
N-(((3aR,6S,7R,7aS)-6-((1R,2S,4S)-4-hydroxy-2-(hydroxymethyl)-1-methylcyclohexyl)-3a-methyl-3a,4,5,6,7,7a-hexahydro-1H-inden-7-yl)methyl)pentanamide.

Another embodiment is a compound of formula (I), as described above in the Summary of the Invention, wherein C1, C4, C11 and C12 are each independently substituted with two hydrogens; C9 is substituted with one hydrogen;

C14 is substituted with one hydrogen when $R^5$ is not a direct bond to C14; C15 is substituted with two hydrogens when $R^7$ is not a direct bond to C15, and one hydrogen when $R^7$ is a direct bond to C15; $R^1$ is $—R^8—OR^9$ or $—R^8—N(R^9)_2$; $R^2$ is $—R^8—OR^9$, $—R^8—CN$, $—R^8—C(O)OR^9$, $—R^8—C(O)N(R^9)_2$, $—R^8—N(R^9)_2$, $—R^8—N(R^9)C(O)R^9$, optionally substituted heterocyclylalkyl or optionally substituted heteroarylalkyl; $R^{4a}$ and $R^{4b}$ are each independently selected from hydrogen and alkyl and $R^3$ is $—CH_2OH$, $—CH_2NH_2$, $—CH_2N(H)CH_3$, $—CH_2N(CH_3)_2$, $—CH_2N(H)CH_2$-cyclopropyl, $—CH_2N(H)CH_2$-pyrrolyl, $—CH_2N(H)C(O)CH_3$, $—CH_2N(H)C(O)$-phenyl, $—CH_2N(H)S(O)_2CH_3$ or $—CH_2N(H)C(=NH)NH_2$; $R^5$ is alkyl or $R^5$ is a direct bond to C14; $R^6$ is hydrogen; $R^7$ is hydrogen, $—R^8—OR^9$ or a direct bond to C15; each $R^8$ is independently a direct bond or a straight or branched alkylene chain; and each $R^9$ is independently hydrogen, alkyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl or optionally substituted heteroarylalkyl.

Another embodiment is a compound of formula (I), as described above in the Summary of the Invention, wherein C1, C4, C11 and C12 are each independently substituted with two hydrogens; C9 is substituted with one hydrogen; C14 is substituted with one hydrogen when $R^5$ is not a direct bond to C14; C15 is substituted with two hydrogens when $R^7$ is not a direct bond to C15, and one hydrogen when $R^7$ is a direct bond to C15; $R^1$ is $—R^8—OR^9$; $R^2$ is $—R^8—OR^9$; $R^{4a}$ and $R^{4b}$ are each independently selected from hydrogen and alkyl and $R^3$ is $—CH_2OH$, $—CH_2NH_2$, $—CH_2N(H)CH_3$, $—CH_2N(CH_3)_2$, $—CH_2N(H)CH_2$-cyclopropyl, $—CH_2N(H)CH_2$-pyrrolyl, $—CH_2N(H)C(O)CH_3$, $—CH_2N(H)C(O)$-phenyl, $—CH_2N(H)S(O)_2CH_3$ or $—CH_2N(H)C(=NH)NH_2$; $R^5$ is alkyl or $R^5$ is a direct bond to C14; $R^6$ is hydrogen; $R^7$ is hydrogen, $—R^8—OR^9$ or a direct bond to C15; each $R^8$ is independently a direct bond or a straight or branched alkylene chain; and each $R^9$ is independently hydrogen, alkyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl or optionally substituted heteroarylalkyl.

Another embodiment is a compound of formula (I), as described above in the Summary of the Invention, wherein C1, C4, C11 and C12 are each independently substituted with two hydrogens; C9 is substituted with one hydrogen; C15 is substituted with two hydrogens; $R^2$ is $—CH_2—OH$; $R^{4a}$ and $R^{4b}$ are each independently selected from hydrogen, methyl or ethyl and $R^3$ is $—CH_2OH$, $—CH_2NH_2$, $—CH_2N(H)CH_3$, $—CH_2N(CH_3)_2$, $—CH_2N(H)CH_2$-cyclopropyl, $—CH_2N(H)CH_2$-pyrrolyl, $—CH_2N(H)C(O)CH_3$, $—CH_2N(H)C(O)$-phenyl, $—CH_2N(H)S(O)_2CH_3$ or $—CH_2N(H)C(=NH)NH_2$; $R^5$ is a direct bond to C14; $R^6$ is hydrogen; and $R^7$ is hydrogen, $—OH$ or a direct bond to C15.

Another embodiment is a compound of formula (I), as described above in the Summary of the Invention, selected from:

1-(((4R,5S)-5-((1R,2S,4S)-4-hydroxy-2-(hydroxymethyl)-1-methylcyclohexyl)-1,1-dimethyl-2,3,4,5,6,7-hexahydro-1H-inden-4-yl)methyl)guanidine hydrochloride;
(1S,3S,4R)-4-((4R,5S)-4-((cyclopropylmethylamino)methyl)-1,1-dimethyl-2,3,4,5,6,7-hexahydro-1H-inden-5-yl)-3-(hydroxymethyl)-4-methylcyclohexanol;
(1S,3S,4R)-4-((4R,5S)-4-((dimethylamino)methyl)-1,1-dimethyl-2,3,4,5,6,7-hexahydro-1H-inden-5-yl)-3-(hydroxymethyl)-4-methylcyclohexanol;
N-(((4R,5S)-5-((1R,2S,4S)-4-hydroxy-2-(hydroxymethyl)-1-methylcyclohexyl)-1,1-dimethyl-2,3,4,5,6,7-hexahydro-1H-inden-4-yl)methyl)acetamide;
(1S,3S,4R)-4-((4R,5S)-1,1-dimethyl-4-((methylamino)methyl)-2,3,4,5,6,7-hexahydro-1H-inden-5-yl)-3-(hydroxymethyl)-4-methylcyclohexanol;
(1S,3S,4R)-4-((4R,5S)-4-(((1H-pyrrol-2-yl)methylamino)methyl)-1,1-dimethyl-2,3,4,5,6,7-hexahydro-1H-inden-5-yl)-3-(hydroxymethyl)-4-methylcyclohexanol;
N-(((4R,5S)-5-((1R,2S,4S)-4-hydroxy-2-(hydroxymethyl)-1-methylcyclohexyl)-1,1-dimethyl-2,3,4,5,6,7-hexahydro-1H-inden-4-yl)methyl)methanesulfonamide;
N-(((4R,5S)-5-((1R,2S,4S)-4-hydroxy-2-(hydroxymethyl)-1-methylcyclohexyl)-1,1-dimethyl-2,3,4,5,6,7-hexahydro-1H-inden-4-yl)methyl)benzamide;
(1S,3S,4R)-3-(hydroxymethyl)-4-((4R,5S)-4-(hydroxymethyl)-1,1-dimethyl-4,5,6,7-tetrahydro-1H-inden-5-yl)-4-methylcyclohexanol; and
(2R,4R,5S)-5-((1R,2S,4S)-4-hydroxy-2-(hydroxymethyl)-1-methylcyclohexyl)-4-(hydroxymethyl)-1,1-dimethyl-2,3,4,5,6,7-hexahydro-1H-inden-2-ol.

Another embodiment is a compound of formula (I), as described above in the Summary of the Invention, wherein C1, C4, C11 and C12 are each independently substituted with two hydrogens; C9 is substituted with one hydrogen; C14 is substituted with one hydrogen; C15 is substituted with two hydrogens when $R^7$ is not a direct bond to C15, and one hydrogen when $R^7$ is a direct bond to C15; $R^1$ is $—R^8—OR^9$; $R^2$ is $—R^8—OR^9$; $R^{4a}$ and $R^{4b}$ are each independently selected from hydrogen and alkyl and $R^3$ is $—CH_2OH$, $—CH_2NH_2$, $—CH_2N(H)CH_3$, $—CH_2N(CH_3)_2$, $—CH_2N(H)CH_2$-cyclopropyl, $—CH_2N(H)CH_2$-pyrrolyl, $—CH_2N(H)C(O)CH_3$, $—CH_2N(H)C(O)$-phenyl, $—CH_2N(H)S(O)_2CH_3$ or $—CH_2N(H)C(=NH)NH_2$; $R^5$ is alkyl; $R^6$ is hydrogen; $R^7$ is hydrogen, $—R^8—OR^9$ or a direct bond to C15; each $R^8$ is independently a direct bond or a straight or branched alkylene chain; and each $R^9$ is independently hydrogen, alkyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl or optionally substituted heteroarylalkyl.

Another embodiment is a compound of formula (I), as described above in the Summary of the Invention, wherein C1, C4, C11 and C12 are each independently substituted with two hydrogens; C9 is substituted with one hydrogen; C14 is substituted with one hydrogen; C15 is substituted with two hydrogens; $R^1$ is $—OH$; $R^2$ is $—CH_2—OH$; $R^{4a}$ and $R^{4b}$ are each independently selected from hydrogen, methyl or ethyl and $R^3$ is $—CH_2NH_2$, $—CH_2N(H)CH_3$ or $—CH_2N(CH_3)_2$; $R^5$ is methyl; $R^6$ is hydrogen; and $R^7$ is hydrogen.

Another embodiment is a compound of formula (I), as described above in the Summary of the Invention, which is (1S,3S,4R)-4-((1S,3aS,4S,5S,7aR)-4-(aminomethyl)-1-ethyl-7a-methyloctahydro-1H-inden-5-yl)-3-(hydroxymethyl)-4-methylcyclohexanol acetate.

Another embodiment is a compound of formula (I), as described above in the Summary of the Invention, wherein C1, C4, C11 and C12 are each independently substituted with two hydrogens; C9 is substituted with one hydrogen; C14 is substituted with one hydrogen when $R^5$ is not a direct bond to C14; C15 is substituted with two hydrogens when $R^7$ is not a direct bond to C15, and one hydrogen when $R^7$ is a direct bond to C15; $R^1$ is —$R^8$—$OR^9$ or —$R^8$—$N(R^9)_2$; $R^2$ is —$R^8$—$OR^9$, —$R^8$—CN, —$R^8$—C(O)$OR^9$, —$R^8$—C(O)N($R^9$)$_2$, —$R^8$—N($R^9$)$_2$, —$R^8$—N($R^9$)C(O)$R^9$, optionally substituted heterocyclylalkyl or optionally substituted heteroarylalkyl; $R^{4a}$ and $R^{4b}$ together form methylene and $R^3$ is —OH, —CH$_2$—OH, —CH$_2$—CH$_2$—OH, —CH$_2$—O-(3,5-dimethoxy)benzyl, —CH$_2$—O-benzyl, —CH$_2$—O—CH$_2$-pyridinyl, —C(O)OH, —CH$_2$—CN, —CH$_2$—C(O)NH$_2$, —CH$_2$—NH$_2$, —CH$_2$—CH$_2$—NH$_2$, —CH$_2$—N(H)—CN, —CH$_2$—N(H)—OCH$_3$, —CH$_2$—N(H)C(O)-(2-methyl)phenyl, —CH$_2$—N(H)C(O)-(3-methyl)phenyl, —CH$_2$—N(H)C(O)-(4-fluoro)phenyl, —CH$_2$—N(H)C(O)-(4-methoxy)phenyl, —CH$_2$—N(H)C(O)-(4-methyl)phenyl, —CH$_2$—N(H)C(O)-(4-trifluoromethyl)phenyl, —CH$_2$—N(H)C(O)-2-pyridinyl, —CH$_2$—N(H)C(O)-2-pyrrolyl, —CH$_2$—N(H)C(O)-3-pyridinyl, —CH$_2$—N(H)C(O)-4-pyridinyl, —CH$_2$—N(H)C(O)-benzodioxolyl, —CH$_2$—N(H)C(O)-butyl, —CH$_2$—N(H)C(O)CF$_3$, —CH$_2$—N(H)C(O)-cyclohexyl, —CH$_2$—N(H)C(O)-cyclopropyl, —CH$_2$—N(H)C(O)-ethyl, —CH$_2$—N(H)C(O)-furanyl, —CH$_2$—N(H)C(O)-isopropyl, —CH$_2$—N(H)C(O)-naphthyl, —CH$_2$—N(H)C(O)-phenyl, —CH$_2$—N(H)C(O)-propyl, —CH$_2$—N(H)C(O)-pyrazinyl, —CH$_2$—N(H)C(O)-t-butyl, —CH$_2$—CH$_2$—N(H)C(O)benzodioxolyl, —CH$_2$—N(H)CH$_2$-(2,2-difluorobenzodioxolyl), —CH$_2$—CH$_2$—N(4-methoxybenzyl)$_2$, —CH$_2$—CH$_2$—N(H)-(4-methoxy)benzyl, —CH$_2$—N(H)-(2-fluoro-4-methoxy)benzyl, —CH$_2$—N(H)-(2-fluoro-4-methyl)benzyl, —CH$_2$—N(H)-(2-methoxy-4-fluoro)benzyl, —CH$_2$—N(H)-(2-methyl)benzyl, —CH$_2$—N(H)-(2-methyl-4-fluoro)benzyl, —CH$_2$—N(H)-(3,5-dimethoxy)benzyl, —CH$_2$—N(H)-(3-methyl)benzyl, —CH$_2$—N(H)-(4-fluoro)benzyl, —CH$_2$—N(H)-(4-methoxy)benzyl, —CH$_2$—N(H)-(4-methyl)benzyl, —CH$_2$—N(H)-(4-nitro)benzyl, —CH$_2$—N(H)-(4-trifluoromethyl)benzyl, —CH$_2$—N(H)-(4-benzoyl)benzyl, —CH$_2$—N(H)CH$_2$-benzimidazolyl, —CH$_2$—CH$_2$—N(H)CH$_2$-benzodioxolyl, —CH$_2$—N(H)CH$_2$CH$_2$-(4-methoxy)phenyl, —CH$_2$—N(H)CH$_2$-pyridinyl, —CH$_2$—N(H)C(O)N(H)-benzyl, —CH$_2$—N(H)C(O)N(H)-ethyl, —CH$_2$—N(H)C(O)N(H)-phenyl, —CH$_2$—N(H)C(S)N(H)CH$_3$, —CH$_2$-benzimidazolyl, —CH$_2$-indolinyl, —CH$_2$-indolyl, —CH$_2$-purinyl, —CH$_2$-pyrazolyl, or —CH$_2$-triazolyl; $R^5$ is alkyl or $R^5$ is a direct bond to C14; $R^6$ is hydrogen; $R^7$ is hydrogen, —$R^8$—$OR^9$ or a direct bond to C15; each $R^8$ is independently a direct bond or a straight or branched alkylene chain; and each $R^9$ is independently hydrogen, alkyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl or optionally substituted heteroarylalkyl.

Another embodiment is a compound of formula (I), as described above in the Summary of the Invention, wherein C1, C4, C11 and C12 are each independently substituted with two hydrogens; C9 is substituted with one hydrogen; C14 is substituted with one hydrogen when $R^5$ is not a direct bond to C14; C15 is substituted with two hydrogens when $R^7$ is not a direct bond to C15, and one hydrogen when $R^7$ is a direct bond to C15; $R^1$ is —$R^8$—$OR^9$ or —$R^8$—$N(R^9)_2$; $R^2$ is —$R^8$—$OR^9$, —$R^8$—CN, —$R^8$—C(O)$OR^9$, —$R^8$—C(O)N($R^9$)$_2$, —$R^8$—N($R^9$)$_2$, —$R^8$—N($R^9$)C(O)$R^9$, optionally substituted heterocyclylalkyl or optionally substituted heteroarylalkyl; $R^{4a}$ and $R^{4b}$ together form methylene and $R^3$ is —OH, —CH$_2$—OH, —CH$_2$—CH$_2$—OH, —CH$_2$—O-(3,5-dimethoxy)benzyl, —CH$_2$—O-benzyl, —CH$_2$—O—CH$_2$-pyridinyl, —C(O)OH, —CH$_2$—CN, —CH$_2$—C(O)NH$_2$, —CH$_2$—NH$_2$, —CH$_2$—CH$_2$—NH$_2$, —CH$_2$—N(H)—CN or —CH$_2$—N(H)—OCH$_3$; $R^5$ is alkyl or $R^5$ is a direct bond to C14; $R^6$ is hydrogen; $R^7$ is hydrogen, —$R^8$—$OR^9$ or a direct bond to C15; each $R^8$ is independently a direct bond or a straight or branched alkylene chain; and each $R^9$ is independently hydrogen, alkyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl or optionally substituted heteroarylalkyl.

Another embodiment is a compound of formula (I), as described above in the Summary of the Invention, wherein C1, C4, C11 and C12 are each independently substituted with two hydrogens; C9 is substituted with one hydrogen; C14 is substituted with one hydrogen; C15 is substituted with two hydrogens when $R^7$ is not a direct bond to C15, and one hydrogen when $R^7$ is a direct bond to C15; $R^1$ is —$R^8$—$OR^9$ or —$R^8$—$N(R^9)_2$; $R^2$ is —$R^8$—$OR^9$; $R^{4a}$ and $R^{4b}$ together form methylene and $R^3$ is —OH, —CH$_2$—OH, —CH$_2$—CH$_2$—OH, —CH$_2$—O-(3,5-dimethoxy)benzyl, —CH$_2$—O-benzyl, —CH$_2$—O—CH$_2$-pyridinyl, —C(O)OH, —CH$_2$—CN, —CH$_2$—C(O)NH$_2$, —CH$_2$—NH$_2$, —CH$_2$—CH$_2$—NH$_2$, —CH$_2$—N(H)—CN or —CH$_2$—N(H)—OCH$_3$; $R^5$ is alkyl; $R^6$ is hydrogen; $R^7$ is hydrogen, —$R^8$—$OR^9$ or a direct bond to C15; each $R^8$ is independently a direct bond or a straight or branched alkylene chain; and each $R^9$ is independently hydrogen, alkyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl or optionally substituted heteroarylalkyl.

Another embodiment is a compound of formula (I), as described above in the Summary of the Invention, wherein C1, C4, C11 and C12 are each independently substituted with two hydrogens; C9 is substituted with one hydrogen; C14 is substituted with one hydrogen; C15 is substituted with two hydrogens when $R^7$ is not a direct bond to C15, and one hydrogen when $R^7$ is a direct bond to C15; $R^1$ is —OH or NH$_2$; $R^2$ is —$R^8$—$OR^9$; $R^{4a}$ and $R^{4b}$ together form methylene and $R^3$ is —OH, —CH$_2$—OH, —CH$_2$—CH$_2$—OH, —CH$_2$—O-(3,5-dimethoxy)benzyl, —CH$_2$—O-benzyl, —CH$_2$—O—CH$_2$-pyridinyl, —C(O)OH, —CH$_2$—CN, —CH$_2$—C(O)NH$_2$, —CH$_2$—NH$_2$, —CH$_2$—CH$_2$—NH$_2$, —CH$_2$—N(H)—CN, or —CH$_2$—N(H)—OCH$_3$; $R^5$ is methyl; $R^6$ is hydrogen; $R^7$ is hydrogen, —OH or a direct bond to C15; $R^8$ is a direct bond, —CH$_2$— or —CH$_2$—CH$_2$—; and $R^9$ is hydrogen, optionally substituted pyridinyl, optionally substituted pyrimidinyl, or optionally substituted pyrazinyl.

Another embodiment is a compound of formula (I), as described above in the Summary of the Invention, selected from:

(1S,3S,4R)-4-((3aS,4R,5S,7aS)-4-(2-aminoethyl)-7a-methyl-1-methyleneoctahydro-1H-inden-5-yl)-3-(hydroxymethyl)-4-methylcyclohexanol;

(1S,3S,4R)-4-((3aS,4S,5S,7aS)-4-(2-hydroxyethyl)-7a-methyl-1-methyleneoctahydro-1H-inden-5-yl)-4-methyl-3-(pyridin-2-yloxy)cyclohexanol;

(1S,3S,4R)-4-((3aS,4R,5S,7aS)-4-(hydroxymethyl)-7a-methyl-1-methyleneoctahydro-1H-inden-5-yl)-4-methyl-3-((pyridin-2-yloxy)methyl)cyclohexanol;

(3aR,4R,5R,7aS)-5-((1S,2S,4S)-4-hydroxy-1-methyl-2-(2-(pyrimidin-2-yloxy)ethyl)cyclohexyl)-7a-methyl-1-methyleneoctahydro-1H-inden-4-ol;

(3aR,4R,5R,7aS)-5-((1S,2S,4S)-4-hydroxy-1-methyl-2-(2-(pyrazin-2-yloxy)ethyl)cyclohexyl)-7a-methyl-1-methyleneoctahydro-1H-inden-4-ol;

(3aR,4R,5R,7aS)-5-((1S,2S,4S)-4-hydroxy-1-methyl-2-(2-(pyridin-2-yloxy)ethyl)cyclohexyl)-7a-methyl-1-methyleneoctahydro-1H-inden-4-ol;

(1S,3S,4R)-3-(hydroxymethyl)-4-methyl-4-((3aS,4R,5S,7aS)-7a-methyl-1-methylene-4-((pyridin-2-ylmethoxy)methyl)octahydro-1H-inden-5-yl)cyclohexanol;

(2S,3aS,4R,5S,7aS)-4-(aminomethyl)-5-((1R,2S,4S)-4-hydroxy-2-(hydroxymethyl)-1-methylcyclohexyl)-7a-methyl-1-methyleneoctahydro-1H-inden-2-ol;

((1S,2R,5S)-5-amino-2-((3aS,4R,5S,7aS)-4-(hydroxymethyl)-7a-methyl-1-methyleneoctahydro-1H-inden-5-yl)-2-methylcyclohexyl)methanol;

(1S,3S,4R)-3-(hydroxymethyl)-4-((3aS,4R,5S,7aS)-4-(hydroxymethyl)-7a-methyl-1-methylene-3a,4,5,6,7,7a-hexahydro-1H-inden-5-yl)-4-methylcyclohexanol;

(1S,3S,4R)-4-((3aS,4R,5S,7aS)-4-(benzyloxymethyl)-7a-methyl-1-methyleneoctahydro-1H-inden-5-yl)-3-(hydroxymethyl)-4-methylcyclohexanol;

(1S,3S,4R)-4-((3aS,4R,5S,7aS)-4-((3,5-dimethoxybenzyloxy)methyl)-7a-methyl-1-methyleneoctahydro-1H-inden-5-yl)-3-(hydroxymethyl)-4-methylcyclohexanol;

2-((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)acetonitrile;

(1S,3S,4R)-3-(hydroxymethyl)-4-((3aS,4R,5S,7aS)-4-((methoxyamino)methyl)-7a-methyl-1-methyleneoctahydro-1H-inden-5-yl)-4-methylcyclohexanol;

N-(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)cyanamide;

2-((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)acetamide; and (3aS,4R,5S,7aS)-5-((1R,2R,4S)-4-hydroxy-2-(hydroxymethyl)-1-methylcyclohexyl)-7a-methyl-1-methyleneoctahydro-1H-indene-4-carboxylic acid.

Another embodiment is a compound of formula (I), as described above in the Summary of the Invention, wherein C1, C4, C11 and C12 are each independently substituted with two hydrogens; C9 is substituted with one hydrogen; C14 is substituted with one hydrogen; C15 is substituted with two hydrogens; $R^1$ is —$R^8$—$OR^9$; $R^2$ is —$R^8$—CN, —$R^8$—C(O)$OR^9$, —$R^8$—C(O)N($R^9$)$_2$, —$R^8$—N($R^9$)$_2$ or —$R^8$—N($R^9$)C(O)$R^9$; $R^{4a}$ and $R^{4b}$ together form methylene and $R^3$ is —OH or —$CH_2$—$NH_2$; $R^5$ is alkyl; $R^6$ is hydrogen; $R^7$ is hydrogen; each $R^8$ is independently a direct bond or a straight or branched alkylene chain; and each $R^9$ is independently hydrogen, alkyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl or optionally substituted heteroarylalkyl.

Another embodiment is a compound of formula (I), as described above in the Summary of the Invention, wherein C1, C4, C11 and C12 are each independently substituted with two hydrogens; C9 is substituted with one hydrogen; C14 is substituted with one hydrogen; C15 is substituted with two hydrogens; $R^1$ is —OH; $R^2$ is —$R^8$—CN, —$R^8$—C(O)OH, —$R^8$—C(O)$NH_2$, —$R^8$—$NH_2$ or —$R^8$—N(H)C(O)$R^9$; $R^{4a}$ and $R^{4b}$ together form methylene and $R^3$ is —OH or —$CH_2$—$NH_2$; $R^5$ is alkyl; $R^6$ is hydrogen; $R^7$ is hydrogen; and $R^9$ is benzodioxolyl.

Another embodiment is a compound of formula (I), as described above in the Summary of the Invention, selected from:

(1S,3S,4R)-3-(aminomethyl)-4-((3aS,4R,5S,7aS)-4-(aminomethyl)-7a-methyl-1-methyleneoctahydro-1H-inden-5-yl)-4-methylcyclohexanol;

3-((1S,2S,5S)-5-hydroxy-2-((3aR,4R,5R,7aS)-4-hydroxy-7a-methyl-1-methyleneoctahydro-1H-inden-5-yl)-2-methylcyclohexyl)propanenitrile;

3-((1S,2S,5S)-5-hydroxy-2-((3aR,4R,5R,7aS)-4-hydroxy-7a-methyl-1-methyleneoctahydro-1H-inden-5-yl)-2-methylcyclohexyl)propanamide;

N-(((1S,2S,5S)-5-hydroxy-2-((3aR,4R,5R,7aS)-4-hydroxy-7a-methyl-1-methyleneoctahydro-1H-inden-5-yl)-2-methylcyclohexyl)methyl)benzo[d][1,3]dioxole-5-carboxamide; and 3-((1R,2S,5S)-5-hydroxy-2-((3aR,4R,5R,7aS)-4-hydroxy-7a-methyl-1-methyleneoctahydro-1H-inden-5-yl)-2-methylcyclohexyl)propanoic acid.

Another embodiment is a compound of formula (I), as described above in the Summary of the Invention, wherein C1, C4, C11 and C12 are each independently substituted with two hydrogens; C9 is substituted with one hydrogen; C14 is substituted with one hydrogen; C15 is substituted with two hydrogens; $R^1$ is —$R^8$—$OR^9$; $R^2$ is optionally substituted heterocyclylalkyl or optionally substituted heteroarylalkyl; $R^{4a}$ and $R^{4b}$ together form methylene and $R^3$ is —OH; $R^5$ is alkyl; $R^6$ is hydrogen; $R^7$ is hydrogen; $R^8$ is a direct bond or a straight or branched alkylene chain; and $R^9$ is hydrogen, alkyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl or optionally substituted heteroarylalkyl.

Another embodiment is a compound of formula (I), as described above in the Summary of the Invention, wherein C1, C4, C11 and C12 are each independently substituted with two hydrogens; C9 is substituted with one hydrogen; C14 is substituted with one hydrogen; C15 is substituted with two hydrogens; $R^1$ is —OH; $R^2$ is optionally substituted heterocyclylalkyl or optionally substituted heteroarylalkyl; $R^{4a}$ and $R^{4b}$ together form methylene and $R^3$ is —OH; $R^5$ is methyl; $R^6$ is hydrogen; and $R^7$ is hydrogen.

Another embodiment is a compound of formula (I), as described above in the Summary of the Invention, selected from:

(3aR,4R,5R,7aS)-5-((1S,2S,4S)-4-hydroxy-1-methyl-2-(2-(pyrrolidin-1-yl)ethyl)cyclohexyl)-7a-methyl-1-methyleneoctahydro-1H-inden-4-ol;

(3aR,4R,5R,7aS)-5-((1S,2S,4S)-4-hydroxy-1-methyl-2-(2-morpholinoethyl)cyclohexyl)-7a-methyl-1-methyleneoctahydro-1H-inden-4-ol;

(3aR,4R,5R,7aS)-5-((1S,2S,4S)-4-hydroxy-1-methyl-2-(2-(4-methylpiperazin-1-yl)ethyl)cyclohexyl)-7a-methyl-1-methyleneoctahydro-1H-inden-4-ol;

(3aR,4R,5R,7aS)-5-((1S,2S,4S)-2-(2-(1H-1,2,4-triazol-1-yl)ethyl)-4-hydroxy-1-methylcyclohexyl)-7a-methyl-1-methyleneoctahydro-1H-inden-4-ol;

(3aR,4R,5R,7aS)-5-((1S,2S,4S)-2-(2-(1H-imidazol-1-yl)ethyl)-4-hydroxy-1-methylcyclohexyl)-7a-methyl-1-methyleneoctahydro-1H-inden-4-ol;

(3aR,4R,5R,7aS)-5-((1S,2S,4S)-2-(2-(1H-pyrazol-1-yl)ethyl)-4-hydroxy-1-methylcyclohexyl)-7a-methyl-1-methyleneoctahydro-1H-inden-4-ol; and (3aR,4R,5R,7aS)-5-((1S,2S,4S)-2-(2-(1H-pyrrol-1-yl)ethyl)-4-hydroxy-1-methylcyclohexyl)-7a-methyl-1-methyleneoctahydro-1H-inden-4-ol.

Another embodiment is a compound of formula (I), as described above in the Summary of the Invention, wherein C1, C4, C11 and C12 are each independently substituted with two hydrogens; C9 is substituted with one hydrogen; C14 is substituted with one hydrogen when $R^5$ is not a direct bond to C14; C15 is substituted with two hydrogens when $R^7$ is not a direct bond to C15, and one hydrogen when $R^7$ is a direct bond to C15; $R^1$ is —$R^8$—$OR^9$ or —$R^8$—$N(R^9)_2$; $R^2$ is —$R^8$—$OR^9$, —$R^8$—CN, —$R^8$—C(O)$OR^9$, —$R^8$—C(O)$N(R^9)_2$, —$R^8$—$N(R^9)_2$, —$R^8$—$N(R^9)C(O)R^9$, optionally substituted heterocyclylalkyl or optionally substituted heteroarylalkyl; $R^{4a}$ and $R^{4b}$ together form methylene and $R^3$ is —$CH_2$—N(H)C(O)-(2-methyl)phenyl, —$CH_2$—N(H)C(O)-(3-methyl)phenyl, —$CH_2$—N(H)C(O)-(4-fluoro)phenyl, —$CH_2$—N(H)C(O)-(4-methoxy)phenyl, —$CH_2$—N(H)C(O)-(4-methyl)phenyl, —$CH_2$—N(H)C(O)-(4-trifluoromethyl)phenyl, —$CH_2$—N(H)C(O)-2-pyridinyl, —$CH_2$—N(H)C(O)-2-pyrrolyl, —$CH_2$—N(H)C(O)-3-pyridinyl, —$CH_2$—N(H)C(O)-4-pyridinyl, —$CH_2$—N(H)C(O)-benzodioxolyl, —$CH_2$—N(H)C(O)-butyl, —$CH_2$—N(H)C(O)$CF_3$, —$CH_2$—N(H)C(O)-cyclohexyl, —$CH_2$—N(H)C(O)-cyclopropyl, —$CH_2$—N(H)C(O)-ethyl, —$CH_2$—N(H)C(O)-furanyl, —$CH_2$—N(H)C(O)-isopropyl, —$CH_2$—N(H)C(O)-naphthyl, —$CH_2$—N(H)C(O)-phenyl, —$CH_2$—N(H)C(O)-propyl, —$CH_2$—N(H)C(O)-pyrazinyl, —$CH_2$—N(H)C(O)-t-butyl or —$CH_2$—$CH_2$—N(H)C(O)benzodioxolyl; $R^5$ is alkyl or $R^5$ is a direct bond to C14; $R^6$ is hydrogen; $R^7$ is hydrogen, —$R^8$—$OR^9$ or a direct bond to C15; each $R^8$ is independently a direct bond or a straight or branched alkylene chain; and each $R^9$ is independently hydrogen, alkyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl or optionally substituted heteroarylalkyl.

Another embodiment is a compound of formula (I), as described above in the Summary of the Invention, wherein C1, C4, C11 and C12 are each independently substituted with two hydrogens; C9 is substituted with one hydrogen; C14 is substituted with one hydrogen; C15 is substituted with two hydrogens; $R^1$ is —$R^8$—$OR^9$; $R^2$ is —$R^8$—$OR^9$; $R^{4a}$ and $R^{4b}$ together form methylene and $R^3$ is —$CH_2$—N(H)C(O)-(2-methyl)phenyl, —$CH_2$—N(H)C(O)-(3-methyl)phenyl, —$CH_2$—N(H)C(O)-(4-fluoro)phenyl, —$CH_2$—N(H)C(O)-(4-methoxy)phenyl, —$CH_2$—N(H)C(O)-(4-methyl)phenyl, —$CH_2$—N(H)C(O)-(4-trifluoromethyl)phenyl, —$CH_2$—N(H)C(O)-2-pyridinyl, —$CH_2$—N(H)C(O)-2-pyrrolyl, —$CH_2$—N(H)C(O)-3-pyridinyl, —$CH_2$—N(H)C(O)-4-pyridinyl, —$CH_2$—N(H)C(O)-benzodioxolyl, —$CH_2$—N(H)C(O)-butyl, —$CH_2$—N(H)C(O)$CF_3$, —$CH_2$—N(H)C(O)-cyclohexyl, —$CH_2$—N(H)C(O)-cyclopropyl, —$CH_2$—N(H)C(O)-ethyl, —$CH_2$—N(H)C(O)-furanyl, —$CH_2$—N(H)C(O)-isopropyl, —$CH_2$—N(H)C(O)-naphthyl, —$CH_2$—N(H)C(O)-phenyl, —$CH_2$—N(H)C(O)-propyl, —$CH_2$—N(H)C(O)-pyrazinyl, —$CH_2$—N(H)C(O)-t-butyl or —$CH_2$—$CH_2$—N(H)C(O)benzodioxolyl; $R^5$ is alkyl; $R^6$ is hydrogen; $R^7$ is hydrogen.

Another embodiment is a compound of formula (I), as described above in the Summary of the Invention, wherein C1, C4, C11 and C12 are each independently substituted with two hydrogens; C9 is substituted with one hydrogen; C14 is substituted with one hydrogen; C15 is substituted with two hydrogens; $R^1$ is —OH; $R^2$ is —OH or —$CH_2OH$; $R^{4a}$ and $R^{4b}$ together form methylene and $R^3$ is —$CH_2$—N(H)C(O)-(2-methyl)phenyl, —$CH_2$—N(H)C(O)-(3-methyl)phenyl, —$CH_2$—N(H)C(O)-(4-fluoro)phenyl, —$CH_2$—N(H)C(O)-(4-methoxy)phenyl, —$CH_2$—N(H)C(O)-(4-methyl)phenyl, —$CH_2$—N(H)C(O)-(4-trifluoromethyl)phenyl, —$CH_2$—N(H)C(O)-2-pyridinyl, —$CH_2$—N(H)C(O)-2-pyrrolyl, —$CH_2$—N(H)C(O)-3-pyridinyl, —$CH_2$—N(H)C(O)-4-pyridinyl, —$CH_2$—N(H)C(O)-benzodioxolyl, —$CH_2$—N(H)C(O)-butyl, —$CH_2$—N(H)C(O)$CF_3$, —$CH_2$—N(H)C(O)-cyclohexyl, —$CH_2$—N(H)C(O)-cyclopropyl, —$CH_2$—N(H)C(O)-ethyl, —$CH_2$—N(H)C(O)-furanyl, —$CH_2$—N(H)C(O)-isopropyl, —$CH_2$—N(H)C(O)-naphthyl, —$CH_2$—N(H)C(O)-phenyl, —$CH_2$—N(H)C(O)-propyl, —$CH_2$—N(H)C(O)-pyrazinyl, —$CH_2$—N(H)C(O)-t-butyl or —$CH_2$—$CH_2$—N(H)C(O)benzodioxolyl; $R^5$ is methyl; $R^6$ is hydrogen; and $R^7$ is hydrogen.

Another embodiment is a compound of formula (I), as described above in the Summary of the Invention, selected from:

N-(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)-2-naphthamide;

N-(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)benzamide;

N-(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)pivalamide;

N-(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)isobutyramide;

N-(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)propionamide;

N-(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)butyramide;

N-(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)pentanamide;

N-(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)nicotinamide;

N-(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)isonicotinamide;

N-(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)pyrazine-2-carboxamide;

N-(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)picolinamide;

N-(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)benzo[d][1,3]dioxole-5-carboxamide;

N-(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)-4-methoxybenzamide;

4-fluoro-N-(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)benzamide;

N-(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)-4-(trifluoromethyl)benzamide;

N-(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)-4-methylbenzamide;

N-(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)-2-methylbenzamide;

N-(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)-1H-pyrrole-2-carboxamide;

N-(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)-3-methylbenzamide;

N-(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)furan-2-carboxamide;

N-(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)cyclopropanecarboxamide;

N-(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)cyclohexanecarboxamide;

2,2,2-trifluoro-N-(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)acetamide; and N-(2-((3aS,4S,5S,7aS)-5-((1R,2S,4S)-2,4-dihydroxy-1-methylcyclohexyl)-7a-methyl-1-methyleneoctahydro-1H-inden-4-yl)ethyl)benzo[d][1,3]dioxole-5-carboxamide.

Another embodiment is a compound of formula (I), as described above in the Summary of the Invention, wherein C1, C4, C11 and C12 are each independently substituted with two hydrogens; C9 is substituted with one hydrogen; C14 is substituted with one hydrogen when $R^5$ is not a direct bond to C14; C15 is substituted with two hydrogens when $R^7$ is not a direct bond to C15, and one hydrogen when $R^7$ is a direct bond to C15; $R^1$ is —$R^8$—$OR^9$ or —$R^8$—$N(R^9)_2$; $R^2$ is —$R^8$—$OR^9$, —$R^8$—CN, —$R^8$—$C(O)OR^9$, —$R^8$—$C(O)N(R^9)_2$, —$R^8$—$N(R^9)_2$, —$R^8$—$N(R^9)C(O)R^9$, optionally substituted heterocyclylalkyl or optionally substituted heteroarylalkyl; $R^{4a}$ and $R^{4b}$ together form methylene and $R^3$ is —$CH_2$—N(H)$CH_2$-(2,2-difluorobenzodioxolyl), —$CH_2$—$CH_2$—N(4-methoxybenzyl)$_2$, —$CH_2$—$CH_2$—N(H)-(4-methoxy)benzyl, —$CH_2$—N(H)-(2-fluoro-4-methoxy)benzyl, —$CH_2$—N(H)-(2-fluoro-4-methyl)benzyl, —$CH_2$—N(H)-(2-methoxy-4-fluoro)benzyl, —$CH_2$—N(H)-(2-methyl)benzyl, —$CH_2$—N(H)-(2-methyl-4-fluoro)benzyl, —$CH_2$—N(H)-(3,5-dimethoxy)benzyl, —$CH_2$—N(H)-(3-methyl)benzyl, —$CH_2$—N(H)-(4-fluoro)benzyl, —$CH_2$—N(H)-(4-methoxy)benzyl, —$CH_2$—N(H)-(4-methyl)benzyl, —$CH_2$—N(H)-(4-nitro)benzyl, —$CH_2$—N(H)-(4-trifluoromethyl)benzyl, —$CH_2$—N(H)-(4-benzoyl)benzyl, —$CH_2$—N(H)$CH_2$-benzimidazolyl, —$CH_2$—$CH_2$—N(H)$CH_2$-benzodioxolyl, —$CH_2$—N(H)$CH_2CH_2$-(4-methoxy)phenyl, or —$CH_2$—N(H)$CH_2$-pyridinyl; $R^5$ is alkyl or $R^5$ is a direct bond to C14; $R^6$ is hydrogen; $R^7$ is hydrogen, —$R^8$—$OR^9$ or a direct bond to C15; each $R^8$ is independently a direct bond or a straight or branched alkylene chain; and each $R^9$ is independently hydrogen, alkyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl or optionally substituted heteroarylalkyl.

Another embodiment is a compound of formula (I), as described above in the Summary of the Invention, wherein C1, C4, C11 and C12 are each independently substituted with two hydrogens; C9 is substituted with one hydrogen; C14 is substituted with one hydrogen; C15 is substituted with two hydrogens; $R^1$ is —$R^8$—$OR^9$; $R^2$ is —$R^8$—$OR^9$; $R^{4a}$ and $R^{4b}$ together form methylene and $R^3$ is —$CH_2$—N(H)$CH_2$-(2,2-difluorobenzodioxolyl), —$CH_2$—$CH_2$—N(4-methoxybenzyl)$_2$, —$CH_2$—$CH_2$—N(H)-(4-methoxy)benzyl, —$CH_2$—N(H)-(2-fluoro-4-methoxy)benzyl, —$CH_2$—N(H)-(2-fluoro-4-methyl)benzyl, —$CH_2$—N(H)-(2-methoxy-4-fluoro)benzyl, —$CH_2$—N(H)-(2-methyl)benzyl, —$CH_2$—N(H)-(2-methyl-4-fluoro)benzyl, —$CH_2$—N(H)-(3,5-dimethoxy)benzyl, —$CH_2$—N(H)-(3-methyl)benzyl, —$CH_2$—N(H)-(4-fluoro)benzyl, —$CH_2$—N(H)-(4-methoxy)benzyl, —$CH_2$—N(H)-(4-methyl)benzyl, —$CH_2$—N(H)-(4-nitro)benzyl, —$CH_2$—N(H)-(4-trifluoromethyl)benzyl, —$CH_2$—N(H)-(4-benzoyl)benzyl, —$CH_2$—N(H)$CH_2$-benzimidazolyl, —$CH_2$—$CH_2$—N(H)$CH_2$-benzodioxolyl, —$CH_2$—N(H)$CH_2CH_2$-(4-methoxy)phenyl, or —$CH_2$—N(H)$CH_2$-pyridinyl; $R^5$ is alkyl; $R^6$ is hydrogen; $R^7$ is hydrogen; each $R^8$ is independently a direct bond or a straight or branched alkylene chain; and each $R^9$ is independently hydrogen, alkyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl or optionally substituted heteroarylalkyl.

Another embodiment is a compound of formula (I), as described above in the Summary of the Invention, wherein C1, C4, C11 and C12 are each independently substituted with two hydrogens; C9 is substituted with one hydrogen; C14 is substituted with one hydrogen; C15 is substituted with two hydrogens; $R^1$ is —OH; $R^2$ is —OH or —$CH_2OH$; $R^{4a}$ and $R^{4b}$ together form methylene and $R^3$ is —$CH_2$—N(H)$CH_2$-(2,2-difluorobenzodioxolyl), —$CH_2$—$CH_2$—N(4-methoxybenzyl)$_2$, —$CH_2$—$CH_2$—N(H)-(4-methoxy)benzyl, —$CH_2$—N(H)-(2-fluoro-4-methoxy)benzyl, —$CH_2$—N(H)-(2-fluoro-4-methyl)benzyl, —$CH_2$—N(H)-(2-methoxy-4-fluoro)benzyl, —$CH_2$—N(H)-(2-methyl)benzyl, —$CH_2$—N(H)-(2-methyl-4-fluoro)benzyl, —$CH_2$—N(H)-(3,5-dimethoxy)benzyl, —$CH_2$—N(H)-(3-methyl)benzyl, —$CH_2$—N(H)-(4-fluoro)benzyl, —$CH_2$—N(H)-(4-methoxy)benzyl, —$CH_2$—N(H)-(4-methyl)benzyl, —$CH_2$—N(H)-(4-nitro)benzyl, —$CH_2$—N(H)-(4-trifluoromethyl)benzyl, —$CH_2$—N(H)-(4-benzoyl)benzyl, —$CH_2$—N(H)$CH_2$-benzimidazolyl, —$CH_2$—$CH_2$—N(H)$CH_2$-benzodioxolyl, —$CH_2$—N(H)$CH_2CH_2$-(4-methoxy)phenyl, or —$CH_2$—N(H)$CH_2$-pyridinyl; $R^5$ is methyl; $R^6$ is hydrogen; and $R^7$ is hydrogen.

Another embodiment is a compound of formula (I), as described above in the Summary of the Invention, selected from:

- (4-(((((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methylamino)methyl)phenyl)(phenyl)methanone;
- (1S,3S,4R)-4-((3aS,4R,5S,7aS)-4-((4-fluorobenzylamino)methyl)-7a-methyl-1-methyleneoctahydro-1H-inden-5-yl)-3-(hydroxymethyl)-4-methylcyclohexanol;
- (1S,3S,4R)-3-(hydroxymethyl)-4-methyl-4-((3aS,4R,5S,7aS)-7a-methyl-1-methylene-4-((pyridin-4-ylmethylamino)methyl)octahydro-1H-inden-5-yl)cyclohexanol;
- (1S,3S,4R)-3-(hydroxymethyl)-4-methyl-4-((3aS,4R,5S,7aS)-7a-methyl-4-((4-methylbenzylamino)methyl)-1-methyleneoctahydro-1H-inden-5-yl)cyclohexanol;
- (1S,3S,4R)-3-(hydroxymethyl)-4-methyl-4-((3aS,4R,5S,7aS)-7a-methyl-4-((3-methylbenzylamino)methyl)-1-methyleneoctahydro-1H-inden-5-yl)cyclohexanol;
- (1S,3S,4R)-3-(hydroxymethyl)-4-methyl-4-((3aS,4R,5S,7aS)-7a-methyl-4-((2-methylbenzylamino)methyl)-1-methyleneoctahydro-1H-inden-5-yl)cyclohexanol;
- (1S,3S,4R)-3-(hydroxymethyl)-4-((3aS,4R,5S,7aS)-4-((4-methoxybenzylamino)methyl)-7a-methyl-1-methyleneoctahydro-1H-inden-5-yl)-4-methylcyclohexanol;
- (1S,3S,4R)-3-(hydroxymethyl)-4-methyl-4-((3aS,4R,5S,7aS)-7a-methyl-1-methylene-4-((4-(trifluoromethyl)benzylamino)methyl)octahydro-1H-inden-5-yl)cyclohexanol;
- (1S,3S,4R)-4-((3aS,4R,5S,7aS)-4-((3,5-dimethoxybenzylamino)methyl)-7a-methyl-1-methyleneoctahydro-1H-inden-5-yl)-3-(hydroxymethyl)-4-methylcyclohexanol;
- (1S,3S,4R)-4-((3aS,4R,5S,7aS)-4-(((1H-benzo[d]imidazol-2-yl)methylamino)methyl)-7a-methyl-1-methyleneoctahydro-1H-inden-5-yl)-3-(hydroxymethyl)-4-methylcyclohexanol;
- (1S,3S,4R)-3-(hydroxymethyl)-4-methyl-4-((3aS,4R,5S,7aS)-7a-methyl-1-methylene-4-((4-nitrobenzylamino)methyl)octahydro-1H-inden-5-yl)cyclohexanol;
- (1S,3S,4R)-4-((3aS,4R,5S,7aS)-4-(((2,2-difluorobenzo[d][1,3]dioxol-5-yl)methylamino)methyl)-7a-methyl-1-methyleneoctahydro-1H-inden-5-yl)-3-(hydroxymethyl)-4-methylcyclohexanol;
- (1S,3S,4R)-4-((3aS,4R,5S,7aS)-4-((4-fluoro-2-methylbenzylamino)methyl)-7a-methyl-1-methyleneoctahydro-1H-inden-5-yl)-3-(hydroxymethyl)-4-methylcyclohexanol;
- (1S,3S,4R)-4-((3aS,4R,5S,7aS)-4-((2-fluoro-4-methoxybenzylamino)methyl)-7a-methyl-1-methyleneoctahydro-1H-inden-5-yl)-3-(hydroxymethyl)-4-methylcyclohexanol;
- (1S,3S,4R)-4-((3aS,4R,5S,7aS)-4-((4-fluoro-2-methoxybenzylamino)methyl)-7a-methyl-1-methyleneoctahydro-1H-inden-5-yl)-3-(hydroxymethyl)-4-methylcyclohexanol;
- (1S,3S,4R)-4-((3aS,4R,5S,7aS)-4-((2-fluoro-4-methylbenzylamino)methyl)-7a-methyl-1-methyleneoctahydro-1H-inden-5-yl)-3-(hydroxymethyl)-4-methylcyclohexanol;
- (1S,3S,4R)-4-((3aS,4S,5S,7aS)-4-(2-(bis(4-methoxybenzyl)amino)ethyl)-7a-methyl-1-methyleneoctahydro-1H-inden-5-yl)-4-methylcyclohexane-1,3-diol;
- (1S,3S,4R)-4-((3aS,4S,5S,7aS)-4-(2-(4-methoxybenzylamino)ethyl)-7a-methyl-1-methyleneoctahydro-1H-inden-5-yl)-4-methylcyclohexane-1,3-diol;
- (1S,3S,4R)-3-(hydroxymethyl)-4-((3aS,4R,5S,7aS)-4-((4-methoxyphenethylamino)methyl)-7a-methyl-1-methyleneoctahydro-1H-inden-5-yl)-4-methylcyclohexanol; and
- (1S,3S,4R)-4-((3aS,4S,5S,7aS)-4-(2-(benzo[d][1,3]dioxol-5-ylmethylamino)ethyl)-7a-methyl-1-methyleneoctahydro-1H-inden-5-yl)-4-methylcyclohexane-1,3-diol.

Another embodiment is a compound of formula (I), as described above in the Summary of the Invention, wherein C1, C4, C11 and C12 are each independently substituted with two hydrogens; C9 is substituted with one hydrogen; C14 is substituted with one hydrogen when $R^5$ is not a direct bond to C14; C15 is substituted with two hydrogens when $R^7$ is not a direct bond to C15, and one hydrogen when $R^7$ is a direct bond to C15; $R^1$ is —$R^8$—$OR^9$ or —$R^8$—$N(R^9)_2$; $R^2$ is —$R^8$—$OR^9$, —$R^8$—CN, —$R^8$—$C(O)OR^9$, —$R^8$—C(O)N($R^9$)$_2$, —$R^8$—N($R^9$)$_2$, —$R^8$—N($R^9$)C(O)$R^9$, optionally substituted heterocyclylalkyl or optionally substituted heteroarylalkyl; $R^{4a}$ and $R^{4b}$ together form methylene and $R^3$ is —$CH_2$—N(H)C(O)N(H)-benzyl, —$CH_2$—N(H)C(O)N(H)-ethyl, —$CH_2$—N(H)C(O)N(H)-phenyl or —$CH_2$—N(H)C(S)N(H)$CH_3$; $R^5$ is alkyl or $R^5$ is a direct bond to C14; $R^6$ is hydrogen; $R^7$ is hydrogen, —$R^8$—$OR^9$ or a direct bond to C15; each $R^8$ is independently a direct bond or a straight or branched alkylene chain; and each $R^9$ is independently hydrogen, alkyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl or optionally substituted heteroarylalkyl.

Another embodiment is a compound of formula (I), as described above in the Summary of the Invention, wherein C1, C4, C11 and C12 are each independently substituted with two hydrogens; C9 is substituted with one hydrogen; C14 is substituted with one hydrogen; C15 is substituted with two hydrogens; $R^1$ is —$R^8$—$OR^9$; $R^2$ is —$R^8$—$OR^9$; $R^{4a}$ and $R^{4b}$ together form methylene and $R^3$ is —$CH_2$—N(H)C(O)N(H)-benzyl, —$CH_2$—N(H)C(O)N(H)-ethyl, —$CH_2$—N(H)C(O)N(H)-phenyl or —$CH_2$—N(H)C(S)N(H)$CH_3$; $R^5$ is alkyl; $R^6$ is hydrogen; $R^7$ is hydrogen; each $R^8$ is independently a direct bond or a straight or branched alkylene chain; and each $R^9$ is independently hydrogen, alkyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl or optionally substituted heteroarylalkyl.

Another embodiment is a compound of formula (I), as described above in the Summary of the Invention, wherein C1, C4, C11 and C12 are each independently substituted with two hydrogens; C9 is substituted with one hydrogen; C14 is substituted with one hydrogen; C15 is substituted with two hydrogens; $R^1$ is —OH; $R^2$ is —$CH_2OH$; $R^{4a}$ and $R^{4b}$ together form methylene and $R^3$ is —$CH_2$—N(H)C(O)N(H)-benzyl, —$CH_2$—N(H)C(O)N(H)-ethyl, —$CH_2$—N(H)C(O)N(H)-phenyl or —$CH_2$—N(H)C(S)N(H)$CH_3$; $R^5$ is methyl; $R^6$ is hydrogen; and $R^7$ is hydrogen.

Another embodiment is a compound of formula (I), as described above in the Summary of the Invention, selected from:

- 1-ethyl-3-(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)urea;
- 1-(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)-3-methylthiourea;
- 1-benzyl-3-(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)urea; and 1-(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)-3-phenylurea.

Another embodiment is a compound of formula (I), as described above in the Summary of the Invention, wherein C1, C4, C11 and C12 are each independently substituted with two hydrogens; C9 is substituted with one hydrogen; C14 is substituted with one hydrogen when R$^5$ is not a direct bond to C14; C15 is substituted with two hydrogens when R$^7$ is not a direct bond to C15, and one hydrogen when R$^7$ is a direct bond to C15; R$^1$ is —R$^8$—OR$^9$ or —R$^8$—N(R$^9$)$_2$; R$^2$ is —R$^8$—OR$^9$, —R$^8$—CN, —R$^8$—C(O)OR$^9$, —R$^8$—C(O)N(R$^9$)$_2$, —R$^8$—N(R$^9$)$_2$, —R$^8$—N(R$^9$)C(O)R$^9$, optionally substituted heterocyclylalkyl or optionally substituted heteroarylalkyl; R$^{4a}$ and R$^{4b}$ together form methylene and R$^3$ is —CH$_2$-benzimidazolyl, —CH$_2$-indolinyl, —CH$_2$-indolyl, —CH$_2$-purinyl, —CH$_2$-pyrazolyl or —CH$_2$-triazolyl; R$^5$ is alkyl or R$^5$ is a direct bond to C14; R$^6$ is hydrogen; R$^7$ is hydrogen, —R$^8$—OR$^9$ or a direct bond to C15; each R$^8$ is independently a direct bond or a straight or branched alkylene chain; and each R$^9$ is independently hydrogen, alkyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl or optionally substituted heteroarylalkyl.

Another embodiment is a compound of formula (I), as described above in the Summary of the Invention, wherein C1, C4, C11 and C12 are each independently substituted with two hydrogens; C9 is substituted with one hydrogen; C14 is substituted with one hydrogen; C15 is substituted with two hydrogens; R$^1$ is —R$^8$—OR$^9$; R$^2$ is —R$^8$—OR$^9$; R$^{4a}$ and R$^{4b}$ together form methylene and R$^3$ is —CH$_2$-benzimidazolyl, —CH$_2$-indolinyl, —CH$_2$-indolyl, —CH$_2$-purinyl, —CH$_2$-pyrazolyl or —CH$_2$-triazolyl; R$^5$ is alkyl; R$^6$ is hydrogen; R$^7$ is hydrogen; each R$^8$ is independently a direct bond or a straight or branched alkylene chain; and each R$^9$ is independently hydrogen, alkyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl or optionally substituted heteroarylalkyl.

Another embodiment is a compound of formula (I), as described above in the Summary of the Invention, wherein C1, C4, C11 and C12 are each independently substituted with two hydrogens; C9 is substituted with one hydrogen; C14 is substituted with one hydrogen; C15 is substituted with two hydrogens; R$^1$ is —OH; R$^2$ is —CH$_2$OH; R$^{4a}$ and R$^{4b}$ together form methylene and R$^3$ is —CH$_2$-benzimidazolyl, —CH$_2$-indolinyl, —CH$_2$-indolyl, —CH$_2$-purinyl, —CH$_2$-pyrazolyl or —CH$_2$-triazolyl; R$^5$ is methyl; R$^6$ is hydrogen; and R$^7$ is hydrogen.

Another embodiment is a compound of formula (I), as described above in the Summary of the Invention, selected from:
(1S,3S,4R)-4-((3aS,4R,5S,7aS)-4-((1H-pyrazol-1-yl)methyl)-7a-methyl-1-methyleneoctahydro-1H-inden-5-yl)-3-(hydroxymethyl)-4-methylcyclohexanol;
(1S,3S,4R)-4-((3aS,4R,5S,7aS)-4-((1H-1,2,4-triazol-1-yl)methyl)-7a-methyl-1-methyleneoctahydro-1H-inden-5-yl)-3-(hydroxymethyl)-4-methylcyclohexanol;
(1S,3S,4R)-4-((3aS,4R,5S,7aS)-4-((1H-benzo[d]imidazol-1-yl)methyl)-7a-methyl-1-methyleneoctahydro-1H-inden-5-yl)-3-(hydroxymethyl)-4-methylcyclohexanol;
(1S,3S,4R)-4-((3aS,4R,5S,7aS)-4-((6-amino-9H-purin-9-yl)methyl)-7a-methyl-1-methyleneoctahydro-1H-inden-5-yl)-3-(hydroxymethyl)-4-methylcyclohexanol;
(1S,3S,4R)-4-((3aS,4R,5S,7aS)-4-((1H-indol-1-yl)methyl)-7a-methyl-1-methyleneoctahydro-1H-inden-5-yl)-3-(hydroxymethyl)-4-methylcyclohexanol; and
(1S,3S,4R)-3-(hydroxymethyl)-4-((3aS,4R,5S,7aS)-4-(indolin-1-ylmethyl)-7a-methyl-1-methyleneoctahydro-1H-inden-5-yl)-4-methylcyclohexanol.

Another embodiment of the Invention is a compound of formula (Ia):

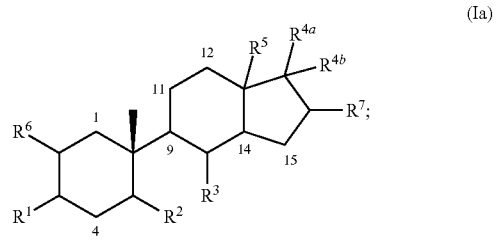

wherein C1, C4, C11 and C12 are each independently substituted with two hydrogens; C9 is substituted with one hydrogen; C14 is substituted with one hydrogen when R$^5$ is not a direct bond to C14; C15 is substituted with two hydrogens when R$^7$ is not a direct bond to C15, and one hydrogen when R$^7$ is a direct bond to C15; R$^1$ is —R$^8$—OR$^9$ or —R$^8$—N(R$^9$)$_2$; R$^2$ is —R$^8$—OR$^9$, —R$^8$—CN, —R$^8$—C(O)OR$^9$, —R$^8$—C(O)N(R$^9$)$_2$, —R$^8$—N(R$^9$)$_2$, —R$^8$—N(R$^9$)C(O)R$^9$, optionally substituted heterocyclylalkyl or optionally substituted heteroarylalkyl; R$^{4a}$ is hydrogen or alkyl, R$^{4b}$ is a direct bond to the carbon to which R$^7$ is attached, and R$^3$ is —CH$_2$NH$_2$ or —CH$_2$N(H)C(O)(CH$_2$)$_3$CH$_3$; or R$^{4a}$ and R$^{4b}$ are each independently selected from hydrogen and alkyl and R$^3$ is —CH$_2$OH, —CH$_2$NH$_2$, —CH$_2$N(H)CH$_3$, —CH$_2$N(CH$_3$)$_2$, —CH$_2$N(H)CH$_2$-cyclopropyl, —CH$_2$N(H)CH$_2$-pyrrolyl, —CH$_2$N(H)C(O)CH$_3$, —CH$_2$N(H)C(O)-phenyl, —CH$_2$N(H)S(O)$_2$CH$_3$ or —CH$_2$N(H)C(═NH)NH$_2$; or R$^{4a}$ and R$^{4b}$ together form methylene and R$^3$ is —CH$_2$—N(H)CH$_2$-benzodioxolyl; R$^5$ is alkyl or R$^5$ is a direct bond to C14; R$^6$ is hydrogen; R$^7$ is hydrogen, —R$^8$—OR$^9$ or a direct bond to C15, provided that when R$^7$ is a direct bond to C15, R$^{4b}$ is not a direct bond to the carbon to which R$^7$ is attached; each R$^8$ is independently a direct bond or a straight or branched alkylene chain; and each R$^9$ is independently hydrogen, alkyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl or optionally substituted heteroarylalkyl; or a stereoisomer, enantiomer or tautomer thereof or mixtures thereof; or a pharmaceutically acceptable salt or solvate thereof.

Of this embodiment, one embodiment is a compound of formula (Ia) wherein C1, C4, C11 and C12 are each independently substituted with two hydrogens; C9 is substituted with one hydrogen; C14 is substituted with one hydrogen when R$^5$ is not a direct bond to C14; C15 is substituted with two hydrogens when R$^7$ is not a direct bond to C15, and one hydrogen when R$^7$ is a direct bond to C15; R$^1$ is —R$^8$—OR$^9$ or —R$^8$—N(R$^9$)$_2$; R$^2$ is —R$^8$—OR$^9$, —R$^8$—CN, —R$^8$—C(O)OR$^9$, —R$^8$—C(O)N(R$^9$)$_2$, —R$^8$—N(R$^9$)$_2$, —R$^8$—N(R$^9$)C(O)R$^9$, optionally substituted heterocyclylalkyl or optionally substituted heteroarylalkyl; R$^{4a}$ and R$^{4b}$ together form methylene and R$^3$ is —CH$_2$—N(H)CH$_2$-benzodioxolyl; R$^5$ is alkyl or R$^5$ is a direct bond to C14; R$^6$ is hydrogen; R$^7$ is hydrogen, —R$^8$—OR$^9$ or a direct bond to C15; each R$^8$ is independently a direct bond or a straight or branched alkylene chain; and each R$^9$ is independently hydrogen, alkyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl or optionally substituted heteroarylalkyl.

Of this embodiment, another embodiment is a compound of formula (Ia) wherein C1, C4, C11 and C12 are each independently substituted with two hydrogens; C9 is substituted with one hydrogen; C14 is substituted with one hydrogen when R$^5$ is not a direct bond to C14; C15 is substituted with two hydrogens when R$^7$ is not a direct bond to C15, and one hydrogen when R$^7$ is a direct bond to C15; R$^1$ is —R$^8$—OR$^9$ or —R$^8$—N(R$^9$)$_2$; R$^2$ is —R$^8$—OR$^9$, —R$^8$—CN, —R$^8$—C(O)OR$^9$, —R$^8$—C(O)N(R$^9$)$_2$, —R$^8$—N(R$^9$)$_2$, —R$^8$—N(R$^9$)C(O)R$^9$, optionally substituted heterocyclylalkyl or optionally substituted heteroarylalkyl; R$^{4a}$ and R$^{4b}$ together form methylene and R$^3$ is —CH$_2$—N(H)CH$_2$-benzodioxolyl; R$^5$ is alkyl or R$^5$ is a direct bond to C14; R$^6$ is hydrogen; R$^7$ is hydrogen, —R$^8$—OR$^9$ or a direct bond to C15; each R$^8$ is independently a direct bond or a straight or branched alkylene chain; and each R$^9$ is independently hydrogen, alkyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl or optionally substituted heteroarylalkyl.

Of this embodiment, another embodiment is a compound of formula (Ia) wherein C1, C4, C11 and C12 are each independently substituted with two hydrogens; C9 is substituted with one hydrogen; C14 is substituted with one hydrogen; C15 is substituted with two hydrogens; R$^1$ is —R$^8$—OR$^9$; R$^2$ is —R$^8$—OR$^9$; R$^{4a}$ and R$^{4b}$ together form methylene and R$^3$ is —CH$_2$—N(H)CH$_2$-benzodioxolyl; R$^5$ is alkyl; R$^6$ is hydrogen; R$^7$ is hydrogen; each R$^8$ is independently a direct bond or a straight or branched alkylene chain; and each R$^9$ is independently hydrogen, alkyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl or optionally substituted heteroarylalkyl.

Of this embodiment, another embodiment is a compound of formula (Ia) wherein C1, C4, C11 and C12 are each independently substituted with two hydrogens; C9 is substituted with one hydrogen; C14 is substituted with one hydrogen; C15 is substituted with two hydrogens; R$^1$ is —OH; R$^2$ is —OH or —CH$_2$OH; R$^{4a}$ and R$^{4b}$ together form methylene and R$^3$ is —CH$_2$—N(H)CH$_2$-benzodioxolyl; R$^5$ is methyl; R$^6$ is hydrogen; and R$^7$ is hydrogen.

Of this embodiment, another embodiment is a compound of formula (Ia) which is (1S,3S,4R)-4-((3aS,4R,5S,7aS)-4-((benzo[d][1,3]dioxol-5-ylmethylamino)methyl)-7a-methyl-1-methyleneoctahydro-1H-inden-5-yl)-3-(hydroxymethyl)-4-methylcyclohexanol.

It is understood that any embodiment of the compounds of the invention, as set forth above, and any specific substituent set forth herein for a particular R group in the compounds of the invention, as set forth above, may be independently combined with other embodiments and/or substituents of compounds of the invention to form embodiments of the inventions not specifically set forth above. In addition, in the event that a list of substituents is listed for any particular R group in a particular embodiment and/or claim, it is understood that each individual substituent may be deleted from the particular embodiment and/or claim and that the remaining list of substituents will be considered to be within the scope of the invention.

Another preferred embodiment of the various aspects of the invention is an embodiment of the methods for treating a disease, disorder or condition in a mammal in need thereof is where the disease, disorder or condition is an autoimmune disease, disorder or condition, an inflammatory disease, disorder or condition, or a neoplastic or cell proliferative disease, disorder or condition.

Another embodiment of the methods for treating a disease, disorder or condition in a mammal in need thereof is where the disease, disorder or condition is an autoimmune disease, disorder or condition selected from idiopathic pulmonary fibrosis, an inflammatory bowel disease, rheumatoid arthritis, Still's Disease, Sjögren's Syndrome, systemic lupus erythematosus, multiple sclerosis, psoriasis and systemic sclerosis.

Another embodiment of the methods for treating a disease, disorder or condition in a mammal in need thereof is where the disease, disorder or condition is an inflammatory bowel disease selected from Crohn's Disease and ulcerative colitis.

Another embodiment of the methods for treating a disease, disorder or condition in a mammal in need thereof is where the disease, disorder or condition is an inflammatory disease, disorder or condition selected from acute respiratory distress syndrome, allergic rhinitis, Alzheimer's Disease, asthma, an ocular inflammatory disease, atopic dermatitis, bladder pain syndrome/interstitial cystitis, chronic obstructive pulmonary disease (COPD) including emphysematous, bronchitic, and alpa 1 anti-trypsin deficiency related COPD; dermal contact hypersensitivity, eczema, eosinophilic gastrointestinal disorder, fibromyalgia, gout, hepatic fibrosis, irritable bowl syndrome, ischemic reperfusion disease, kidney fibrosis, pancreatitis, Parkisons Disease, post operative inflammation, a seronegative spondyloarthropathy, and vasculitis.

Another embodiment of the methods for treating a disease, disorder or condition in a mammal in need thereof is where the disease, disorder or condition is an ocular inflammatory disease selected from allergic conjunctivitis, dry eye, and uveitis.

Another embodiment of the methods for treating a disease, disorder or condition in a mammal in need thereof is where the disease, disorder or condition is a seronegative spondyloarthropathy selected from anklyosing spondylitis, psoriatic arthritis, and Reiter's Syndrome.

Another embodiment of the methods for treating a disease, disorder or condition in a mammal in need thereof is where the disease, disorder or condition is vasculitis selected from Wegener's Granulomatosis, polyarteritis nodosa, leucocytoclastic vasculitis, Churg-Strauss Syndrome, cryoglobulinemic vasculitis, and giant cell arteritis.

Another embodiment of the methods for treating a disease, disorder or condition in a mammal in need thereof is where the disease, disorder or condition is a neoplastic or cell proliferative disease, disorder or condition selected from acute myelogenous leukemia, chronic myelogenous leukemia, acute lymphocytic leukemia, chronic lymphocytic leukemia, basophilic leukemia, cutaneous T-cell lymphoma, Sezary Syndrome, Hodgkin's Disease, Non-Hodgkin's Lymphoma, multiple myeloma, hypereosinophilic syndromes, mastocytosis and thrombocythemia.

Another embodiment of the invention is a method of using the compounds of formula (I) as standards or controls in in vitro or in vivo assays in determining the efficacy of test compounds in modulating SHIP1 activity.

In another embodiment of the invention, the compounds of formula (I) are isotopically-labeled by having one or more atoms therein replaced by an atom having a different atomic mass or mass number. Such isotopically-labeled (i.e., radio-labelled) compounds of formula (I) are considered to be within the scope of this invention. Examples of isotopes that can be incorporated into the compounds of formula (I) include isotopes of hydrogen, carbon, nitrogen, oxygen, phosphorous, sulfur, fluorine, chlorine, and iodine, such as, but not limited to, $^2H$, $^3H$, $^{11}C$, $^{13}O$, $^{14}O$ $^{13}N$, $^{15}N$, $^{15}O$, $^{17}O$, $^{18}O$, $^{31}P$, $^{32}P$, $^{35}S$, $^{18}F$, $^{36}CL$, $^{123}I$, and $^{125}I$, respectively. These isotopically-labeled compounds would be useful to help determine or measure the effectiveness of the compounds, by characterizing, for example, the site or mode of action for SHIP1 modulation, or binding affinity to pharmacologically important site of action for SHIP1 modulation. Certain isotopically-labeled compounds of formula (I), for example, those incorporating a radioactive isotope, are useful in drug and/or substrate tissue distribution studies. The radioactive isotopes tritium, i.e. $^3H$, and carbon-14, i.e., $^{14}C$, are particularly useful for this purpose in view of their ease of incorporation and ready means of detection.

Substitution with heavier isotopes such as deuterium, i.e. $^2H$, may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled compounds of formula (I) can generally be prepared by conventional techniques known to those skilled in the art or by processes analogous to those described in the Examples as set out below using an appropriate isotopically-labeled reagent in place of the non-labeled reagent previously employed.

In other embodiments, preferred stereochemistry of the compounds of formula (I) is shown below:

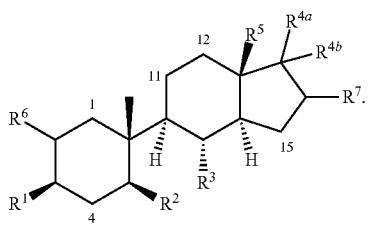

Specific embodiments of the compounds of the invention are described in more detail below in the Preparation of the Compounds of the Invention and in the Examples.

Utility and Testing of the Compounds of the Invention

Compounds of formula (I) above have activity as SHIP1 modulators and utility over a wide range of therapeutic applications, and may be used to treat any of a variety of diseases, disorders or conditions that would benefit from SHIP1 modulation. For example, such diseases, disorders or conditions include (but are not limited to) autoimmune diseases such as idiopathic pulmonary fibrosis, inflammatory bowel disease (including Crohn's Disease and ulcerative colitis), rheumatoid arthritis, Still's Disease, Sjögren's Syndrome, systemic lupus erythematosus, multiple sclerosis, psoriasis, and systemic sclerosis; inflammatory diseases such as acute respiratory distress syndrome (ARDS), allergic rhinitis, Alzheimer's Disease, asthma, ocular inflammatory diseases (including allergic conjunctivitis, dry eye, and uveitis), chronic obstructive pulmonary disease (COPD) including emphysematous, bronchitic, and COPD due to alpha 1 anti-trypsin deficiency, atopic dermatitis, dermal contact hypersensitivity, eczema, eosinophilic gastrointestinal disorder, fibromyalgia, gout, hepatic fibrosis, irritable bowel syndrome, bladder pain syndrome/interstitial cystitis, post operative inflammation, ischemic reperfusion disease, kidney fibrosis, pancreatitis, Parkinsons Disease, seronegative spondyloarthropathies (including anklyosing spondylitis, psoriatic arthritis, and Reiter's Syndrome), and vasculitis (including Wegener's Granulomatosis, polyarteritis nodosa, leucocytoclastic vasculitis, Churg-Strauss Syndrome, cryoglobulinemic vasculitis and giant cell arteritis); and neoplastic diseases or other cell proliferative disorders such as acute myelogenous leukemia, chronic myelogenous leukemia, acute lymphocytic leukemia, chronic lymphocytic leukemia, basophilic leukemia, cutaneous T-cell lymphoma, Sezary Syndrome, Hodgkin's Disease, Non-Hodgkin's Lymphoma, multiple myeloma, hypereosinophilic syndromes, mastocytosis and thrombocythemia.

The effectiveness of a compound as a SHIP1 modulator may be determined by any number of known techniques, including the assays set forth below in Examples 98-101.

Pharmaceutical Compositions of the Invention and Administration

For the purposes of administration, the compounds of the present invention may be formulated as pharmaceutical compositions. Pharmaceutical compositions comprise one or more compounds of this invention in combination with a pharmaceutically acceptable carrier and/or diluent. The compound is present in the composition in an amount which is effective to treat a particular disorder, that is, in an amount sufficient to achieve SHIP1 modulation activity, and preferably with acceptable toxicity to the patient. Typically, the pharmaceutical compositions of the present invention may include a compound in an amount from 0.1 mg to 250 mg per dosage depending upon the route of administration, and more typically from 1 mg to 60 mg. Appropriate concentrations and dosages can be readily determined by one skilled in the art.

Pharmaceutically acceptable carrier and/or diluents are familiar to those skilled in the art. For compositions formulated as liquid solutions, acceptable carriers and/or diluents include saline and sterile water, and may optionally include antioxidants, buffers, bacteriostats and other common additives. The compositions can also be formulated as pills, capsules, granules, or tablets which contain, in addition to a compound of this invention, diluents, dispersing and surface active agents, binders, and lubricants. One skilled in this art may further formulate the compounds in an appropriate manner, and in accordance with accepted practices, such as those disclosed in *Remington's Pharmaceutical Sciences* (Mack Pub. Co., N.J. current edition).

In another embodiment, the present invention provides a method for modulation SHIP1 generally and, more specifically, to treating the diseases, disorders and conditions as discussed above. Such methods include administering of a compound of the present invention to a mammal, preferably a human, in an amount sufficient to treat the condition. In this context, "treat" includes prophylactic administration. Such methods include systemic administration of a compound of this invention, preferably in the form of a pharmaceutical composition as discussed above. As used herein, systemic administration includes oral and parenteral methods of administration. For oral administration, suitable pharmaceutical compositions include powders, granules, pills, tablets, and capsules as well as liquids, syrups, suspensions, and emulsions. These compositions may also include flavorants, preservatives, suspending, thickening and emulsifying agents, and other pharmaceutically acceptable additives. For parenteral administration, the compounds of the present invention can be prepared in aqueous injection solutions which may contain buffers, antioxidants, bacteriostats, and other additives commonly employed in such solutions.

Preparation of the Compounds of the Invention

The following Reaction Schemes illustrate methods to make compounds of the present invention, i.e., compounds of formula (I), as set forth above in the Summary of the Invention.

The compounds of the present invention may be prepared by known organic synthesis techniques, including the methods described in more detail in the Examples. In general, the compounds of formula (I) may be made by the following Reaction Schemes, wherein all substituents are as defined above unless indicated otherwise. Although not generally depicted in the following schemes, one skilled in the art will understand that appropriate protecting group strategies may be useful in preparing compounds of formula (I). Protecting group methodology is well known to those skilled in the art (see, for example, Greene, T. W. and Wuts, P. G. M. *Greene's Protective Groups in Organic Synthesis* (2006), 4$^{th}$ Ed. Wiley).

It is also understood that one skilled in the art would be able to make the compounds of the invention by similar methods, by methods known to one skilled in the art, or by methods similar to the methods disclosed in U.S. Pat. Nos. 6,635,629 and 7,601,874. It is also understood that one skilled in the art would be able to make in a similar manner as described below other compounds of the invention not specifically illustrated below by using the appropriate starting components and modifying the parameters of the synthesis as needed. In general, starting components may be obtained from sources such as Sigma Aldrich, Lancaster Synthesis, Inc., Maybridge, Matrix Scientific, TCI, and Fluorochem USA, etc. or synthesized according to sources known to those skilled in the art (see, e.g., Smith, M. B. and J. March, *March's Advanced Organic Chemistry: Reactions, Mechanisms, and Structure*, 6th edition (Wiley, 2007)) or prepared as described herein. Certain starting materials, or their salts thereof, may be prepared according to the methods disclosed in U.S. Pat. Nos. 6,635,629 and 7,601,874, the relevant disclosures therein are incorporated in reference herein, or by methods known to one skilled in the art.

It is also understood that in the following description, combinations of substituents and/or variables of the depicted formulae are permissible only if such contributions result in stable compounds.

It will also be appreciated by those skilled in the art, although protected derivatives of compounds of this invention may not possess pharmacological activity as such, they may be administered to a mammal and thereafter metabolized in the body to form compounds of the invention which are pharmacologically active. Such derivatives may therefore be described as "prodrugs". All prodrugs of compounds of this invention are included within the scope of the invention.

Although depicted without stereochemistry, one skilled in the art will recognize that the compounds depicted in the following general Reaction Schemes can also be prepared in an optically pure form by utilizing methods known to one skilled in the art, such as the use of stereoselective reagents, chiral starting materials and phase transfer catalysts.

ABBREVIATIONS

The following abbreviations may be used herein in the following general reaction schemes and the Examples:
$Ac_2O$ for acetic anhydride;
AcOH for acetic acid;
$AlMe_3$ for trimethylaluminum;
Boc for tert-butoxycarbonyl;
$BH_3$.THF for borane tetrahydrofuran complex;
BnBr for benzyl bromide;
$Bu_3SnH$ for tributyltin hydride;
n-BuLi for n-butyl lithium;
t-BuOOH for tert-butyl hydroperoxide;
CDI for 1,1'-carbonyldiimidazole;
d for days;
DABCO for 1,4-diazabicyclo[2.2.2]octane;
DBU for 1,8-diazabicyclo[5.4.0]undec-7-ene;
DCC for N,N'-dicyclohexylcarbodiimide;
DCE for dichloroethane;
DIAD for diisopropyl azodicarboxylate;
Diglyme for diethylene glycol dimethyl ether;
DIPEA/DIEA for N, N-diisopropylethylamine;
DMAP for 4-dimethylaminopyridine;
DMF for N,N-dimethylformamide;
DMSO for dimethyl sulfoxide;
DPPA for diphenylphosphoryl azide;
$Et_2O$ for diethyl ether;
$Et_3N$ for triethylamine;
EtNCO for ethyl isocyanate;
EtOAc for ethyl acetate;
EtOH for ethanol;
h for hours;
$H_2$/Pd/C for hydrogen on palladium on charcoal;
$H_2$NMe.HCl for methylamine hydrochloride;
HBTU for O-(benzotriazol-1-yl)-N,N,N',N'-tetramethyluronium hexafluorophosphate;
IBX for 2-iodoxybenzoic acid;
Imid for imidazole;
i-PrOH for iso-propanol;
Imid. for imidazole;
KO$^t$Bu for potassium tert-butoxide;
$LiAlH_4$/LAH for lithium aluminum hydride;
$LiEt_3BH$ for lithium triethylborohydride (Super hydride);
m-CPBA/MCPBA for m-chloroperoxybenzoic acid;
m for minutes;
MeCN for acetonitrile;
MeI for methyl iodide;
MeNCS for methyl isocyanate;
2-MePhCO$_2$H for o-toluic acid;
3-MePhCO$_2$H for m-toluic acid;
4-MePhCO$_2$H for p-toluic acid;
Me$_4$Phen for 3,4,7,8-tetramethyl-[1,10]-phenanthroline;
MeOCH$_2$PPh$_3$Cl for methoxymethyl triphenylphosphonium chloride;
MeOH for methanol;
MePPh$_3$Br for methyl triphenylphosphonium bromide;
MeSO$_3$SiMe$_3$ for trimethylsilylmethanesulfonate;
MsCl for mesyl chloride;
MW for microwave;
NaOMe for sodium acetate;

NaSEt for sodium ethanethiolate;
NaBH(OAc)$_3$ for sodium triacetoxyborohydride;
n-BuLi for n-butyllithium;
NMO for N-methylmorpholine N-oxide;
NMP for N-methyl-2-pyrrolidone;
NMR for nuclear magnetic resonance;
pTsNHNH$_2$ for para-toluenesulfonyl hydrazide;
PCC for pyridinium chlorochromate;
Pd/C for palladium metal on charcoal;
PhCO$_2$H for benzoic acid;
PPh$_3$ for triphenylphosphine;
Ph$_3$PMeBr for methyltriphenylphosphonium bromide;
PhMe for toluene;
PivCl for trimethylacetyl chloride;
POCl$_3$ for phosphoryl chloride;
PTSA/PTSA.H$_2$O for para-toluenesulfonic acid/para-toluenesulfonic acid monohydrate;
PyBOP for benzotriazol-1-yl-oxytripyrrolidinophosphonium hexafluorophosphate;
Pyr for pyridine;
SEMCl for 2-(trimethylsilyl)ethoxymethyl chloride;
SEM for 2-(trimethylsilyl)ethoxymethyl;
TBAF for tetrabutylammonium fluoride;
TBDPS for tert-butyldiphenylsilyl;
TBDPS for tert-butyldiphenylsilyl;
TBDPSCl for tert-butyldiphenylsilyl chloride;
TBS/TBDMS for tert-butyldimethylsilyl;
TBSCl for tert-butyldimethylsilyl chloride;
TBTU for O-(benzotriazol-1-yl)-N,N,N',N'-tetramethyluronium tetrafluoroborate;
TEA for triethylamine;
TFA for trifluoroacetic acid;
TFAA for trifluoroacetic anhydride;
THF for tetrahydrofuran;
TLC for thin layer chromatography;
TMSOTf for trimethylsilyl triflate;
TPAP for tetrapropylammonium perruthenate;
TPSH for 2,4,6-triisopropylbenzenesulfonyl hydrazide; and
VAZO® for 1,1'-azobis(cyclohexanecarbonitrile).

A. Preparation of Compounds of Formula (I-1)

Compounds of formula (I-1) are compounds of formula (I), as defined above in the Summary of the Invention, where $R^1$ and $R^2$ are both —$R^8$—OH, $R^{4a}$ and $R^{4b}$ together form methylene and $R^3$ is —CH$_2$-benzimidazolyl, —CH$_2$-indolinyl, —CH$_2$-indolyl, —CH$_2$-purinyl, —CH$_2$-pyrazolyl, —CH$_2$-triazolyl, and are prepared as described below in Reaction Scheme 1 where $R^5$, $R^6$, $R^7$ and each $R^8$ are as described above in the Summary of the Invention for compounds of formula (I), $R^{3a}$ is benzimidazole, imidazole, indoline, indole, purine, pyrazole or triazole, Pg$^1$ and Pg$^2$ are each independently selected from an oxygen-protecting group, such as, but not limited to, tert-butyldimethylsilyl, tert-butyldiphenylsilyl or acetyl, Lg$^1$ is a functional group which forms a leaving group with the oxygen to which it is attached, such as mesyl or tosyl, and X is bromo or chloro.

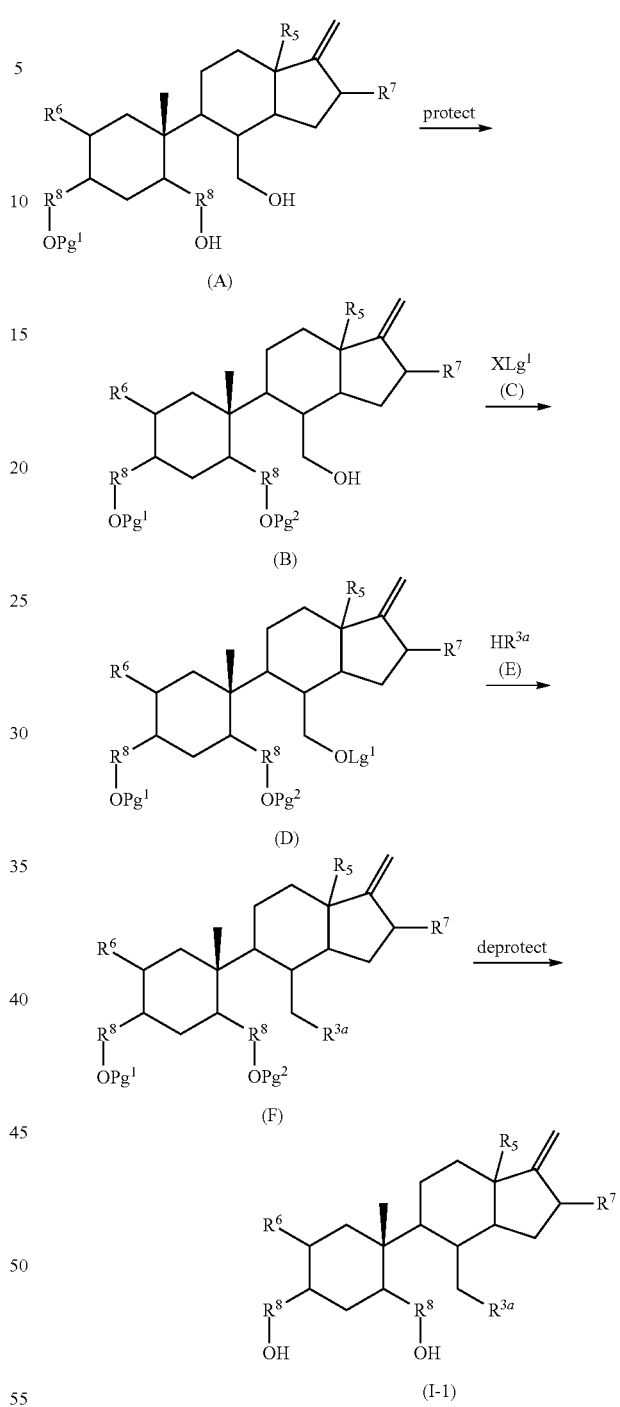

REACTION SCHEME 1

Compounds of formula (A) may be prepared by methods known to one skilled in the art or by the methods disclosed in U.S. Pat. No. 7,601,874. Compounds of formula (C) and (E) are commercially available, or can be prepared according to methods known to one skilled in the art.

In general, compounds of formula (I-1) are prepared, as described above in Reaction Scheme 1, by first protecting a compound of formula (A) under standard oxygen protecting conditions, such as treating the compound of formula (A) with the appropriate oxygen-protecting group under basic conditions in an aprotic solvent. The resulting oxygen-protected compound of formula (B) is then treated with a compound of formula (C) under standard leaving group formation conditions, such as treatment with the appropriate oxygen-activating group under basic conditions in an aprotic solvent, to yield the compound of formula (D). The compound of formula (D) is then treated with a compound of formula (E) under standard nucleophilic substitution conditions, such as treatment of the compound of formula (D) with the appropriate nucleophile under basic conditions in an aprotic solvent, to yield the compound of formula (F). Deprotection of the oxygens in the compound of formula (F) under standard conditions, such as treatment with the appropriate oxygen-deprotecting reagent in a protic solvent, yields the compound of formula (I-1).

Compounds of formula (D) can be treated with the appropriate cyanating agent, such as potassium cyanide, under standard conditions, such as in the presence of an aprotic solvent, such as DMSO, to yield a compound of formula (F) where $R^{3a}$ is —CN, which can be deprotected to yield a compound of formula (I-1) wherein $R^{3a}$ is —CN, or which can then be reduced under standard conditions to yield a compound of formula (I-1) where $R^{3a}$ is —$CH_2NH_2$.

The compound of formula (I-1) wherein $R^{3a}$ is —CN can be hydrolyzed in the presence of hydrogen peroxide to yield a compound of formula (I-1) wherein $R^{3a}$ is —$C(O)NH_2$.

Compounds of formula (B) can be treated under standard oxidizing conditions to form the corresponding aldehyde, which can then further oxidized to form the corresponding carboxy and then deprotected to form a compound of formula (I) where $R^3$ is —C(O)OH.

B. Preparation of Compounds of Formula (I-2)

Compounds of formula (I-2) are compounds of formula (I), as defined above in the Summary of the Invention, where $R^1$ and $R^3$ are both —$R^8$—OH, $R^{4a}$ and $R^{4b}$ together form methylene, and $R^2$ is heteroarylalkyl, and are prepared as described below in Reaction Scheme 2A where $R^5$, $R^6$, $R^7$ and each $R^8$ are as described above in the Summary of the Invention for compounds of formula (I), $R^{2a}$ is heteroaryl, $Pg^1$ and $Pg^2$ are each independently selected from an oxygen-protecting group, such as, but not limited to, tert-butyldimethylsilyl, tert-butyldiphenylsilyl or acetyl, $Lg^1$ is a functional group which forms a leaving group with the oxygen to which it is attached, such as mesyl or tosyl, and X is bromo or chloro.

REACTION SCHEME 2A

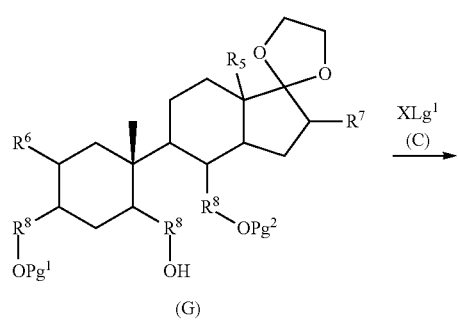

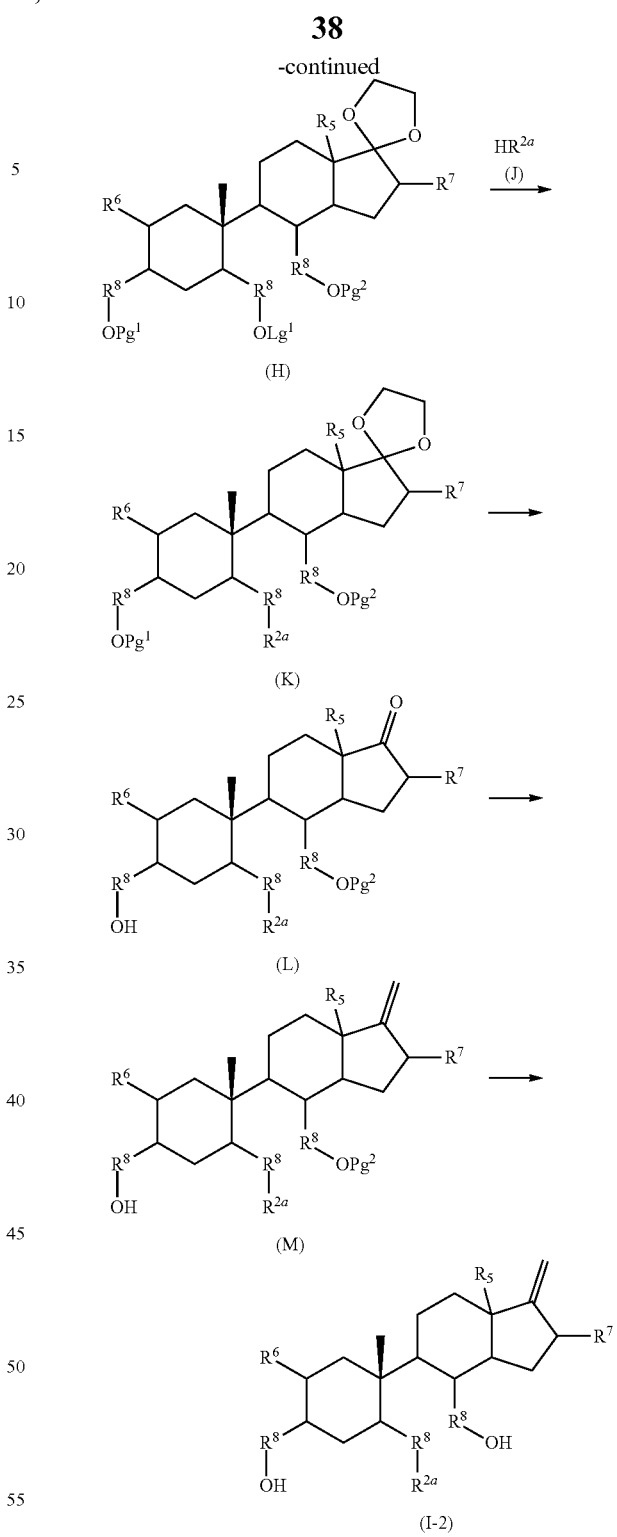

Compounds of formula (G) may be prepared by methods known to one skilled in the art or by the methods disclosed in U.S. Pat. No. 7,601,874. Compounds of formula (C) and (J) are commercially available, or can be prepared according to methods known to one skilled in the art.

In general, compounds of formula (I-2) are prepared, as described above in Reaction Scheme 2A, by first treating a compound of formula (G) with the compound of formula (C) under standard leaving group formation conditions, such as treating the compound of formula (G) with the appropriate oxygen-activating group under basic conditions in an aprotic solvent, to yield a compound of formula (H). The compound of formula (H) is then treated with a compound of formula (J) under standard nucleophilic substitution conditions, such as basic conditions in an aprotic solvent, to form a compound of formula (K). Treatment of the compound of formula (K) with acetic acid under standard conditions removes the ketal and $Pg^1$ to form the compound of formula (L). Olefination of the compound of formula (L) with the appropriate agent, such as methyl triphenylphosphonium bromide, in the presence of a base, such as KO$^t$Bu, provides the compound of formula (M). Treatment of the compound of formula (M) under standard deprotecting conditions, such as treatment with the appropriate oxygen-deprotecting reagent in an aprotic solvent, yields the compound of formula (I-2).

Alternatively, compounds of formula (I-2) can be prepared according the process described below in Reaction Scheme 2B wherein $R^5$, $R^6$, $R^7$, $R^8$, $R^{2a}$, $Pg^1$, $Pg^2$, $Lg^1$ and X are as described above for Reaction Scheme 2A.

Compounds of formula (N) may be prepared by methods known to one skilled in the art or by the methods disclosed in U.S. Pat. No. 7,601,874. Compounds of formula (J) are commercially available, or can be prepared according to methods known to one skilled in the art.

In general, compounds of formula (I-2) are prepared, as described above in Reaction Scheme 2B, by first treating a compound of formula (N) with a compound of formula (J) under standard nucleophilic substitution conditions, such as basic conditions in an aprotic solvent, to form a compound of formula (O). Treatment of compound of formula (O) under standard deprotecting conditions, such as treatment with the appropriate oxygen-deprotecting reagent in an aprotic solvent, yields the compound of formula (P), which is further deprotected to yield the compound of formula (I-2).

Alternatively, compounds of formula (I-2) can be prepared by treating a compound of formula (N), as described above in Reaction Scheme 2B, with a compound of formula (J) under standard conditions, such as under basic conditions in an aprotic solvent, to yield a compound of formula (I-2), as described above.

Alternatively, compounds of formula (I-2) can be prepared from compounds of formula (V), which can be prepared by the process described below in Reaction Scheme 2C wherein $R^5$, $R^6$, $R^7$, $R^8$, $Pg^1$ and $Pg^2$ are as described above for Reaction Schemes 2A and 2C, and $Pg^3$ is acetyl.

Compounds of formula (N) can be treated with a cyanating agent, such as potassium cyanide, and then deprotected to form compounds of formula (I-2) where $R^{2a}$ is cyano. Such compounds can be further hydrolyzed to the corresponding amide or carboxylic acid by procedures known to one skilled in the art.

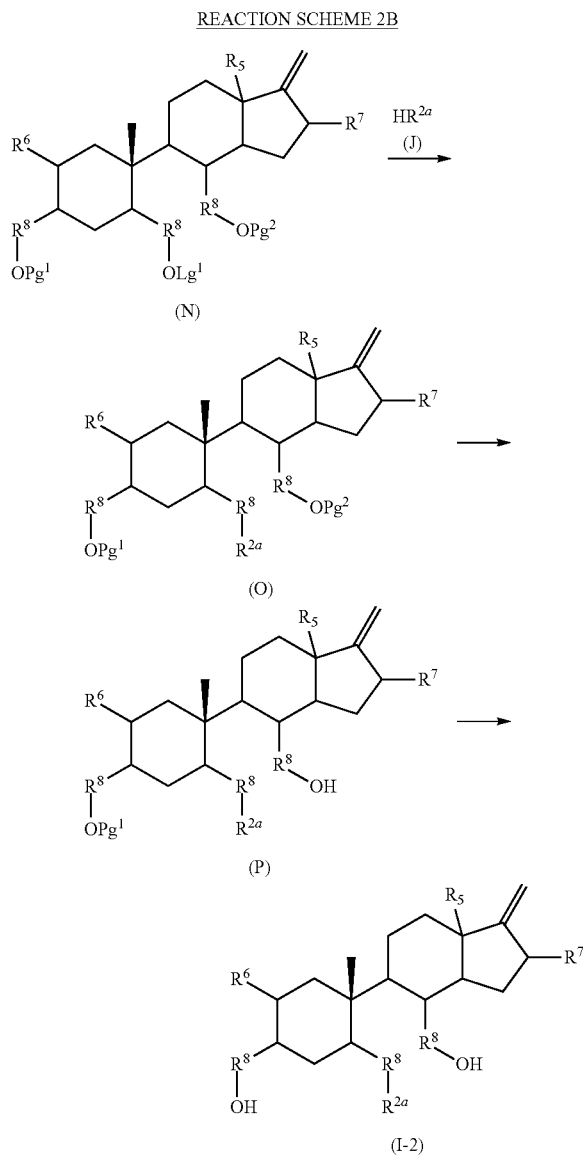

REACTION SCHEME 2B

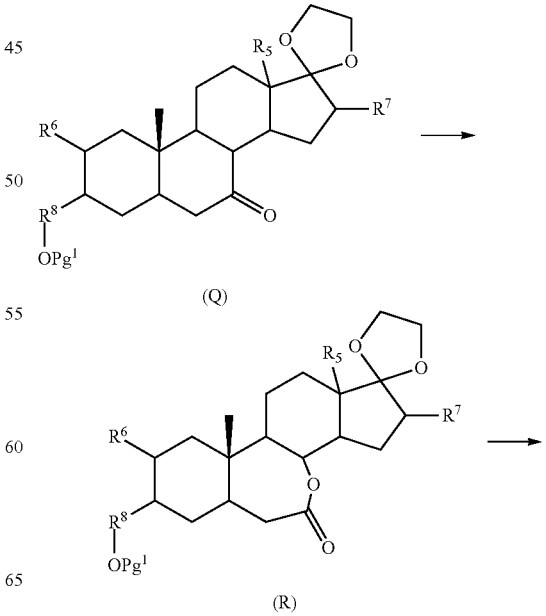

REACTION SCHEME 2C

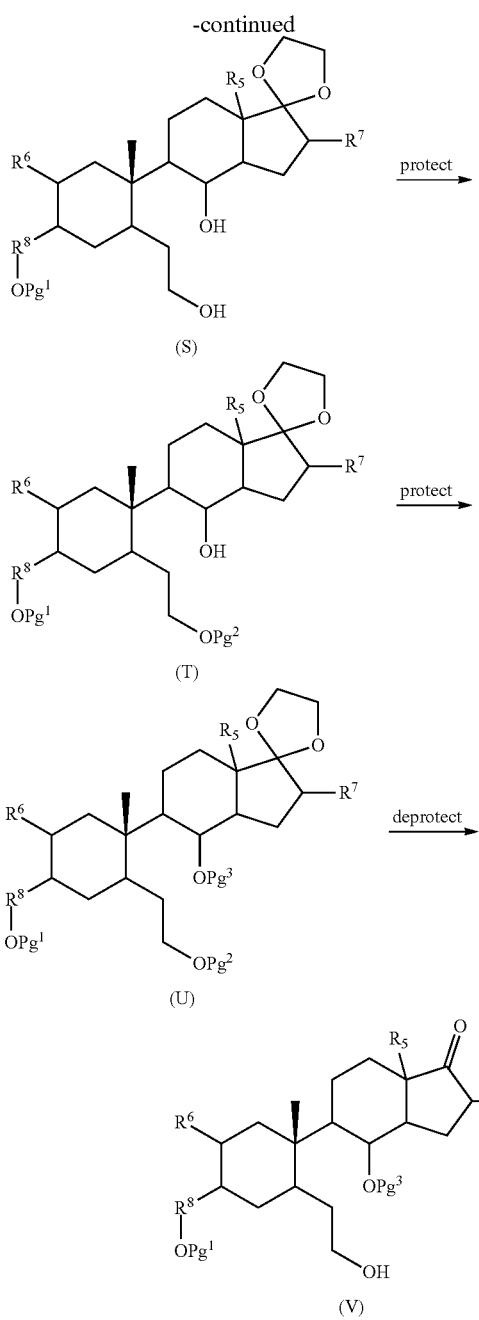

removes the ketal and Pg² to yield the compound of formula (V). The compound of formula (V) can then treated with the appropriate reagent under standard nucleophilic substitution conditions to form the compound of formula (I-2).

C. Preparation of Compounds of Formula (I-3)

Compounds of formula (I-3) are compounds of formula (I), as defined above in the Summary of the Invention, where $R^1$ and $R^2$ are both —$R^8$—OH, $R^{4a}$ and $R^{4b}$ together form methylene and $R^3$ is —$CH_2$—N(H)—CN, —$CH_2$—N(H)-(4-benzoyl)benzyl, and —$CH_2$—N(H)-(3,5-dimethoxy)benzyl, and are prepared as described below in Reaction Scheme 3 where $R^5$, $R^6$, $R^7$ and each $R^8$ are as described above in the Summary of the Invention for compounds of formula (I), $R^{3b}$ is cyano, methylbenzophenone or dimethoxybenzyl, $Pg^1$ and $Pg^2$ are each independently selected from an oxygen-protecting group, such as, but not limited to, tert-butyldimethylsilyl, tert-butyldiphenylsilyl or acetyl, and X is bromo or chloro.

REACTION SCHEME 3

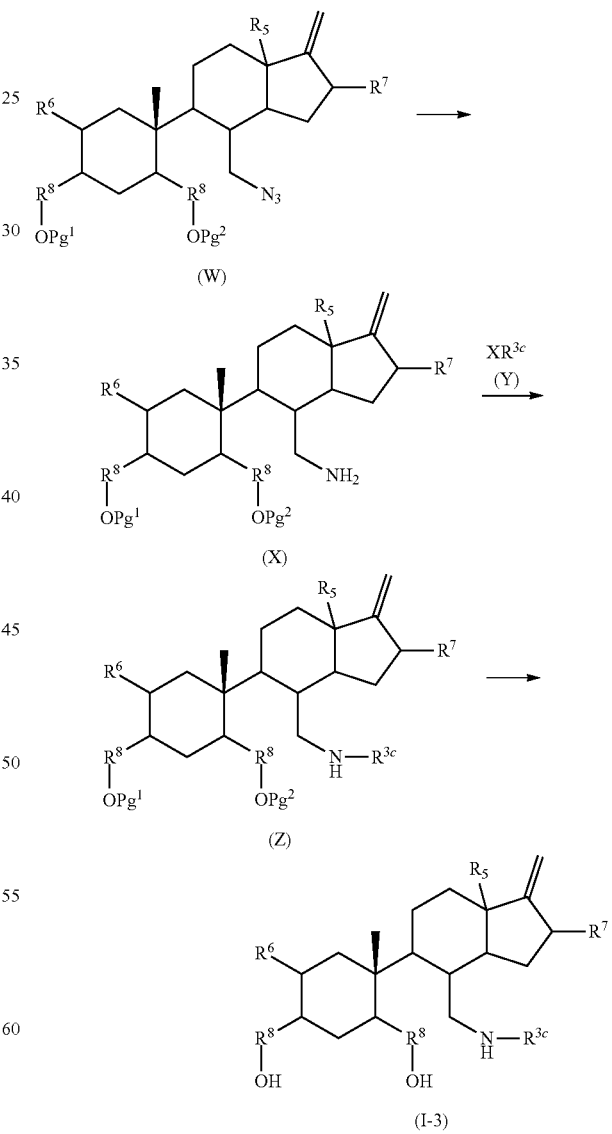

Compounds of formula (Q) are prepared by methods known to one skilled in the art or by methods disclosed in U.S. Pat. No. 6,635,629 or by methods disclosed herein.

In general, compounds of formula (V) are prepared by the process disclosed in Reaction Scheme 3 by first treating a compound of formula (Q) under standard Baeyer-Villager oxidation conditions, such as using 3-chloroperoxybenzoic acid (MCPBA) in $CHCl_3$ to yield the lactone compound of formula (R). Reduction of the lactone under standard procedures, such as treating the compound of formula (R) with the appropriate reducing agent in an aprotic solvent, yields the diol compound of formula (S). Sequential protection of the primary hydroxyl groups in the compound of formula (S) under standard procedures yields the compounds of formula (T) and (U), respectively. Treatment of the compound of formula (U) with acetic acid under standard conditions Compounds of formula (W) are prepared by methods known to one skilled in the art or by methods similar to those described in U.S. Pat. No. 7,601,874 or by methods disclosed herein. Compounds of formula (Y) are commercially available or can be prepared by methods known to one skilled in the art.

In general, compounds of formula (I-3) are prepared, as described above in Reaction Scheme 3, by first treating a compound of formula (Q) under standard reduction conditions, such as Staudinger reaction conditions, to yield a compound of formula (X). The compound of formula (X) is then treated with a compound of formula (Y) under standard alkylation conditions, such as under basic conditions in an aprotic solvent, to yield the compound of formula (Z), which is then deprotected under standard deprotecting conditions, such as treating the compound of formula (Z) with the appropriate oxygen-deprotecting reagent in a protic solvent, to yield the compound of formula (I-3).

D. Preparation of Compounds of Formula (I-4)

Compounds of formula (I-4) are compounds of formula (I), as defined above in the Summary of the Invention, or compounds of formula (Ia), as defined above in the Embodiments, where $R^1$ and $R^2$ are both —$R^8$—OH, $R^{4a}$ and $R^{4b}$ together form methylene and $R^3$ is —$CH_2$—N(H)-(4-fluoro)benzyl, —$CH_2$—N(H)—$CH_2$-pyridinyl, —$CH_2$—N(H)-(4-methyl)benzyl, —$CH_2$—N(H)-(3-methyl)benzyl, —$CH_2$—N(H)-(2-methyl)benzyl, —$CH_2$—N(H)-(4-methoxy)benzyl, —$CH_2CH_2$—N(H)-(4-methoxy)benzyl, —$CH_2$—N(H)-(4-trifluoromethyl)benzyl, —$CH_2$—N(H)—$CH_2$-benzimidazolyl, —$CH_2$—N(H)—$CH_2$-benzodioxolyl, —$CH_2CH_2$—N(H)—$CH_2$-benzodioxolyl, —$CH_2$—N(H)-(4-nitro)benzyl, —$CH_2$—N(H)—$CH_2$-(2,2-difluorobenzodioxolyl), —$CH_2$—N(H)-(2-methyl-4-fluoro)benzyl, —$CH_2$—N(H)-(2-fluoro-4-methyl)benzyl, —$CH_2$—N(H)-(2-methoxy-4-fluoro)benzyl, —$CH_2$—N(H)-(2-fluoro-4-methoxy)benzyl, —$CH_2$—N(H)-(4-methoxybenzyl)$_2$, or —$CH_2$—N(H)—$CH_2CH_2$-(4-methoxy)phenyl, and are prepared as described below in Reaction Scheme 4 where $R^5$, $R^6$, $R^7$ and each $R^8$ are as described above in the Summary of the Invention for compounds of formula (I), $R^{3d}$ is -(4-fluoro)phenyl, -pyridinyl, -(4-methyl)phenyl, -(3-methyl)phenyl, -(2-methyl)phenyl, -(4-methoxy)phenyl, -(4-trifluoromethyl)phenyl, -benzimidazolyl, -benzodioxolyl, -(4-nitro)phenyl, -(2,2-difluorobenzodioxolyl), -(2-methyl-4-fluoro)phenyl, -(2-fluoro-4-methyl)phenyl, -(2-methoxy-4-fluoro)phenyl, -(2-fluoro-4-methoxy)phenyl, -(4-methoxyphenyl)$_2$, or —$CH_2$-(4-methoxy)phenyl.

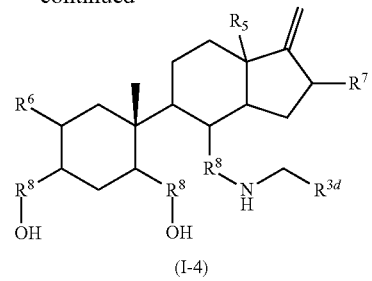

(I-4)

Compounds of formula (AA) can be prepared by methods known to one skilled in the art, by methods similar to the methods disclosed in U.S. Pat. No. 7,601,874 or by methods disclosed herein. Compounds of formula (BB) are commercially available or can be prepared by methods known to one skilled in the art.

In general, compounds of formula (I-4) are prepared, as described above in Reaction Scheme 4, by treating a compound of formula (AA) with a compound of formula (BB) under standard reductive amination conditions, such as the appropriate reducing agent in a solvent mixture. The hydroxyls of compound (AA) may optionally be protected by standard oxygen-protecting procedures known to one skilled in the art prior to the reaction of the compound of formula (AA) with the compound of formula (BB), and the resulting compound may then be deprotected according to methods known to one skilled in the art to arrive at the compound of formula (I-4).

Alternatively, compounds of formula (AA) can be treated with ethyl isocyanate, phenyl, isocyanate, benzyl isocyanate or methyl isothiocyanate under conditions known to one skilled in the art to yield compounds of formula (I) wherein $R^3$ is —$CH_2$—N(H)C(O)N(H)-benzyl, —$CH_2$—N(H)C(O)N(H)-ethyl, —$CH_2$—N(H)C(O)N(H)-phenyl or —$CH_2$—N(H)C(S)N(H)CH_3$.

E. Preparation of Compounds of Formula (I-5)

Compounds of formula (I-5) are compounds of formula (I), as defined above in the Summary of the Invention, where $R^1$ and $R^3$ are both —$R^8$—OH, $R^{4a}$ and $R^{4b}$ together form methylene and $R^2$ is heterocyclylalkyl, and are prepared as described below in Reaction Scheme 5 where $R^5$, $R^6$, $R^7$ and each $R^8$ are as described above in the Summary of the Invention for compounds of formula (I), $R^{2b}$ is heterocyclyl and $Pg^1$ and $Pg^2$ are each independently selected from an oxygen-protecting group, such as, but not limited to, tert-butyldimethylsilyl, tert-butyldiphenylsilyl or acetyl.

REACTION SCHEME 4

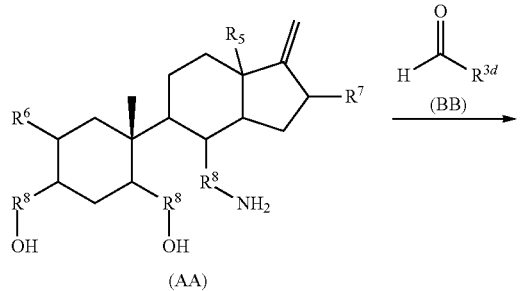

REACTION SCHEME 5

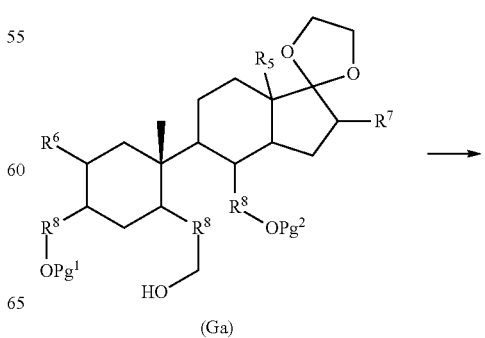

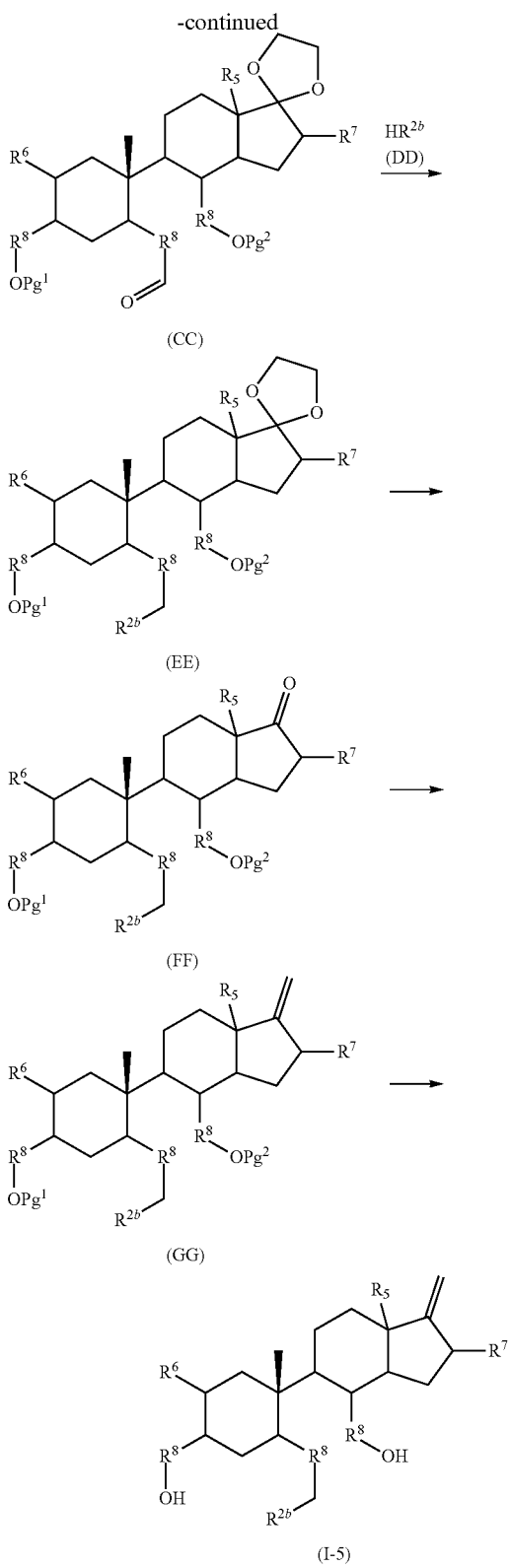

Compounds of formula (Ga) are compounds of formula (G) as described above in Reaction Scheme 2A. Compounds of formula (DD) can be prepared by methods known to one skilled in the art or by methods disclosed herein.

In general, compounds of formula (I-5) are prepared, as described above in Reaction Scheme 5, by treating a compound of formula (Ga) with an oxidizing agent, such as TPAP and NMO, to form the ketone compound of formula (CC). The compound of formula (CC) is then treated with a compound of formula (DD) under standard reductive amination conditions, such as treatment with the appropriate reducing agent combination in an aprotic solvent, to form the compound of formula (EE). Treatment of the compound of formula (EE) with acetic acid under standard conditions removes the ketal and $Pg^1$ to form the compound of formula (FF). Olefination of the compound of formula (FF) with the appropriate agent, such as methyl triphenylphosphonium bromide, in the presence of a base, such as KO$^t$Bu, provides the compound of formula (GG). Treatment of the compound of formula (GG) under standard deprotecting conditions, such as treatment with the appropriate oxygen-deprotecting reagent in an aprotic solvent, yields the compound of formula (I-5).

Alternatively, the hydroxyl group in the compound of formula (Ga) can first be optionally protected under standard oxygen-protecting procedures and the protected compound can then be treated under similar conditions as the treatment of compounds of formula (EE) and formula (FF) to form the corresponding compound where $R^{4a}$ and $R^{4b}$ form methylene, which can then be deprotected, oxidized and treated with a compounds of formula (DD) to produce a compound of formula (GG), which is then treated to deprotecting conditions to form the compound of formula (I-5).

F. Preparation of Compounds of Formula (I-6)

Compounds of formula (I-6) are compounds of formula (I), as defined above in the Summary of the Invention, where $R^1$ and $R^2$ are both —$R^8$—OH, $R^3$ is —$CH_2N(H)C(O)CH_3$, —$CH_2$—N(H)C(O)-(2-methyl)phenyl, —$CH_2$—N(H)C(O)-(3-methyl)phenyl, —$CH_2$—N(H)C(O)-(4-fluoro)phenyl, —$CH_2$—N(H)C(O)-(4-methoxy)phenyl, —$CH_2$—N(H)C(O)-(4-methyl)phenyl, —$CH_2$—N(H)C(O)-(4-trifluoromethyl)phenyl, —$CH_2$—N(H)C(O)-2-pyridinyl, —$CH_2$—N(H)C(O)-2-pyrrolyl, —$CH_2$—N(H)C(O)-3-pyridinyl, —$CH_2$—N(H)C(O)-4-pyridinyl, —$CH_2$—N(H)C(O)-benzodioxolyl, —$CH_2$—N(H)C(O)-butyl, —$CH_2$—N(H)C(O)CF_3$, —$CH_2$—N(H)C(O)-cyclohexyl, —$CH_2$—N(H)C(O)-cyclopropyl, —$CH_2$—N(H)C(O)-ethyl, —$CH_2$—N(H)C(O)-furanyl, —$CH_2$—N(H)C(O)-isopropyl, —$CH_2$—N(H)C(O)-naphthyl, —$CH_2$—N(H)C(O)-phenyl, —$CH_2$—N(H)C(O)-propyl, —$CH_2$—N(H)C(O)-pyrazinyl, —$CH_2$—N(H)C(O)-t-butyl or —$CH_2$—$CH_2$—N(H)C(O)benzodioxolyl, and are prepared as described below in Reaction Scheme 6 where $R^{4a}$, $R^{4b}$, $R^5$, $R^6$, $R^7$ and each $R^8$ are as described above in the Summary of the Invention for compounds of formula (I) and $R^{3e}$ is —$CH_3$, -(2-methyl)phenyl, -(3-methyl)phenyl, -(4-fluoro)phenyl, -(4-methoxy)phenyl, -(4-methyl)phenyl, -(4-trifluoromethyl)phenyl, -2-pyridinyl, -2-pyrrolyl, -3-pyridinyl, -4-pyridinyl, -benzodioxolyl, -butyl, —$CF_3$, -cyclohexyl, -cyclopropyl, -ethyl, -furanyl, -isopropyl, -naphthyl, -phenyl, -propyl, -pyrazinyl, -t-butyl or -benzodioxolyl.

REACTION SCHEME 6

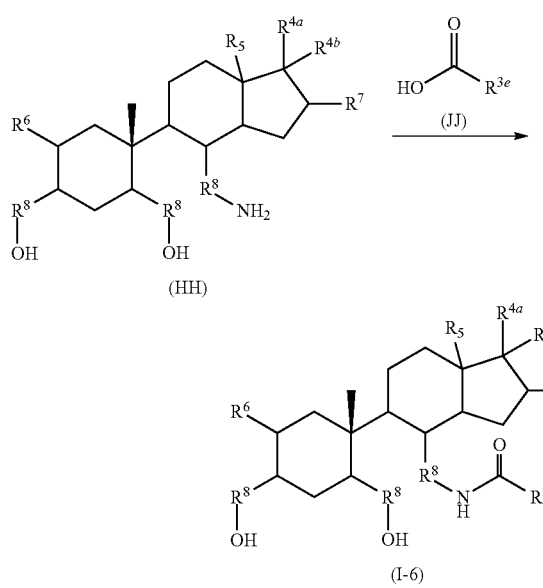

Compounds of (HH) can be prepared according to methods known to one skilled in the art or by methods similar to the methods disclosed in U.S. Pat. No. 7,601,874 or by methods disclosed herein. Compounds of formula (JJ) are commercially available or can be prepared by methods known to one skilled in the art.

In general, compounds of formula (I-6) are prepared, as described above in Reaction Scheme 6, by treating a compound of formula (HH) with a compound of formula (JJ) under suitable conditions, such as treatment with a coupling reagent in an aprotic solvent, to form a compound of formula (I-6). The hydroxyls of the compound of formula (HH) may first be optionally protected by treating the compound of formula (HH) under the appropriate oxygen-protecting conditions. The resulting protected compound of formula (HH) may then be treated with the compound of formula (JJ) under suitable conditions to form the protected compound of formula (I-6), which can then be deprotected under standard deprotection conditions to form the compound of formula (I-6).

Compounds of formula (HH) where $R^{4a}$ and $R^{4b}$ together form ethylidene are prepared by methods disclosed in U.S. Pat. No. 7,601,874 and can be treated to standard reducing conditions to form compounds of formula (HH) where $R^{4a}$ is ethyl and $R^{4b}$ is hydrogen.

Alternatively, compounds of formula (HH) where $R^{4a}$ and $R^{4b}$ together form methylene can be treated with the appropriate acid, such as p-toulenesulfonic acid, to yield a compound of formula (I) where $R^{4a}$ is alkyl and $R^{4b}$ is a direct bond to the carbon to which $R^7$ is attached.

G. Preparation of Compounds of Formula (I-7)

Compounds of formula (I-7) are compounds of formula (I), as defined above in the Summary of the Invention, where $R^1$ and $R^3$ are both —$R^8$—OH, $R^{4a}$ and $R^{4b}$ together form methylene and $R^2$ is —$R^8$—N($R^9$)C(O)$R^9$ where $R^9$ is as defined above in the Summary of the Invention for compounds of formula (I), and are prepared as described below in Reaction Scheme 7 where $R^5$, $R^6$, $R^7$ and each $R^8$ are as described above in the Summary of the Invention for compounds of formula (I), $R^{2C}$ is $R^9$ as defined above in the Summary of the Invention for compounds of formula (I), and $Pg^1$ and $Pg^2$ are each independently selected from an oxygen-protecting group, such as, but not limited to, tert-butyldimethylsilyl, tert-butyldiphenylsilyl or acetyl.

REACTION SCHEME 7

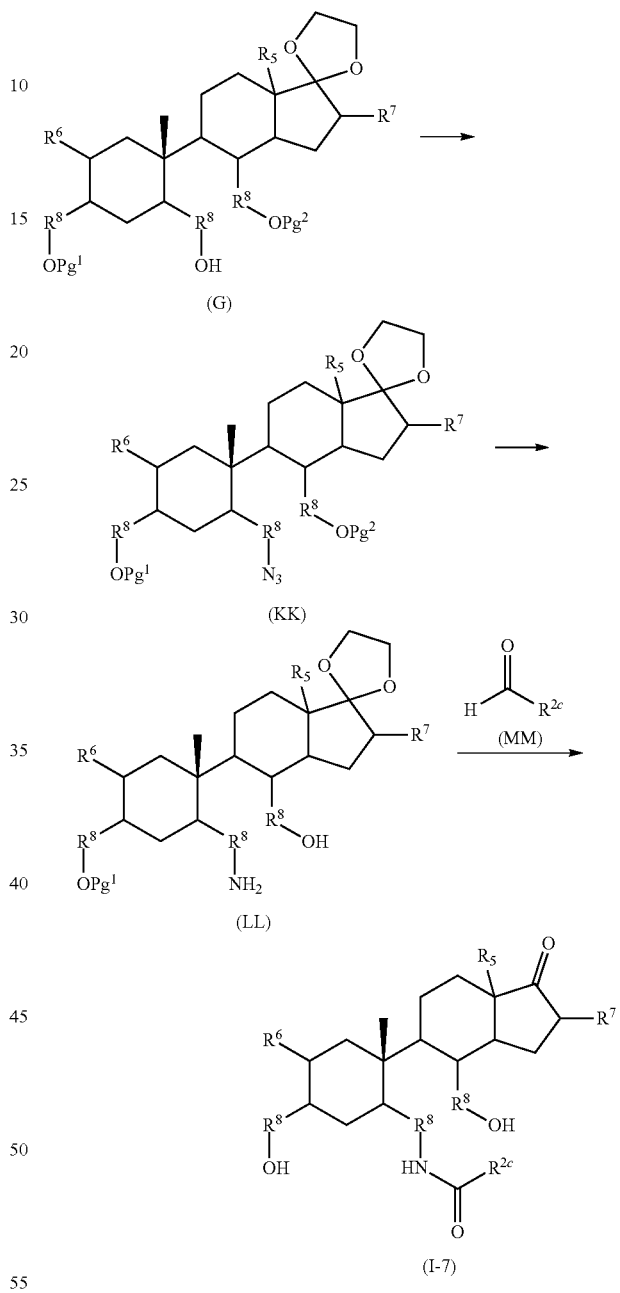

Compounds of formula (G) are described above in Reaction Scheme 2A. Compounds of formula (MM) are commercially available or can be prepared by methods known to one skilled in the art.

In general, compounds of formula (I-7) are prepared, as described above in Reaction Scheme 7, by first treating a compound of formula (G) with a suitable azide, such as diphenylphosphoryl azide under standard Mitsunobu reaction conditions in an aprotic solvent, to form the azide compound of formula (KK). The $Pg^2$ group of the compound of formula (KK) is then removed by standard procedures, such as treatment with the appropriate oxygen-deprotecting reagent in an aprotic solvent, to form the compound of formula (LL), which is then reacted with a compound of formula (MM) under standard amidation conditions, such as treatment with a coupling reagent in an aprotic solvent, to form the compound of formula (I-7).

H. Preparation of Compounds of Formula (I-8)

Compounds of formula (I-8) are compounds of formula (I), as defined above in the Summary of the Invention, where $R^1$ and $R^2$ are both —$R^8$—OH, $R^{4a}$ and $R^{4b}$ together form methylene and $R^3$ is —$CH_2$—O-(3,5-dimethoxy)benzyl, —$CH_2$—O-benzyl, or —$CH_2$—O—$CH_2$-pyridinyl, and are prepared as described below in Reaction Scheme 8 where $R^5$, $R^6$, $R^7$ and each $R^8$ are as described above in the Summary of the Invention for compounds of formula (I), $R^{3f}$ is -(3,5-dimethoxy)benzyl, -benzyl, or —$CH_2$-pyridinyl, and $Pg^1$, $Pg^2$ and $Pg^3$ are each independently selected from an oxygen-protecting group, such as, but not limited to, tert-butyldimethylsilyl, tert-butyldiphenylsilyl or acetyl.

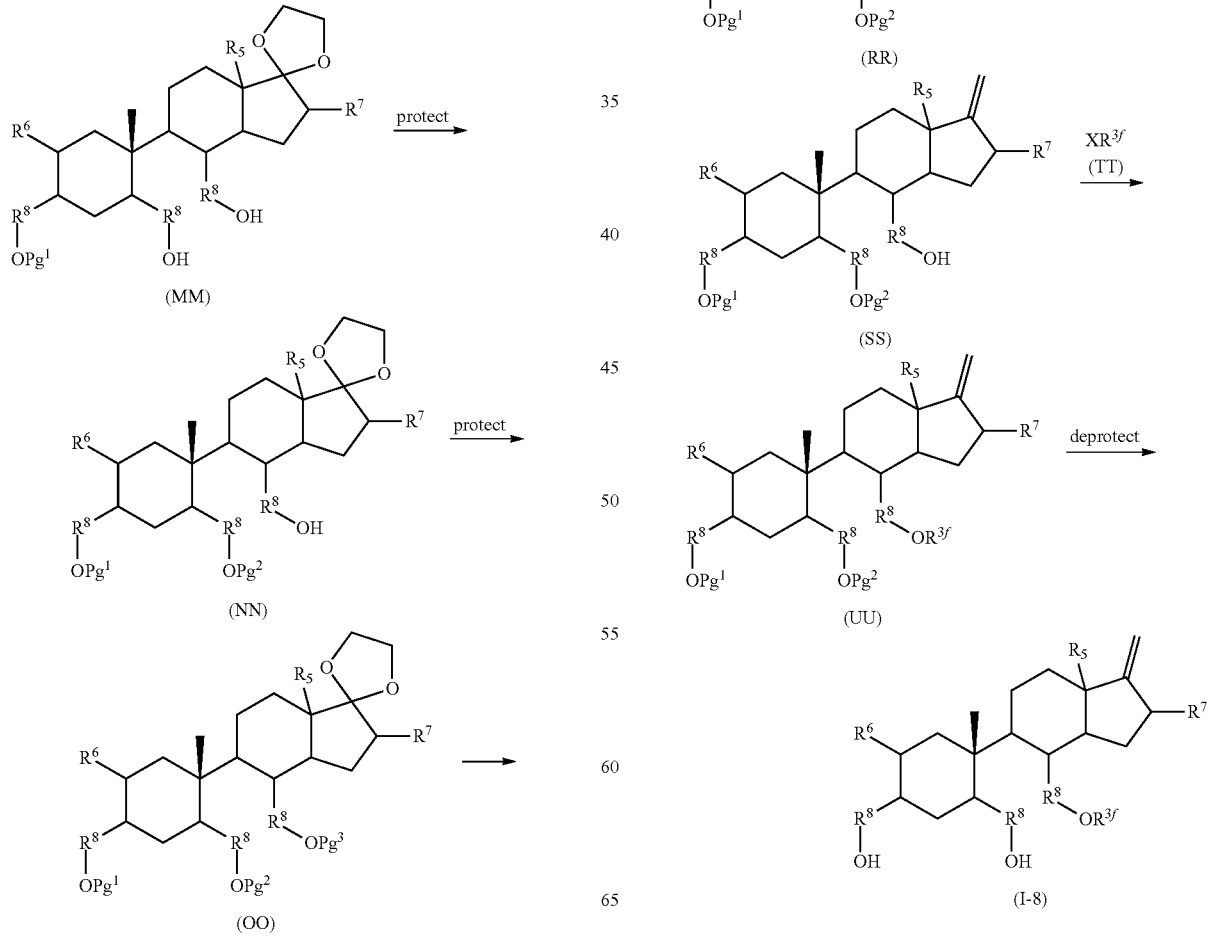

REACTION SCHEME 8

Compounds of formula (MM) may be prepared by methods known to one skilled in the art or by the methods disclosed in U.S. Pat. No. 7,601,874. Compounds of formula (TT) are commercially available, or can be prepared according to methods known to one skilled in the art.

In general, compounds of formula (I-8) are prepared, as described above in Reaction Scheme 8, by first treating a compound of formula (MM) to suitable oxygen-protecting conditions, such as treatment with the appropriate oxygen-protecting group under basic conditions in an aprotic solvent, to form a compound of formula (NN), which is further treated to suitable oxygen-protecting conditions, under basic conditions in an aprotic solvent, to form a compound of formula (OO). Treatment of the compound of formula (OO) with acetic acid under standard conditions removes the ketal and $Pg^1$ and $Pg^2$ to form the compound of formula (PP), which is then treated with suitable oxygen-protecting conditions to form the compound of formula (QQ). $Pg^3$ is removed from the compound of formula (QQ) by standard procedures, such as treatment with the appropriate oxygen-deprotecting reagent under basic conditions in an aprotic solvent, to form the compound of formula (RR). Olefination of the compound of formula (RR) with the appropriate agent, such as methyl triphenylphosphonium bromide, in the presence of a base, such as KO$^t$Bu, provides the compound of formula (SS), which is then treated with a compound of formula (TT) under suitable Williamson ether synthesis conditions, such as treatment with the appropriate alkylating agent under basic conditions in an aprotic solvent, to form the compound of formula (UU). The protecting groups on the compound of formula (UU) are then removed by standard procedures to form the compound of formula (I-8).

I. Preparation of Compounds of Formula (I-9)

Compounds of formula (I-9) are compounds of formula (I), as defined above in the Summary of the Invention, where $R^1$ and $R^3$ are both —$R^8$—OH, $R^{4a}$ and $R^{4b}$ together form methylene and $R^2$ is —$R^8$—$OR^9$ where $R^9$ is alkyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl or optionally substituted heteroarylalkyl, and are prepared as described below in Reaction Scheme 8 where $R^5$, $R^6$, $R^7$ and each $R^8$ are as described above in the Summary of the Invention for compounds of formula (I), $R^{2d}$ is alkyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl or optionally substituted heteroarylalkyl, and $Pg^1$ and $Pg^2$ are each independently selected from an oxygen-protecting group, such as, but not limited to, tert-butyldimethylsilyl, tert-butyldiphenylsilyl or acetyl.

REACTION SCHEME 9

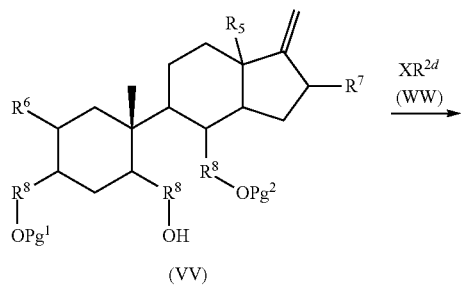

(VV)

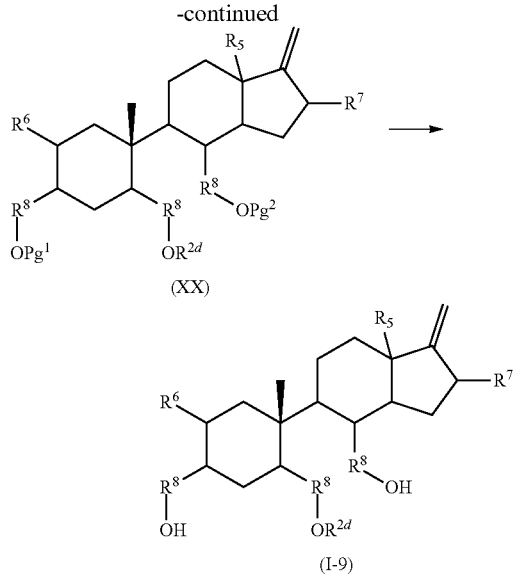

Compounds of formula (VV) may be prepared by methods known to one skilled in the art or by the methods disclosed in U.S. Pat. No. 7,601,874. Compounds of formula (WW) are commercially available, or can be prepared according to methods known to one skilled in the art.

In general, compounds of formula (I-9) are prepared, as described above in Reaction Scheme 9, by first treating a compound of formula (W) with a compound of formula (WW) under standard Williamson ether synthesis conditions, such as under basic conditions in an aprotic solvent, to form a compound of formula (XX). The oxygen-protecting groups on the compound of formula (XX) are removed by standard procedures, such as treating the compound of formula (XX) with the appropriate oxygen-deprotecting reagent in an aprotic solvent, to form the compound of formula (I-9).

J. Preparation of Compounds of Formula (I-11)

Compounds of formula (I-11) are compounds of formula (I), as defined above in the Summary of the Invention, where $R^{4a}$ and $R^{4b}$ are both methyl and $R^5$ is a direct bond to C14, and are prepared as described below in Reaction Scheme 10 where $R^1$, $R^2$, $R^3$, $R^6$ and $R^7$ are as described above in the Summary of the Invention for compounds of formula (I).

REACTION SCHEME 10

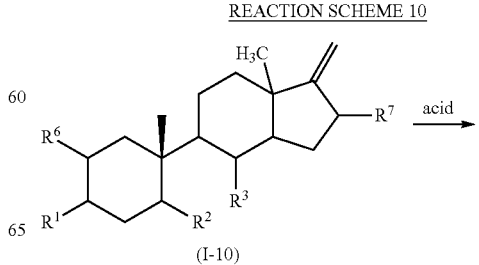

(I-10)

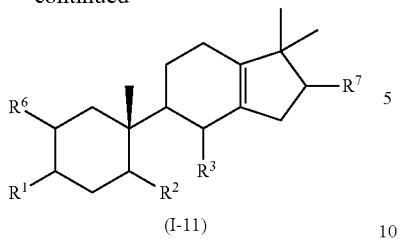

(I-11)

Compounds of formula (I-10) are compounds of formula (I), as defined above in the Summary of the Invention, where $R^5$ is methyl and $R^{4a}$ and $R^{4b}$ together form methlylene, and are prepared as described herein.

In general, compound of formula (I-11) are prepared, as described above in Reaction Scheme 10, by treating the compound of formula (I-10) with an acid, preferably HCl, to form the compound of formula (I-11).

Compounds of formula (I-11) where $R^3$ is —CH$_2$NH$_2$ can be further treated with a sulfonating agent, such as mesyl chloride, under standard conditions to form compounds of formula (I-11) wherein $R^3$ is —CH$_2$N(H)S(O)$_2$CH$_3$.

K. Preparation of Compounds of Formula (I-12)

Compounds of formula (I-12) are compounds of formula (I), as defined above in the Summary of the Invention, where $R^{4a}$ and $R^{4b}$ are both methyl, $R^5$ is a direct bond to C14 and $R^7$ is —OH, and are prepared as described below in Reaction Scheme 11 where $R^6$ and each $R^8$ are as described above in the Summary of the Invention for compounds of formula (I) and Pg$^1$, Pg$^2$ and Pg$^3$ are each independently selected from an oxygen-protecting group, such as, but not limited to, tert-butyldimethylsilyl or tert-butyldiphenylsilyl, and Pg$^4$ is acetyl.

REACTION SCHEME 11

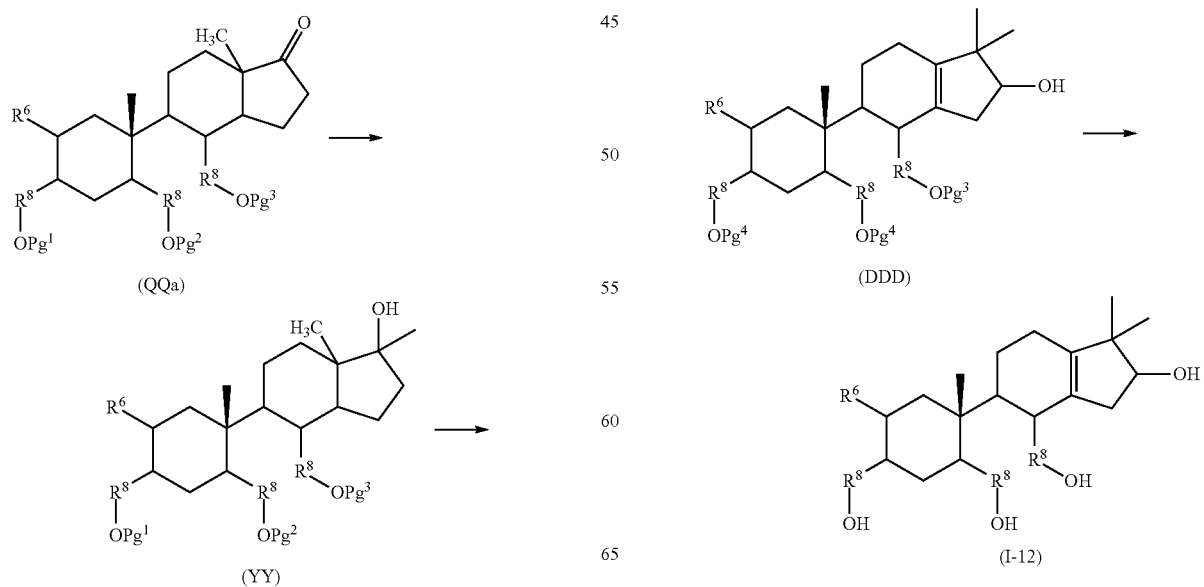

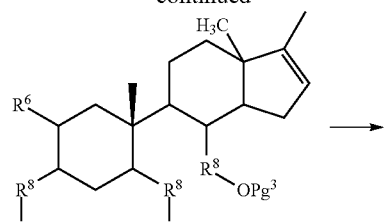

(ZZ)

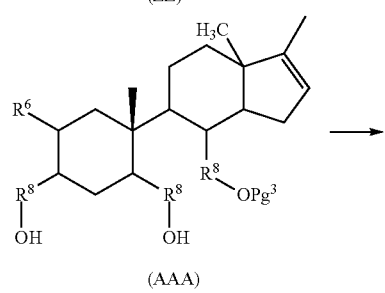

(AAA)

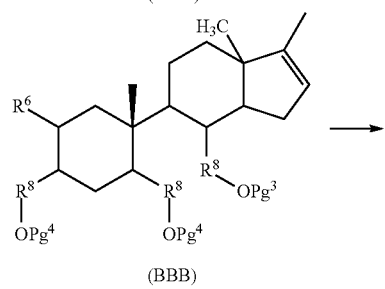

(BBB)

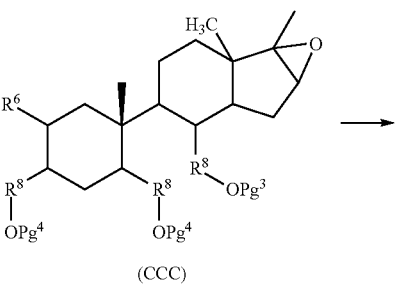

(CCC)

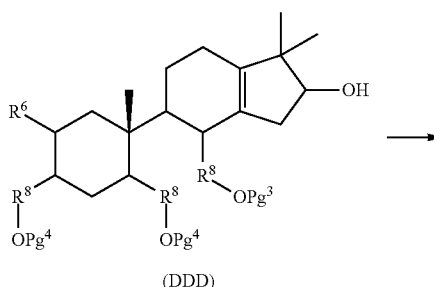

(DDD)

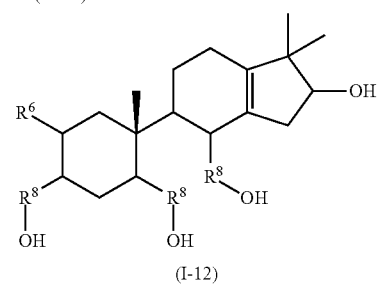

(I-12)

Compounds of formula (QQa) are compounds of formula (QQ) as described above in Reaction Scheme 8 where $R^5$ is methyl and $R^7$ is hydrogen and are prepared as described herein.

In general, compounds of formula (I-12) are prepared, as described above in Reaction Scheme 11, by treating a compound of formula (QQa) with methyl lithium under standard conditions, such as treating the compound of formula (QQa) with the appropriate alkyl lithium in an aprotic solvent, to form a compound of formula (YY), which is then subjected to dehydrating conditions, such as treatment with phosphoryl chloride in the presence of an base, to form the compound of formula (ZZ). $Pg^1$ and $Pg^2$ in the compound of formula (ZZ) are then removed by standard procedures, such as treating the compound of formula (ZZ) with the appropriate oxygen-deprotecting reagent in a protic solvent, to yield the compound of formula (AAA). Treatment of the compound of formula (AAA) with the acetic anhydride under standard conditions, such as treating the compound of formula (ZZ) with the acetylating agent in an aprotic solvent, yields the compound of formula (BBB). Treatment of the compound of formula (BBB) with an appropriate oxidizing agent, such as MCPBA, under standard conditions, such as in an aprotic solvent, yields the compound of formula (CCC). Treatment of the compound of formula (CCC) to acidic conditions yields the compound of formula (DDD), which is then subjected to deprotecting conditions, such as treating the compound of formula (CCC) with deprotecting agent in a protic solvent, to remove each $Pg^4$ and $Pg^3$ to yield the compound of formula (I-12).

L. Preparation of Compounds of Formula (I-13)

Compound of formula (I-13) are compound of formula (I), as described above in the Summary of the Invention, where $R^1$ is —$R^8$—OH, $R^2$ is —$R^8$—$NH_2$, $R^3$ is —$CH_2$—$NH_2$, and $R^{4a}$ and $R^{4b}$ together form methylene, and are prepared as described below in Reaction Scheme 12 where $R^5$, $R^6$, $R^7$ and each $R^8$ are as described above in the Summary of the Invention for compounds of formula (I), $Pg^1$ is an oxygen-protecting group, such as, but not limited to, tert-butyldimethylsilyl, tert-butyldiphenylsilyl or acetyl, $Lg^1$ is a functional group which forms a leaving group with the oxygen to which it is attached, such as mesyl or tosyl, and X is bromo or chloro.

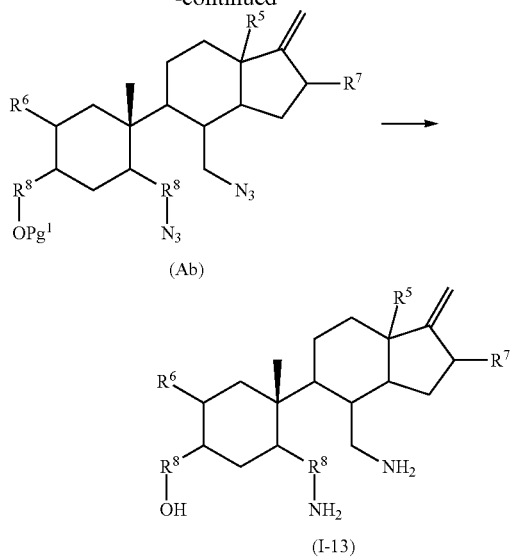

Compounds of formula (A) are described above in Reaction Scheme 1. Compounds of formula (C) and $NaN_3$ are commercially available or can be prepared by methods known to one skilled in the art.

In general, compounds of formula (I-13) are prepared, as described above in Reaction Scheme 12, by first treating a compound of formula (A) with a compound of formula (C) under standard leaving group formation conditions, such as under basic conditions in an aprotic solvent, and then treating the resulting mixture with sodium azide under standard conditions, such as treatment with the appropriate nucleophilic azide in an aprotic solvent, to yield the compound of formula (Aa). Treatment of the compound of formula (Aa) with sodium azide under standard conditions, such as the above at higher temperatures, yields the compound of formula (Ac), with is then deprotected under standard conditions to yield the compound of formula (I-13).

M. Preparation of Compounds of Formula (I-14)

Compound of formula (I-14) are compounds of formula (I), as described above in the Summary of the Invention, where $R^1$ and $R^2$ are each —$R^8$—OH, $R^3$ is —$CH_2N(H)C(O)(CH_2)_3CH_3$, and $R^7$ is hydrogen, and are prepared as described below in Reaction Scheme 13 where $R^5$, $R^6$, and each $R^8$ are as described above in the Summary of the Invention for compounds of formula (I), $Pg^1$ and $Pg^2$ are each independently an oxygen-protecting group, such as, but not limited to, tert-butyldimethylsilyl, tert-butyldiphenylsilyl or acetyl, and $R^{3g}$ is n-butyl.

REACTION SCHEME 12

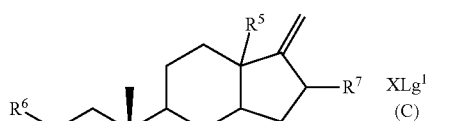

REACTION SCHEME 13

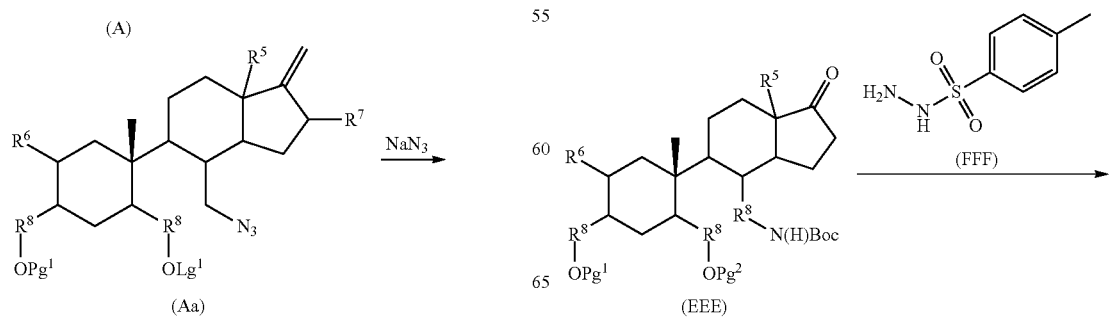

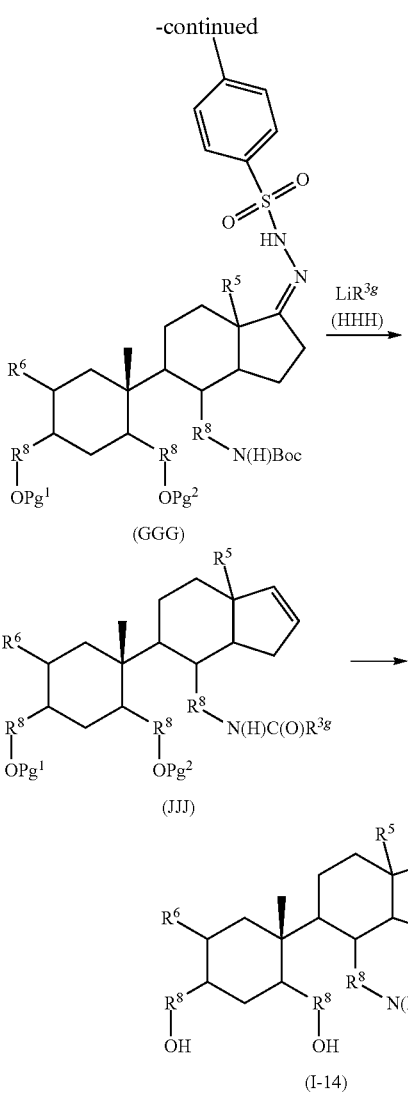

(GGG)

(JJJ)

(I-14)

Compounds of formula (EEE) may be prepared by methods known to one skilled in the art from compounds disclosed herein or by methods similar to the methods disclosed in U.S. Pat. No. 7,601,874. Compounds of formula (FFF) and formula (HHH) are commercially available or can be prepared by methods known to one skilled in the art.

In general, compounds of formula (I-14) are prepared, as described above in Reaction Scheme 13, by first treating a compound of formula (EEE) with a compound of formula (FFF) under standard conditions, such as in the presence of a drying agent in an aprotic solvent, to yield the compound of formula (GGG). Treatment of the compound of formula (GGG) with a compound of formula (HHH) under standard conditions, in an aprotic solvent, yields the compound of formula (JJJ), with is then deprotected under standard conditions to yield the compound of formula (I-14).

N. Preparation of Compounds of Formula (I-15)

Compound of formula (I-15) are compounds of formula (I), as described above in the Summary of the Invention, where $R^1$ and $R^2$ are each —$R^8$—OH, $R^3$ is —$CH_2NH_2$, $R^{4a}$ and $R^{4b}$ together form methylene and $R^7$ is —$R^8$—$OR^9$ where $R^8$ is a direct bond and $R^9$ is hydrogen, and are prepared as described below in Reaction Scheme 14 where $R^5$, $R^6$, and each $R^8$ are as described above in the Summary of the Invention for compounds of formula (I), $Pg^1$, $Pg^2$, $Pg^3$ and $Pg^4$ are each independently an oxygen-protecting group, such as, but not limited to, tert-butyldimethylsilyl, tert-butyldiphenylsilyl or acetyl, $Lg^1$ is a functional group which forms a leaving group with the oxygen to which it is attached, such as mesyl or tosyl, and X is bromo or chloro.

REACTION SCHEME 14

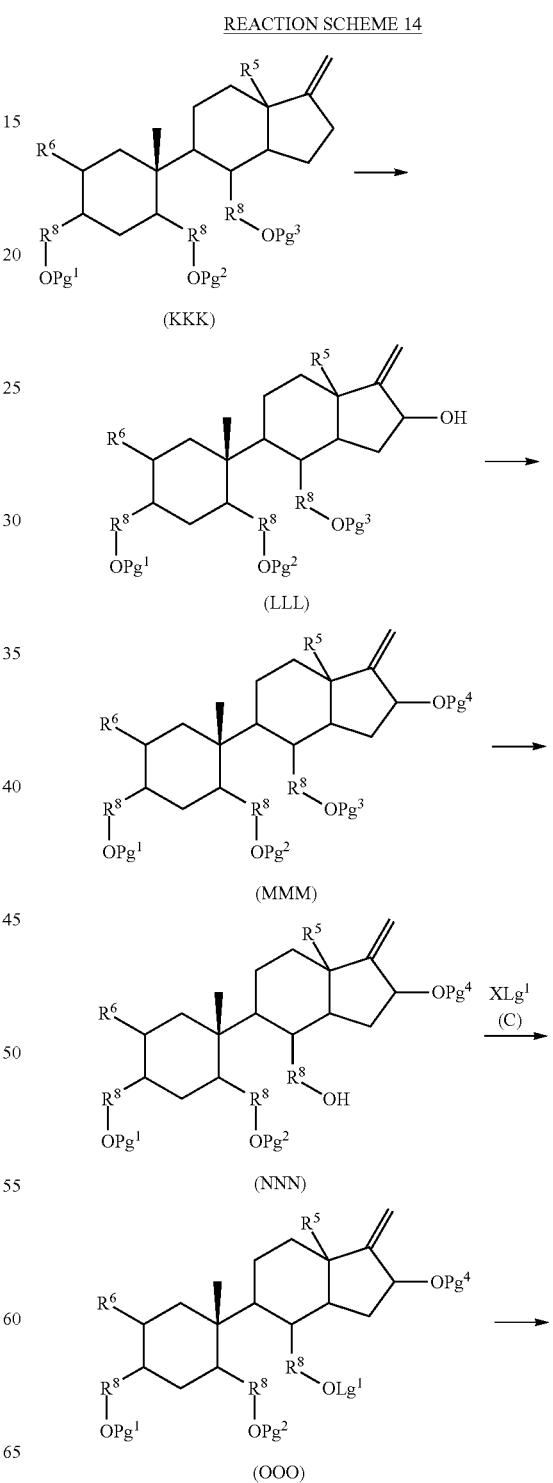

(KKK)

(LLL)

(MMM)

(NNN)

(OOO)

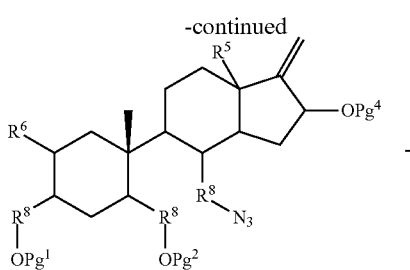

(PPP)

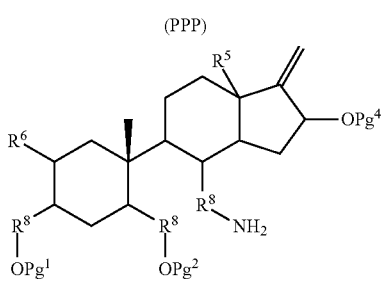

(QQQ)

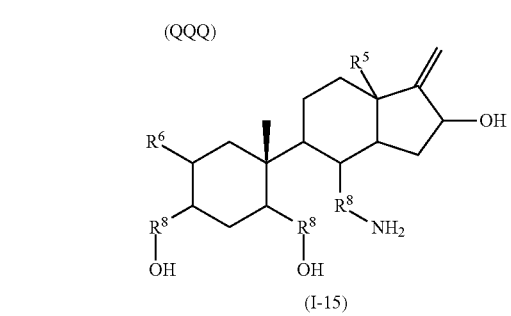

(I-15)

Compounds of formula (KKK) may be prepared by methods known to one skilled in the art from compounds disclosed herein or by methods similar to the methods disclosed in U.S. Pat. No. 7,601,874. Compounds of formula (C) are commercially available or can be prepared by methods known to one skilled in the art.

In general, compounds of formula (I-15) are prepared, as described above in Reaction Scheme 14, by first treating a compound of formula (KKK) with a appropriate oxidizing agent, under standard conditions, such as in an aprotic solvent, to yield the compound of formula (LLL). Protection of the hydroxyl on the compound of formula (LLL) under standard conditions, such as treatment with acetic anhydride in pyridine yields the compound of formula (MMM). Removal of the $Pg^3$ protecting group under standard conditions yields the compound of formula (NNN). Treatment of the compound of formula (NNN) with a compound of formula (C) under standard conditions, such as treatment with the appropriate oxygen-activating group under basic conditions in an aprotic solvent, yields the compound of formula (OOO). Azide displacement of the mesylate using sodium azide in DMF gives compound formula (PPP). Reduction of the azide under standard conditions, such as Staudinger reaction conditions, yields the compound of formula (QQQ). $Pg^1$ and $Pg^2$ are removed from the compound of formula (QQQ) by standard techniques, such as treating the compound of formula (QQQ) with the appropriate oxygen-deprotecting reagent in a protic solvent, to yield the compound of formula (I-15).

O. Preparation of Compounds of Formula (I-16)

Compound of formula (I-16) are compounds of formula (I), as described above in the Summary of the Invention, where $R^1$ is —$R^8$—$N(R^9)_2$ where $R^8$ is a direct bond and each $R^9$ is hydrogen, $R^2$ and $R^3$ are each —$CH_2$—OH, $R^{4a}$ and $R^{4b}$ together form methylene, and are prepared as described below in Reaction Scheme 15 where $R^5$, $R^6$ and $R^7$ are as described above in the Summary of the Invention for compounds of formula (I) and $Pg^5$ is a nitrogen-protecting group, such as trifluoromethylcarbonyl.

REACTION SCHEME 15

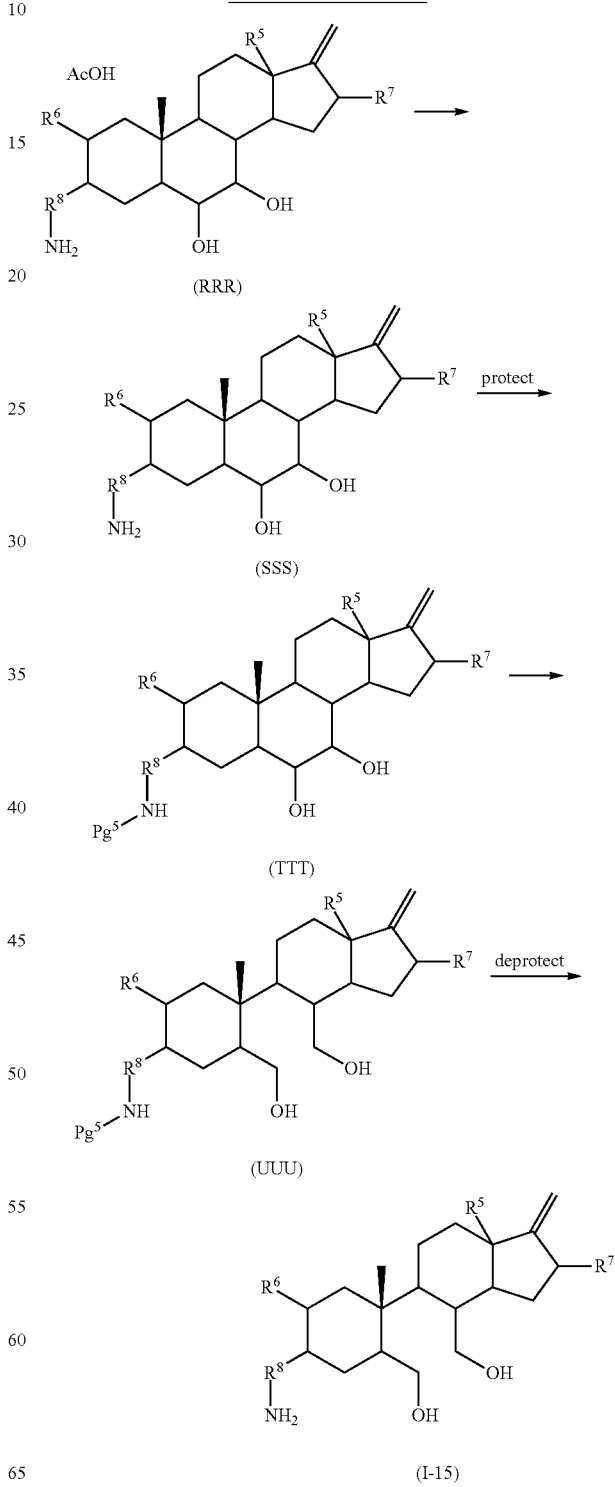

Compounds of formula (RRR) may be prepared by methods known to one skilled in the art or by methods similar to the methods disclosed in U.S. Pat. No. 6,635,629.

In general, compounds of formula (I-16) are prepared, as described above in Reaction Scheme 15, by first treating a compound of formula (RRR) with an appropriate base, such as sodium hydroxide in a protic solvent, to form the free base compound of formula (SSS). The free amino group in the compound of formula (SSS) is then protected by standard nitrogen protecting procedures, such as treatment with trifluoroacetic anhydride under basic conditions in a protic solvent, to yield a compound of formula (TTT). Treatment of the compound of formula (TTT) with sodium periodate in THF to oxidatively cleave the diol yields a dialdehyde intermediate, which is then reduced with sodium borohydride in THF to yield the compound of formula (UUU), which is then deprotected under standard conditions, such as treatment with a base in a protic solvent, to yield the compound of formula (I-16).

P. Preparation of Compounds of Formula (I-17)

Compound of formula (I-17) are compounds of formula (I), as described above in the Summary of the Invention, where $R^1$, $R^2$ and $R^3$ are each —$R^8$—OH, $R^{4a}$ and $R^{4b}$ together form methylene and $R^7$ is a direct bond to C15, and are prepared as described below in Reaction Scheme 16 where $R^5$, $R^6$ and each $R^8$ are as described above in the Summary of the Invention for compounds of formula (I), and $Pg^1$, $Pg^2$, and $Pg^3$ are each independently an oxygen-protecting group, such as, but not limited to, tert-butyldimethylsilyl, tert-butyldiphenylsilyl or acetyl.

REACTION SCHEME 16

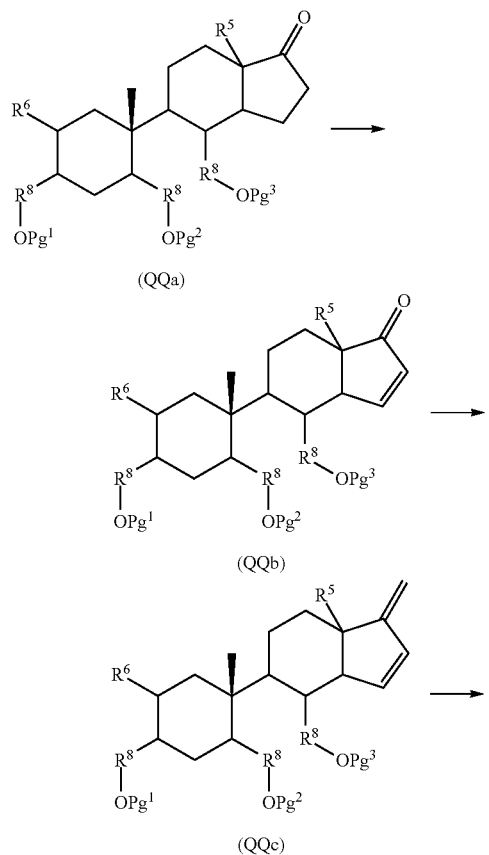

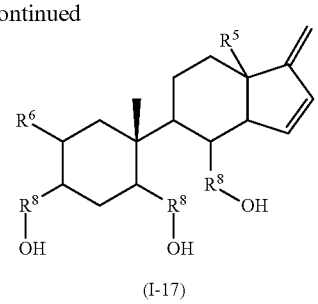

(I-17)

Compounds of formula (QQa) are compounds of formula (QQ) as described above in Reaction Scheme 8 where $R^7$ is hydrogen.

In general, compounds of formula (I-17) are prepared, as described above in Reaction Scheme 16, by first treating a compound of formula (QQa) with an appropriate silylating reagent under basic conditions in an aprotic solvent followed by oxidation under Saegusa-Ito oxidation conditions to yield a compound of formula (QQb). Olefination of the compound of formula (QQb) with the appropriate agent, such as methyl triphenylphosphonium bromide, in the presence of a base, such as KO$^t$Bu, provides the compound of formula (QQc), which is then deprotected under standard deprotecting conditions, such as treatment with the appropriate oxygen-deprotecting reagent in an aprotic solvent, to yield the compound of formula (I-17).

Q. Preparation of Compounds of Formula (I-18)

Compound of formula (I-18) are compounds of formula (I), as described above in the Summary of the Invention, where $R^1$ and $R^2$ are each —$R^8$—OH, $R^3$ is —CH$_2$N(H)OCH$_3$, and $R^{4a}$ and $R^{4b}$ together form methylene, and are prepared as described below in Reaction Scheme 17 where $R^5$, $R^6$ and each $R^8$ are as described above in the Summary of the Invention for compounds of formula (I), and $Pg^1$ and $Pg^2$, are each independently an oxygen-protecting group, such as, but not limited to, tert-butyldimethylsilyl, tert-butyldiphenylsilyl or acetyl.

REACTION SCHEME 17

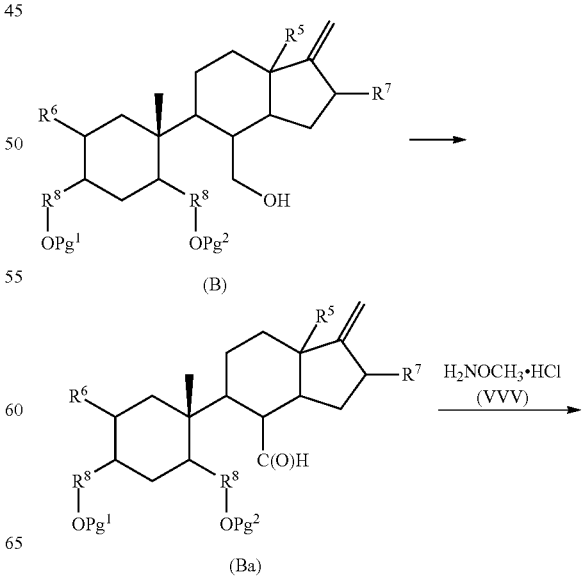

-continued

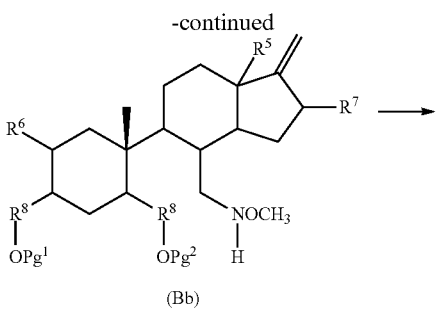

(Bb)

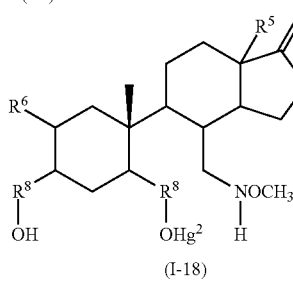

(I-18)

Compounds of formula (B) are described above in Reaction Scheme 1. Compounds of formula (VVV) are commercially available or can be prepared by methods known to one skilled in the art.

In general, compounds of formula (I-18) are prepared, as described above in Reaction Scheme 17, by first oxidizing a compound of formula (B) under standard conditions, such as Swern oxidation conditions, to yield a compound of formula (Ba). Compounds of formula (Ba) are then treated with a compound of formula (VVV) under standard reductive amination conditions, such as the appropriate reducing agent in a solvent mixture, to yield the compound of formula (Bb), which is then deprotected under standard conditions known to one skilled in the art to yield the compound of formula (I-18).

All of the compounds described herein as being prepared which may exist in free base or acid form may be converted to their pharmaceutically acceptable salts by treatment with the appropriate inorganic or organic base or acid. Salts of the compounds prepared below may be converted to their free base or acid form by standard techniques. Furthermore, all compounds of the invention which contain an acid or an ester group can be converted to the corresponding ester or acid, respectively, by methods known to one skilled in the art or by methods described herein.

Representative compounds of the invention which were prepared by the methods disclosed herein include (but are not limited to) the compounds listed below in Table 1. The compound (Cpd) numbers in this table correspond to the compound numbers in Examples 98-99 below (but do not correspond with the compound numbers in Examples 1-97 below).

TABLE 1

| Cpd. No. | Compound Name |
|---|---|
| Cpd. No. 1 | 1-(((4R,5S)-5-((1R,2S,4S)-4-hydroxy-2-(hydroxymethyl)-1-methylcyclohexyl)-1,1-dimethyl-2,3,4,5,6,7-hexahydro-1H-inden-4-yl)methyl)guanidine hydrochloride |
| Cpd. No. 2 | (1S,3S,4R)-4-((4R,5S)-4-((cyclopropylmethylamino)methyl)-1,1-dimethyl-2,3,4,5,6,7-hexahydro-1H-inden-5-yl)-3-(hydroxymethyl)-4-methylcyclohexanol |
| Cpd. No. 3 | (1S,3S,4R)-4-((4R,5S)-4-((dimethylamino)methyl)-1,1-dimethyl-2,3,4,5,6,7-hexahydro-1H-inden-5-yl)-3-(hydroxymethyl)-4-methylcyclohexanol |
| Cpd. No. 4 | N-(((4R,5S)-5-((1R,2S,4S)-4-hydroxy-2-(hydroxymethyl)-1-methylcyclohexyl)-1,1-dimethyl-2,3,4,5,6,7-hexahydro-1H-inden-4-yl)methyl)acetamide |
| Cpd. No. 5 | (1S,3S,4R)-4-((4R,5S)-1,1-dimethyl-4-((methylamino)methyl)-2,3,4,5,6,7-hexahydro-1H-inden-5-yl)-3-(hydroxymethyl)-4-methylcyclohexanol |
| Cpd. No. 6 | (1S,3S,4R)-4-((4R,5S)-4-(((1H-pyrrol-2-yl)methylamino)methyl)-1,1-dimethyl-2,3,4,5,6,7-hexahydro-1H-inden-5-yl)-3-(hydroxymethyl)-4-methylcyclohexanol |
| Cpd. No. 7 | N-(((4R,5S)-5-((1R,2S,4S)-4-hydroxy-2-(hydroxymethyl)-1-methylcyclohexyl)-1,1-dimethyl-2,3,4,5,6,7-hexahydro-1H-inden-4-yl)methyl)methanesulfonamide |
| Cpd. No. 8 | N-(((4R,5S)-5-((1R,2S,4S)-4-hydroxy-2-(hydroxymethyl)-1-methylcyclohexyl)-1,1-dimethyl-2,3,4,5,6,7-hexahydro-1H-inden-4-yl)methyl)benzamide |
| Cpd. No. 9 | (4-((((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methylamino)methyl)phenyl)(phenyl)methanone |
| Cpd. No. 10 | (1S,3S,4R)-4-((3aS,4R,5S,7aS)-4-((4-fluorobenzylamino)methyl)-7a-methyl-1-methyleneoctahydro-1H-inden-5-yl)-3-(hydroxymethyl)-4-methylcyclohexanol |
| Cpd. No. 11 | (3aR,4R,5R,7aS)-5-((1S,2S,4S)-4-hydroxy-1-methyl-2-(2-(pyrrolidin-1-yl)ethyl)cyclohexyl)-7a-methyl-1-methyleneoctahydro-1H-inden-4-ol |
| Cpd. No. 12 | (1S,3S,4R)-3-(hydroxymethyl)-4-methyl-4-((3aS,4R,5S,7aS)-7a-methyl-1-methylene-4-((pyridin-4-ylmethylamino)methyl)octahydro-1H-inden-5-yl)cyclohexanol |
| Cpd. No. 13 | (1S,3S,4R)-3-(hydroxymethyl)-4-methyl-4-((3aS,4R,5S,7aS)-7a-methyl-4-((4-methylbenzylamino)methyl)-1-methyleneoctahydro-1H-inden-5-yl)cyclohexanol |
| Cpd. No. 14 | (1S,3S,4R)-3-(hydroxymethyl)-4-methyl-4-((3aS,4R,5S,7aS)-7a-methyl-4-((3-methylbenzylamino)methyl)-1-methyleneoctahydro-1H-inden-5-yl)cyclohexanol |

TABLE 1-continued

| Cpd. No. | Compound Name |
| --- | --- |
| Cpd. No. 15 | (1S,3S,4R)-3-(hydroxymethyl)-4-methyl-4-((3aS,4R,5S,7aS)-7a-methyl-4-((2-methylbenzylamino)methyl)-1-methyleneoctahydro-1H-inden-5-yl)cyclohexanol |
| Cpd. No. 16 | N-(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)-2-naphthamide |
| Cpd. No. 17 | N-(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)benzamide |
| Cpd. No. 18 | (1S,3S,4R)-3-(hydroxymethyl)-4-((3aS,4R,5S,7aS)-4-((4-methoxybenzylamino)methyl)-7a-methyl-1-methyleneoctahydro-1H-inden-5-yl)-4-methylcyclohexanol |
| Cpd. No. 19 | (1S,3S,4R)-3-(hydroxymethyl)-4-methyl-4-((3aS,4R,5S,7aS)-7a-methyl-1-methylene-4-((4-(trifluoromethyl)benzylamino)methyl)octahydro-1H-inden-5-yl)cyclohexanol |
| Cpd. No. 20 | N-(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)pivalamide |
| Cpd. No. 21 | N-(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)isobutyramide |
| Cpd. No. 22 | N-(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)propionamide |
| Cpd. No. 23 | N-(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)butyramide |
| Cpd. No. 24 | N-(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)pentanamide |
| Cpd. No. 26 | (1S,3S,4R)-4-((3aS,4R,5S,7aS)-4-((1H-pyrazol-1-yl)methyl)-7a-methyl-1-methyleneoctahydro-1H-inden-5-yl)-3-(hydroxymethyl)-4-methylcyclohexanol |
| Cpd. No. 27 | (1S,3S,4R)-4-((3aS,4R,5S,7aS)-4-((1H-1,2,4-triazol-1-yl)methyl)-7a-methyl-1-methyleneoctahydro-1H-inden-5-yl)-3-(hydroxymethyl)-4-methylcyclohexanol |
| Cpd. No. 28 | (1S,3S,4R)-4-((3aS,4R,5S,7aS)-4-((1H-benzo[d]imidazol-1-yl)methyl)-7a-methyl-1-methyleneoctahydro-1H-inden-5-yl)-3-(hydroxymethyl)-4-methylcyclohexanol |
| Cpd. No. 29 | (1S,3S,4R)-4-((3aS,4R,5S,7aS)-4-(2-aminoethyl)-7a-methyl-1-methyleneoctahydro-1H-inden-5-yl)-3-(hydroxymethyl)-4-methylcyclohexanol |
| Cpd. No. 30 | (1S,3S,4R)-4-((3aS,4R,5S,7aS)-4-((1H-indol-1-yl)methyl)-7a-methyl-1-methyleneoctahydro-1H-inden-5-yl)-3-(hydroxymethyl)-4-methylcyclohexanol |
| Cpd. No. 31 | (1S,3S,4R)-3-(hydroxymethyl)-4-((3aS,4R,5S,7aS)-4-(indolin-1-ylmethyl)-7a-methyl-1-methyleneoctahydro-1H-inden-5-yl)-4-methylcyclohexanol |
| Cpd. No. 32 | (1S,3S,4R)-4-((3aS,4R,5S,7aS)-4-((3,5-dimethoxybenzylamino)methyl)-7a-methyl-1-methyleneoctahydro-1H-inden-5-yl)-3-(hydroxymethyl)-4-methylcyclohexanol |
| Cpd. No. 33 | (1S,3S,4R)-4-((3aS,4R,5S,7aS)-4-(((1H-benzo[d]imidazol-2-yl)methylamino)methyl)-7a-methyl-1-methyleneoctahydro-1H-inden-5-yl)-3-(hydroxymethyl)-4-methylcyclohexanol |
| Cpd. No. 34 | (1S,3S,4R)-4-((3aS,4R,5S,7aS)-4-((benzo[d][1,3]dioxol-5-ylmethylamino)methyl)-7a-methyl-1-methyleneoctahydro-1H-inden-5-yl)-3-(hydroxymethyl)-4-methylcyclohexanol |
| Cpd. No. 35 | (1S,3S,4R)-4-((3aS,4R,5S,7aS)-4-((6-amino-9H-purin-9-yl)methyl)-7a-methyl-1-methyleneoctahydro-1H-inden-5-yl)-3-(hydroxymethyl)-4-methylcyclohexanol |
| Cpd. No. 36 | (1S,3S,4R)-3-(hydroxymethyl)-4-methyl-4-((3aS,4R,5S,7aS)-7a-methyl-1-methylene-4-((4-nitrobenzylamino)methyl)octahydro-1H-inden-5-yl)cyclohexanol |
| Cpd. No. 37 | (1S,3S,4R)-4-((3aS,4R,5S,7aS)-4-(((2,2-difluorobenzo[d][1,3]dioxol-5-yl)methylamino)methyl)-7a-methyl-1-methyleneoctahydro-1H-inden-5-yl)-3-(hydroxymethyl)-4-methylcyclohexanol |
| Cpd. No. 38 | (1S,3S,4R)-4-((3aS,4R,5S,7aS)-4-((4-fluoro-2-methylbenzylamino)methyl)-7a-methyl-1-methyleneoctahydro-1H-inden-5-yl)-3-(hydroxymethyl)-4-methylcyclohexanol |
| Cpd. No. 39 | (1S,3S,4R)-4-((3aS,4R,5S,7aS)-4-((2-fluoro-4-methoxybenzylamino)methyl)-7a-methyl-1-methyleneoctahydro-1H-inden-5-yl)-3-(hydroxymethyl)-4-methylcyclohexanol |
| Cpd. No. 40 | (1S,3S,4R)-4-((3aS,4R,5S,7aS)-4-((4-fluoro-2-methoxybenzylamino)methyl)-7a-methyl-1-methyleneoctahydro-1H-inden-5-yl)-3-(hydroxymethyl)-4-methylcyclohexanol |

TABLE 1-continued

| Cpd. No. | Compound Name |
|---|---|
| Cpd. No. 41 | (1S,3S,4R)-4-((3aS,4R,5S,7aS)-4-((2-fluoro-4-methylbenzylamino)methyl)-7a-methyl-1-methyleneoctahydro-1H-inden-5-yl)-3-(hydroxymethyl)-4-methylcyclohexanol |
| Cpd. No. 42 | (1S,3S,4R)-3-(hydroxymethyl)-4-((3aS,4R,5S,7aS)-4-((4-methoxyphenethylamino)methyl)-7a-methyl-1-methyleneoctahydro-1H-inden-5-yl)-4-methylcyclohexanol |
| Cpd. No. 43 | (1S,3S,4R)-4-((3aS,4S,5S,7aS)-4-(2-(bis(4-methoxybenzyl)amino)ethyl)-7a-methyl-1-methyleneoctahydro-1H-inden-5-yl)-4-methylcyclohexane-1,3-diol |
| Cpd. No. 44 | (1S,3S,4R)-4-((3aS,4S,5S,7aS)-4-(2-(4-methoxybenzylamino)ethyl)-7a-methyl-1-methyleneoctahydro-1H-inden-5-yl)-4-methylcyclohexane-1,3-diol |
| Cpd. No. 45 | (1S,3S,4R)-4-((3aS,4S,5S,7aS)-4-(2-(benzo[d][1,3]dioxol-5-ylmethylamino)ethyl)-7a-methyl-1-methyleneoctahydro-1H-inden-5-yl)-4-methylcyclohexane-1,3-diol |
| Cpd. No. 46 | (3aR,4R,5R,7aS)-5-((1S,2S,4S)-4-hydroxy-1-methyl-2-(2-morpholinoethyl)cyclohexyl)-7a-methyl-1-methyleneoctahydro-1H-inden-4-ol |
| Cpd. No. 47 | (1S,3S,4R)-3-(aminomethyl)-4-((3aS,4R,5S,7aS)-4-(aminomethyl)-7a-methyl-1-methyleneoctahydro-1H-inden-5-yl)-4-methylcyclohexanol |
| Cpd. No. 48 | (3aR,4R,5R,7aS)-5-((1S,2S,4S)-4-hydroxy-1-methyl-2-(2-(4-methylpiperazin-1-yl)ethyl)cyclohexyl)-7a-methyl-1-methyleneoctahydro-1H-inden-4-ol |
| Cpd. No. 49 | (3aR,4R,5R,7aS)-5-((1S,2S,4S)-2-(2-(1H-1,2,4-triazol-1-yl)ethyl)-4-hydroxy-1-methylcyclohexyl)-7a-methyl-1-methyleneoctahydro-1H-inden-4-ol |
| Cpd. No. 50 | (3aR,4R,5R,7aS)-5-((1S,2S,4S)-2-(2-(1H-imidazol-1-yl)ethyl)-4-hydroxy-1-methylcyclohexyl)-7a-methyl-1-methyleneoctahydro-1H-inden-4-ol |
| Cpd. No. 51 | (3aR,4R,5R,7aS)-5-((1S,2S,4S)-2-(2-(1H-pyrazol-1-yl)ethyl)-4-hydroxy-1-methylcyclohexyl)-7a-methyl-1-methyleneoctahydro-1H-inden-4-ol |
| Cpd. No. 52 | (3aR,4R,5R,7aS)-5-((1S,2S,4S)-2-(2-(1H-pyrrol-1-yl)ethyl)-4-hydroxy-1-methylcyclohexyl)-7a-methyl-1-methyleneoctahydro-1H-inden-4-ol |
| Cpd. No. 53 | (1S,3S,4R)-4-((3aS,4S,5S,7aS)-4-(2-hydroxyethyl)-7a-methyl-1-methyleneoctahydro-1H-inden-5-yl)-4-methyl-3-(pyridin-2-yloxy)cyclohexanol |
| Cpd. No. 54 | (1S,3S,4R)-4-((3aS,4R,5S,7aS)-4-(hydroxymethyl)-7a-methyl-1-methyleneoctahydro-1H-inden-5-yl)-4-methyl-3-((pyridin-2-yloxy)methyl)cyclohexanol |
| Cpd. No. 55 | (3aR,4R,5R,7aS)-5-((1S,2S,4S)-4-hydroxy-1-methyl-2-(2-(pyrimidin-2-yloxy)ethyl)cyclohexyl)-7a-methyl-1-methyleneoctahydro-1H-inden-4-ol |
| Cpd. No. 56 | (3aR,4R,5R,7aS)-5-((1S,2S,4S)-4-hydroxy-1-methyl-2-(2-(pyrazin-2-yloxy)ethyl)cyclohexyl)-7a-methyl-1-methyleneoctahydro-1H-inden-4-ol |
| Cpd. No. 57 | (3aR,4R,5R,7aS)-5-((1S,2S,4S)-4-hydroxy-1-methyl-2-(2-(pyridin-2-yloxy)ethyl)cyclohexyl)-7a-methyl-1-methyleneoctahydro-1H-inden-4-ol |
| Cpd. No. 58 | (1S,3S,4R)-4-((3aS,6S,7R,7aS)-7-(aminomethyl)-3,3a-dimethyl-3a,4,5,6,7,7a-hexahydro-1H-inden-6-yl)-3-(hydroxymethyl)-4-methylcyclohexanol |
| Cpd. No. 59 | N-(((3aR,6S,7R,7aS)-6-((1R,2S,4S)-4-hydroxy-2-(hydroxymethyl)-1-methylcyclohexyl)-3a-methyl-3a,4,5,6,7,7a-hexahydro-1H-inden-7-yl)methyl)pentanamide |
| Cpd. No. 60 | (1S,3S,4R)-4-((1S,3aS,4S,5S,7aR)-4-(aminomethyl)-1-ethyl-7a-methyloctahydro-1H-inden-5-yl)-3-(hydroxymethyl)-4-methylcyclohexanol acetate |
| Cpd. No. 61 | (1S,3S,4R)-3-(hydroxymethyl)-4-methyl-4-((3aS,4R,5S,7aS)-7a-methyl-1-methylene-4-((pyridin-2-ylmethoxy)methyl)octahydro-1H-inden-5-yl)cyclohexanol |
| Cpd. No. 62 | (2S,3aS,4R,5S,7aS)-4-(aminomethyl)-5-((1R,2S,4S)-4-hydroxy-2-(hydroxymethyl)-1-methylcyclohexyl)-7a-methyl-1-methyleneoctahydro-1H-inden-2-ol |
| Cpd. No. 63 | ((1S,2R,5S)-5-amino-2-((3aS,4R,5S,7aS)-4-(hydroxymethyl)-7a-methyl-1-methyleneoctahydro-1H-inden-5-yl)-2-methylcyclohexyl)methanol |
| Cpd. No. 64 | (1S,3S,4R)-3-(hydroxymethyl)-4-((3aS,4R,5S,7aS)-4-(hydroxymethyl)-7a-methyl-1-methylene-3a,4,5,6,7,7a-hexahydro-1H-inden-5-yl)-4-methylcyclohexanol |
| Cpd. No. 65 | (1S,3S,4R)-3-(hydroxymethyl)-4-((4R,5S)-4-(hydroxymethyl)-1,1-dimethyl-4,5,6,7-tetrahydro-1H-inden-5-yl)-4-methylcyclohexanol |
| Cpd. No. 66 | (2R,4R,5S)-5-((1R,2S,4S)-4-hydroxy-2-(hydroxymethyl)-1-methylcyclohexyl)-4-(hydroxymethyl)-1,1-dimethyl-2,3,4,5,6,7-hexahydro-1H-inden-2-ol |

TABLE 1-continued

| Cpd. No. | Compound Name |
|---|---|
| Cpd. No. 67 | (1S,3S,4R)-4-((3aS,4R,5S,7aS)-4-(benzyloxymethyl)-7a-methyl-1-methyleneoctahydro-1H-inden-5-yl)-3-(hydroxymethyl)-4-methylcyclohexanol |
| Cpd. No. 68 | (1S,3S,4R)-4-((3aS,4R,5S,7aS)-4-((3,5-dimethoxybenzyloxy)methyl)-7a-methyl-1-methyleneoctahydro-1H-inden-5-yl)-3-(hydroxymethyl)-4-methylcyclohexanol |
| Cpd. No. 69 | N-(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)nicotinamide |
| Cpd. No. 70 | N-(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)isonicotinamide |
| Cpd. No. 71 | N-(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)pyrazine-2-carboxamide |
| Cpd. No. 72 | N-(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)picolinamide |
| Cpd. No. 73 | N-(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)benzo[d][1,3]dioxole-5-carboxamide |
| Cpd. No. 74 | N-(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)-4-methoxybenzamide |
| Cpd. No. 75 | 4-fluoro-N-(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)benzamide |
| Cpd. No. 76 | N-(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)-4-(trifluoromethyl)benzamide |
| Cpd. No. 77 | N-(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)-4-methylbenzamide |
| Cpd. No. 78 | N-(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)-2-methylbenzamide |
| Cpd. No. 79 | N-(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)-1H-pyrrole-2-carboxamide |
| Cpd. No. 80 | N-(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)-3-methylbenzamide |
| Cpd. No. 81 | N-(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)furan-2-carboxamide |
| Cpd. No. 82 | N-(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)cyclopropanecarboxamide |
| Cpd. No. 83 | N-(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)cyclohexanecarboxamide |
| Cpd. No. 84 | 1-ethyl-3-(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)urea |
| Cpd. No. 85 | 1-(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)-3-methylthiourea |
| Cpd. No. 86 | 2,2,2-trifluoro-N-(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)acetamide |
| Cpd. No. 87 | 2-((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)acetonitrile |
| Cpd. No. 88 | (1S,3S,4R)-3-(hydroxymethyl)-4-((3aS,4R,5S,7aS)-4-((methoxyamino)methyl)-7a-methyl-1-methyleneoctahydro-1H-inden-5-yl)-4-methylcyclohexanol |
| Cpd. No. 89 | N-(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)cyanamide |
| Cpd. No. 90 | 2-((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)acetamide |
| Cpd. No. 91 | 1-benzyl-3-(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)urea |
| Cpd. No. 92 | 1-(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)-3-phenylurea |

TABLE 1-continued

| Cpd. No. | Compound Name |
| --- | --- |
| Cpd. No. 93 | N-(2-((3aS,4S,5S,7aS)-5-((1R,2S,4S)-2,4-dihydroxy-1-methylcyclohexyl)-7a-methyl-1-methyleneoctahydro-1H-inden-4-yl)ethyl)benzo[d][1,3]dioxole-5-carboxamide |
| Cpd. No. 94 | 3-((1S,2S,5S)-5-hydroxy-2-((3aR,4R,5R,7aS)-4-hydroxy-7a-methyl-1-methyleneoctahydro-1H-inden-5-yl)-2-methylcyclohexyl)propanenitrile |
| Cpd. No. 95 | 3-((1S,2S,5S)-5-hydroxy-2-((3aR,4R,5R,7aS)-4-hydroxy-7a-methyl-1-methyleneoctahydro-1H-inden-5-yl)-2-methylcyclohexyl)propanamide |
| Cpd. No. 96 | N-(((1S,2S,5S)-5-hydroxy-2-((3aR,4R,5R,7aS)-4-hydroxy-7a-methyl-1-methyleneoctahydro-1H-inden-5-yl)-2-methylcyclohexyl)methyl)benzo[d][1,3]dioxole-5-carboxamide |
| Cpd. No. 97 | 3-((1R,2S,5S)-5-hydroxy-2-((3aR,4R,5R,7aS)-4-hydroxy-7a-methyl-1-methyleneoctahydro-1H-inden-5-yl)-2-methylcyclohexyl)propanoic acid |
| Cpd. No. 98 | (3aS,4R,5S,7aS)-5-((1R,2R,4S)-4-hydroxy-2-(hydroxymethyl)-1-methylcyclohexyl)-7a-methyl-1-methyleneoctahydro-1H-indene-4-carboxylic acid |

The following Examples are provided for purposes of illustration, not limitation. In summary, the following Examples disclose the synthesis of representative compounds of this invention and compounds used in the preparation of compounds of the invention, as well as representative assays for the same.

Example 1

Synthesis of 1-(((4R,5S)-5-((1R,2S,4S)-4-hydroxy-2-(hydroxymethyl)-1-methylcyclohexyl)-1,1-dimethyl-2,3,4,5,6,7-hexahydro-1H-inden-4-yl)methyl)guanidine hydrochloride (Compound No. 3)

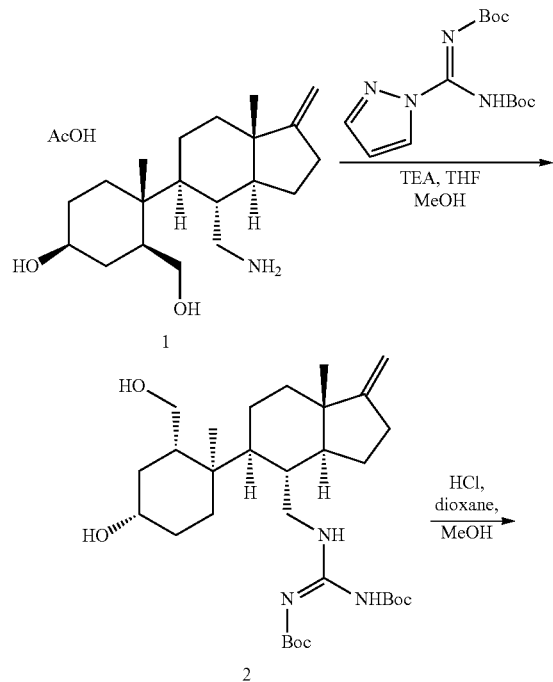

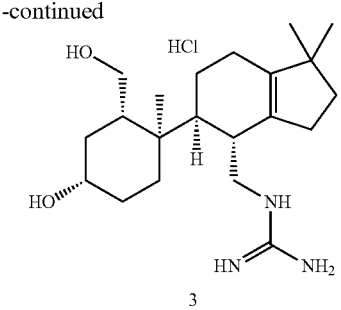

A. A solution of (1S,3S,4R)-4-((3aS,4R,5S,7aS)-4-(aminomethyl)-7a-methyl-1-methyleneoctahydro-1H-inden-5-yl)-3-(hydroxymethyl)-4-methylcyclohexanol acetate (Compound No. 1, 105 mg, 0.28 mmol), N,N'-bis(tert-butoxycarbonyl)-1H-pyrazole-1-carboxamidine (94 mg, 0.30 mmol) and triethylamine (80 μL, 0.57 mmol) in MeOH (1 mL) and THF (5 mL) was stirred at room temperature overnight. The mixture was diluted with $CH_2Cl_2$ (35 mL), washed with saturated $NaHCO_3$ solution (2×10 mL), dried ($Na_2SO_4$) and concentrated. The residue was purified using chromatography on silica gel (4% then 6% MeOH/$CH_2Cl_2$) to afford (Z)-tert-butyl (tert-butoxycarbonylamino)(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methylamino)methylenecarbamate (Compound No. 2, 142 mg, 90%) as a white solid.

B. A solution of (Z)-tert-butyl (tert-butoxycarbonylamino)(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methylamino) methylenecarbamate (Compound No. 2, 142 mg) in 4N HCl/dioxane (2 mL) and MeOH (1 mL) was stirred at room temperature for 3 d. The mixture was concentrated, thrice taken up in MeOH (10 mL) and concentrated and thrice triturated with $Et_2O$ (20 mL) to afford 1-(((4R,5S)-5-((1R,2S,4S)-4-hydroxy-2-(hydroxymethyl)-1-methylcyclohexyl)-1,1-dimethyl-2,3,4,5,6,7-hexahydro-1H-inden-4-yl)methyl)guanidine hydrochloride (Compound No. 3, 103 mg) as a beige solid. $^1$H NMR ($CDCl_3$): δ 7.20 (m, 1H), 3.65 (m, 1H), 3.45 (m, 1H), 3.20 (m, 1H), 3.05 (m, 1H), 2.40 (m, 1H), 2.25-1.55 (12H), 1.2 (4H), 1.00 (s, 3H), 0.92 (s, 3H), 0.85 (s, 3H). ES-MS m/z 364 ([M+1]$^+$)

Example 2

Synthesis of (1S,3S,4R)-4-((4R,5S)-4-((cyclopropylmethylamino)methyl)-1,1-dimethyl-2,3,4,5,6,7-hexahydro-1H-inden-5-yl)-3-(hydroxymethyl)-4-methylcyclohexanol (Compound No. 4a)

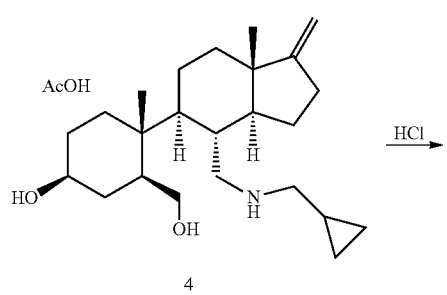

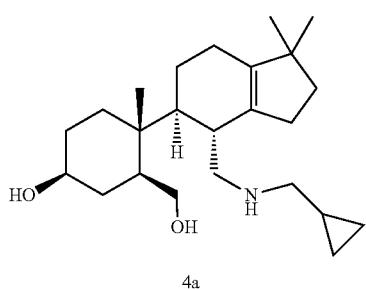

A solution of (1S,3S,4R)-4-((3aS,4R,5S,7aS)-4-(((cyclopropylmethyl)amino)methyl)-7a-methyl-1-methyleneoctahydro-1H-inden-5-yl)-3-(hydroxymethyl)-4-methylcyclohexanol acetate (Compound No. 4, 95 mg, 0.22 mmol) in 1 N HCl (aq) (5.5 mL) was stirred at 60° C. overnight. The solution was cooled to 0° C., adjusted to pH 12 using 10 N NaOH (aq), and extracted with EtOAc (30 mL then 2×10 mL). The combined organic layers were dried (MgSO$_4$) and concentrated to give (1S,3S,4R)-4-((4R,5S)-4-((cyclopropylmethylamino)methyl)-1,1-dimethyl-2,3,4,5,6,7-hexahydro-1H-inden-5-yl)-3-(hydroxymethyl)-4-methylcyclohexanol (Compound No. 4a, 55 mg, 67%) as a yellow foam. $^1$H NMR (CD$_3$OD): δ3.83 (m, 1H), 3.44 (m, 1H), 3.22 (m, 1H), 2.77 (m, 1H), 2.57 (m, 3H), 2.39 (m, 1H), 1.20-2.22 (m, 17H), 0.99 (s, 3H), 0.93 (s, 3H), 0.91 (s, 3H), 0.54 (m, 2H), 0.19 (m, 2H); $^{13}$C NMR (CD$_3$OD): δ144.5, 135.3, 71.4, 63.4, 55.6, 53.8, 46.7, 43.6, 42.5, 40.2, 38.8, 37.3, 35.7, 34.2, 33.1, 32.2, 27.3, 25.7, 20.9, 20.8, 20.1, 11.2, 4.1, 4.0. ES-MS m/z 376 ([M+1]$^+$).

Example 3

Synthesis of (1S,3S,4R)-4-((4R,5S)-4-((dimethylamino)methyl)-1,1-dimethyl-2,3,4,5,6,7-hexahydro-1H-inden-5-yl)-3-(hydroxymethyl)-4-methylcyclohexanol (Compound No. 6)

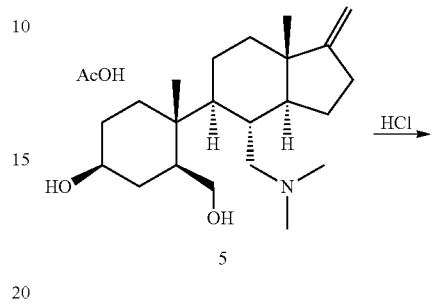

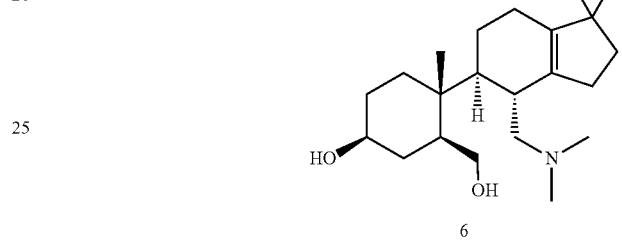

A solution of (1S,3S,4R)-4-((3aS,4R,5S,7aS)-4-((dimethylamino)methyl)-7a-methyl-1-methyleneoctahydro-1H-inden-5-yl)-3-(hydroxymethyl)-4-methylcyclohexanol acetate (Compound No. 5, 172 mg, 0.420 mmol) in 1 N HCl (aq) (7.5 mL) was stirred at 60° C. overnight. The solution was cooled to 0° C., adjusted to pH 12 using 10 N NaOH (aq), and extracted with EtOAc (20 mL then 2×10 mL). The combined organic layers were dried (MgSO$_4$) and concentrated to give (1S,3S,4R)-4-((4R,5S)-4-((dimethylamino)methyl)-1,1-dimethyl-2,3,4,5,6,7-hexahydro-1H-inden-5-yl)-3-(hydroxymethyl)-4-methylcyclohexanol (Compound No. 6, 114 mg, 78%) as a colourless foam. $^1$H NMR (CD$_3$OD): δ3.82 (m, 1H), 3.43 (m, 1H), 3.19 (m, 1H), 2.38 (m, 2H), 1.16-2.25 (m, 23H), 0.98 (s, 3H), 0.92 (s, 3H), 0.90 (s, 3H); $^{13}$C NMR (CD$_3$OD): δ143.5, 136.1, 71.4, 64.9, 63.4, 46.7, 46.3 (2C), 43.6, 41.7, 40.2, 38.7, 35.7, 35.6, 34.6, 33.1, 32.2, 27.4, 25.6, 20.8, 20.4, 20.1. ES-MS m/z 350 ([M+1]$^+$).

Example 4

Synthesis of N-(((4R,5S)-5-((1R,2S,4S)-4-hydroxy-2-(hydroxymethyl)-1-methylcyclohexyl)-1,1-dimethyl-2,3,4,5,6,7-hexahydro-1H-inden-4-yl)methyl)acetamide (Compound No. 9)

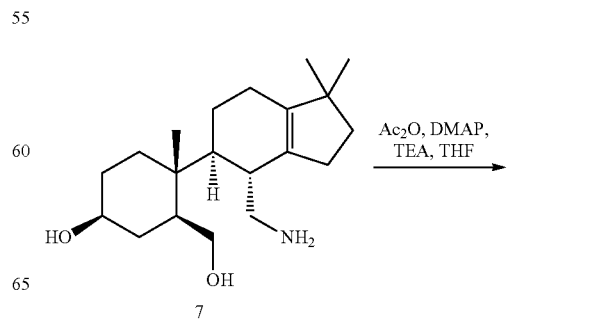

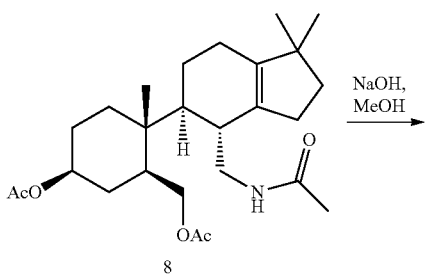

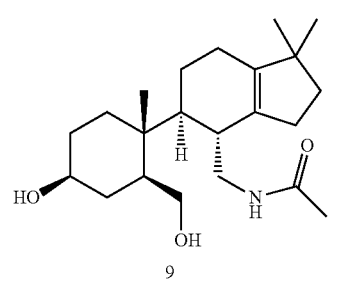

A. To a solution of (1S,3S,4R)-4-((4R,5S)-4-(aminomethyl)-1,1-dimethyl-2,3,4,5,6,7-hexahydro-1H-inden-5-yl)-3-(hydroxymethyl)-4-methylcyclohexanol (Compound No. 7, 153 mg, 0.476 mmol), Et₃N (0.20 mL, 1.4 mmol) and DMAP (5 mg, 0.04 mmol) in THF (4.8 mL) at 0° C. under argon was added Ac₂O (0.14 mL, 1.5 mmol), and the solution was stirred for 5 min at 0° C. then at room temperature for 1 h. The solution was concentrated, and the residue was dissolved in EtOAc (50 mL). The solution was washed with saturated aqueous NaHCO₃ (4×20 mL) and brine (2×20 mL) then dried (MgSO₄) and concentrated to give (1S,3S,4R)-4-((4R,5S)-4-(acetamidomethyl)-1,1-dimethyl-2,3,4,5,6,7-hexahydro-1H-inden-5-yl)-3-(acetoxymethyl)-4-methylcyclohexyl acetate (Compound No. 8, 186 mg) as a colourless foam.

B. To a solution of (1S,3S,4R)-4-((4R,5S)-4-(acetamidomethyl)-1,1-dimethyl-2,3,4,5,6,7-hexahydro-1H-inden-5-yl)-3-(acetoxymethyl)-4-methylcyclohexyl acetate (Compound No. 8, 186 mg) in MeOH (4.2 mL) was added 10 N NaOH (aq) (0.42 mL, 4.2 mmol) then stirred vigorously at room temperature for 1 h. The solution was concentrated, and the residue was partitioned between EtOAc (40 mL) and H₂O (20 mL). The aqueous layer was extracted with EtOAc (2×20 mL), and the combined organic layers were dried (MgSO₄) and concentrated. The residue was purified by chromatography on silica gel (100:10:2 CH₂Cl₂/MeOH/NH₄OH) to give N-(((4R,5S)-5-((1R,2S,4S)-4-hydroxy-2-(hydroxymethyl)-1-methylcyclohexyl)-1,1-dimethyl-2,3,4,5,6,7-hexahydro-1H-inden-4-yl)methyl)acetamide (Compound No. 9, 103 mg, 60% over 2 steps) as a colourless foam. ¹H NMR (CD₃OD): δ3.79 (dd, J=11, 2.3 Hz, 1H), 3.42 (m, 1H), 3.18 (m, 1H), 2.94 (dd, J=13, 10 Hz, 1H), 2.44 (m, 1H), 1.12-2.21 (m, 20H), 0.99 (s, 3H), 0.92 (s, 3H), 0.81 (s, 3H); ¹³C NMR (CD₃OD): δ173.0, 144.5, 135.1, 71.3, 63.3, 46.6, 43.6, 43.5, 41.5, 40.2, 38.5, 38.1, 35.6, 33.9, 32.9, 32.2, 27.2, 25.8, 22.7, 20.8, 20.5, 19.7. ES-MS m/z 364 ([M+1]⁺).

Example 5

Synthesis of (1S,3S,4R)-4-((4R,5S)-1,1-dimethyl-4-((methylamino)methyl)-2,3,4,5,6,7-hexahydro-1H-inden-5-yl)-3-(hydroxymethyl)-4-methylcyclohexanol (Compound No. 11)

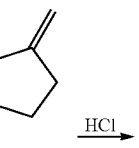

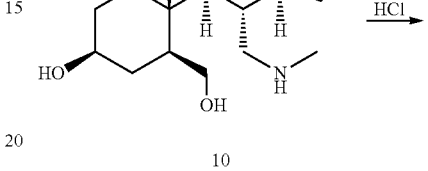

A solution of (1S,3S,4R)-4-((3aS,4R,5S,7aS)-4-(aminomethyl)-7a-methyl-1-methyleneoctahydro-1H-inden-5-yl)-3-(hydroxymethyl)-4-methylcyclohexanol acetate (Compound No. 10, 112 mg, 0.283 mmol) in 1 N HCl (aq) (7.0 mL) was stirred at 60° C. overnight. The solution was cooled to 0° C., adjusted to pH 12 using 10 N NaOH (aq), and extracted with EtOAc (3×20 mL). The combined organic layers were dried (MgSO₄) and concentrated to give (1S,3S,4R)-4-((4R,5S)-1,1-dimethyl-4-((methylamino)methyl)-2,3,4,5,6,7-hexahydro-1H-inden-5-yl)-3-(hydroxymethyl)-4-methylcyclohexanol (Compound No. 11, 75 mg, 79%) as a yellow foam. ¹H NMR (CD₃OD): δ3.82 (m, 1H), 3.43 (m, 1H), 3.21 (m, 1H), 2.67 (dd, J=12, 3.1 Hz, 1H), 2.51 (m, 1H), 2.42 (s, 3H), 1.15-2.21 (m, 17H), 0.99 (s, 3H), 0.92 (s, 3H), 0.90 (s, 3H); ¹³C NMR (CD₃OD): δ144.3, 135.3, 71.4, 63.4, 56.2, 46.7, 43.6, 42.2, 40.2, 38.7, 37.3, 36.3, 35.7, 34.3, 33.0, 32.2, 27.3, 25.6, 20.8, 20.7, 20.0. ES-MS m/z 336 ([M+1]⁺).

Example 6

Synthesis of (1S,3S,4R)-4-((4R,5S)-4-(((1H-pyrrol-2-yl)methylamino)methyl)-1,1-dimethyl-2,3,4,5,6,7-hexahydro-1H-inden-5-yl)-3-(hydroxymethyl)-4-methylcyclohexanol (Compound No. 13)

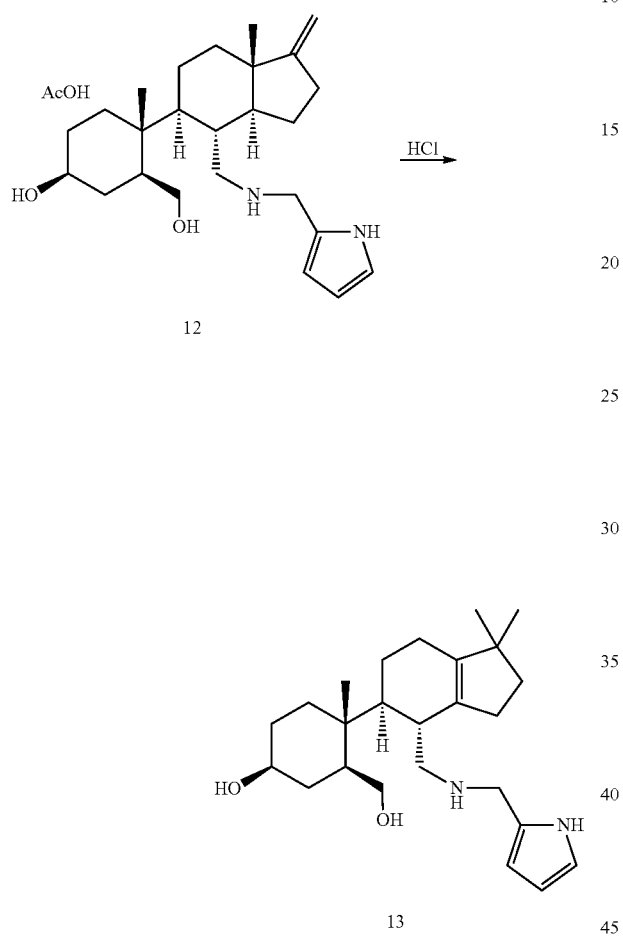

A suspension of (1S,3S,4R)-4-((3aS,4R,5S,7aS)-4-((((1H-pyrrol-2-yl)methyl)amino)methyl)-7a-methyl-1-methyleneoctahydro-1H-inden-5-yl)-3-(hydroxymethyl)-4-methylcyclohexanol acetate (Compound No. 12, 49 mg, 0.11 mmol) in 1 N HCl (aq) (5.0 mL) was stirred at 60° C. overnight. The solution was cooled to 0° C., adjusted to pH 12 using 10 N NaOH (aq), and extracted with EtOAc (3×20 mL). The combined organic layers were dried (MgSO$_4$) and concentrated to give (1S,3S,4R)-4-((4R,5S)-4-(((1H-pyrrol-2-yl)methylamino)methyl)-1,1-dimethyl-2,3,4,5,6,7-hexahydro-1H-inden-5-yl)-3-(hydroxymethyl)-4-methylcyclohexanol (Compound No. 13, 41 mg, 95%) as a brown foam. $^1$H NMR (CD$_3$OD): δ6.69 (m, 1H), 6.03 (m, 2H), 3.78 (m, 3H), 3.43 (m, 1H), 3.20 (m, 1H), 2.70 (dd, J=12, 3.2 Hz, 1H), 2.51 (dd, J=12, 9.2 Hz, 1H), 1.13-2.32 (m, 17H), 0.98 (s, 3H), 0.91 (s, 3H), 0.89 (s, 3H); $^{13}$C NMR (CD$_3$OD): δ 144.6, 135.1, 129.0, 118.8, 108.7, 108.6, 71.4, 63.4, 52.5, 46.7, 46.6, 43.6, 42.3, 40.2, 38.8, 37.2, 35.7, 34.2, 32.9, 32.2, 27.3, 25.6, 20.8, 20.7, 20.0. ES-MS m/z 401 ([M+1]$^+$).

Example 7

Synthesis of N-(((4R,5S)-5-((1R,2S,4S)-4-hydroxy-2-(hydroxymethyl)-1-methylcyclohexyl)-1,1-dimethyl-2,3,4,5,6,7-hexahydro-1H-inden-4-yl)methyl) methanesulfonamide (Compound No. 16)

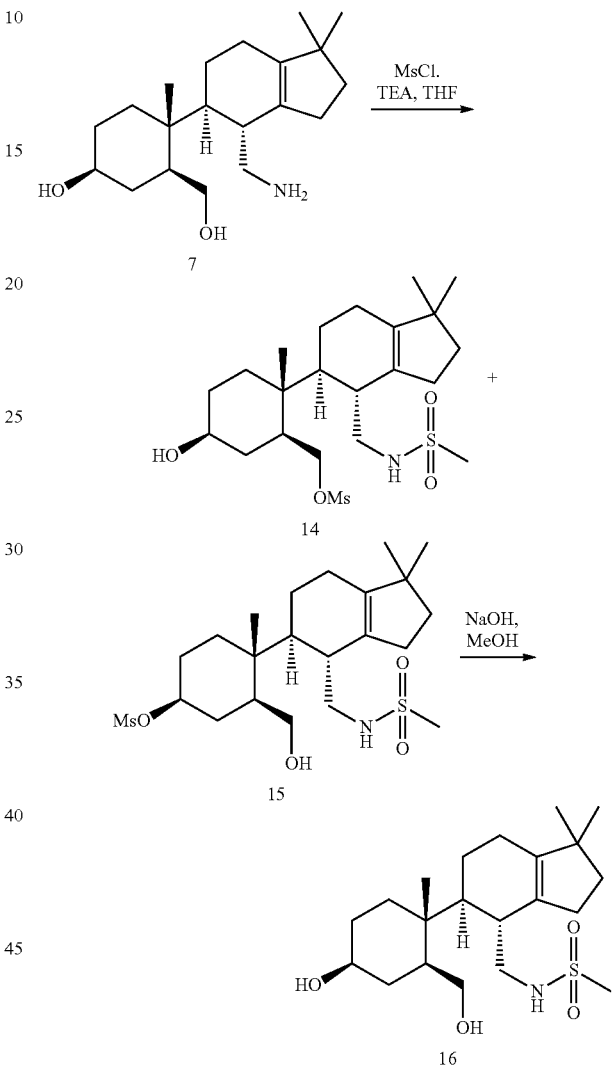

A. To a solution of (1S,3S,4R)-4-((4R,5S)-4-(aminomethyl)-1,1-dimethyl-2,3,4,5,6,7-hexahydro-1H-inden-5-yl)-3-(hydroxymethyl)-4-methylcyclohexanol (Compound No. 7, 101 mg, 0.314 mmol) and Et$_3$N (0.15 mL, 1.1 mmol) in THF (3.2 mL) at 0° C. under argon was added MsCl (0.07 mL, 0.9 mmol), and the solution was stirred at room temperature for 18 h. The mixture was concentrated, and the residue was partitioned between EtOAc (30 mL) and H$_2$O (10 mL). The organic layer was washed with saturated aqueous NaHCO$_3$ (5×15 mL) and brine (2×15 mL) then dried (MgSO$_4$) and concentrated. The residue was purified by chromatography on silica gel (10:90-50:50 EtOAc/CH$_2$Cl$_2$) to give ((1S,2R,5S)-2-((4R,5S)-1,1-dimethyl-4-(methylsulfonamidomethyl)-2,3,4,5,6,7-hexahydro-1H-inden-5-yl)-2-methyl-5-((methylsulfonyl)oxy)cyclohexyl) methyl methanesulfonate (Compound No. 14, 24 mg, 14%)

as a colourless oil and a by-product, possibly (1S,3S,4R)-4-(((4R,5S)-1,1-dimethyl-4-(methylsulfonamidomethyl)-2,3,4,5,6,7-hexahydro-1H-inden-5-yl)-3-(hydroxymethyl)-4-methylcyclohexyl methanesulfonate, (Compound No. 15, 37 mg, 25%) as a brown oil. Compound No. 14 (24 mg) and Compound No. 15 (37 mg) were combined to use in the next step.

B. To a solution of the above mixture (61 mg, 0.12 mmol) in MeOH (2.2 mL) was added 10 N NaOH (aq) (0.11 mL, 1.1 mmol) then heated to 60° C. for 22 h. The solution was concentrated, and the residue was partitioned between EtOAc (30 mL) and H$_2$O (10 mL). The aqueous layer was extracted with EtOAc (3×15 mL), and the combined the organic layers were dried (MgSO$_4$) and concentrated. The residue was purified by chromatography on silica gel (20:80 EtOAc/CH$_2$Cl$_2$) to give N-(((4R,5S)-5-((1R,2S,4S)-4-hydroxy-2-(hydroxymethyl)-1-methylcyclohexyl)-1,1-dimethyl-2,3,4,5,6,7-hexahydro-1H-inden-4-yl)methyl)methanesulfonamide (Compound No. 16, 21 mg, 44%) as a colourless foam. $^1$H NMR (CD$_3$OD): δ4.24 (m, 1H), 4.05 (d, J=8.1 Hz, 1H), 3.70 (dd, J=4.7, 8.3 Hz, 1H), 3.19 (dd, J=3.5, 13 Hz, 1H), 2.93 (s, 3H), 2.87 (dd, J=9.9, 13 Hz, 1H), 1.29-2.49 (m, 17H), 1.00 (s, 3H), 0.93 (s, 3H), 0.74 (s, 3H); $^{13}$C NMR (CD$_3$OD): δ145.3, 134.3, 76.3, 70.6, 47.1, 46.8, 45.8, 40.2, 39.7, 39.6, 38.4, 35.2, 34.1, 33.0, 30.3, 30.0, 27.3, 25.7, 23.7, 20.4 (2C). ES-MS m/z 400 ([M+1]$^+$).

stirred under argon for 20 h. The mixture was concentrated, and the residue was dissolved in EtOAc (40 mL). The solution was washed with saturated aqueous NaHCO$_3$ (5×10 mL) and brine (2×10 mL) then dried (MgSO$_4$) and concentrated. The residue was purified by chromatography on silica gel (100:10:2 CH$_2$Cl$_2$/MeOH/NH$_4$OH) to give N-(((4R,5S)-5-((1R,2S,4S)-4-hydroxy-2-(hydroxymethyl)-1-methylcyclohexyl)-1,1-dimethyl-2,3,4,5,6,7-hexahydro-1H-inden-4-yl)methyl)benzamide (Compound No. 17, 42 mg, 56%) as a colourless foam. $^1$H NMR (CD$_3$OD): δ8.63 (m, 1H), 7.79 (d, J=7.2 Hz, 2H), 7.49 (m, 3H), 3.78 (m, 1H), 3.53 (m, 1H), 3.43 (m, 1H), 3.08-3.24 (m, 2H), 2.52 (m, 1H), 2.38 (m, 1H), 1.13-2.20 (m, 15H), 1.02 (s, 3H), 0.94 (s, 3H), 0.76 (s, 3H); $^{13}$C NMR (CD$_3$OD): δ170.3, 144.6, 136.0, 135.2, 132.5, 129.6 (2C), 128.1 (2C), 71.4, 63.3, 46.7, 44.0, 43.5, 41.5, 40.3, 38.6, 38.2, 35.6, 34.0, 33.0, 32.2, 27.3, 25.7, 20.9, 20.6, 19.9. ES-MS m/z 426 ([M+1]$^+$).

Example 9

Synthesis of (4-(((((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methylamino)methyl)phenyl)(phenyl)methanone (Compound No. 21)

Example 8

Synthesis of N-(((4R,5S)-5-((1R,2S,4S)-4-hydroxy-2-(hydroxymethyl)-1-methylcyclohexyl)-1,1-dimethyl-2,3,4,5,6,7-hexahydro-1H-inden-4-yl)methyl)benzamide (Compound No. 17)

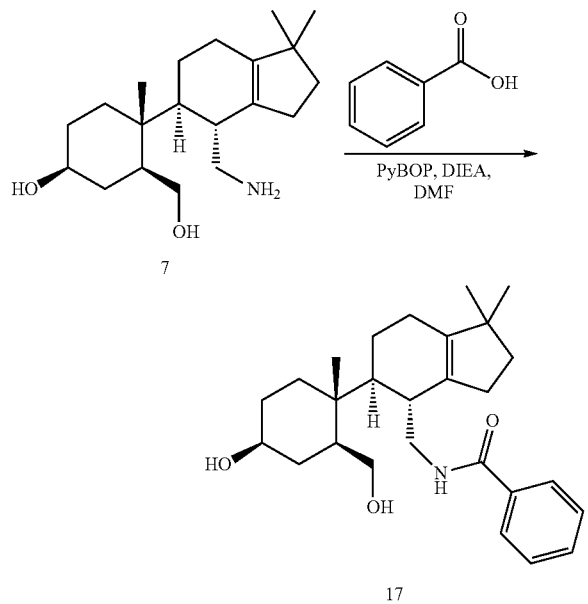

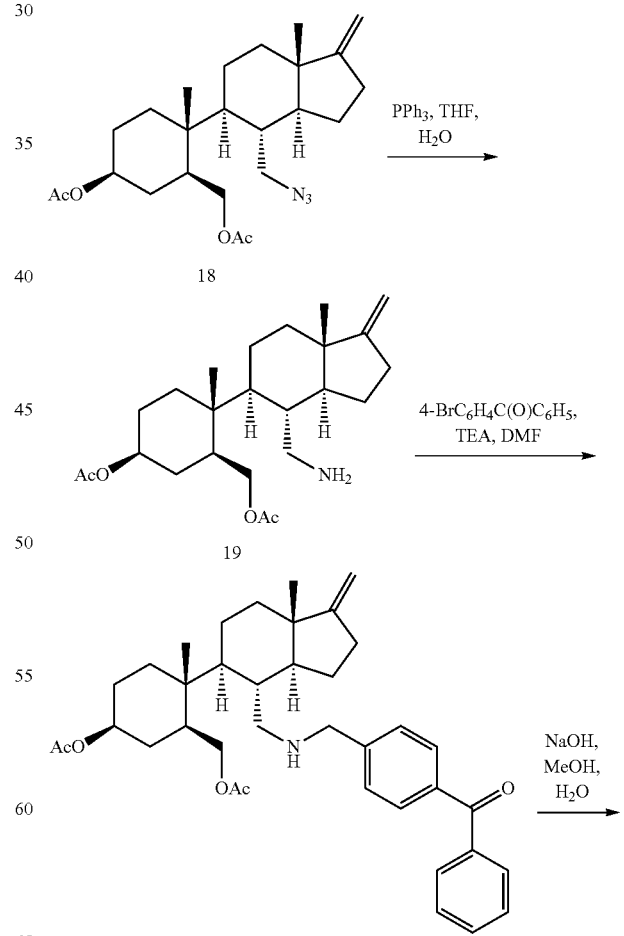

To a solution of (1S,3S,4R)-4-(((4R,5S)-4-(aminomethyl)-1,1-dimethyl-2,3,4,5,6,7-hexahydro-1H-inden-5-yl)-3-(hydroxymethyl)-4-methylcyclohexanol (Compound No. 7, 57 mg, 0.18 mmol), (benzotriazol-1-yl-oxy)tripyrrolidinophosphonium hexafluorophosphate (112 mg, 0.22 mmol), and benzoic acid (27 mg, 0.22 mmol) in DMF (1.8 mL) was added DIEA (0.075 mL, 0.43 mmol), and the solution was -continued

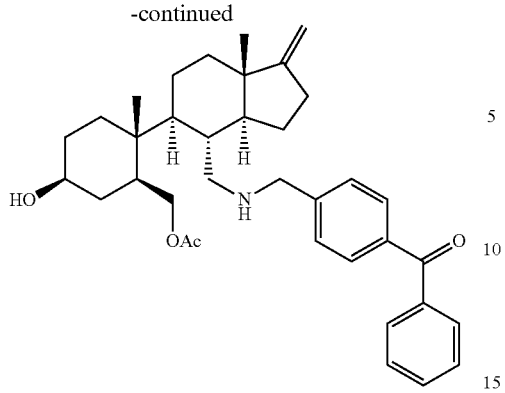

21

A. A mixture of ((1S,2R,5S)-5-acetoxy-2-((3aS,4R,5S, 7aS)-4-(azidomethyl)-7a-methyl-1-methyleneoctahydro-1H-inden-5-yl)-2-methylcyclohexyl)methyl acetate (Compound No. 18, 283 mg, 0.65 mmol), PPh₃ (516 mg, 1.95 mmol) and water (0.12 mL, 6.5 mmol) in THF (10 mL) was stirred at room temperature for 20 h then at 50° C. for 5 h. The mixture was cooled to room temperature, diluted with saturated NaHCO₃ solution (20 mL), extracted with EtOAc (3×15 mL), dried (Na₂SO₄) and concentrated. The residue was purified using chromatography on silica gel (9:1 EtOAc:MeOH) to afford ((1S,2R,5S)-5-acetoxy-2-((3aS,4R,5S,7aS)-4-(aminomethyl)-7a-methyl-1-methyleneoctahydro-1H-inden-5-yl)-2-methylcyclohexyl)methyl acetate (Compound No. 19, 129 mg) as a white foam.

B. A mixture of ((1S,2R,5S)-5-acetoxy-2-((3aS,4R,5S, 7aS)-4-(aminomethyl)-7a-methyl-1-methyleneoctahydro-1H-inden-5-yl)-2-methylcyclohexyl)methyl acetate (Compound No. 19, 129 mg), TEA (0.27 mL, 1.9 mmol) and 4-bromomethylbenzophenone (160 mg, 0.59 mmol) in DMF was stirred under argon at room temperature overnight. The resultant mixture was diluted with Et₂O (25 mL), washed with water (3×5 mL), dried (Na₂SO₄) and concentrated. The residue was purified by chromatography on silica gel (4:1 to 2:1 Hexanes:EtOAc) to afford ((1S,2R,5S)-5-acetoxy-2-((3aS,4R,5S,7aS)-4-(((4-benzoylbenzyl)amino)methyl)-7a-methyl-1-methyleneoctahydro-1H-inden-5-yl)-2-methylcyclohexyl)methyl acetate (Compound No. 20, 140 mg) as a colourless oil.

C. A mixture of ((1S,2R,5S)-5-acetoxy-2-((3aS,4R,5S, 7aS)-4-(((4-benzoylbenzyl)amino)methyl)-7a-methyl-1-methyleneoctahydro-1H-inden-5-yl)-2-methylcyclohexyl) methyl acetate (Compound No. 20, 140 mg) and 1 N NaOH (2.4 mL, 2.4 mmol) in MeOH (3 mL) at room temperature was allowed to stir for 2 d. The resultant mixture was concentrated then suspended in water (15 mL). The pH was adjusted to ~7 with 1 M aqueous HCl. The mixture was extracted successively with CH₂Cl₂ (3×20 mL), and EtOAc (20 mL), dried (Na₂SO₄) and concentrated. The residue was purified using chromatography on silica gel (1:1 CH₂Cl₂:MeOH to load, EtOAc to elute) to afford (4-((((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methylamino)methyl)phenyl)(phenyl)methanone (Compound No. 21, 20 mg, 6% over 3 steps) as a white solid. ¹H NMR (300 MHz, CD₃OD) δ7.74 (t, J=7.5, 4H), 7.64 (m, 1H), 7.52 (dd, J=7.9, 13.6, 4H), 4.61 (s, 2H), 3.78 (m, 2H), 3.74-3.61 (m, 1H), 3.54-3.36 (m, 1H), 3.13 (m, 1H), 2.82 (d, J=12.4, 1H), 2.62 (d, J=12.1, 1H), 2.53-2.37 (m, 1H), 2.34-2.18 (m, 1H), 2.18-2.03 (m, 1H), 1.93-1.11 (m, 15H), 1.00 (s, 3H), 0.78 (s, 3H); ¹³C NMR (75 MHz, CD₃OD) δ198.5, 162.9, 147.0, 139.0, 137.5, 133.7, 131.1, 130.9, 129.7, 129.5, 101.5, 71.1, 62.9, 55.0, 52.4, 50.8, 46.4, 44.7, 41.1, 39.3, 38.2, 37.2, 35.2, 32.1, 30.0, 25.8, 21.1, 18.6; MS m/z: 516.5 [M+H]⁺.

Example 10

Synthesis of (1S,3S,4R)-4-((3aS,4R,5S,7aS)-4-((4-fluorobenzylamino)methyl)-7a-methyl-1-methyl-eneoctahydro-1H-inden-5-yl)-3-(hydroxymethyl)-4-methylcyclohexanol (Compound No. 23)

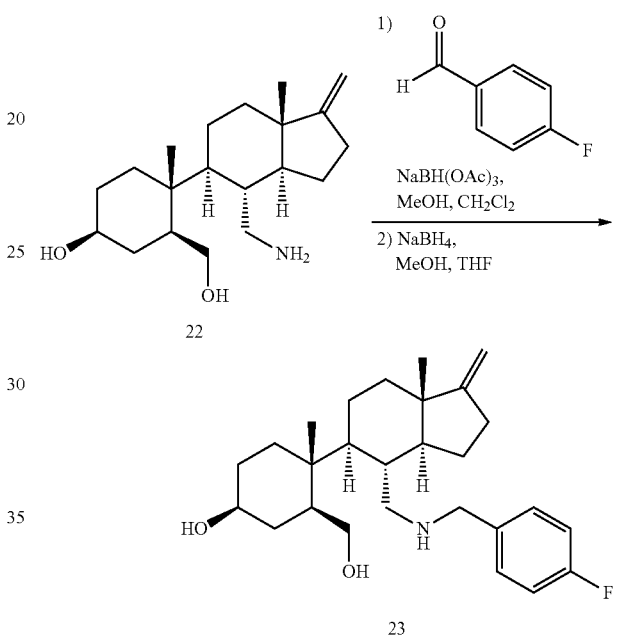

A mixture of (1S,3S,4R)-4-((3aS,4R,5S,7aS)-4-(aminomethyl)-7a-methyl-1-methyleneoctahydro-1H-inden-5-yl)-3-(hydroxymethyl)-4-methylcyclohexanol (Compound No. 22, 100 mg, 0.310 mmol), NaBH(OAc)₃ (197 mg, 0.93 mmol), 4 Å molecular sieves (100 mg) and 4-fluorobenzaldehyde (0.17 mL, 1.55 mmol) in CH₂Cl₂:MeOH (5:1, 6 mL) under argon was stirred at room temperature for 72 h. The mixture was filtered through Celite using EtOAc and was concentrated to a white solid. A solution of the residue and NaBH₄ (15 mg, 0.40 mmol) in MeOH:EtOAc (5:1, 6 mL), was allowed to stir at room temperature for 48 h. The solution was quenched with NH₄Cl solution (10 mL), extracted with EtOAc (2×20 mL), washed with NaHCO₃ (2×10 mL), and brine (10 mL). The organic layer was dried (Na₂SO₄), and concentrated to afford a white solid. The residue was purified using a chromatography on silica gel (0%, 10% then 100% MeOH/EtOAc) to afford (1S,3S,4R)-4-((3aS,4R,5S,7aS)-4-((4-fluorobenzylamino)methyl)-7a-methyl-1-methyleneoctahydro-1H-inden-5-yl)-3-(hydroxymethyl)-4-methylcyclohexanol (Compound No. 23, 98 mg, 74%). ¹H NMR (300 MHz, CD₃OD) δ7.32 (m, 2H), 7.03 (m, 2H), 4.61 (s, 2H), 3.70 (s, 1H), 3.65 (s, 2H), 3.41 (s, 1H), 3.31 (s, 1H), 3.12 (m, 1H), 2.78 (m, 1H), 2.49 (m, 1H), 2.18 (m, 2H), 1.78 (m, 5H), 1.61 (m, 1H), 1.42 (m, 5H), 1.24 (m, 4H), 0.96 (s, 3H), 0.77 (s, 3H); ¹³C NMR (75 MHz, CD₃OD) δ162.8, 137.1, 131.6, 131.5, 115.9, 115.7, 101.5, 71.1, 62.8, 54.4, 52.3, 50.5, 46.4, 44.7, 39.2, 38.1, 37.2, 35.1, 31.9, 29.9, 25.8, 24.4, 21.1, 18.6; MS m/z: 430.5 [M+H]+.

Example 11

Synthesis of (3aR,4R,5R,7aS)-5-((1S,2S,4S)-4-hydroxy-1-methyl-2-(2-(pyrrolidin-1-yl)ethyl)cyclohexyl)-7a-methyl-1-methyleneoctahydro-1H-inden-4-ol (Compound No. 29)

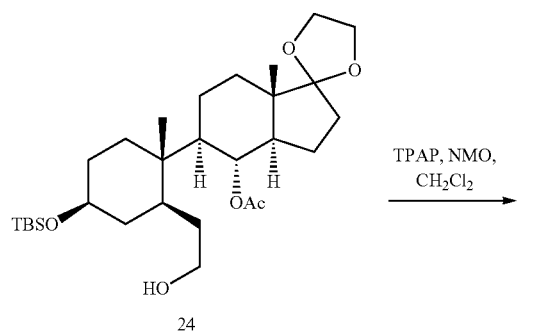

24

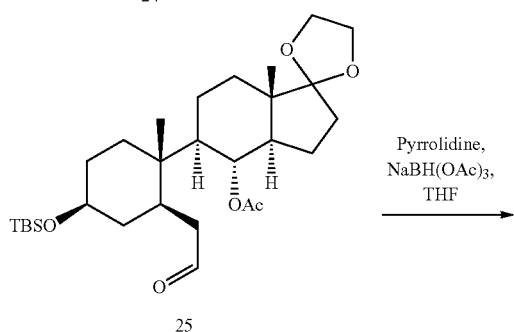

25

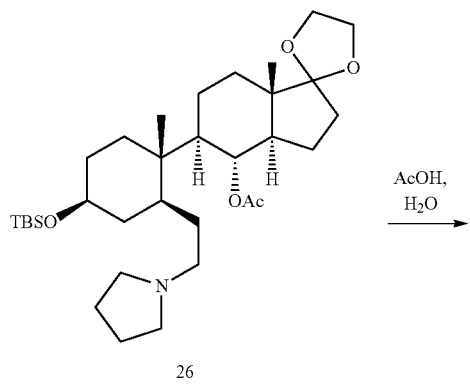

26

27

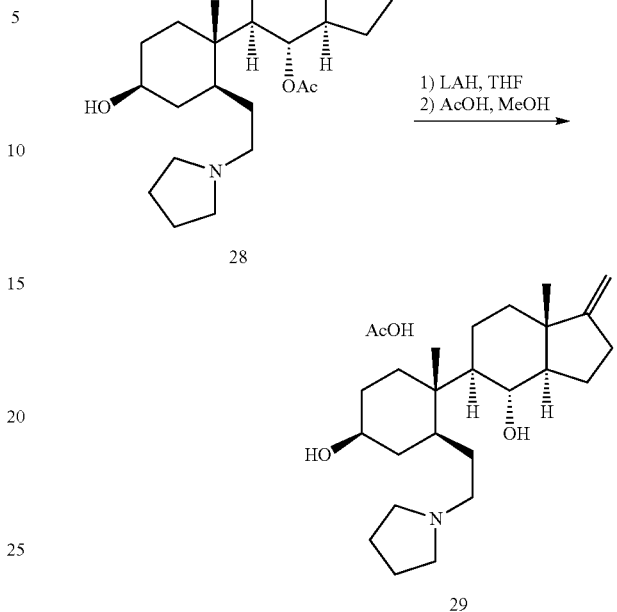

A. A mixture of (3a'R,4'R,5'R,7a'S)-5'-((1S,2S,4S)-4-((tert-butyldimethylsilyl)oxy)-2-(2-hydroxyethyl)-1-methylcyclohexyl)-7a'-methyloctahydrospiro[[1,3]dioxolane-2,1'-inden]-4'-yl acetate (Compound No. 24, 2.00 g, 3.8 mmol), TPAP (200 mg, 0.57 mmol) and NMO (1.33 g, 11.4 mmol) in CH$_2$Cl$_2$ (25 mL) under argon at 0° C. was allowed to warm to room temperature over 1 h. The mixture was filtered through a pad of silica then concentrated. The residue was purified using chromatography on silica gel (2% to 5% to 10% to 20% EtOAc in Hexanes) to afford (3a'R, 4'R,5'R,7a'S)-5'-((1S,2R,4S)-4-((tert-butyldimethylsilyl) oxy)-1-methyl-2-(2-oxoethyl)cyclohexyl)-7a'-methyloctahydrospiro[[1,3]dioxolane-2,1'-inden]-4'-yl as the acetate salt (Compound No. 25, 0.66 g, 33%) as a white foam.

B. A mixture of (3a'R,4'R,5'R,7a'S)-5'-((1S,2R,4S)-4-((tert-butyldimethylsilyl)oxy)-1-methyl-2-(2-oxoethyl)cyclohexyl)-7a'-methyloctahydrospiro[[1,3]dioxolane-2,1'-inden]-4'-yl acetate (Compound No. 25, 0.66 g, 1.3 mmol) and pyrrolidine (0.13 mL, 1.6 mmol) in THF (10 mL) under argon at room temperature was allowed to stir for 5 min. To the resultant mixture was added NaBH(OAc)$_3$ (0.40 g, 1.9 mmol) and the solution was stirred for 19 h. To the mixture was added pyrollidine (0.13 mL, 1.6 mmol) and NaBH(OAc)$_3$ (0.40 g, 1.9 mmol) and the solution was stirred for 3 d. The reaction was quenched with saturated NaHCO$_3$ solution (20 mL), extracted with EtOAc (3×20 mL), dried (Na$_2$SO$_4$) and concentrated. The residue was purified using chromatography on silica gel (9:1 EtOAc:MeOH+1% NH4Cl) to afford (3a'R,4'R,5'R,7a'S)-5'-((1S,2S,4S)-4-((tert-butyldimethylsilyl)oxy)-1-methyl-2-(2-(pyrrolidin-1-yl)ethyl)cyclohexyl)-7a'-methyloctahydrospiro[[1,3]dioxolane-2,1'-inden]-4'-yl acetate (Compound No. 26, 0.67 g, 89%) as a colourless oil.

B. A mixture of (3a'R,4'R,5'R,7a'S)-5'-((1S,2S,4S)-4-((tert-butyldimethylsilyl)oxy)-1-methyl-2-(2-(pyrrolidin-1-yl)ethyl)cyclohexyl)-7a'-methyloctahydrospiro[[1,3]dioxolane-2,1'-inden]-4'-yl acetate (Compound No. 26, 0.65 g, 1.1 mmol) and water (8 mL) in AcOH (32 mL) was heated at 50°

C. for 2 d. The mixture was concentrated and azeotroped from toluene (2×20 mL). The residue was purified using chromatography on silica gel (9:1 EtOAc:MeOH+2% NH$_4$Cl) to afford (3aR,4R,5R,7aS)-5-((1S,2S,4S)-4-hydroxy-1-methyl-2-(2-(pyrrolidin-1-yl)ethyl)cyclohexyl)-7a-methyl-1-oxooctahydro-1H-inden-4-yl acetate (Compound No. 27, 0.36 g, 78%) as a white foam.

C. To a suspension of Ph$_3$PMeBr (768 mg, 2.15 mmol) in THF (30 mL) under argon at 0° C. was added KOtBu (241 mg, 2.15 mmol). After 20 min a solution of (3aR,4R,5R,7aS)-5-((1S,2S,4S)-4-hydroxy-1-methyl-2-(2-(pyrrolidin-1-yl)ethyl)cyclohexyl)-7a-methyl-1-oxooctahydro-1H-inden-4-yl acetate (Compound No. 27, 0.36 g, 0.86 mmol) in THF (10 mL) was added via cannula and the mixture was stirred at room temperature for 60 h. The reaction was quenched with brine (40 mL), extracted with EtOAc (3×40 mL), dried (Na$_2$SO$_4$) and concentrated. The residue was purified by chromatography on silica gel (9:1 EtOAc:MeOH+1% NH4Cl) to afford (3aR,4R,5R,7aS)-5-((1S,2S,4S)-4-hydroxy-1-methyl-2-(2-(pyrrolidin-1-yl)ethyl)cyclohexyl)-7a-methyl-1-methyleneoctahydro-1H-inden-4-yl acetate (Compound No. 28, 0.35 g, 97%) as a white foam.

D. A mixture of (3aR,4R,5R,7aS)-5-((1S,2S,4S)-4-hydroxy-1-methyl-2-(2-(pyrrolidin-1-yl)ethyl)cyclohexyl)-7a-methyl-1-methyleneoctahydro-1H-inden-4-yl acetate (Compound No. 28, 0.35 g, 0.8 mmol) and LiAlH$_4$ (1 mL of a 2 M solution in THF, 2 mmol) in THF (8 mL) under argon at 0° C. was warmed to room temperature over 90 min. The mixture was cooled to 0° C. before the slow addition of water (76 µL), NaOH (2 M, 76 µL) then water (228 µL). The mixture was stirred for 90 min, filtered and concentrated. The residue was purified using chromatography on silica gel (9:1 EtOAc:MeOH+1% NH$_4$Cl) to afford the free base (143 mg, 50%) as a clear film. A mixture of the free base (143 mg, 0.39 mmol) and AcOH (114 µL, 2 mmol) in MeOH (8 mL) was stirred at room temperature for 10 min. The mixture was concentrated and azeotroped from MeOH:toluene (1:3, 2×10 mL). The residue was dissolved in CH$_2$Cl$_2$ (5 mL) and hexanes (10 mL) were added. The mixture was concentrated. The material was dissolved in CH$_2$Cl$_2$ (5 mL) and hexanes (10 mL) were added. The mixture was concentrated to afford (3aR,4R,5R,7aS)-5-((1S,2S,4S)-4-hydroxy-1-methyl-2-(2-(pyrrolidin-1-yl)ethyl)cyclohexyl)-7a-methyl-1-methyleneoctahydro-1H-inden-4-ol (Compound No. 29, 167 mg, 97%) as a white solid. $^1$H NMR (300 MHz, CD$_3$OD) δ4.62 (s, 2H), 3.62 (m, 1H), 3.43 (m, 1H), 3.15 (m, 2H), 2.51 (m, 1H), 2.24 (m, 1H), 2.04 (m, 4H), 1.93 (s, 6H), 1.79-1.23 (s, 18H), 1.18 (s, 3H), 0.79 (s, 3H); $^{13}$C NMR (75 MHz, CDCl$_3$) δ177.7, 161.1, 161.0, 101.1, 71.6, 69.7, 69.7, 56.2, 54.2, 54.1, 53.0, 51.9, 51.8, 45.4, 38.3, 37.5, 35.5, 35.3, 35.3, 31.0, 30.9, 29.2, 25.7, 24.0, 23.5, 23.4, 23.2, 23.1, 22.9, 20.8, 20.7, 18.4; MS m/z: 376.4 [M+H]$^+$ free base.

Example 12

Synthesis of (1S,3S,4R)-3-(hydroxymethyl)-4-methyl-4-((3aS,4R,5S,7aS)-7a-methyl-1-methylene-4-((pyridin-4-ylmethylamino)methyl)octahydro-1H-inden-5-yl)cyclohexanol (Compound No. 30)

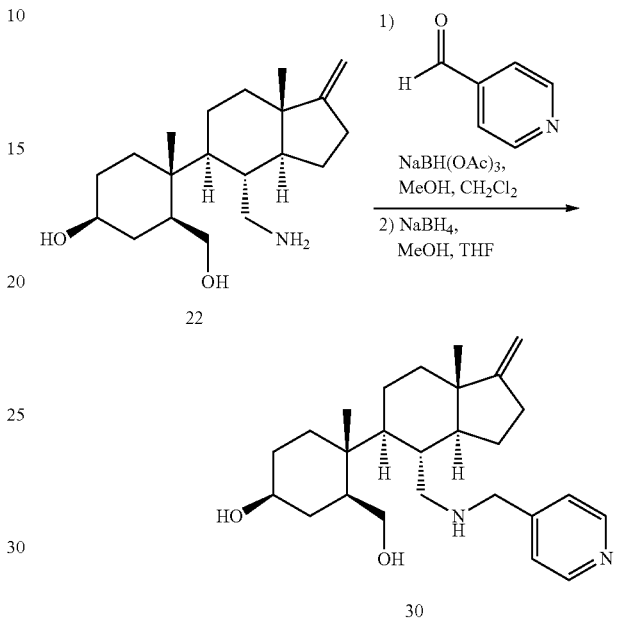

A mixture of (1S,3S,4R)-4-((3aS,4R,5S,7aS)-4-(aminomethyl)-7a-methyl-1-methyleneoctahydro-1H-inden-5-yl)-3-(hydroxymethyl)-4-methylcyclohexanol (Compound No. 22, 100 mg, 0.310 mmol), NaBH(OAc)$_3$ (197 mg, 0.93 mmol), 4 Å molecular sieves (100 mg) and 4-pyridinecarboxaldehyde (0.15 mL, 1.6 mmol) in CH$_2$Cl$_2$:MeOH (5:1, 6 mL) under argon was stirred at room temperature for 72 h. The mixture was filtered through Celite with EtOAc and was concentrated to a white solid. The residue was purified using chromatography on silica gel (0% to 10% MeOH/EtOAc) to afford an off-white solid. A solution of the solid (70 mg, 0.17 mmol) and NaBH$_4$ (10 mg, 0.26 mmol) in MeOH:THF (2:1, 9 mL) was stirred at room temperature for 24 h. Additional NaBH$_4$ (3 equivalents) was added and the mixture was heated at reflux for 24 h. The reaction was quenched with a solution of NH$_4$Cl (10 mL), extracted with EtOAc (2×10 mL), washed successively with saturated NaHCO$_3$ solution (2×10 mL) and brine (10 mL), dried (Na$_2$SO$_4$) and concentrated. The residue was purified using chromatography on silica gel (0% to 100% MeOH/EtOAc) to afford (1S,3S,4R)-3-(hydroxymethyl)-4-methyl-4-((3aS,4R,5S,7aS)-7a-methyl-1-methylene-4-((pyridin-4-ylmethylamino)methyl)octahydro-1H-inden-5-yl)cyclohexanol (Compound No. 30, 39 mg, 30%). $^1$H NMR (300 MHz, CD$_3$OD) δ8.44 (d, J=5.6 Hz, 2H), 7.42 (d, J=6.4 Hz, 2H), 4.61 (s, 2H), 3.42 (m, 1H), 3.31 (m, 1H), 3.13 (m, 1H), 2.83 (d, J=11.7 Hz, 1H), 2.58 (m, 1H), 2.45 (m, 1H), 2.19 (m, 2H), 1.77 (m, 5H), 1.62 (m, 1H), 1.44 (m, 5H), 1.27 (m, 4H), 1.02 (s, 3H), 0.78 (s, 3H); $^{13}$C NMR (75 MHz, CD$_3$OD) δ162.9, 152.5, 149.8, 125.2, 101.6, 71.1, 62.9, 54.1, 52.3, 50.9, 46.4, 44.7, 39.3, 38.2, 37.2, 35.2, 32.1, 30.0, 25.8, 24.4, 21.0, 18.6; MS m/z: 413.4 [M+H]$^+$.

Example 13

Synthesis of (1S,3S,4R)-3-(hydroxymethyl)-4-methyl-4-((3aS,4R,5S,7aS)-7a-methyl-4-((4-methylbenzylamino)methyl)-1-methyleneoctahydro-1H-inden-5-yl)cyclohexanol (Compound No. 31)

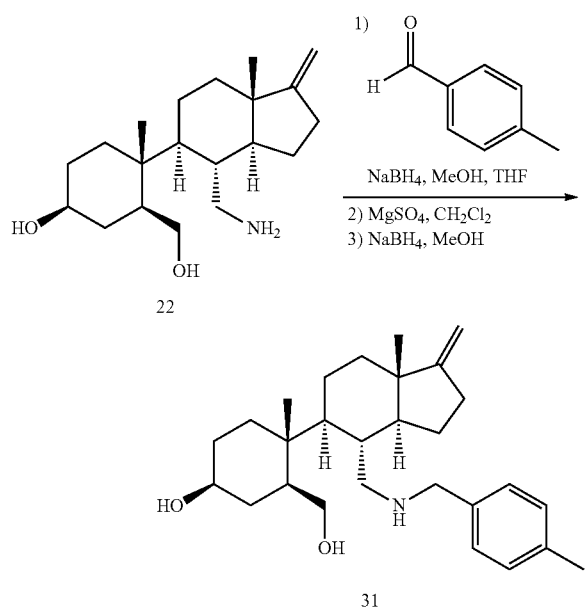

Example 14

Synthesis of (1S,3S,4R)-3-(hydroxymethyl)-4-methyl-4-((3aS,4R,5S,7aS)-7a-methyl-4-((3-methylbenzylamino)methyl)-1-methyleneoctahydro-1H-inden-5-yl)cyclohexanol (Compound No. 32)

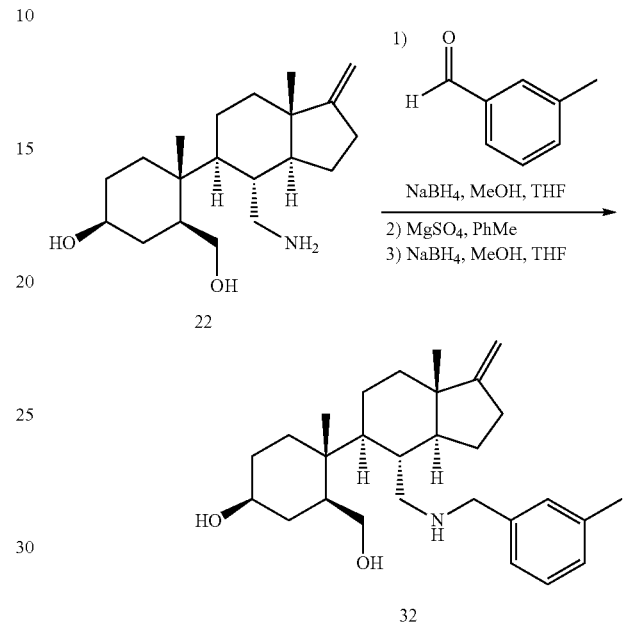

A. A mixture of (1S,3S,4R)-4-((3aS,4R,5S,7aS)-4-(aminomethyl)-7a-methyl-1-methyleneoctahydro-1H-inden-5-yl)-3-(hydroxymethyl)-4-methylcyclohexanol (Compound No. 22, 100 mg, 0.310 mmol) p-tolualdehyde (0.18 mL, 1.55 mmol) and NaBH$_4$ (41 mg, 1.1 mmol) in MeOH:THF (2:1, 9 mL) under argon was allowed to stir at room temperature for 48 h. The solution was concentrated and then dissolved in CH$_2$Cl$_2$ (4 mL). p-Tolualdehyde (0.4 mL, 0.34 mmol) and anhydrous Mg$_2$SO$_4$ (1.1 g, 9.3 mmol) were added and the solution was stirred at room temperature under argon for 24 h then was filtered through Celite with EtOAc, and concentrated. A solution of the residue and NaBH$_4$ (18 mg, 0.46 mmol) in MeOH was stirred at room temperature for 20 h. The reaction was quenched with saturated aqueous NH$_4$Cl (10 mL), extracted with EtOAc (2×10 mL), washed successively with saturated NaHCO$_3$ solution (2×10 mL) and brine (10 mL), dried (Na$_2$SO$_4$) and concentrated. The residue was purified using chromatography on silica gel (0% to 100% MeOH/EtOAc) to afford (1S,3S,4R)-3-(hydroxymethyl)-4-methyl-4-((3aS,4R,5S,7aS)-7a-methyl-4-((4-methylbenzylamino)methyl)-1-methyleneoctahydro-1H-inden-5-yl)cyclohexanol (Compound No. 31, 69 mg, 63%) as a white solid. $^1$H NMR (300 MHz, CD$_3$OD) δ7.18 (d, J=7.7 Hz, 2H), 7.11 (d, J=8.1 Hz, 2H), 4.61 (s, 2H), 3.69 (m, 1H), 3.63 (m, 2H), 3.39 (m, 1H), 3.11 (m, 1H), 2.78 (m, 1H), 2.55 (m, 1H), 2.44 (m, 1H), 2.31 (s, 3H), 2.18 (m, 2H), 1.81 (m, 5H), 1.60 (m, 1H), 1.41 (m, 5H), 1.25 (m, 4H), 0.96 (s, 3H), 0.77 (s, 3H); $^{13}$C NMR (75 MHz, CD$_3$OD) δ162.8, 137.9, 137.8, 129.9, 129.7, 101.5, 71.0, 62.9, 55.0, 52.5, 50.6, 46.5, 44.7, 39.3, 38.5, 37.2, 35.2, 32.0, 30.0, 25.8, 21.1, 18.6; MS m/z: 426.5 [M+H]$^+$.

A mixture of (1S,3S,4R)-4-((3aS,4R,5S,7aS)-4-(aminomethyl)-7a-methyl-1-methyleneoctahydro-1H-inden-5-yl)-3-(hydroxymethyl)-4-methylcyclohexanol (Compound No. 22, 100 mg, 0.310 mmol), m-tolualdehyde (0.18 mL, 1.55 mmol) and NaBH$_4$ (41 mg, 1.1 mmol) in MeOH:THF (2:1, 9 mL) under argon was allowed to stir at room temperature for 48 h. The solution was concentrated and then dissolved in toluene (4 mL). m-Tolualdehyde (0.4 mL, 0.34 mmol) and anhydrous Mg$_2$SO$_4$ (1.1 g, 9.3 mmol) were added and the solution was stirred at room temperature under argon for 24 h. The solution was filtered through Celite with EtOAc, and concentrated. A solution of the residue and NaBH$_4$ (18 mg, 0.46 mmol) in MeOH, was stirred at room temperature for 20 h. The solution was quenched with saturated aqueous NH$_4$Cl (10 mL), extracted with EtOAc (2×10 mL), washed successively with saturated NaHCO$_3$ solution (2×10 mL) and brine (10 mL), dried (Na$_2$SO$_4$) and concentrated. The residue was purified using chromatography on silica gel (0% to 100% MeOH/EtOAc) to afford (1S,3S,4R)-3-(hydroxymethyl)-4-methyl-4-((3aS,4R,5S,7aS)-7a-methyl-4-((3-methylbenzylamino)methyl)-1-methyleneoctahydro-1H-inden-5-yl)cyclohexanol (Compound No. 32, 83 mg, 63%) as a white solid. $^1$H NMR (300 MHz, CD$_3$OD) δ7.13 (m, 1H), 7.07 (m, 3H), 4.60 (s, 2H), 3.68 (m, 1H), 3.61 (s, 2H), 3.40 (m, 1H), 3.11 (m, 1H), 2.76 (m, 1H), 2.56 (m, 1H), 2.43 (m, 1H), 2.31 (s, 3H), 2.18 (m, 2H), 1.72 (m, 5H), 1.56 (m, 1H), 1.39 (m, 5H), 1.23 (m, 4H), 0.97 (s, 3H), 0.76 (s, 3H); $^{13}$C NMR (75 MHz, CD$_3$OD) δ161.6, 139.9, 137.7, 129.3, 128.1, 127.6, 125.7, 100.5, 69.9, 61.8, 54.2, 51.3, 49.6, 45.3, 43.6, 38.1, 36.9, 36.0, 34.1, 30.9, 28.9, 24.7, 20.5, 19.9, 17.6; MS m/z: 426.5 [M+H]$^+$.

Example 15

Synthesis of (1S,3S,4R)-3-(hydroxymethyl)-4-methyl-4-((3aS,4R,5S,7aS)-7a-methyl-4-((2-methylbenzylamino)methyl)-1-methyleneoctahydro-1H-inden-5-yl)cyclohexanol (Compound No. 33)

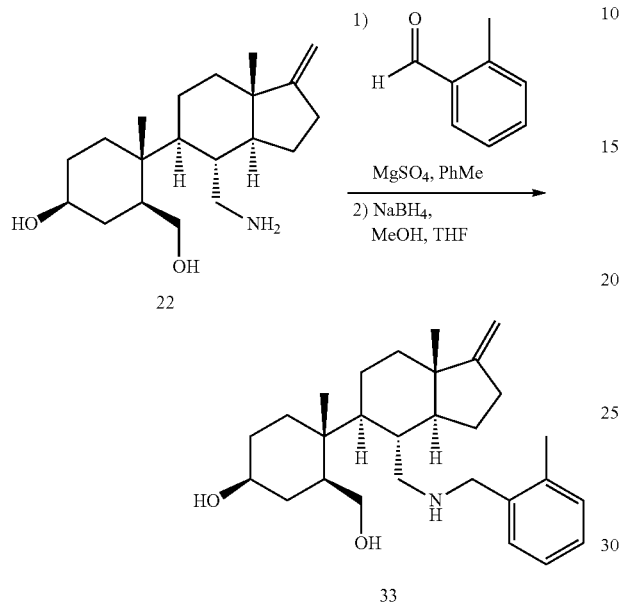

A mixture of (1S,3S,4R)-4-((3aS,4R,5S,7aS)-4-(aminomethyl)-7a-methyl-1-methyleneoctahydro-1H-inden-5-yl)-3-(hydroxymethyl)-4-methylcyclohexanol (Compound No. 22, 100 mg, 0.310 mmol), o-tolualdehyde (0.04 mL, 0.34 mmol) and anhydrous $Mg_2SO_4$ (1.1 g, 9.3 mmol) in $CH_2Cl_2$ (4 mL) was stirred at room temperature under argon for 24 h. The solution was filtered through Celite with EtOAc and concentrated. A solution of the residue and $NaBH_4$ (11 mg, 0.29 mmol) in MeOH was stirred at room temperature under argon for 20 h. The reaction was quenched with saturated aqueous $NH_4Cl$ (10 mL), extracted with EtOAc (2×10 mL), washed with saturate $NaHCO_3$ solution (2×10 mL) and brine (10 mL), dried ($Na_2SO_4$) and concentrated. The residue was purified using chromatography on silica gel (0%-100% MeOH/EtOAc) to afford (1S,3S,4R)-3-(hydroxymethyl)-4-methyl-4-((3aS,4R,5S,7aS)-7a-methyl-4-((2-methylbenzylamino)methyl)-1-methyleneoctahydro-1H-inden-5-yl)cyclohexanol (Compound No. 33, 56 mg, 42%) as a white solid. $^1$H NMR (300 MHz, $CD_3OD$) δ7.20 (m, 1H), 7.13 (s, 3H), 4.60 (s, 2H), 3.67 (m, 3H), 3.40 (m, 1H), 3.10 (m, 1H), 2.87 (m, 1H), 2.62 (m, 1H), 2.45 (m, 1H), 2.35 (s, 3H), 2.17 (m, 2H), 1.74 (m, 5H), 1.60 (m, 1H), 1.39 (m, 5H), 1.23 (m, 4H), 0.98 (s, 3H), 0.78 (s, 3H); $^{13}$C NMR (75 MHz, $CD_3OD$) δ161.7, 137.9, 136.6, 130.0, 129.3, 127.0, 125.6, 100.4, 69.9, 61.8, 51.9, 51.3, 49.8, 46.9, 45.3, 43.5, 38.1, 36.9, 36.0, 34.0, 30.9, 28.9, 24.6, 19.8, 18.0, 17.5.

Example 16

Synthesis of N-(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)-2-naphthamide (Compound No. 34)

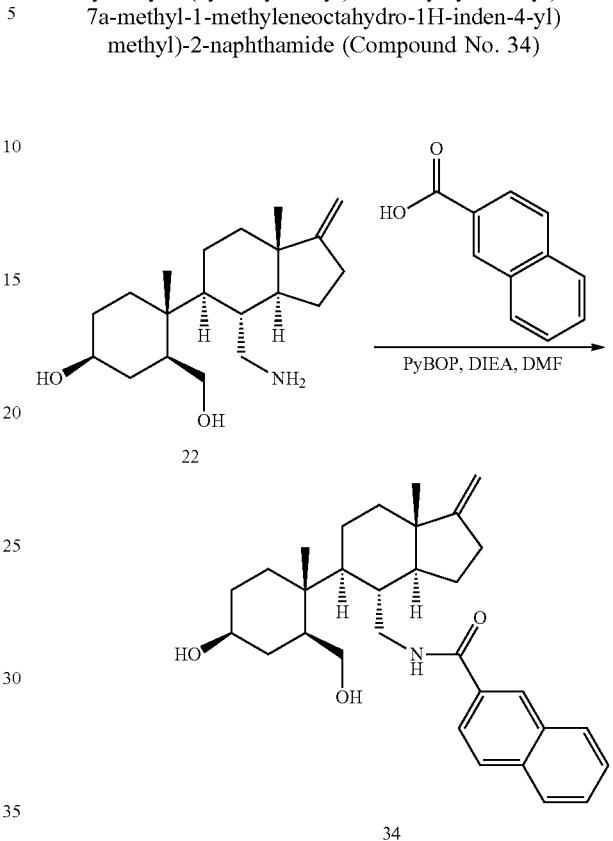

To a mixture of (1S,3S,4R)-4-((3aS,4R,5S,7aS)-4-(aminomethyl)-7a-methyl-1-methyleneoctahydro-1H-inden-5-yl)-3-(hydroxymethyl)-4-methylcyclohexanol (Compound No. 22, 100 mg, 0.310 mmol), PyBOP (210 mg, 0.400 mmol), 2-naphthoic acid (69 mg, 0.40 mmol) under argon were added DIEA (0.81 mL, 0.81 mmol) and DMF (3.0 mL). The solution was stirred for 24 h then was diluted with EtOAc (20 mL), washed successively with saturated $NaHCO_3$ solution (2×10 mL) and brine (2×10 mL) then was concentrated. The residue was purified using chromatography on silica gel (0% to 10% MeOH/EtOAc) to afford N-(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)-2-naphthamide (Compound No. 34, 123 mg, 84%) as a white solid. $^1$H NMR (300 MHz, $CD_3OD$) δ8.30 (s, 1H), 7.91 (m 3H), 6.81 (m, 1H), 7.57 (m, 2H), 4.65 (s, 2H), 3.76 (m, 1H), 3.67 (m, 2H), 3.48 (m, 1H), 3.14 (m, 1H), 2.51 (m, 1H), 2.23 (m, 2H), 1.87 (m, 5H), 1.74 (m, 1H), 1.50 (m, 5H), 1.29 (m, 4H), 1.08 (s, 3H), 0.86 (s, 3H); $^{13}$C NMR (75 MHz, $CD_3OD$) δ171.1, 162.6, 136.2, 134.0, 133.3, 129.9, 129.2, 128.8, 127.8, 125.1, 101.8, 71.1, 62.9, 52.9, 47.5, 45.0, 44.8, 43.9, 38.2, 36.9, 35.2, 32.1, 30.2, 26.2, 24.4, 21.7, 18.8; MS m/z: 474.1 [M−H]⁻.

Example 17

Synthesis of N-(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)benzamide (Compound No. 35)

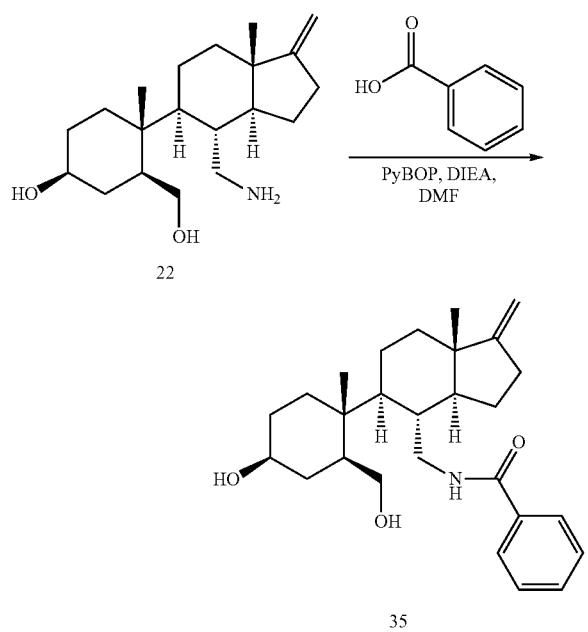

Example 18

Synthesis of (1S,3S,4R)-3-(hydroxymethyl)-4-((3aS,4R,5S,7aS)-4-((4-methoxybenzylamino)methyl)-7a-methyl-1-methyleneoctahydro-1H-inden-5-yl)-4-methylcyclohexanol (Compound No. 36)

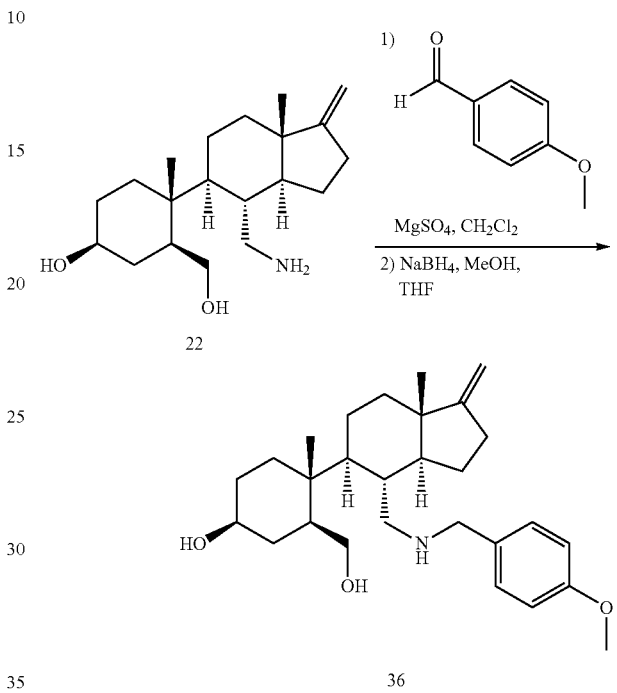

To a mixture of (1S,3S,4R)-4-((3aS,4R,5S,7aS)-4-(aminomethyl)-7a-methyl-1-methyleneoctahydro-1H-inden-5-yl)-3-(hydroxymethyl)-4-methylcyclohexanol (Compound No. 22, 100 mg, 0.310 mmol), PyBOP (210 mg, 0.400 mmol), benzoic acid (49 mg, 0.40 mmol) under argon were added DIEA (0.81 mL, 0.81 mmol) and DMF (3.0 mL). The solution was stirred for 24 h then was diluted with EtOAc (20 mL), washed successively with saturated NaHCO$_3$ solution (2×10 mL) and brine (2×10 mL) then was concentrated. The residue was purified using chromatography on silica gel (0% to 10% MeOH/EtOAc) to afford N-(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)benzamide (Compound No. 35, 89 mg, 68%) as a white solid. $^1$H NMR (300 MHz, CD$_3$OD) δ7.74 (d, J=6.93 Hz, 2H), 7.48 (m, 3H), 4.64 (s, 2H), 3.73 (m, 1H), 3.61 (m, 2H), 3.47 (m, 1H), 3.13 (m, 1H), 2.49 (m, 1H), 2.21 (m, 2H), 1.86 (m, 5H), 1.69 (m, 1H), 1.49 (m, 5H), 1.30 (m, 4H), 1.05 (s, 3H), 0.84 (s, 3H); $^{13}$C NMR (75 MHz, CD$_3$OD) δ170.0, 161.3, 134.9, 131.3, 128.3, 127.2, 100.6, 69.9, 61.7, 51.7, 46.9, 46.4, 43.9, 43.7, 42.6, 39.9, 35.8, 34.0, 30.9, 29.0, 24.9, 23.2, 20.5, 17.6; MS m/z: 423.9 [M−H]$^-$.

A mixture of (1S,3S,4R)-4-((3aS,4R,5S,7aS)-4-(aminomethyl)-7a-methyl-1-methyleneoctahydro-1H-inden-5-yl)-3-(hydroxymethyl)-4-methylcyclohexanol (Compound No. 22, 100 mg, 0.310 mmol), 4-methoxybenzaldehyde (0.04 mL, 0.34 mmol) and anhydrous Mg$_2$SO$_4$ (1.1 g, 9.3 mmol) in CH$_2$Cl$_2$ (4 mL) was stirred at room temperature under argon for 18 h. The solution was filtered through Celite with EtOAc and concentrated. A solution of the residue and NaBH$_4$ (35 mg, 0.92 mmol) in MeOH (5 mL) was stirred at room temperature under argon for 48 h. The reaction was quenched with saturated aqueous NH$_4$Cl (10 mL), extracted with EtOAc (2×10 mL), washed successively with saturated NaHCO$_3$ solution (2×10 mL) and brine (10 mL), dried (Na$_2$SO$_4$) and concentrated. The residue was purified using chromatography on silica gel (0% to 100% MeOH/EtOAc) to afford (1S,3S,4R)-3-(hydroxymethyl)-4-((3aS,4R,5S,7aS)-4-((4-methoxybenzylamino)methyl)-7a-methyl-1-methyleneoctahydro-1H-inden-5-yl)-4-methylcyclohexanol (Compound No. 36, 83 mg, 61%) as a white solid. $^1$H NMR (300 MHz, CD$_3$OD) δ7.22 (d, J=8.5, 2H), 6.86 (d, J=8.5, 2H), 4.61 (s, 2H), 3.78 (s, 3H), 3.69 (d, J=10.3, 1H), 3.62 (s, 2H), 3.40 (m, 1H), 3.11 (t, J=10.0, 1H), 2.78 (d, J=11.1, 1H), 2.58 (d, J=11.1, 1H), 2.44 (m, 1H), 2.18 (m, 2H), 1.87-1.04 (m, 15H), 0.96 (s, 3H), 0.78 (s, 3H).; $^{13}$C NMR (75 MHz, CD$_3$OD) δ 164.5, 162.9 160.4, 131.0, 131.0, 114.7, 101.5, 71.1, 62.9, 55.7, 54.6, 52.5, 50.5, 46.5, 46.4, 44.7, 39.2, 38.1, 37.2, 35.2, 32.0, 30.0, 25.8, 21.1, 18.6.

Example 19

Synthesis of (1S,3S,4R)-3-(hydroxymethyl)-4-methyl-4-((3aS,4R,5S,7aS)-7a-methyl-1-methylene-4-((4-(trifluoromethyl)benzylamino)methyl)octahydro-1H-inden-5-yl)cyclohexanol (Compound No. 37)

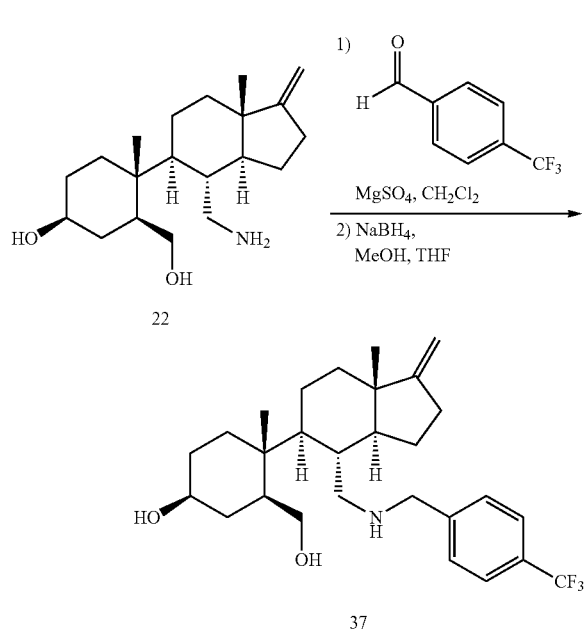

A mixture of (1S,3S,4R)-4-((3aS,4R,5S,7aS)-4-(aminomethyl)-7a-methyl-1-methyleneoctahydro-1H-inden-5-yl)-3-(hydroxymethyl)-4-methylcyclohexanol (Compound No. 22, 100 mg, 0.310 mmol), 4-trifluoromethylbenzaldehyde (63 mg mL, 0.36 mmol) and anhydrous Mg$_2$SO$_4$ (1.1 g, 9.3 mmol) in CH$_2$Cl$_2$ (3 mL) was stirred at room temperature under argon for 24 h. The solution was filtered through Celite with EtOAc and concentrated. A solution of the residue and NaBH$_4$ (5.3 mg, 0.14 mmol) in MeOH (5 mL) was stirred at room temperature under argon for 24 h. The reaction was quenched with saturated aqueous NH$_4$Cl (10 mL), extracted with EtOAc (2×10 mL), washed successively with saturated NaHCO$_3$ solution (2×10 mL) and brine (10 mL), dried (Na$_2$SO$_4$) and concentrated. The residue was purified using chromatography on silica gel (EtOAc) to afford (1S,3S,4R)-3-(hydroxymethyl)-4-methyl-4-((3aS,4R,5S,7aS)-7a-methyl-1-methylene-4-((4-(trifluoromethyl)benzylamino)methyl)octahydro-1H-inden-5-yl)cyclohexanol (Compound No. 37, 20 mg, 13%) as a white solid. $^1$H NMR (300 MHz, CDCl$_3$) δ7.57 (d, J=7.7, 2H), 7.42 (d, J=7.5, 2H), 4.63 (m 2H), 3.71 (s, 2H), 3.58 (m, 1H), 3.30 (m, 1H), 2.86 (d, J=12.3, 1H), 2.61 (d, J=12.3, 1H), 2.46 (m, 1H), 2.23 (m, 2H), 1.81-1.19 (m, 15H), 1.04 (s, 3H), 0.77 (s, 3H); $^{13}$C NMR (75 MHz, CDCl$_3$) δ161.5, 144.9, 128.6, 125.4, 101.3, 63.2, 63.1, 63.1, 54.3, 51.1, 50.2, 43.8, 38.2, 37.2, 36.1, 34.5, 31.3, 29.2, 24.8, 23.5, 20.6, 18.3.

Example 20

Synthesis of N-(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)pivalamide (Compound No. 38)

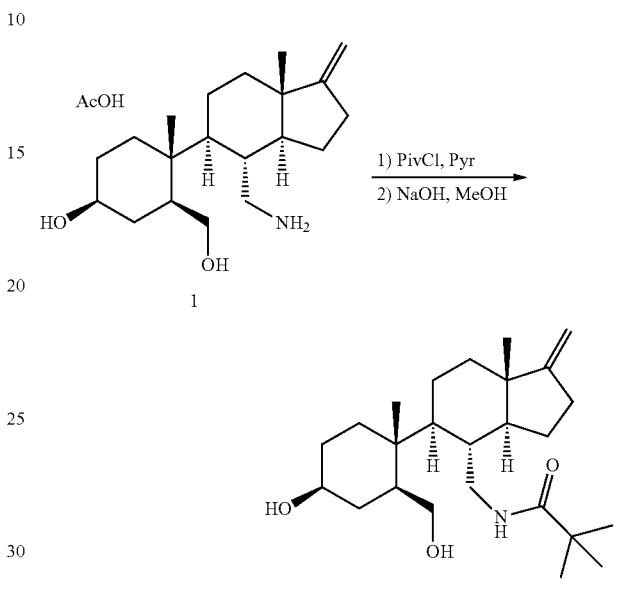

To a suspension of (1S,3S,4R)-4-((3aS,4R,5S,7aS)-4-(aminomethyl)-7a-methyl-1-methyleneoctahydro-1H-inden-5-yl)-3-(hydroxymethyl)-4-methylcyclohexanol acetate (Compound No. 1, 116 mg, 0.304 mmol) in pyridine (3.0 mL) was added trimethylacetyl chloride (0.11 mL, 0.89 mmol), and the mixture was stirred at room temperature under argon for 24 h then concentrated. Azeotropic removal of remaining pyridine was carried out with toluene (2×4 mL). The residue was dissolved in MeOH (3 mL), and 10 N NaOH (aq) (0.3 mL, 3 mmol) was added then heated to reflux for 2.3 h. The mixture was concentrated, and the residue was partitioned between EtOAc (35 mL) and H$_2$O (10 mL). The organic layer was washed with brine (10 mL) then dried (MgSO$_4$) and concentrated. The residue was purified by chromatography on silica gel (4:96-6:94 MeOH/CH$_2$Cl$_2$) to give N-(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)pivalamide (Compound No. 38, 82 mg, 67% over 2 steps) as a colourless solid. $^1$H NMR (CD$_3$OD): δ6.50 (br s, 1H), 4.64 (s, 2H), 3.71 (m, 1H), 3.47 (m, 2H), 3.32 (m, 1H), 3.13 (m, 1H), 2.50 (m, 1H), 2.12-2.26 (m, 2H), 1.18-1.87 (m, 24H), 1.00 (s, 3H), 0.82 (s, 3H). ES-MS m/z 406 ([M+1]$^+$).

Example 21

Synthesis of N-(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)isobutyramide (Compound No. 39)

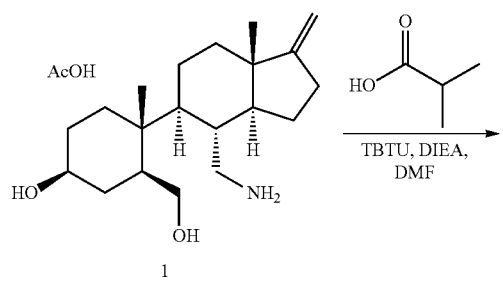

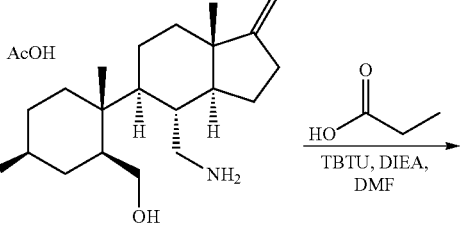

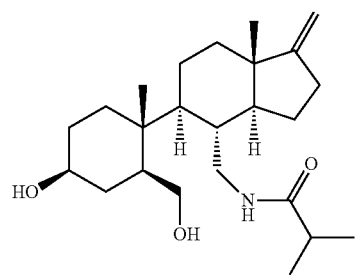

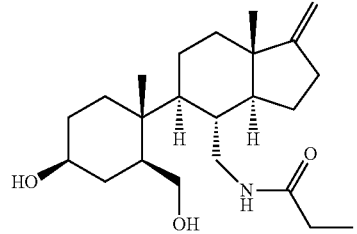

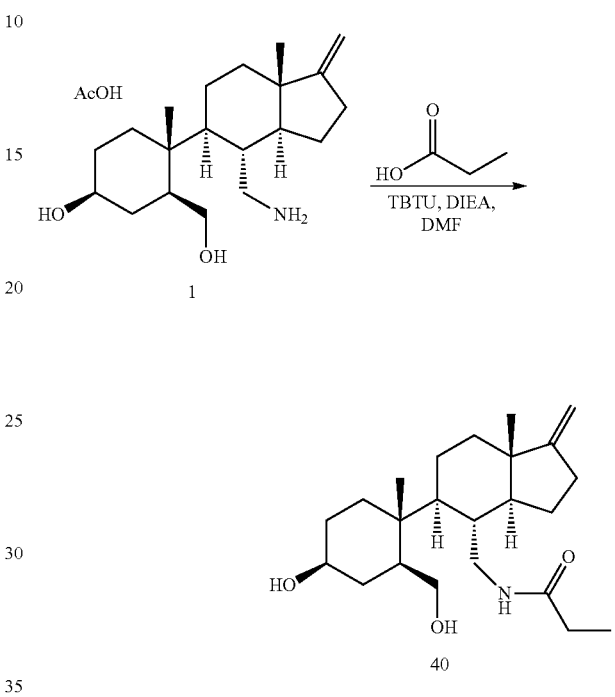

Example 22

Synthesis of N-(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)propionamide (Compound No. 40)

To a solution of (1S,3S,4R)-4-((3aS,4R,5S,7aS)-4-(aminomethyl)-7a-methyl-1-methyleneoctahydro-1H-inden-5-yl)-3-(hydroxymethyl)-4-methylcyclohexanol acetate (Compound No. 1, 104 mg, 0.273 mmol), O-(benzotriazol-1-yl)-N,N,N',N'-tetramethyluronium tetrafluoroborate (96 mg, 0.30 mmol), and isobutyric acid (0.028 mL, 0.30 mmol) in DMF (1.4 mL) was added N,N-diisopropylethylamine (0.11 mL, 0.63 mmol), and the solution was stirred at room temperature for 24 h. The mixture was concentrated, and the residue was partitioned between EtOAc (35 mL) and saturated aqueous NaHCO$_3$ (10 mL). The organic layer was washed with brine (5×10 mL) then dried (MgSO$_4$) and concentrated. The residue was purified by chromatography on silica gel (7:93 MeOH/CH$_2$Cl$_2$) to give N-(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)isobutyramide (Compound No. 39, 41 mg, 38%) as a colourless solid. $^1$H NMR (CD$_3$OD): δ4.64 (s, 2H), 3.72 (m, 1H), 3.44 (m, 2H), 3.33 (m, 1H), 3.13 (m, 1H), 2.45-2.65 (m, 2H), 2.13-2.28 (m, 2H), 1.20-1.89 (m, 15H), 1.07 (m, 6H), 0.99 (s, 3H), 0.82 (s, 3H). ES-MS m/z 392 ([M+1]$^+$).

To a solution of (1S,3S,4R)-4-((3aS,4R,5S,7aS)-4-(aminomethyl)-7a-methyl-1-methyleneoctahydro-1H-inden-5-yl)-3-(hydroxymethyl)-4-methylcyclohexanol acetate (Compound No. 1, 97 mg, 0.25 mmol), O-(benzotriazol-1-yl)-N,N,N',N'-tetramethyluronium tetrafluoroborate (90 mg, 0.28 mmol), and propionic acid (0.021 mL, 0.28 mmol) in DMF (1.3 mL) was added N,N-diisopropylethylamine (0.11 mL, 0.63 mmol), and the solution was stirred at room temperature for 18 h. The mixture was concentrated, and the residue was partitioned between EtOAc (35 mL) and saturated aqueous NaHCO$_3$ (10 mL). The organic layer was washed with brine (5×10 mL) then dried (MgSO$_4$) and concentrated. The residue was purified by chromatography on silica gel (5:95-7:93 MeOH/CH$_2$Cl$_2$) to give N-(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)propionamide (Compound No. 40, 38 mg, 40%) as colourless crystals. $^1$H NMR (CD$_3$OD): δ7.53 (br s, 1H), 4.63 (s, 2H), 3.72 (m, 1H), 3.46 (m, 2H), 3.33 (m, 1H), 3.13 (m, 1H), 2.50 (m, 1H), 2.13-2.28 (m, 4H), 1.20-1.86 (m, 15H), 1.10 (t, J=7.7 Hz, 3H), 0.98 (s, 3H), 0.82 (s, 3H). ES-MS m/z 378 ([M+1]$^+$).

Example 23

Synthesis of N-(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)butyramide (Compound No. 41)

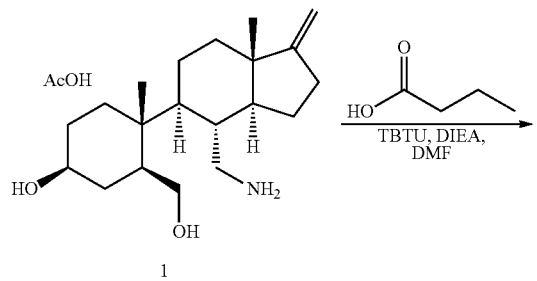

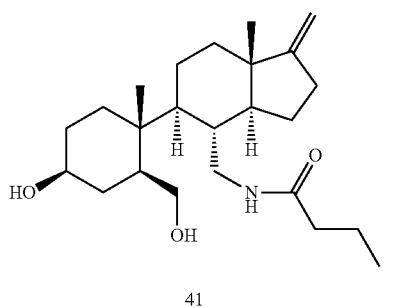

To a solution of (1S,3S,4R)-4-((3aS,4R,5S,7aS)-4-(aminomethyl)-7a-methyl-1-methyleneoctahydro-1H-inden-5-yl)-3-(hydroxymethyl)-4-methylcyclohexanol acetate (Compound No. 1, 96 mg, 0.25 mmol), O-(benzotriazol-1-yl)-N,N,N',N'-tetramethyluronium tetrafluoroborate (89 mg, 0.28 mmol), and butyric acid (0.025 mL, 0.27 mmol) in DMF (1.3 mL) was added N,N-diisopropylethylamine (0.11 mL, 0.63 mmol), and the solution was stirred at room temperature for 18 h. The mixture was concentrated, and the residue was partitioned between EtOAc (35 mL) and saturated aqueous NaHCO$_3$ (10 mL). The organic layer was washed with brine (5×10 mL) then dried (MgSO$_4$) and concentrated. The residue was purified by chromatography on silica gel (7:93 MeOH/CH$_2$Cl$_2$) to give N-(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)butyramide (Compound No. 41, 39 mg, 39%) as colourless crystals. $^1$H NMR (CD$_3$OD): δ7.55 (br s, 1H), 4.64 (s, 2H), 3.72 (m, 1H), 3.31-3.48 (m, 3H), 3.13 (m, 1H), 2.49 (m, 1H), 2.13-2.28 (m, 4H), 1.20-1.89 (m, 17H), 0.99 (s, 3H), 0.93 (t, J=7.2 Hz, 3H), 0.82 (s, 3H). ES-MS m/z 392 ([M+1]$^+$).

Example 24

Synthesis of N-(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)pentanamide (Compound No. 42)

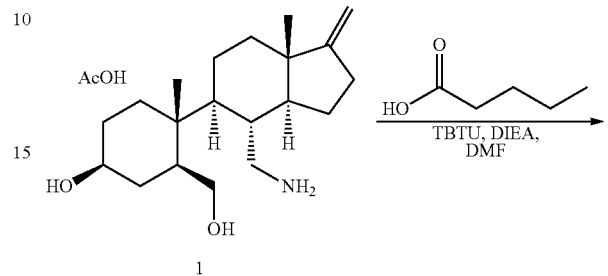

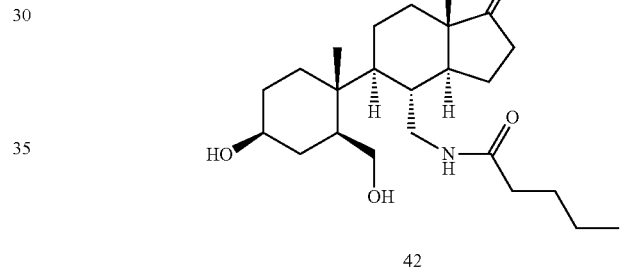

To a solution of (1S,3S,4R)-4-((3aS,4R,5S,7aS)-4-(aminomethyl)-7a-methyl-1-methyleneoctahydro-1H-inden-5-yl)-3-(hydroxymethyl)-4-methylcyclohexanol acetate (Compound No. 1, 94 mg, 0.25 mmol), O-(benzotriazol-1-yl)-N,N,N',N'-tetramethyluronium tetrafluoroborate (87 mg, 0.27 mmol), and valeric acid (0.054 mL, 0.50 mmol) in DMF (1.2 mL) was added N,N-diisopropylethylamine (0.10 mL, 0.57 mmol), and the solution was stirred at room temperature for 21 h. The mixture was concentrated, and the residue was partitioned between EtOAc (35 mL) and saturated aqueous NaHCO$_3$ (10 mL). The organic layer was washed with brine (5×10 mL) then dried (MgSO$_4$) and concentrated. The residue was purified by chromatography on silica gel (7:93 MeOH/CH$_2$Cl$_2$) to give N-(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)pentanamide (Compound No. 42, 41 mg, 41%) as a colourless solid. $^1$H NMR (CD$_3$OD): δ7.55 (br s, 1H), 4.64 (s, 2H), 3.72 (m, 1H), 3.31-3.48 (m, 3H), 3.13 (m, 1H), 2.49 (m, 1H), 2.13-2.27 (m, 4H), 1.20-1.86 (m, 19H), 0.99 (s, 3H), 0.93 (t, J=7.2 Hz, 3H), 0.82 (s, 3H). ES-MS m/z 406 ([M+1]$^+$).

Example 25

Synthesis of (1S,3S,4R)-4-((3aS,4R,5S,7aS)-4-((1H-pyrazol-1-yl)methyl)-7a-methyl-1-methyleneoctahydro-1H-inden-5-yl)-3-(hydroxymethyl)-4-methyl-cyclohexanol (Compound No. 48)

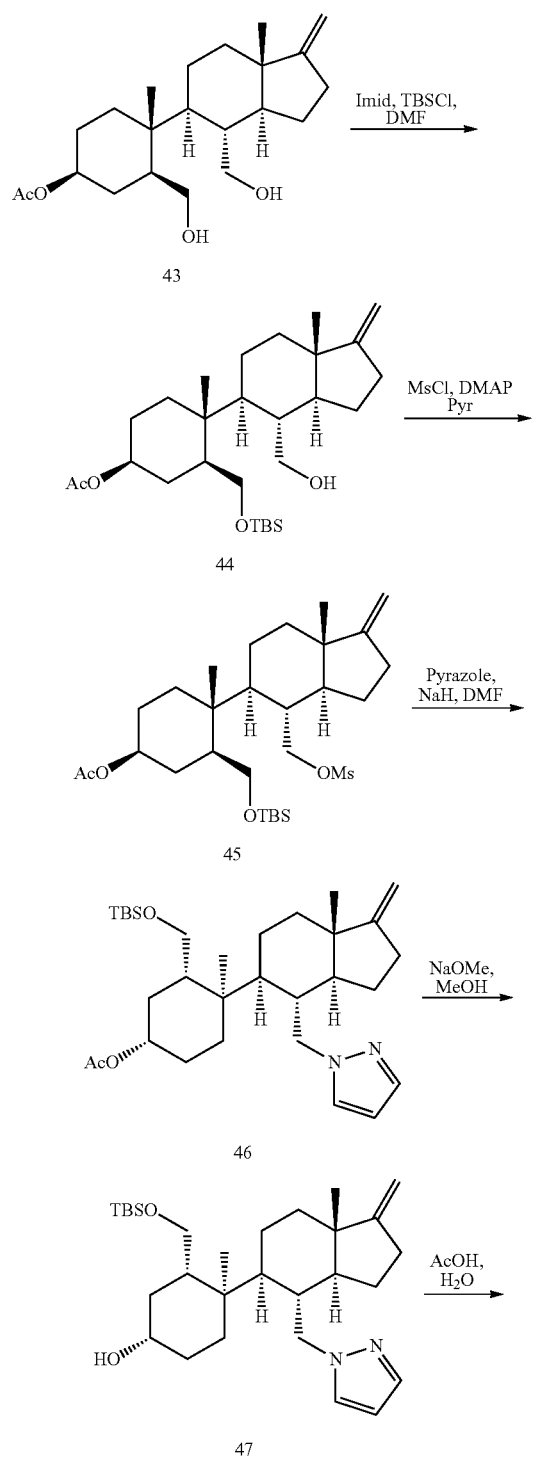

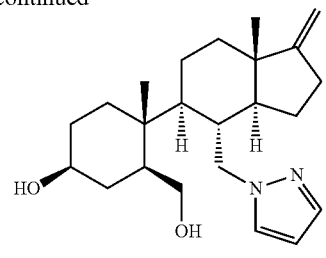

A. A solution of (1S,3S,4R)-3-(hydroxymethyl)-4-((3aS,4R,5S,7aS)-4-(hydroxymethyl)-7a-methyl-1-methyleneoctahydro-1H-inden-5-yl)-4-methylcyclohexyl acetate (Compound No. 43, 3.60 g, 9.90 mmol), TBSCl (1.64 g, 10.9 mmol), imidazole (1.48 g, 21.8 mmol) in DMF (50 mL) was stirred 5 h at room temperature under nitrogen. The solution was poured into water (90 mL), extracted with Et$_2$O (2×100 mL), dried (MgSO$_4$) and concentrated. The residue was purified using chromatography on silica gel (15% EtOAc/hexanes) to afford (1S,3S,4R)-3-(((tert-butyldimethylsilyl)oxy)methyl)-4-((3aS,4R,5S,7aS)-4-(hydroxymethyl)-7a-methyl-1-methyleneoctahydro-1H-inden-5-yl)-4-methylcyclohexyl acetate (Compound No. 44, 3.61 g, 76%) as a white foam.

B. To a solution of (1S,3S,4R)-3-(((tert-butyldimethylsilyl)oxy)methyl)-4-((3aS,4R,5S,7aS)-4-(hydroxymethyl)-7a-methyl-1-methyleneoctahydro-1H-inden-5-yl)-4-methylcyclohexyl acetate (Compound No. 44, 1.00 g, 2.09 mmol) and DMAP (24 mg, 0.2 mmol) in pyridine (10 mL) at 0° C. under nitrogen was added MsCl (0.50 mL, 6.3 mmol). After 2.5 h saturated NaHCO$_3$ solution (10 mL) was added and the solution was stirred at room temperature for 20 min. The solution was diluted with EtOAc (200 mL), washed with brine, dried (MgSO$_4$) and concentrated to afford (1S,3S,4R)-3-(((tert-butyldimethylsilyl)oxy)methyl)-4-methyl-4-((3aS,4R,5S,7aS)-7a-methyl-1-methylene-4-(((methylsulfonyl)oxy)methyl)octahydro-1H-inden-5-yl)cyclohexyl acetate (Compound No. 45, 1.15 g, 99%) as a white solid.

C. To a solution of pyrazole (73 mg, 1.1 mmol) in DMF (5 mL) at 0° C. under nitrogen was added NaH (43 mg of a 60% solution in mineral oil, 1.1 mmol). After 45 min, (1S,3S,4R)-3-(((tert-butyldimethylsilyl)oxy)methyl)-4-methyl-4-((3aS,4R,5S,7aS)-7a-methyl-1-methylene-4-(((methylsulfonyl)oxy)methyl)octahydro-1H-inden-5-yl)cyclohexyl acetate (Compound No. 45, 200 mg, 0.36 mmol) was added and the reaction was stirred at room temperature for 22 h. The solution was cooled in ice then saturated NaHCO$_3$ solution (3 mL) was added. The solution was diluted with Et$_2$O (100 mL), washed with brine, dried (MgSO$_4$) and concentrated. The resulting colourless oil was purified using chromatography on silica gel (10%, 30% and 40% EtOAc/hexanes) to afford (1S,3S,4R)-4-((3aS,4R,5S,7aS)-4-((1H-1,2,4-triazol-1-yl)methyl)-7a-methyl-1-methyleneoctahydro-1H-inden-5-yl)-3-(((tert-butyldimethylsilyl)oxy)methyl)-4-methylcyclohexyl acetate (Compound 46, 124 mg, 65%) as a colourless film and (1S,3S,4R)-4-((3aS,4R,5S,7aS)-4-((1H-pyrazol-1-yl)methyl)-7a-methyl-1-methyleneoctahydro-1H-inden-5-yl)-3-(((tert-butyldimethylsilyl)oxy)methyl)-4-methylcyclohexanol (Compound No. 5, 65 mg, 37%) as a colourless film.

D. A solution of (1S,3S,4R)-4-((3aS,4R,5S,7aS)-4-((1H-1,2,4-triazol-1-yl)methyl)-7a-methyl-1-methyleneoctahydro-1H-inden-5-yl)-3-(((tert-butyldimethylsilyl)oxy)

methyl)-4-methylcyclohexyl acetate (Compound No. 46, 124 mg, 0.23 mmol) and sodium methoxide (0.4 mL of a 5.4 M solution in methanol, 2.3 mmol) in methanol (5 mL) was stirred at room temperature for 23 h. The solution was cooled in ice then was added (1S,3S,4R)-4-((3aS,4R,5S,7aS)-4-((1H-pyrazol-1-yl)methyl)-7a-methyl-1-methyleneoctahydro-1H-inden-5-yl)-3-(((tert-butyldimethylsilyl)oxy)methyl)-4-methylcyclohexanol (Compound No. 47, 65 mg, 0.13 mmol) in acetic acid (16 mL) and water (4 mL). The solution was stirred at room temperature for 20 hours then was concentrated and purified by chromatography on silica gel (40% then 80% EtOAc/hexanes) to afford (1S,3S,4R)-4-((3aS,4R,5S,7aS)-4-((1H-pyrazol-1-yl)methyl)-7a-methyl-1-methyleneoctahydro-1H-inden-5-yl)-3-(hydroxymethyl)-4-methylcyclohexanol (Compound No. 48, 77 mg, 56%) as a white solid. $^1$H NMR (CDCl$_3$): δ7.42 (s, 1H), 7.35 (s, 1H), 6.20 (s, 1H), 4.58 (s, 2H), 4.50 (s, 1H), 3.98 (m, 1H), 3.70 (m, 1H), 3.48 (m, 1H), 3.19 (m, 1H), 2.28 (m, 2H), 2.05 (m, 2H), 1.80 (m, 4H), 1.1-1.4 (9H), 1.02 (s, 3H), 0.85 (m, 1H), 0.70 (s, 3H). ES-MS m/z 373 ([M+1]$^+$).

Example 26

Synthesis of (1S,3S,4R)-4-((3aS,4R,5S,7aS)-4-((1H-1,2,4-triazol-1-yl)methyl)-7a-methyl-1-methyleneoctahydro-1H-inden-5-yl)-3-(hydroxymethyl)-4-methylcyclohexanol (Compound No. 50)

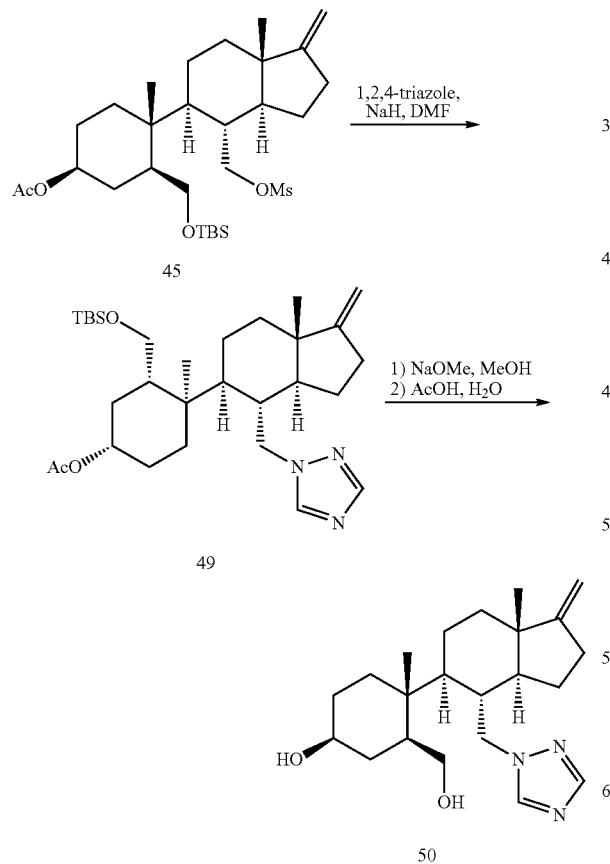

A. To a solution of 1,2,4-triazole (253 mg, 3.60 mmol) in DMF (5 mL) at 0° C. under nitrogen was added NaH (144 mg of a 60% solution in mineral oil, 3.60 mmol). After 70 min, (1S,3S,4R)-3-(((tert-butyldimethylsilyl)oxy)methyl)-4-methyl-4-((3aS,4R,5S,7aS)-7a-methyl-1-methylene-4-(((methylsulfonyl)oxy)methyl)octahydro-1H-inden-5-yl)cyclohexyl acetate (Compound No. 45, 200 mg, 0.36 mmol) was added and the reaction was stirred at room temperature for 25 h then was heated at 50° C. for 18 h then was heated at 80° C. for 4 h. The solution was cooled in ice then saturated NaHCO$_3$ solution (3 mL) was added. The solution was diluted with Et$_2$O (100 mL), washed with brine, dried (MgSO$_4$) and concentrated. The resulting colourless film was purified using chromatography on silica gel (30%, 40% and 50% EtOAc/hexanes) to afford (1S,3S,4R)-4-((3aS,4R,5S,7aS)-4-((1H-1,2,4-triazol-1-yl)methyl)-7a-methyl-1-methyleneoctahydro-1H-inden-5-yl)-3-(((tert-butyldimethylsilyl)oxy)methyl)-4-methylcyclohexyl acetate (Compound 49, 0.17 g, 89%) as a colourless film.

B. A solution of (1S,3S,4R)-4-((3aS,4R,5S,7aS)-4-((1H-1,2,4-triazol-1-yl)methyl)-7a-methyl-1-methyleneoctahydro-1H-inden-5-yl)-3-(((tert-butyldimethylsilyl)oxy)methyl)-4-methylcyclohexyl acetate (Compound No. 49, 0.17 g, 0.32 mmol) and sodium methoxide (0.66 mL of a 5.4 M solution in methanol, 3.6 mmol) in methanol (23 mL) was stirred at room temperature for 4 h. To the solution was added acetic acid (32 mL) and water (8 mL). The solution was stirred at 40° C. for 3 d then was concentrated and purified by chromatography on silica gel (5% then 10% MeOH/EtOAc) to afford (1S,3S,4R)-4-((3aS,4R,5S,7aS)-4-((1H-1,2,4-triazol-1-yl)methyl)-7a-methyl-1-methyleneoctahydro-1H-inden-5-yl)-3-(hydroxymethyl)-4-methylcyclohexanol (Compound No. 50, 110 mg, 92%) as a white foam. $^1$H NMR (CDCl$_3$): δ8.04 (s, 1H), 7.92 (s, 1H), 4.62 (s, 2H), 4.45 (m, 1H), 4.25 (m, 1H), 3.78 (m, 1H), 3.60 (m, 1H), 3.32 (m, 1H), 2.40 (m, 1H), 2.20 (m, 3H), 1.0-2.0 (15H), 1.18 (s, 3H), 0.85 (m, 1H), 0.80 (s, 3H). ES-MS m/z 374 ([M+1]$^+$).

Example 27

Synthesis of (1S,3S,4R)-4-((3aS,4R,5S,7aS)-4-((1H-benzo[d]imidazol-1-yl)methyl)-7a-methyl-1-methyleneoctahydro-1H-inden-5-yl)-3-(hydroxymethyl)-4-methylcyclohexanol (Compound No. 53)

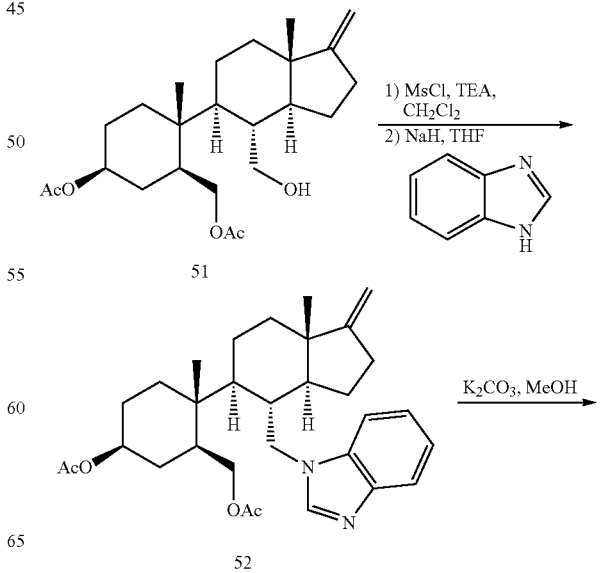

-continued

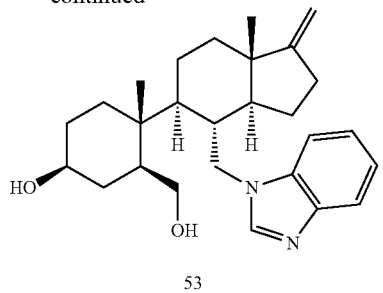

53

A. To a solution of ((1S,2R,5S)-5-acetoxy-2-((3aS,4R,5S,7aS)-4-(hydroxymethyl)-7a-methyl-1-methyleneoctahydro-1H-inden-5-yl)-2-methylcyclohexyl)methyl acetate (Compound No. 51, 222 mg, 0.546 mmol) and Et$_3$N (0.099 mL, 0.71 mmol) in CH$_2$Cl$_2$ (5.5 mL) at 0° C. under argon was added MsCl (0.047 mL, 0.61 mmol), and the solution was stirred at room temperature for 1 h. The solution was diluted with CH$_2$Cl$_2$ (15 mL) and washed with saturated aqueous NaHCO$_3$ (15 mL), and the aqueous layer was extracted with CH$_2$Cl$_2$ (2×10 mL). The combined organic layers were dried (MgSO$_4$) and concentrated. Azeotropic removal of impurities was carried out with toluene (3×10 mL), and the mesylate residue was dissolved in THF (1.1 mL). A solution of benzimidazole (52 mg, 0.44 mmol) in THF (1.1 mL) was cooled to 0° C. under argon and NaH (35 mg of a 60% solution, 0.88 mmol) was added then stirred at room temperature for 0.5 h. The mesylate solution from above (1.1 mL) was added and heated to 65° C. for 17 h. The mixture was diluted with H$_2$O (10 mL) followed by EtOAc (30 mL), and the organic layer was washed with H$_2$O (10 mL) and brine (10 mL) then dried (MgSO$_4$) and concentrated. The residue was partially purified by chromatography on silica gel (3:97 MeOH/CH$_2$Cl$_2$) to give (1S,3S,4R)-4-((3aS,4R,5S,7aS)-4-((1H-benzo[d]imidazol-1-yl)methyl)-7a-methyl-1-methyleneoctahydro-1H-inden-5-yl)-3-(acetoxymethyl)-4-methylcyclohexyl acetate (Compound No. 52, 74 mg) as a colourless oil.

B. To a solution of (1S,3S,4R)-4-((3aS,4R,5S,7aS)-4-((1H-benzo[d]imidazol-1-yl)methyl)-7a-methyl-1-methyleneoctahydro-1H-inden-5-yl)-3-(acetoxymethyl)-4-methylcyclohexyl acetate (Compound No. 52, 74 mg) in MeOH (3 mL) was added potassium carbonate (81 mg, 0.59 mmol) and heated to 40° C. for 1 h. The mixture was concentrated, and the residue was purified by chromatography on silica gel (10:90 MeOH/EtOAc) to give (1S,3S,4R)-4-((3aS,4R,5S,7aS)-4-((1H-benzo[d]imidazol-1-yl)methyl)-7a-methyl-1-methyleneoctahydro-1H-inden-5-yl)-3-(hydroxymethyl)-4-methylcyclohexanol (Compound No. 53, 16 mg, 9% over 3 steps) as a colourless solid. $^1$H NMR (CD$_3$OD): δ8.29 (s, 1H), 7.67 (d, J=7.8 Hz, 1H), 7.56 (d, J=8.1 Hz, 1H), 7.26-7.37 (m, 2H), 4.70 (m, 1H), 4.62 (s, 1H), 4.56 (s, 1H), 4.19 (dd, J=14, 9.8 Hz, 1H), 3.76 (m, 1H), 3.52 (m, 1H), 3.18 (m, 1H), 2.53 (m, 1H), 2.19 (m, 2H), 1.23-2.01 (m, 13H), 1.09 (s, 3H), 0.94 (m, 1H), 0.73 (m, 4H). ES-MS m/z 423 ([M+1]$^+$).

Example 28

Synthesis of (1S,3S,4R)-4-((3aS,4R,5S,7aS)-4-(2-aminoethyl)-7a-methyl-1-methyleneoctahydro-1H-inden-5-yl)-3-(hydroxymethyl)-4-methylcyclohexanol (Compound No. 56)

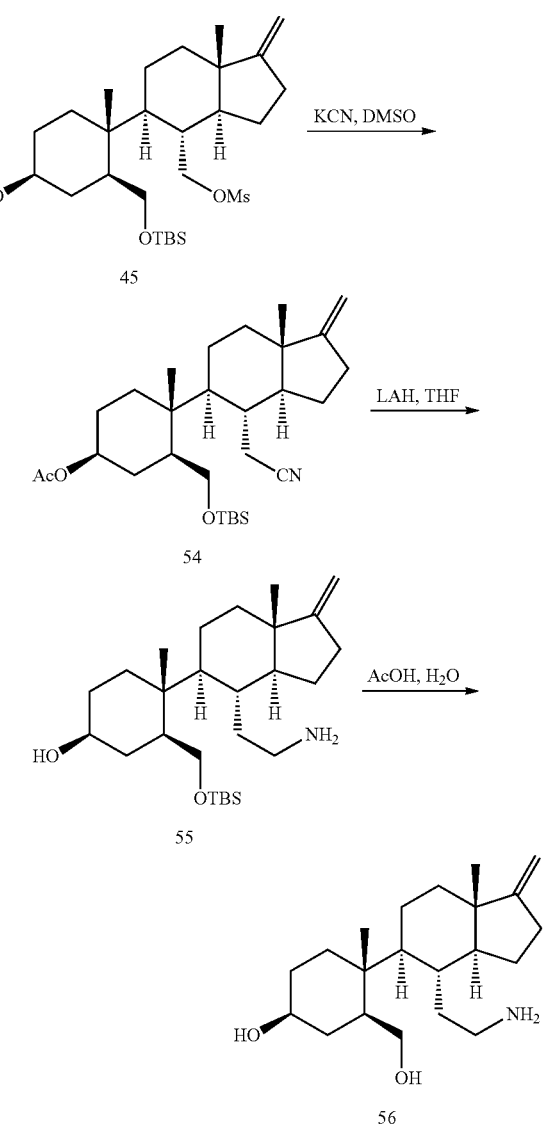

A. A solution of (1S,3S,4R)-3-(((tert-butyldimethylsilyl)oxy)methyl)-4-methyl-4-((3aS,4R,5S,7aS)-7a-methyl-1-methylene-4-(((methylsulfonyl)oxy)methyl)octahydro-1H-inden-5-yl)cyclohexyl acetate (Compound No. 45, 1.14 g, 2.05 mmol) and KCN (0.42 g, 6.14 mmol) in DMSO (10 mL) was stirred at 60° C. under nitrogen for 16 h. THF (10 mL) was added, then after 1 h the solution was cooled to room temperature, poured into water (40 mL), extracted with Et$_2$O (2×100 mL), washed with brine, dried (MgSO$_4$) and concentrated. The solid residue was purified by chromatography on silica gel (10% then 20% EtOAc/hexanes) to afford (1S,3S,4R)-3-(((tert-butyldimethylsilyl)oxy)methyl)-4-((3aS,4R,5S,7aS)-4-(cyanomethyl)-7a-methyl-1-methyleneoctahydro-1H-inden-5-yl)-4-methylcyclohexyl acetate (Compound No. 54, 0.92 g, 92%) as a white solid.

B. To a solution of (1S,3S,4R)-3-(((tert-butyldimethylsilyl)oxy)methyl)-4-((3aS,4R,5S,7aS)-4-(cyanomethyl)-7a-methyl-1-methyleneoctahydro-1H-inden-5-yl)-4-methylcyclohexyl acetate (Compound No. 54, 0.92 g, 1.9 mmol) in THF (10 mL) at 0° C. under nitrogen was added LAH (1.9 mL of a 2 M solution in THF, 3.8 mmol). After 22 h, the solution was cooled in ice then added Na$_2$SO$_4$.10H$_2$O (1.22 g) and stirred the solution at room temperature for 40 min. The solution was filtered through Celite and eluted with EtOAc. The residue was purified using chromatography on silica gel (20% MeOH/EtOAc then 20% MeOH/EtOAc with 5% Et$_3$N) to afford (1S,3S,4R)-4-((3aS,4R,5S,7aS)-4-(2-aminoethyl)-7a-methyl-1-methyleneoctahydro-1H-inden-5-yl)-3-(((tert-butyldimethylsilyl)oxy)methyl)-4-methylcyclohexanol (Compound No. 55, 0.48 g, 56%) as a white film.

C. A solution of (1S,3S,4R)-4-((3aS,4R,5S,7aS)-4-(2-aminoethyl)-7a-methyl-1-methyleneoctahydro-1H-inden-5-yl)-3-(((tert-butyldimethylsilyl)oxy)methyl)-4-methylcyclohexanol (Compound No. 55, 0.48 g, 1.1 mmol) in acetic acid (32 mL) and water (8 mL) was stirred at room temperature for 24 h then was concentrated. The residue was purified using chromatography on silica gel (20% MeOH/EtOAc then 20% MeOH/EtOAc with 5% Et$_3$N) to afford (1S,3S,4R)-4-((3aS,4R,5S,7aS)-4-(2-aminoethyl)-7a-methyl-1-methyleneoctahydro-1H-inden-5-yl)-3-(hydroxymethyl)-4-methylcyclohexanol (Compound No. 56, 364 mg, 100%) as a white foam.

Example 29

Synthesis of (1S,3S,4R)-4-((3aS,4R,5S,7aS)-4-((1H-indol-1-yl)methyl)-7a-methyl-1-methyleneoctahydro-1H-inden-5-yl)-3-(hydroxymethyl)-4-methylcyclohexanol (Compound No. 57)

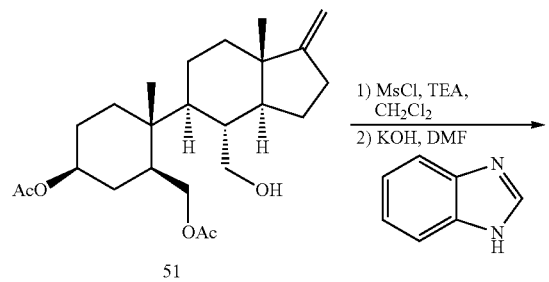

To a solution of ((1S,2R,5S)-5-acetoxy-2-((3aS,4R,5S,7aS)-4-(hydroxymethyl)-7a-methyl-1-methyleneoctahydro-1H-inden-5-yl)-2-methylcyclohexyl)methyl acetate (Compound No. 51, 243 mg, 0.598 mmol) and Et$_3$N (0.11 mL, 0.79 mmol) in CH$_2$Cl$_2$ (6.0 mL) at 0° C. under argon was added MsCl (0.051 mL, 0.66 mmol), and the solution was stirred at room temperature for 1 h. The solution was diluted with CH$_2$Cl$_2$ (15 mL) and washed with saturated aqueous NaHCO$_3$ (15 mL), and the aqueous layer was extracted with CH$_2$Cl$_2$ (2×10 mL). The combined organic layers were dried (MgSO$_4$) and concentrated. Azeotropic removal of impurities was carried out with toluene (3×10 mL), and the mesylate residue was dissolved in DMF (0.9 mL). To a suspension of KOH (168 mg, 2.99 mmol) in DMF (0.3 mL) was added indole (140 mg, 1.20 mmol), and the mixture was stirred under argon at room temperature for 15 min. The mesylate solution from above (0.9 mL) was added dropwise, and the mixture was stirred at room temperature for 1 h then heated to 50° C. for 20 h. The mixture was diluted with EtOAc (35 mL), and the organic layer was washed with brine (6×15 mL) then dried (MgSO$_4$) and concentrated. The residue was purified by chromatography on silica gel (90:10 EtOAc/hexanes) to give (1S,3S,4R)-4-((3aS,4R,5S,7aS)-4-((1H-indol-1-yl)methyl)-7a-methyl-1-methyleneoctahydro-1H-inden-5-yl)-3-(hydroxymethyl)-4-methylcyclohexanol (Compound No. 57, 43 mg, 17%) as a colourless solid ($^1$H NMR (CDCl$_3$): δ7.62 (d, J=7.8 Hz, 1H), 7.19-7.32 (m, 3H), 7.09 (m, 1H), 6.52 (d, J=2.7 Hz, 1H), 4.61 (s, 1H), 4.58 (s, 1H), 4.52 (dd, J=14, 3.0 Hz, 1H), 3.93 (dd, J=14, 9.0 Hz, 1H), 3.78 (m, 1H), 3.62 (m, 1H), 3.32 (m, 1H), 2.39 (m, 1H), 2.20 (m, 2H), 1.25-1.99 (m, 13H), 1.03 (m, 4H), 0.83 (m, 4H). ES-MS m/z 480 ([M−1+60]$^-$).

Example 30

Synthesis of (1S,3S,4R)-3-(hydroxymethyl)-4-((3aS,4R,5S,7aS)-4-(indolin-1-ylmethyl)-7a-methyl-1-methyleneoctahydro-1H-inden-5-yl)-4-methylcyclohexanol (Compound No. 59)

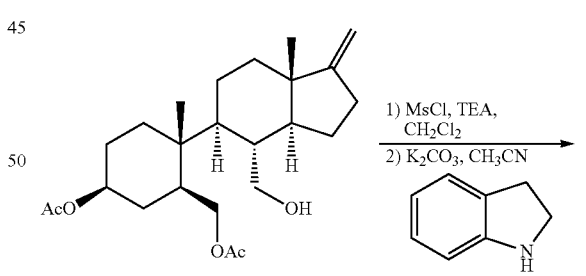

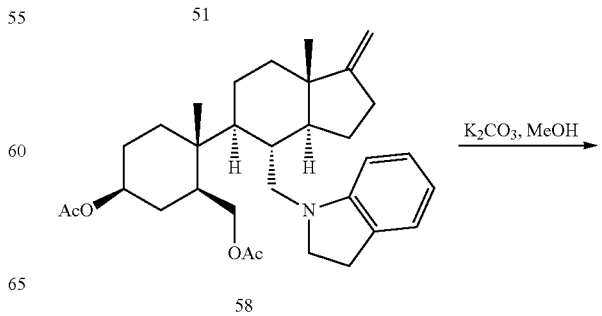

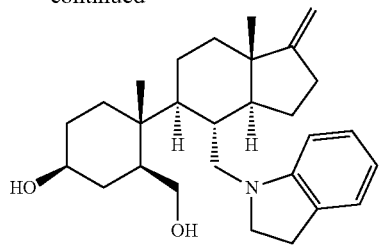

59

A. To a solution of ((1S,2R,5S)-5-acetoxy-2-((3aS,4R,5S,7aS)-4-(hydroxymethyl)-7a-methyl-1-methyleneoctahydro-1H-inden-5-yl)-2-methylcyclohexyl)methyl acetate (Compound No. 51, 244 mg, 0.600 mmol) and Et$_3$N (0.11 mL, 0.79 mmol) in CH$_2$Cl$_2$ (6.0 mL) at 0° C. under argon was added MsCl (0.051 mL, 0.66 mmol), and the solution was stirred at room temperature for 1.5 h. The solution was diluted with CH$_2$Cl$_2$ (15 mL) and washed with saturated aqueous NaHCO$_3$ (15 mL), and the aqueous layer was extracted with CH$_2$Cl$_2$ (2×10 mL). The combined organic layers were dried (MgSO$_4$) and concentrated, and azeotropic removal of impurities was carried out with toluene (3×10 mL). To the mesylate residue was added indoline (143 mg, 1.20 mmol), potassium carbonate (415 mg, 3.00 mmol) and CH$_3$CN (2.0 mL), and the mixture was heated to reflux under argon for 19 h. The mixture was partitioned between CH$_2$Cl$_2$ (15 mL) and H$_2$O (10 mL), and the aqueous phase was extracted with CH$_2$Cl$_2$ (2×10 mL). The combined organic layers were dried (MgSO$_4$) and concentrated, and the residue was purified by chromatography on silica gel (12:88 EtOAc/hexanes) to give ((1S,2R,5S)-5-acetoxy-2-((3aS,4R,5S,7aS)-4-(indolin-1-ylmethyl)-7a-methyl-1-methyleneoctahydro-1H-inden-5-yl)-2-methylcyclohexyl) methyl acetate (Compound No. 58, 81 mg, 27% over 2 steps) as a colourless film.

B. To a solution of ((1S,2R,5S)-5-acetoxy-2-((3aS,4R,5S,7aS)-4-(indolin-1-ylmethyl)-7a-methyl-1-methyleneoctahydro-1H-inden-5-yl)-2-methylcyclohexyl)methyl acetate (Compound No. 58, 81 mg, 0.16 mmol) in MeOH (3.2 mL) was added potassium carbonate (88 mg, 0.64 mmol) and heated to 40° C. for 1 h then concentrated. Acetone (20 mL) was added, and the mixture was filtered and concentrated. The residue was purified by chromatography on silica gel (85:15 EtOAc/hexanes) to give (1S,3S,4R)-3-(hydroxymethyl)-4-((3aS,4R,5S,7aS)-4-(indolin-1-ylmethyl)-7a-methyl-1-methyleneoctahydro-1H-inden-5-yl)-4-methylcyclohexanol (Compound No. 59, 31 mg, 46%) as a colourless solid. $^1$H NMR (CDCl$_3$): δ7.06 (m, 2H), 6.64 (m, 1H), 6.41 (d, J=7.8 Hz, 1H), 4.64 (s, 2H), 3.74 (m, 1H), 3.57 (m, 1H), 3.27-3.39 (m, 4H), 2.92 (m, 3H), 2.44 (m, 1H), 2.16 (m, 2H), 1.25-1.92 (m, 15H), 1.07 (s, 3H), 0.83 (s, 3H). ES-MS m/z 424 ([M+1]$^+$).

Example 31

Synthesis of (1S,3S,4R)-4-((3aS,4R,5S,7aS)-4-((3,5-dimethoxybenzylamino)methyl)-7a-methyl-1-methyleneoctahydro-1H-inden-5-yl)-3-(hydroxymethyl)-4-methylcyclohexanol (Compound No. 64)

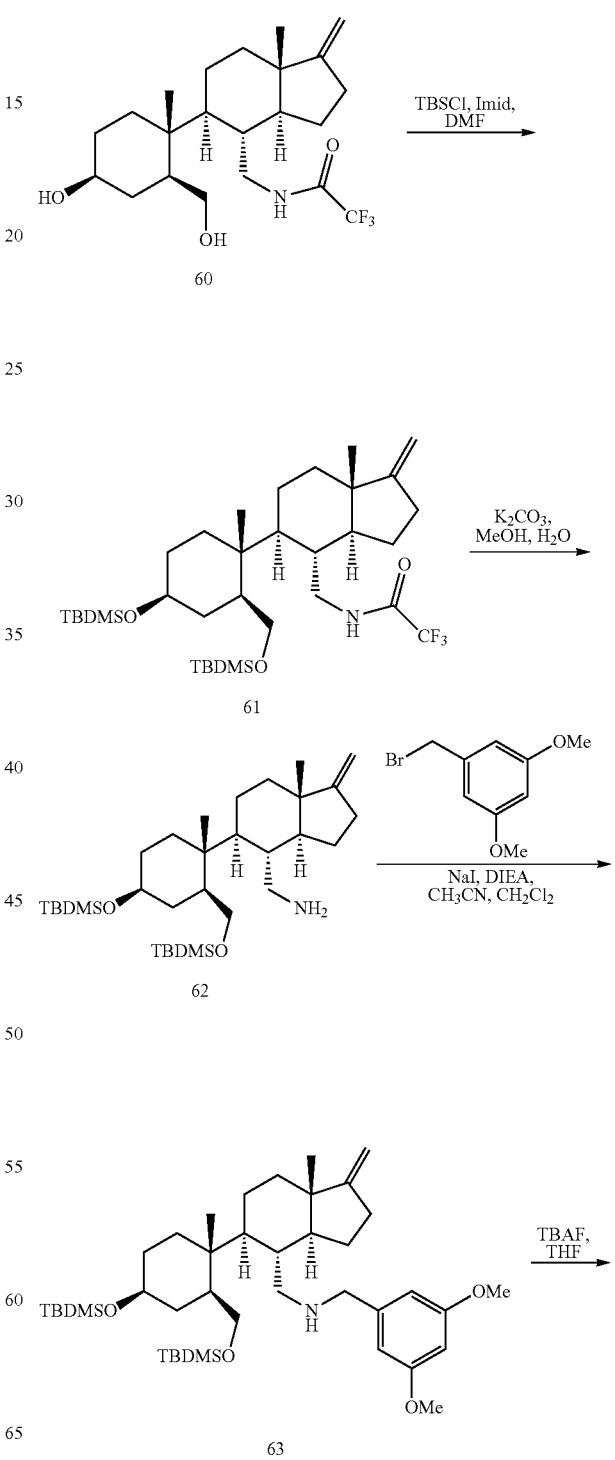

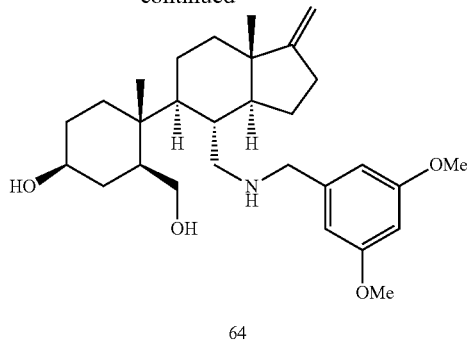

64

A. To a solution of 2,2,2-trifluoro-N-(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)acetamide (Compound No. 60, 3.21 g, 7.69 mmol) and imidazole (1.20 g, 17.6 mmol) in DMF (15 mL) at 0° C. was added TBSCl (2.43 g, 16.1 mmol), and the solution was stirred at room temperature under argon for 3 d. The mixture was diluted with EtOAc (70 mL) and washed with H₂O (2×20 mL) and brine (6×20 mL) then dried (MgSO₄) and concentrated. The residue was purified by chromatography on silica gel (10:90 EtOAc/hexanes) to give N-(((3aS,4R,5S,7aS)-5-((1R,2S,4S)-4-((tert-butyldimethylsilyl)oxy)-2-(((tert-butyldimethylsilyl)oxy)methyl)-1-methylcyclohexyl)-7a-methyl-1-methyleneoctahydro-1H-inden-4-yl)methyl)-2,2,2-trifluoroacetamide (Compound No. 61, 4.60 g, 93%) as a colourless foam.

B. To a solution of N-(((3aS,4R,5S,7aS)-5-((1R,2S,4S)-4-((tert-butyldimethylsilyl)oxy)-2-(((tert-butyldimethylsilyl)oxy)methyl)-1-methylcyclohexyl)-7a-methyl-1-methyleneoctahydro-1H-inden-4-yl)methyl)-2,2,2-trifluoroacetamide (Compound No. 61, 4.59 g, 7.10 mmol) in 9:1 MeOH/H₂O (71 mL) was added potassium carbonate (2.95 g, 21.3 mmol) and heated to 60° C. for 18 h. The mixture was concentrated and H₂O (10 mL) was added. The mixture was extracted with CH₂Cl₂ (40 mL then 2×15 mL), and the combined organic layers were dried (MgSO₄) and concentrated. The residue was purified by chromatography on silica gel (5:95 MeOH/CH₂Cl₂) to give ((3aS,4R,5S,7aS)-5-((1R,2S,4S)-4-((tert-butyldimethylsilyl)oxy)-2-(((tert-butyldimethylsilyl)oxy)methyl)-1-methylcyclohexyl)-7a-methyl-1-methyleneoctahydro-1H-inden-4-yl)methanamine (Compound No. 62, 3.68 g, 94%) as a colourless foam.

C. To a mixture of ((3aS,4R,5S,7aS)-5-((1R,2S,4S)-4-((tert-butyldimethylsilyl)oxy)-2-(((tert-butyldimethylsilyl)oxy)methyl)-1-methylcyclohexyl)-7a-methyl-1-methyleneoctahydro-1H-inden-4-yl)methanamine (Compound No. 62, 167 mg, 0.304 mmol), NaI (6 mg, 0.04 mmol) and DIEA (0.063 mL, 0.36 mmol) in CH₃CN (3.0 mL) was added 3,5-dimethoxybenzyl bromide (95%, 74 mg, 0.30 mmol) followed by CH₂Cl₂ (1 mL). The mixture was stirred at room temperature for 24 h then concentrated. The residue was partitioned between EtOAc (40 mL) and saturated aqueous NaHCO₃ (15 mL). The organic layer was washed with brine (4×15 mL) then dried (MgSO₄) and concentrated to give 1-((3aS,4R,5S,7aS)-5-((1R,2S,4S)-4-((tert-butyldimethylsilyl)oxy)-2-(((tert-butyldimethylsilyl)oxy)methyl)-1-methylcyclohexyl)-7a-methyl-1-methyleneoctahydro-1H-inden-4-yl)-N-(3,5-dimethoxybenzyl)methanamine (Compound No. 63, 216 mg) as a colourless foam.

D. TBAF (1.2 mL of a 1 M solution in THF, 1.2 mmol) was added to a solution of 1-((3aS,4R,5S,7aS)-5-((1R,2S,4S)-4-((tert-butyldimethylsilyl)oxy)-2-(((tert-butyldimethylsilyl)oxy)methyl)-1-methylcyclohexyl)-7a-methyl-1-methyleneoctahydro-1H-inden-4-yl)-N-(3,5-dimethoxybenzyl)methanamine (Compound No 63, 216 mg) in THF (6.0 mL) and stirred at room temperature for 18 h. The solution was concentrated, and the residue was purified by chromatography on silica gel (6:94 MeOH/EtOAc) to give (1S,3S,4R)-4-((3aS,4R,5S,7aS)-4-((3,5-dimethoxybenzylamino)methyl)-7a-methyl-1-methyleneoctahydro-1H-inden-5-yl)-3-(hydroxymethyl)-4-methylcyclohexanol (Compound No. 64 127 mg, 89% over 2 steps) as a colourless solid. ¹H NMR (CD₃OD): δ6.48 (s, 2H), 6.36 (s, 1H), 4.61 (s, 2H), 3.55-3.76 (m, 9H), 3.40 (m, 1H), 3.12 (m, 1H), 2.77 (m, 1H), 2.41-2.58 (m, 2H), 2.10-2.29 (m, 2H), 1.18-1.82 (m, 15H), 1.00 (s, 3H), 0.77 (s, 3H). ES-MS m/z 472 ([M+1]⁺).

Example 32

Synthesis of (1S,3S,4R)-4-((3aS,4R,5S,7aS)-4-(((1H-benzo[d]imidazol-2-yl)methylamino)methyl)-7a-methyl-1-methyleneoctahydro-1H-inden-5-yl)-3-(hydroxymethyl)-4-methylcyclohexanol (Compound No. 68)

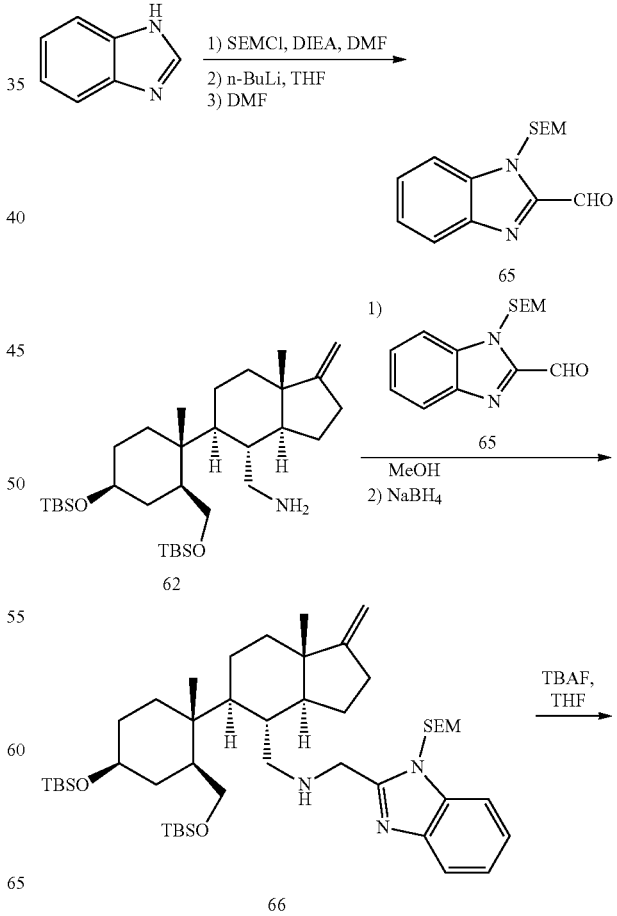

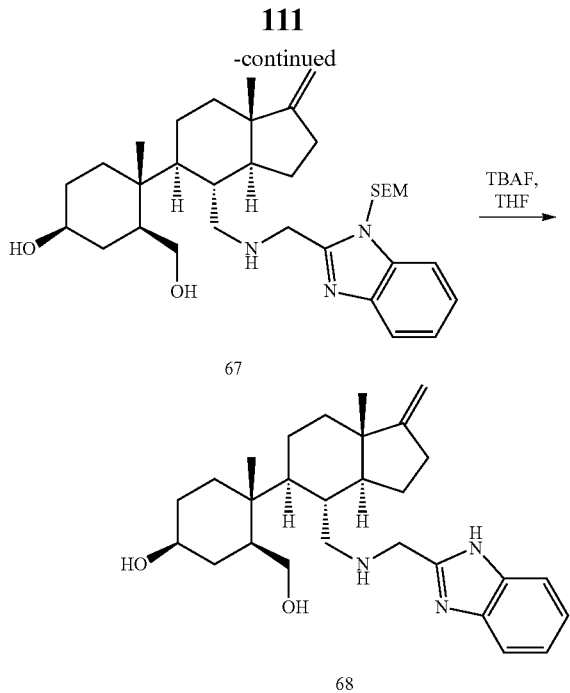

A. A solution of 2-(trimethylsilyl)ethoxymethyl chloride (531 mg, 3.18 mmol) in DMF (2.0 mL) was added to a solution of benzimidazole (314 mg, 2.66 mmol) and DIEA (0.69 mL, 4.0 mmol) in DMF (3.3 mL) then heated to 80° C. for 1.5 h. The mixture was diluted with EtOAc (40 mL) and washed with brine (6×18 mL) then dried (MgSO$_4$) and concentrated. Azeotropic removal of impurities was carried out with MeOH (10 mL) then CH$_2$Cl$_2$ (3×10 mL). The residue was dissolved in THF (13 mL) and cooled to −40° C. under argon. n-Butyllithium (1.7 mL of a 1.9 M solution in hexanes, 3.2 mmol) was added and stirred at −40° C. for 20 min then DMF (0.51 mL, 6.6 mmol) was added at −40° C. The mixture was allowed to warm to room temperature over 4 h then stirred at room temperature for 3 d. The mixture was diluted with EtOAc (30 mL) and washed with H$_2$O (10 mL) and brine (3×10 mL). The organic layer was dried (MgSO$_4$) and concentrated, and the residue was partially purified by chromatography on silica gel (1:99 MeOH/CH$_2$Cl$_2$) to give 1-((2-(trimethylsilyl)ethoxy)methyl)-1H-benzo[d]imidazole-2-carbaldehyde (Compound No. 65, 579 mg) as a yellow oil.

B. A solution of ((3aS,4R,5S,7aS)-5-((1R,2S,4S)-4-((tert-butyldimethylsilyl)oxy)-2-(((tert-butyldimethylsilyl)oxy)methyl)-1-methylcyclohexyl)-7a-methyl-1-methyleneoctahydro-1H-inden-4-yl)methanamine (Compound No. 62, 164 mg, 0.298 mmol) and 1-((2-(trimethylsilyl)ethoxy)methyl)-1H-benzo[d]imidazole-2-carbaldehyde (Compound No. 65, 99 mg) in MeOH (4.3 mL) was heated to reflux under argon for 0.5 h then allowed to cool to room temperature. NaBH$_4$ (14 mg, 0.37 mmol) was added and stirred at room temperature for 17 h. More NaBH$_4$ (14 mg, 0.37 mmol) was added and heated to 60° C. for 1 h. The mixture was diluted with H$_2$O (0.5 mL) and concentrated then 1 N NaOH (aq) (10 mL) was added to the residue. The mixture was extracted with CH$_2$Cl$_2$ (15 mL then 2×10 mL), and the combined organic layers were dried (MgSO$_4$) and concentrated. The residue was purified by chromatography on silica gel (20:80 EtOAc/hexanes) to give 1-((3aS,4R,5S,7aS)-5-((1R,2S,4S)-4-((tert-butyldimethylsilyl)oxy)-2-(((tert-butyldimethylsilyl)oxy)methyl)-1-methylcyclohexyl)-7a-methyl-1-methyleneoctahydro-1H-inden-4-yl)-N-((1-((2-(trimethylsilyl)ethoxy)methyl)-1H-benzo[d]imidazol-2-yl)methyl)methanamine (Compound No. 66, 170 mg, 70%) as a yellow oil.

C. TBAF (1.0 mL of a 1 M solution in THF, 1.0 mmol) was added to a solution of 1-((3aS,4R,5S,7aS)-5-((1R,2S,4S)-4-((tert-butyldimethylsilyl)oxy)-2-(((tert-butyldimethylsilyl)oxy)methyl)-1-methylcyclohexyl)-7a-methyl-1-methyleneoctahydro-1H-inden-4-yl)-N-((1-((2-(trimethylsilyl)ethoxy)methyl)-1H-benzo[d]imidazol-2-yl)methyl)methanamine (Compound No. 66, 170 mg, 0.210 mmol) in THF (4.2 mL) and heated to 50° C. for 16 h. The solution was concentrated, and the residue was purified by chromatography on silica gel (5:95 MeOH/EtOAc) to give (1S,3S,4R)-3-(hydroxymethyl)-4-methyl-4-((3aS,4R,5S,7aS)-7a-methyl-1-methylene-4-((((1-((2-(trimethylsilyl)ethoxy)methyl)-1H-benzo[d]imidazol-2-yl)methyl)amino)methyl)octahydro-1H-inden-5-yl)cyclohexanol (Compound No. 67, 85 mg, 70%) as a colourless film.

D. TBAF (0.44 mL of a 1 M solution in THF, 0.44 mmol) was added to a solution of (1S,3S,4R)-3-(hydroxymethyl)-4-methyl-4-((3aS,4R,5S,7aS)-7a-methyl-1-methylene-4-((((1-((2-(trimethylsilyl)ethoxy)methyl)-1H-benzo[d]imidazol-2-yl)methyl)amino)methyl)octahydro-1H-inden-5-yl)cyclohexanol (Compound No. 67, 85 mg, 0.15 mmol) in THF (2.9 mL) and heated to 70° C. for 26.5 h. The solution was concentrated, and the residue was purified by chromatography on silica gel (100:5:1 EtOAc/MeOH/NH$_4$OH) to give (1S,3S,4R)-4-((3aS,4R,5S,7aS)-4-(((1H-benzo[d]imidazol-2-yl)methylamino)methyl)-7a-methyl-1-methyleneoctahydro-1H-inden-5-yl)-3-(hydroxymethyl)-4-methylcyclohexanol (Compound No. 68, 57 mg, 86%) as a colourless solid. $^1$H NMR (CD$_3$OD): δ7.52 (m, 2H), 7.21 (m, 2H), 4.60 (s, 2H), 3.95 (d, J=15 Hz, 1H), 3.88 (d, J=15 Hz, 1H), 3.70 (m, 1H), 3.40 (m, 1H), 3.12 (m, 1H), 2.92 (m, 1H), 2.62 (m, 1H), 2.43 (m, 1H), 2.09-2.28 (m, 2H), 1.20-1.82 (m, 15H), 0.99 (s, 3H), 0.77 (s, 3H). ES-MS m/z 452 ([M+1]$^+$).

Example 33

Synthesis of (1S,3S,4R)-4-((3aS,4R,5S,7aS)-4-((benzo[d][1,3]dioxol-5-ylmethylamino)methyl)-7a-methyl-1-methyleneoctahydro-1H-inden-5-yl)-3-(hydroxymethyl)-4-methylcyclohexanol (Compound No. 70)

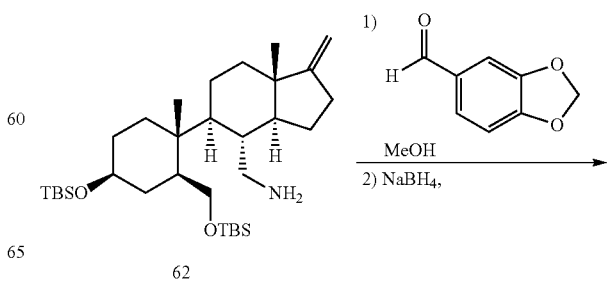

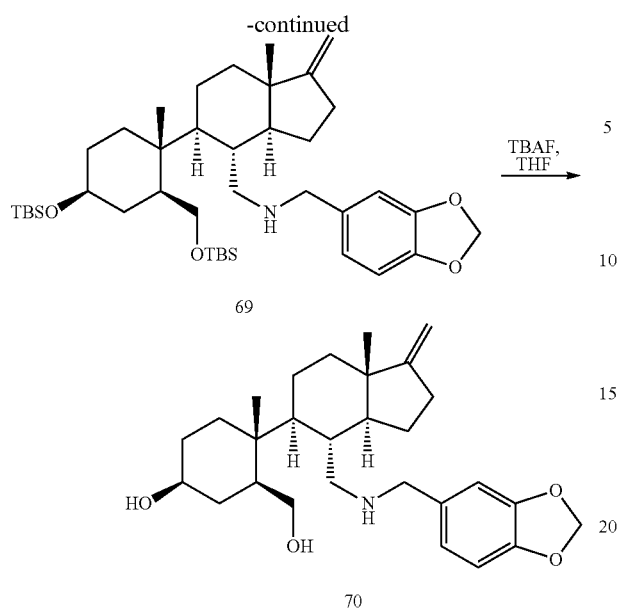

A. A solution of ((3aS,4R,5S,7aS)-5-((1R,2S,4S)-4-((tert-butyldimethylsilyl)oxy)-2-(((tert-butyldimethylsilyl)oxy)methyl)-1-methylcyclohexyl)-7a-methyl-1-methyleneoctahydro-1H-inden-4-yl)methanamine (Compound No. 62, 125 mg, 0.227 mmol) and piperonal (41 mg, 0.27 mmol) in MeOH (4.5 mL) was heated to reflux under argon for 25 min then allowed to cool to room temperature. NaBH$_4$ (17 mg, 0.44 mmol) was added and stirred at room temperature for 1.5 h. The mixture was diluted with H$_2$O (0.5 mL) and concentrated, and the residue was partitioned between 1 N NaOH (aq) (10 mL) and CH$_2$Cl$_2$ (15 mL). The aqueous layer was extracted with CH$_2$Cl$_2$ (2×10 mL), and the combined organic layers were dried (MgSO$_4$) and concentrated. The residue was purified by chromatography on silica gel (20:80 EtOAc/hexanes) to give 1-(benzo[d][1,3]dioxol-5-yl)-N-(((3aS,4R,5S,7aS)-5-((1R,2S,4S)-4-((tert-butyldimethylsilyl)oxy)-2-(((tert-butyldimethylsilyl)oxy)methyl)-1-methylcyclohexyl)-7a-methyl-1-methyleneoctahydro-1H-inden-4-yl)methyl)methanamine (Compound No. 69, 137 mg, 88%) as a colourless oil.

B. TBAF (0.80 mL of a 1 M solution in THF, 0.80 mmol) was added to a solution of 1-(benzo[d][1,3]dioxol-5-yl)-N-(((3aS,4R,5S,7aS)-5-((1R,2S,4S)-4-((tert-butyldimethylsilyl)oxy)-2-(((tert-butyldimethylsilyl)oxy)methyl)-1-methylcyclohexyl)-7a-methyl-1-methyleneoctahydro-1H-inden-4-yl)methyl)methanamine (Compound No. 69, 137 mg, 0.200 mmol) in THF (4.0 mL) and stirred at room temperature for 16 h. The solution was concentrated, and the residue was purified by chromatography on silica gel (4:96 MeOH/EtOAc) to give (1S,3S,4R)-4-((3aS,4R,5S,7aS)-4-((benzo[d][1,3]dioxol-5-ylmethylamino)methyl)-7a-methyl-1-methyleneoctahydro-1H-inden-5-yl)-3-(hydroxymethyl)-4-methylcyclohexanol (Compound No. 70, 56 mg, 62%) as a colourless solid. $^1$H NMR (CD$_3$OD): δ6.82 (s, 1H), 6.74 (s, 2H), 5.91 (s, 2H), 4.61 (s, 2H), 3.69 (m, 1H), 3.59 (m, 2H), 3.40 (m, 1H), 3.12 (m, 1H), 2.77 (m, 1H), 2.42-2.57 (m, 2H), 2.10-2.29 (m, 2H), 1.22-1.82 (m, 15H), 0.98 (s, 3H), 0.78 (s, 3H). ES-MS m/z 456 ([M+1]$^+$).

Example 34

Synthesis of (1S,3S,4R)-4-((3aS,4R,5S,7aS)-4-((6-amino-9H-purin-9-yl)methyl)-7a-methyl-1-methyleneoctahydro-1H-inden-5-yl)-3-(hydroxymethyl)-4-methylcyclohexanol (Compound No. 73)

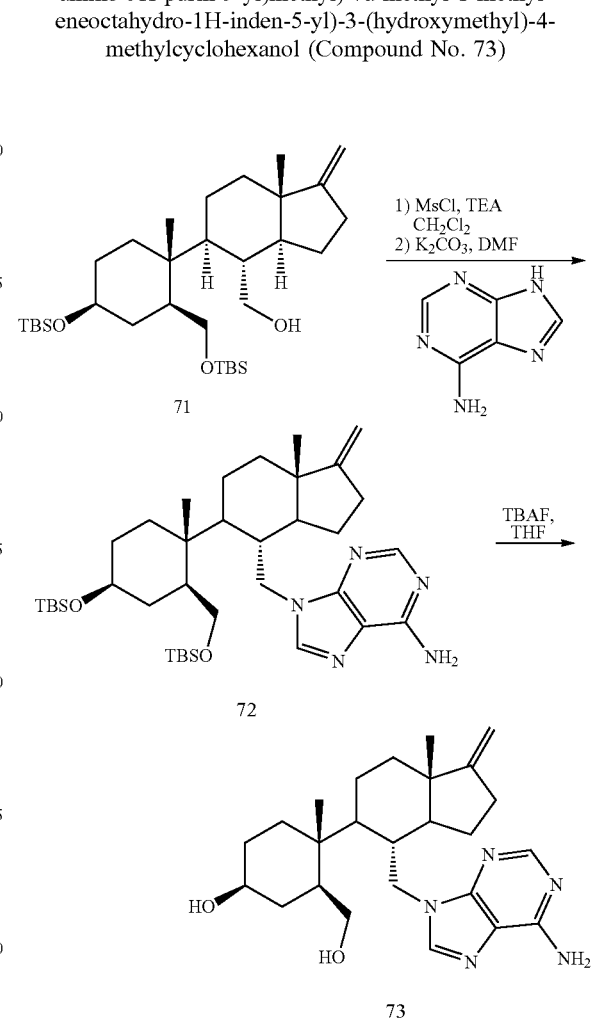

A. To a solution of ((3aS,4R,5S,7aS)-5-((1R,2S,4S)-4-((tert-butyldimethylsilyl)oxy)-2-(((tert-butyldimethylsilyl)oxy)methyl)-1-methylcyclohexyl)-7a-methyl-1-methyleneoctahydro-1H-inden-4-yl)methanol (Compound No. 71, 311 mg, 0.56 mmol) and Et$_3$N (0.10 mL, 0.72 mmol) in CH$_2$Cl$_2$ (5.6 mL) at 0° C. under argon was added MsCl (0.048 mL, 0.62 mmol), and the solution was stirred at room temperature for 3 h. The solution was diluted with CH$_2$Cl$_2$ (15 mL) and washed with saturated aqueous NaHCO$_3$ (15 mL). The aqueous layer was extracted with CH$_2$Cl$_2$ (2×10 mL), and the combined organic layers were dried (MgSO$_4$) and concentrated. Azeotropic removal of impurities was carried out with toluene (3×10 mL), and the residue was dissolved in DMF (1.9 mL). Adenine (84 mg, 0.62 mmol) and potassium carbonate (234 mg, 1.69 mmol) were added, and the mixture was heated to 80° C. under argon for 17.5 h. The mixture was partitioned between EtOAc (40 mL) and H$_2$O (15 mL), and the organic layer was washed with brine (3×10 mL) then dried (MgSO$_4$) and concentrated. The residue was purified by chromatography on silica gel (3:97 MeOH/CH$_2$Cl$_2$) to give 9-(((3aS,4R,5S,7aS)-5-((1R,2S,4S)-4-((tert-butyldimethylsilyl)oxy)-2-(((tert-butyldimethylsilyl)oxy)methyl)-1-methylcyclohexyl)-7a-methyl-1- methyleneoctahydro-1H-inden-4-yl)methyl)-9H-purin-6-amine (Compound No. 72, 187 mg, 50%) as a pale foam.

B. TBAF (1.1 mL of a 1 M solution in THF, 1.1 mmol) was added to a solution of 9-(((3aS,4R,5S,7aS)-5-((1R,2S,4S)-4-((tert-butyldimethylsilyl)oxy)-2-(((tert-butyldimethylsilyl)oxy)methyl)-1-methylcyclohexyl)-7a-methyl-1-methyleneoctahydro-1H-inden-4-yl)methyl)-9H-purin-6-amine (Compound No. 72, 187 mg, 0.280 mmol) in THF (5.6 mL) and heated to 40° C. for 3 d. The solution was concentrated, and the residue was purified by chromatography on silica gel (100:10:2 EtOAc/MeOH/NH$_4$OH) to give (1S,3S,4R)-4-((3aS,4R,5S,7aS)-4-((6-amino-9H-purin-9-yl)methyl)-7a-methyl-1-methyleneoctahydro-1H-inden-5-yl)-3-(hydroxymethyl)-4-methylcyclohexanol (Compound No. 73, 104 mg, 85%) as a colourless solid. $^1$H NMR (CD$_3$OD): δ8.21 (s, 2H), 4.62 (m, 3H), 4.17 (dd, J=14, 9.6 Hz, 1H), 3.75 (m, 1H), 3.51 (m, 1H), 3.18 (m, 1H), 2.62 (m, 1H), 2.17-2.29 (m, 2H), 1.23-2.08 (m, 13H), 1.07 (m, 4H), 0.72 (m, 4H). ES-MS m/z 440 ([M+1]$^+$).

Example 35

Synthesis of (1S,3S,4R)-3-(hydroxymethyl)-4-methyl-4-((3aS,4R,5S,7aS)-7a-methyl-1-methylene-4-((4-nitrobenzylamino)methyl)octahydro-1H-inden-5-yl)cyclohexanol (Compound No. 74)

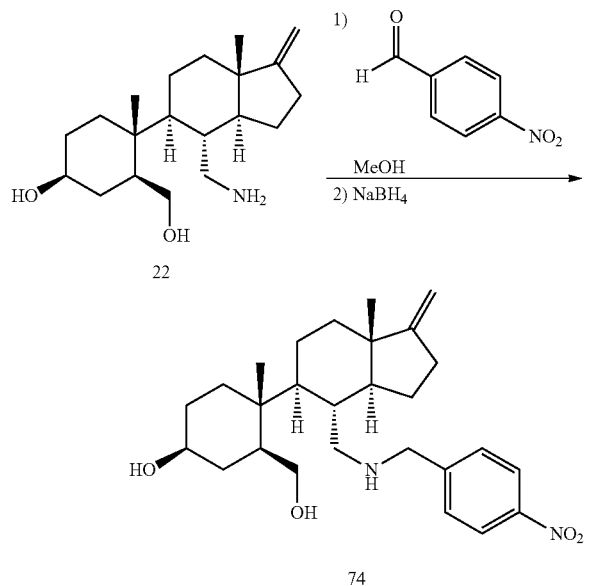

A solution of (1S,3S,4R)-4-((3aS,4R,5S,7aS)-4-(aminomethyl)-7a-methyl-1-methyleneoctahydro-1H-inden-5-yl)-3-(hydroxymethyl)-4-methylcyclohexanol (Compound No. 22, 109 mg, 0.339 mmol) and 4-nitrobenzaldehyde (61 mg, 0.40 mmol) in MeOH (6.7 mL) was heated to reflux under argon for 35 min then allowed to cool to room temperature. NaBH$_4$ (26 mg, 0.69 mmol) and THF (2.5 mL) were added and stirred at room temperature for 3 d. The mixture was heated to 60° C. for 19 h and more NaBH$_4$ (29 mg, 0.77 mmol) was added. The mixture was heated to 60° C. for 1 h then concentrated. The residue was dissolved in CH$_2$Cl$_2$ (20 mL) and washed with 1 N NaOH (aq) (10 mL). The aqueous layer was extracted with CH$_2$Cl$_2$ (2×10 mL), and the combined organic layers were dried (MgSO$_4$) and concentrated. The residue was purified by chromatography on silica gel (0.5:99.5 MeOH/EtOAc) to give (1S,3S,4R)-3-(hydroxymethyl)-4-methyl-4-((3aS,4R,5S,7aS)-7a-methyl-1-methylene-4-((4-nitrobenzylamino)methyl)octahydro-1H-inden-5-yl)cyclohexanol (Compound No. 74, 66 mg, 43%) as a colourless solid. $^1$H NMR (CD$_3$OD): δ8.18 (d, J=8.4 Hz, 2H), 7.58 (d, J=8.4 Hz, 2H), 4.61 (s, 2H), 3.83 (d, J=14 Hz, 1H), 3.76 (d, J=14 Hz, 1H), 3.70 (m, 1H), 3.41 (m, 1H), 3.13 (m, 1H), 2.83 (m, 1H), 2.57 (m, 1H), 2.46 (m, 1H), 2.11-2.29 (m, 2H), 1.18-1.83 (m, 15H), 1.01 (s, 3H), 0.78 (s, 3H). ES-MS m/z 457 ([M+1]$^+$).

Example 36

Synthesis of (1S,3S,4R)-4-((3aS,4R,5S,7aS)-4-(((2,2-difluorobenzo[d][1,3]dioxol-5-yl)methylamino)methyl)-7a-methyl-1-methyleneoctahydro-1H-inden-5-yl)-3-(hydroxymethyl)-4-methylcyclohexanol (Compound No. 75)

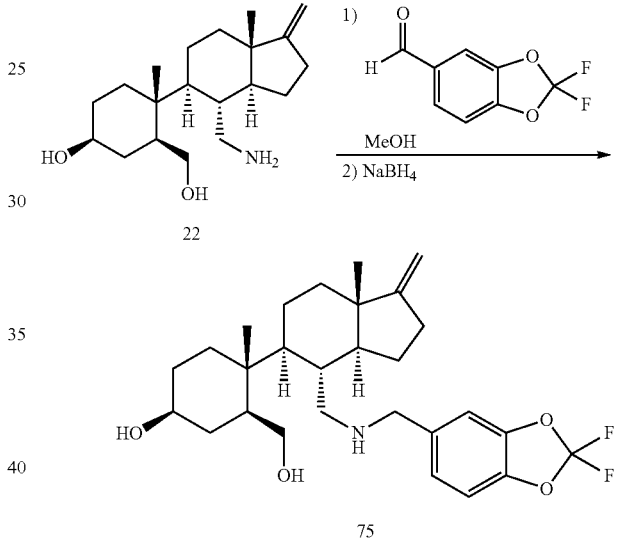

A solution of (1S,3S,4R)-4-((3aS,4R,5S,7aS)-4-(aminomethyl)-7a-methyl-1-methyleneoctahydro-1H-inden-5-yl)-3-(hydroxymethyl)-4-methylcyclohexanol (Compound No. 22, 68 mg, 0.21 mmol) and 2,2-difluoro-1,3-benzodioxole-5-carbaldehyde (47 mg, 0.25 mmol) in MeOH (4.2 mL) was heated to reflux under argon for 0.5 h then allowed to cool to room temperature. NaBH$_4$ (16 mg, 0.42 mmol) was added and stirred at room temperature overnight. The mixture was concentrated, and the residue was dissolved in 1:9 MeOH/CH$_2$Cl$_2$ (15 mL) then washed with 1 N NaOH (aq) (10 mL). The aqueous layer was extracted with CH$_2$Cl$_2$ (2×10 mL), and the combined organic layers were dried (MgSO$_4$) and concentrated. The residue was purified by chromatography on silica gel (6:94 MeOH/CH$_2$Cl$_2$) to give (1S,3S,4R)-4-((3aS,4R,5S,7aS)-4-(((2,2-difluorobenzo[d][1,3]dioxol-5-yl)methylamino)methyl)-7a-methyl-1-methyleneoctahydro-1H-inden-5-yl)-3-(hydroxymethyl)-4-methylcyclohexanol (Compound No. 75, 84 mg, 81%) as a colourless solid ($^1$H NMR (CD$_3$OD): δ7.21 (s, 1H), 7.11 (s, 2H), 4.61 (s, 2H), 3.69 (m, 3H), 3.42 (m, 1H), 3.13 (m, 1H), 2.80 (m, 1H), 2.42-2.57 (m, 2H), 2.11-2.29 (m, 2H), 1.18-1.83 (m, 15H), 0.99 (s, 3H), 0.78 (s, 3H). ES-MS m/z 492 ([M+1]$^+$).

Example 37

Synthesis of (1S,3S,4R)-4-((3aS,4R,5S,7aS)-4-((4-fluoro-2-methylbenzylamino)methyl)-7a-methyl-1-methyleneoctahydro-1H-inden-5-yl)-3-(hydroxymethyl)-4-methylcyclohexanol (Compound No. 76)

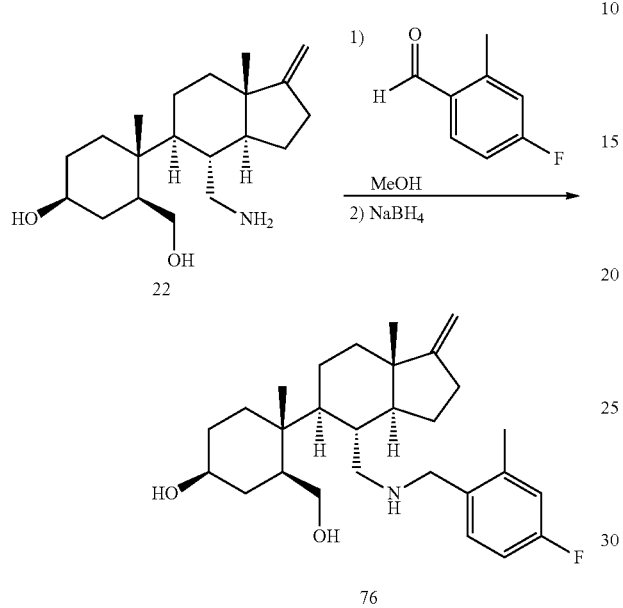

A solution of (1S,3S,4R)-4-((3aS,4R,5S,7aS)-4-(aminomethyl)-7a-methyl-1-methyleneoctahydro-1H-inden-5-yl)-3-(hydroxymethyl)-4-methylcyclohexanol (Compound No. 22, 93 mg, 0.29 mmol) and 4-fluoro-2-methylbenzaldehyde (48 mg, 0.35 mmol) in MeOH (5.8 mL) was heated to reflux under argon for 0.5 h then allowed to cool to room temperature. NaBH$_4$ (22 mg, 0.58 mmol) was added and stirred at room temperature for 1.75 h. The mixture was concentrated, and the residue was dissolved in CH$_2$Cl$_2$ (15 mL) then washed with 1 N NaOH (aq) (10 mL). The aqueous layer was extracted with CH$_2$Cl$_2$ (2×10 mL), and the combined organic layers were dried (MgSO$_4$) and concentrated. The residue was purified by chromatography on silica gel (6:94 MeOH/CH$_2$Cl$_2$) to give (1S,3S,4R)-4-((3aS,4R,5S,7aS)-4-((4-fluoro-2-methylbenzylamino)methyl)-7a-methyl-1-methyleneoctahydro-1H-inden-5-yl)-3-(hydroxymethyl)-4-methylcyclohexanol (Compound No. 76, 113 mg, 88%) as a colourless solid. $^1$H NMR (CD$_3$OD): δ7.24 (dd, J=8.4, 6.0 Hz, 1H), 6.87 (m, 2H), 4.61 (s, 2H), 3.67 (m, 3H), 3.41 (m, 1H), 3.11 (m, 1H), 2.89 (m, 1H), 2.64 (m, 1H), 2.37-2.51 (m, 4H), 2.10-2.28 (m, 2H), 1.21-1.82 (m, 15H), 0.97 (s, 3H), 0.79 (s, 3H). ES-MS m/z 444 ([M+1]$^+$).

Example 38

Synthesis of (1S,3S,4R)-4-((3aS,4R,5S,7aS)-4-((2-fluoro-4-methoxybenzylamino)methyl)-7a-methyl-1-methyleneoctahydro-1H-inden-5-yl)-3-(hydroxymethyl)-4-methylcyclohexanol (Compound No. 77)

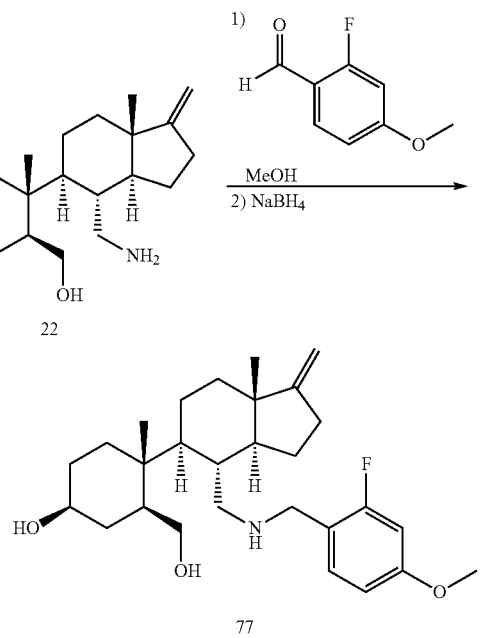

A solution of (1S,3S,4R)-4-((3aS,4R,5S,7aS)-4-(aminomethyl)-7a-methyl-1-methyleneoctahydro-1H-inden-5-yl)-3-(hydroxymethyl)-4-methylcyclohexanol (Compound No. 22, 60 mg, 0.19 mmol) and 2-fluoro-4-methoxybenzaldehyde (35 mg, 0.23 mmol) in MeOH (3.7 mL) was heated to reflux under argon for 0.5 h then allowed to cool to room temperature. NaBH$_4$ (14 mg, 0.37 mmol) was added and stirred at room temperature for 3 h then THF (1.2 mL) was added. The mixture was stirred at room temperature for 1.25 h then concentrated. The residue was dissolved in 1:9 MeOH/CH$_2$Cl$_2$ (15 mL) and washed with 1 N NaOH (aq) (10 mL). The aqueous layer was extracted with CH$_2$Cl$_2$ (2×10 mL), and the combined organic layers were dried (MgSO$_4$) and concentrated. The residue was purified by chromatography on silica gel (8:92 MeOH/CH$_2$Cl$_2$) to give (1S,3S,4R)-4-((3aS,4R,5S,7aS)-4-((2-fluoro-4-methoxybenzylamino)methyl)-7a-methyl-1-methyleneoctahydro-1H-inden-5-yl)-3-(hydroxymethyl)-4-methylcyclohexanol (Compound No. 77, 71 mg, 83%) as a colourless solid. $^1$H NMR (CD$_3$OD): δ7.27 (m, 1H), 6.71 (m, 2H), 4.62 (s, 2H), 3.67-3.79 (m, 6H), 3.31 (m, 1H), 3.11 (m, 1H), 2.87 (m, 1H), 2.64 (m, 1H), 2.48 (m, 1H), 2.10-2.30 (m, 2H), 1.17-1.83 (m, 15H), 0.94 (s, 3H), 0.78 (s, 3H). ES-MS m/z 460 ([M+1]$^+$).

Example 39

Synthesis of (1S,3S,4R)-4-((3aS,4R,5S,7aS)-4-((4-fluoro-2-methoxybenzylamino)methyl)-7a-methyl-1-methyleneoctahydro-1H-inden-5-yl)-3-(hydroxymethyl)-4-methylcyclohexanol (Compound No. 78)

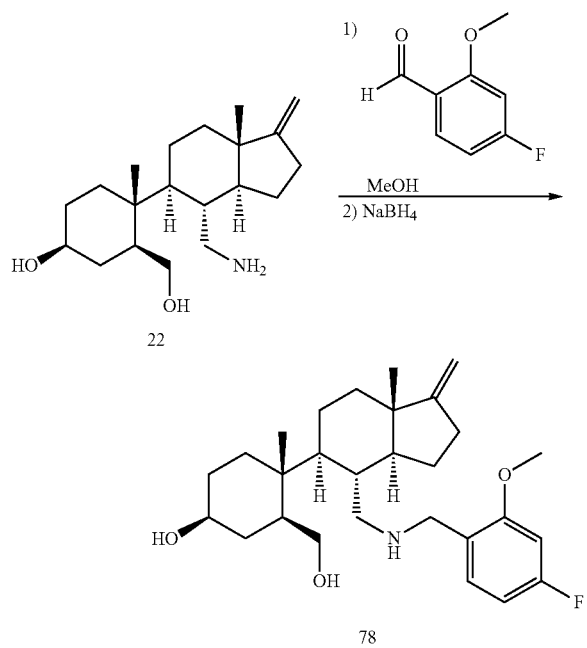

A solution of (1S,3S,4R)-4-((3aS,4R,5S,7aS)-4-(aminomethyl)-7a-methyl-1-methyleneoctahydro-1H-inden-5-yl)-3-(hydroxymethyl)-4-methylcyclohexanol (Compound No. 22, 61 mg, 0.19 mmol) and 4-fluoro-2-methoxybenzaldehyde (35 mg, 0.23 mmol) in MeOH (3.8 mL) was heated to reflux under argon for 0.5 h then allowed to cool to room temperature. NaBH$_4$ (14 mg, 0.37 mmol) was added and stirred at room temperature for 5 h. The mixture was concentrated, and the residue was dissolved in 1:9 MeOH/CH$_2$Cl$_2$ (15 mL) then washed with 1 N NaOH (aq) (10 mL). The aqueous layer was extracted with CH$_2$Cl$_2$ (2×10 mL), and the combined organic layers were dried (MgSO$_4$) and concentrated. The residue was purified by chromatography on silica gel (10:90 MeOH/CH$_2$Cl$_2$) to give (1S,3S,4R)-4-((3aS,4R,5S,7aS)-4-((4-fluoro-2-methoxybenzylamino)methyl)-7a-methyl-1-methyleneoctahydro-1H-inden-5-yl)-3-(hydroxymethyl)-4-methylcyclohexanol (Compound No. 78, 80 mg, 92%) as a colourless foam. $^1$H NMR (CD$_3$OD): δ7.23 (m, 1H), 6.80 (dd, J=11, 2.1 Hz, 1H), 6.65 (m, 1H), 4.63 (s, 2H), 3.85 (s, 3H), 3.73 (m, 3H), 3.41 (m, 1H), 3.12 (m, 1H), 2.87 (m, 1H), 2.64 (m, 1H), 2.49 (m, 1H), 2.10-2.31 (m, 2H), 1.18-1.83 (m, 15H), 0.96 (s, 3H), 0.79 (s, 3H). ES-MS m/z 460 ([M+1]$^+$).

Example 40

Synthesis of (1S,3S,4R)-4-((3aS,4R,5S,7aS)-4-((2-fluoro-4-methylbenzylamino)methyl)-7a-methyl-1-methyleneoctahydro-1H-inden-5-yl)-3-(hydroxymethyl)-4-methylcyclohexanol (Compound No. 79)

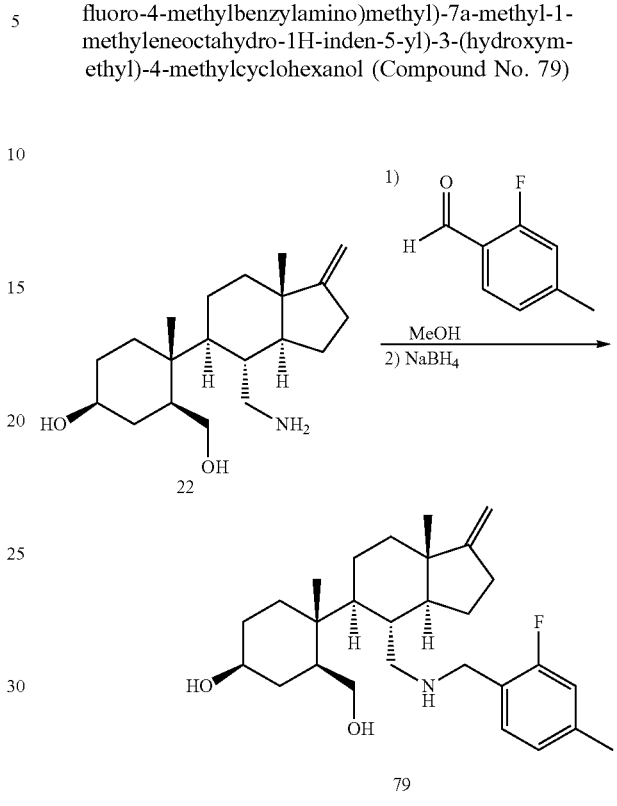

A solution of (1S,3S,4R)-4-((3aS,4R,5S,7aS)-4-(aminomethyl)-7a-methyl-1-methyleneoctahydro-1H-inden-5-yl)-3-(hydroxymethyl)-4-methylcyclohexanol (Compound No. 22, 60 mg, 0.19 mmol) and 2-fluoro-4-methylbenzaldehyde (31 mg, 0.22 mmol) in MeOH (3.7 mL) was heated to reflux under argon for 0.5 h then allowed to cool to room temperature. NaBH$_4$ (14 mg, 0.37 mmol) was added and stirred at room temperature overnight. The mixture was concentrated, and the residue was dissolved in 1:9 MeOH/CH$_2$Cl$_2$ (15 mL) then washed with 1 N NaOH (aq) (10 mL). The aqueous layer was extracted with CH$_2$Cl$_2$ (2×10 mL), and the combined organic layers were dried (MgSO$_4$) and concentrated. The residue was purified by chromatography on silica gel (6:94 MeOH/CH$_2$Cl$_2$) to give (1S,3S,4R)-4-((3aS,4R,5S,7aS)-4-((2-fluoro-4-methylbenzylamino)methyl)-7a-methyl-1-methyleneoctahydro-1H-inden-5-yl)-3-(hydroxymethyl)-4-methylcyclohexanol (Compound No. 79, 64 mg, 77%) as a colourless solid. $^1$H NMR (CD$_3$OD): δ7.23 (m, 1H), 6.93 (m, 2H), 4.61 (s, 2H), 3.67-3.79 (m, 3H), 3.39 (m, 1H), 3.11 (m, 1H), 2.85 (m, 1H), 2.61 (m, 1H), 2.47 (m, 1H), 2.10-2.33 (m, 5H), 1.16-1.82 (m, 15H), 0.94 (s, 3H), 0.78 (s, 3H). ES-MS m/z 444 ([M+1]$^+$).

Example 41

Synthesis of (1S,3S,4R)-3-(hydroxymethyl)-4-((3aS, 4R,5S,7aS)-4-((4-methoxyphenethylamino)methyl)-7a-methyl-1-methyleneoctahydro-1H-inden-5-yl)-4-methylcyclohexanol (Compound No. 81)

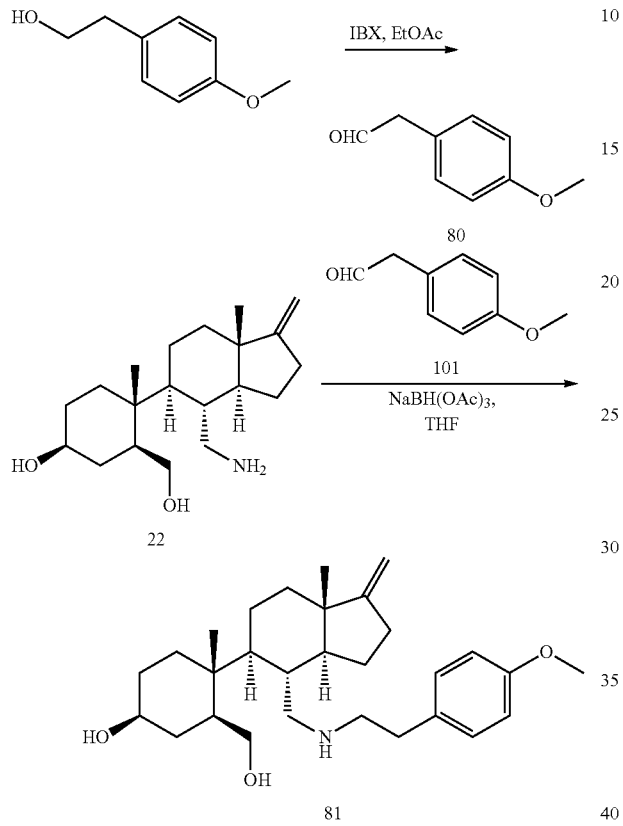

A. To a solution of 4-methoxyphenethyl alcohol (184 mg, 1.21 mmol) in EtOAc (24 mL) was added 2-iodoxybenzoic acid (1.02 g, 3.64 mmol), and the mixture was heated to 80° C. open to air for 3 h. The mixture was cooled to 0° C. for 10 min then filtered through Celite and concentrated to give Compound No. 80 (185 mg) as a yellow oil.

B. To a mixture of Compound No. 80 (33 mg) and (1S,3S,4R)-4-((3aS,4R,5S,7aS)-4-(aminomethyl)-7a-methyl-1-methyleneoctahydro-1H-inden-5-yl)-3-(hydroxymethyl)-4-methylcyclohexanol (Compound No. 22, 59 mg, 0.18 mmol) in THF (1.8 mL) was added sodium triacetoxyborohydride (78 mg, 0.37 mmol), and the mixture was stirred at room temperature for 25 h. The mixture was diluted with 1:9 MeOH/CH$_2$Cl$_2$ (15 mL) and washed with 1 N NaOH (aq) (10 mL). The aqueous layer was extracted with CH$_2$Cl$_2$ (2×10 mL), and the combined organic layers were dried (MgSO$_4$) and concentrated. The residue was purified by chromatography on silica gel (100:5:1 CH$_2$Cl$_2$/MeOH/NH$_4$OH) to give (1S,3S,4R)-3-(hydroxymethyl)-4-((3aS,4R,5S,7aS)-4-((4-methoxyphenethylamino)methyl)-7a-methyl-1-methyleneoctahydro-1H-inden-5-yl)-4-methylcyclohexanol (Compound No. 81, 49 mg, 58%) as a colourless foam. $^1$H NMR (CD$_3$OD): δ7.13 (d, J=8.4 Hz, 2H), 6.86 (d, J=8.7 Hz, 2H), 4.61 (s, 2H), 3.77 (s, 3H), 3.58 (m, 1H), 3.40 (m, 1H), 2.98 (m, 1H), 2.61-2.75 (m, 6H), 2.44 (m, 1H), 2.09-2.24 (m, 2H), 1.12-1.80 (m, 15H), 0.76 (s, 3H), 0.70 (s, 3H). ES-MS m/z 456 ([M+1]$^+$).

Example 42

Synthesis of (1S,3S,4R)-4-((3aS,4S,5S,7aS)-4-(2-(bis(4-methoxybenzyl)amino)ethyl)-7a-methyl-1-methyleneoctahydro-1H-inden-5-yl)-4-methylcyclohexane-1,3-diol (Compound No. 83)

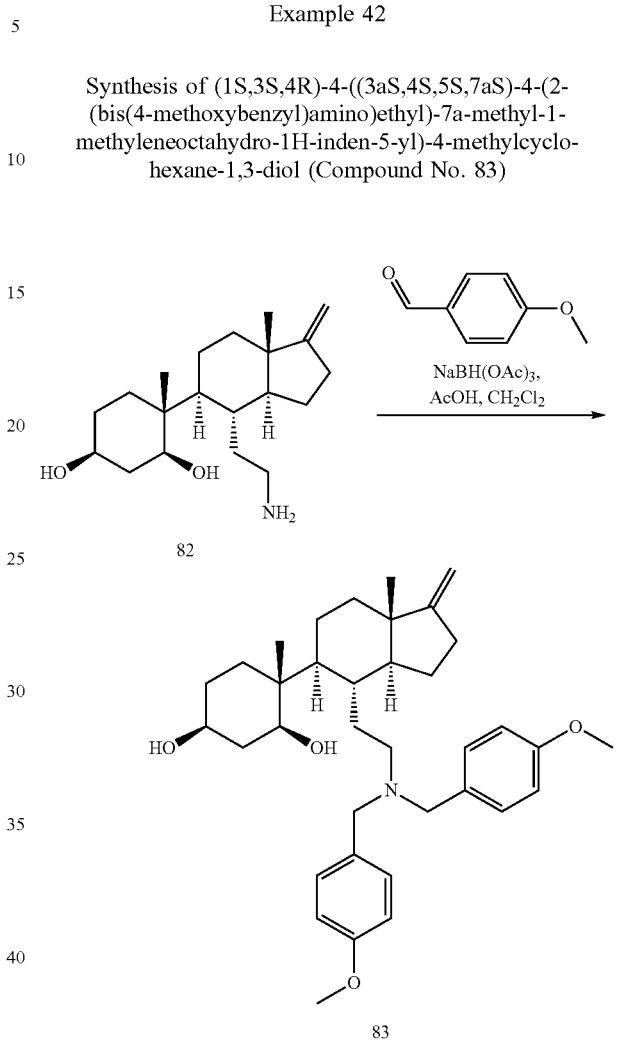

A mixture of (1S,3S,4R)-4-((3aS,4S,5S,7aS)-4-(2-aminoethyl)-7a-methyl-1-methyleneoctahydro-1H-inden-5-yl)-4-methylcyclohexane-1,3-diol (Compound No. 82, 68 mg, 0.21 mmol), p-anisaldehyde (51 μL, 0.42 mmol), AcOH (24 μL, 0.42 mmol) and NaBH(OAc)$_3$ (133 mg, 0.63 mmol) in CH$_2$Cl$_2$ (5 mL) under argon was stirred at room temperature for 24 h. A 1 M aqueous solution of NaOH (10 mL) was added and the mixture was extracted with CH$_2$Cl$_2$ (3×10 mL). The combined organic layers were dried (Na$_2$SO$_4$) and concentrated. The residue was purified using chromatography on silica gel (1:1 EtOAc:hexanes) to afford (1S,3S,4R)-4-((3aS,4S,5S,7aS)-4-(2-(bis(4-methoxybenzyl)amino)ethyl)-7a-methyl-1-methyleneoctahydro-1H-inden-5-yl)-4-methylcyclohexane-1,3-diol (Compound No. 83, 46 mg, 39%) as a white solid. $^1$H NMR (300 MHz, CDCl$_3$) δ7.25 (d, J=7.9, 4H), 6.84 (d, J=7.9, 4H), 4.60 (s, 1H), 4.58 (s 1H), 3.77 (s, 6H), 3.71 (m, 1H), 3.43 (s, 4H and m, 1H), 2.36 (m, 3H), 2.11 (m, 1H), 1.86-1.09 (m, 17H), 0.91 (s, 3H), 0.72 (s, 3H); $^{13}$C NMR (75 MHz, CDCl$_3$) δ161.9, 158.8, 132.4, 130.1, 113.8, 101.1, 72.2, 68.4, 58.2, 55.5, 52.4, 48.6, 43.8, 40.7, 36.2, 36.1, 30.4, 29.9, 29.7, 29.2, 25.1, 24.0, 19.1, 18.3; MS m/z: 562.6 [M+H]$^+$.

Example 43

Synthesis of (1S,3S,4R)-4-((3aS,4S,5S,7aS)-4-(2-(4-methoxybenzylamino)ethyl)-7a-methyl-1-methyleneoctahydro-1H-inden-5-yl)-4-methylcyclohexane-1,3-diol (Compound No. 84)

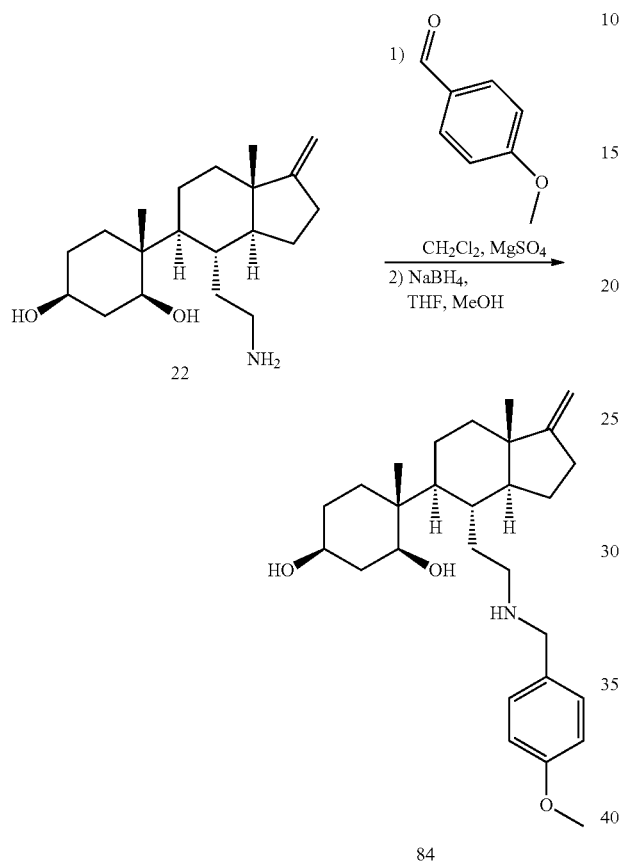

A mixture of (1S,3S,4R)-4-((3aS,4S,5S,7aS)-4-(2-aminoethyl)-7a-methyl-1-methyleneoctahydro-1H-inden-5-yl)-4-methylcyclohexane-1,3-diol (Compound No. 22, 40 mg, 0.12 mmol), p-anisaldehyde (21 µL, 0.19 mmol) and anhydrous MgSO$_4$ (0.5 g) in CH$_2$Cl$_2$ (5 mL) at room temperature was stirred for 24 h. The mixture was filtered and concentrated. The residue and NaBH$_4$ (23 mg, 0.61 mmol) in THF (3 mL) and MeOH (1 mL) under argon at room temperature was stirred for 18 h. 80% AcOH (1 mL) was added and the mixture was stirred for 10 min before being concentrated. The residue was taken up in EtOAc (20 mL), washed successively with saturated NaHCO$_3$ solution (3×5 mL) and brine (2×5 mL), dried (Na$_2$SO$_4$) and concentrated. The residue was purified using chromatography on silica gel (1:1 EtOAc:MeOH) to afford (1S,3S,4R)-4-((3aS,4S,5S,7aS)-4-(2-(4-methoxybenzylamino)ethyl)-7a-methyl-1-methyleneoctahydro-1H-inden-5-yl)-4-methylcyclohexane-1,3-diol (Compound No. 84, 26 mg, 49% over 2 steps) as a white solid. $^1$H NMR (300 MHz, CD$_3$OD) δ7.26 (d, J=8.4, 2H), 6.89 (d, J=8.4, 2H), 4.60 (s, 2H), 3.93-3.63 (m, 6H), 3.50 (m, 1H), 2.71-2.42 (s, 3H), 2.21 (s, 1H), 1.96-1.12 (m, 19H), 1.06 (s, 3H), 0.77 (s, 3H); $^{13}$C NMR (75 MHz, CD$_3$OD) δ162.8, 160.6, 130.9, 114.9, 101.6, 72.1, 69.5, 55.7, 53.6, 46.5, 44.8, 44.2, 41.3, 40.2, 37.2, 37.0, 31.5, 31.4, 30.0, 29.0, 25.9, 24.6, 19.4, 18.5; MS m/z: 442.4 [M+H]$^+$.

Example 44

Synthesis of (1S,3S,4R)-4-((3aS,4S,5S,7aS)-4-(2-(benzo[d][1,3]dioxol-5-ylmethylamino)ethyl)-7a-methyl-1-methyleneoctahydro-1H-inden-5-yl)-4-methylcyclohexane-1,3-diol (Compound No. 85)

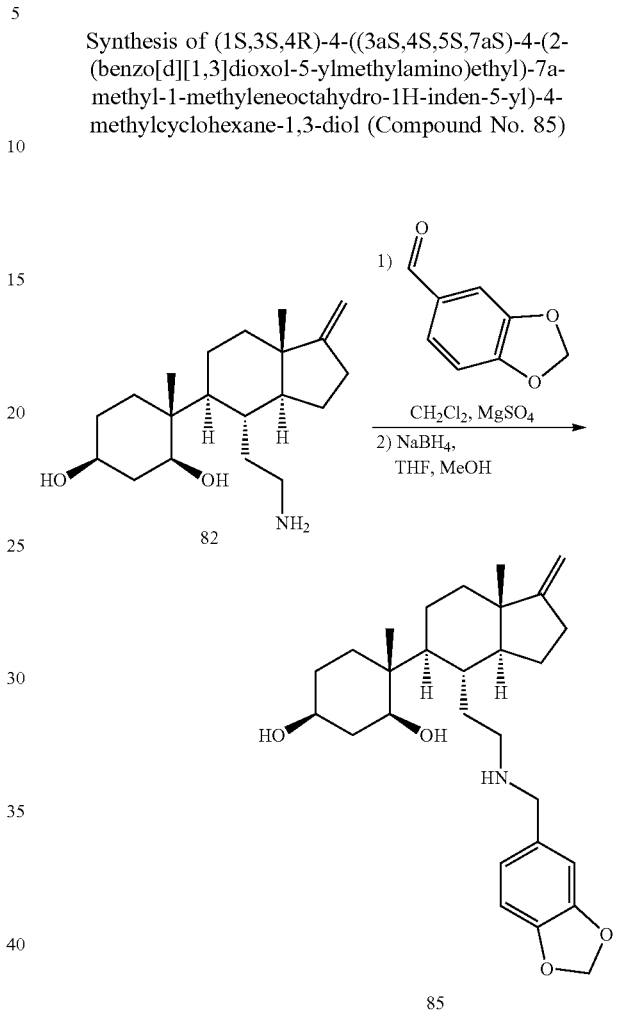

A mixture of (1S,3S,4R)-4-((3aS,4S,5S,7aS)-4-(2-aminoethyl)-7a-methyl-1-methyleneoctahydro-1H-inden-5-yl)-4-methylcyclohexane-1,3-diol (Compound No. 82, 38 mg, 0.12 mmol), piperonal (27 mg, 0.18 mmol) and anhydrous MgSO$_4$ (0.5 g) in CH$_2$Cl$_2$ (5 mL) at room temperature was stirred for 20 h. The mixture was filtered and concentrated. The residue and NaBH$_4$ (23 mg, 0.61 mmol) in THF (3 mL) and MeOH (1 mL) under argon at room temperature was stirred for 22 h. 80% AcOH (1 mL) was added and the mixture was stirred for 10 min before being concentrated. The residue was taken up in EtOAc (25 mL), washed with saturated NaHCO$_3$ solution (3×5 mL) and brine (5 mL), dried (Na$_2$SO$_4$) and concentrated. The residue was purified using chromatography on silica gel (0% to 25% to 50% MeOH:EtOAc) to afford (1S,3S,4R)-4-((3aS,4S,5S,7aS)-4-(2-(benzo[d][1,3]dioxol-5-ylmethylamino)ethyl)-7a-methyl-1-methyleneoctahydro-1H-inden-5-yl)-4-methylcyclohexane-1,3-diol (Compound No. 85, 23 mg, 42% over 2 steps) as a white solid. $^1$H NMR (300 MHz, CD$_3$OD) δ6.85 (s, 1H), 6.76 (m, 2H), 5.91 (s, 2H), 4.59 (s, 2H), 3.66 (m, 3H), 3.50 (m, 1H), 2.65 (m, 1H), 2.50 (m, 2H), 2.15 (m, 1H), 1.87-1.16 (m, 18H), 1.06 (s, 3H), 0.77 (s, 3H). $^{13}$C NMR (75 MHz, CD$_3$OD) δ162.8, 149.2, 148.2, 134.4, 122.9, 109.8, 109.0, 102.3, 101.6, 72.1, 69.5, 54.2, 53.6, 46.5, 44.8, 44.0, 41.3, 40.2, 37.2, 37.0, 31.8, 31.4, 30.0, 29.0, 25.9, 24.7, 19.3, 18.5; MS m/z: 456.2 [M+H]$^+$.
Example 45
Synthesis of (3aR,4R,5R,7aS)-5-((1S,2S,4S)-4-hydroxy-1-methyl-2-(2-morpholinoethyl)cyclohexyl)-7a-methyl-1-methyleneoctahydro-1H-inden-4-ol (Compound No. 96)
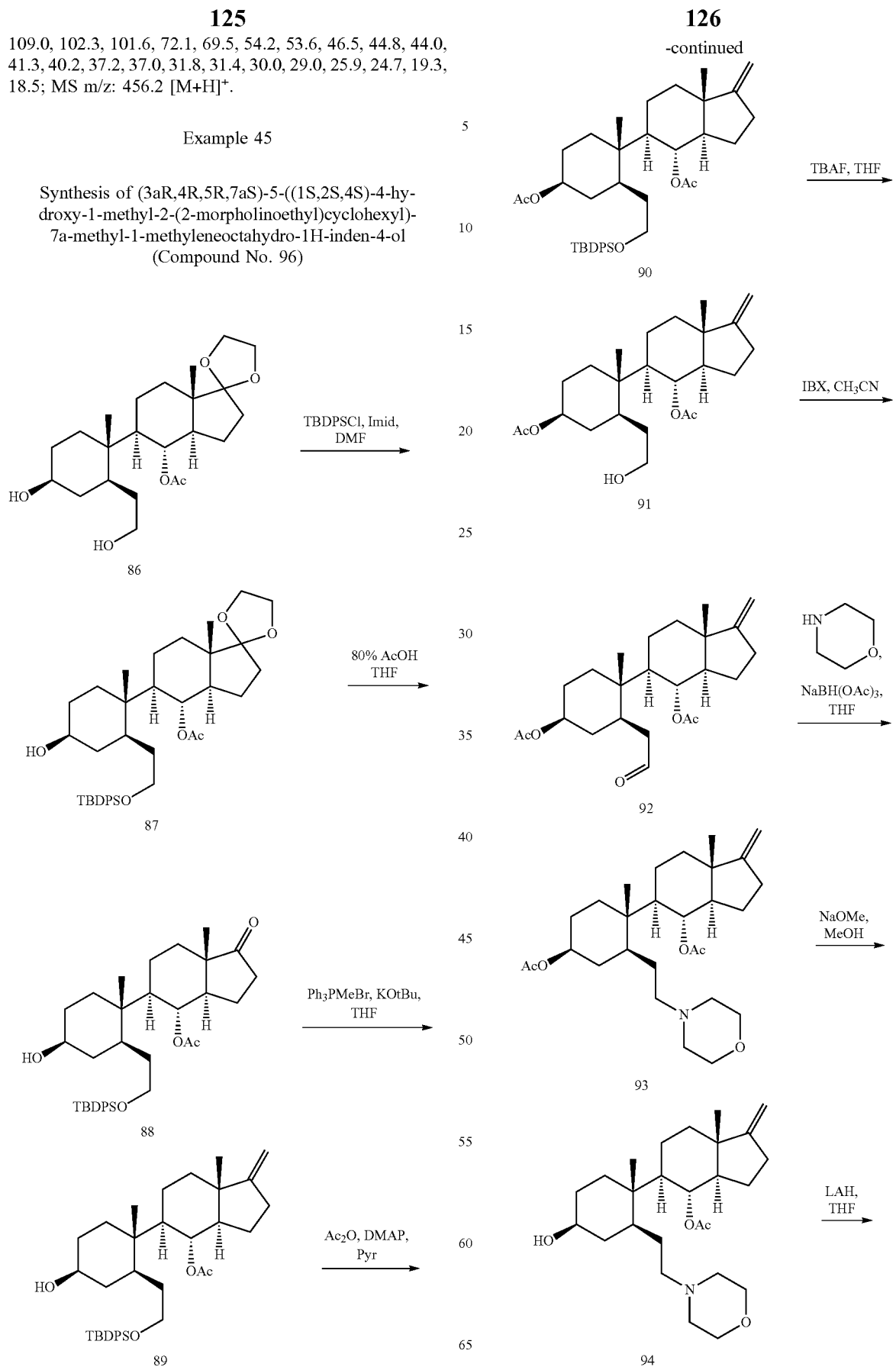

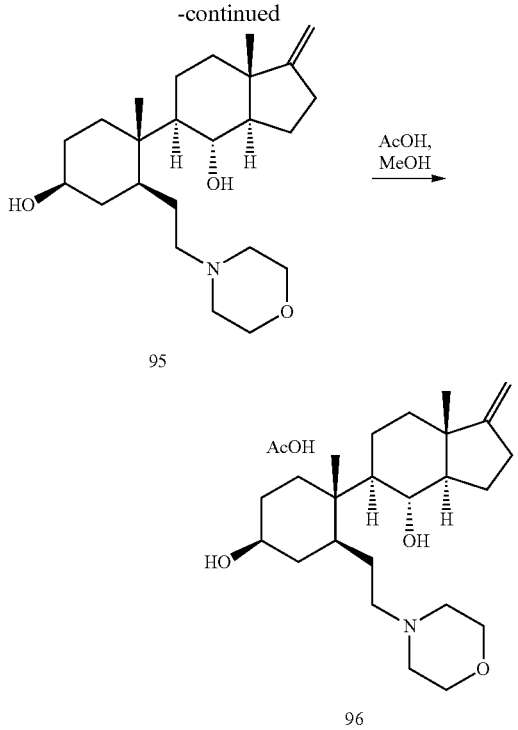

95

96

A. A mixture of (3a'R,4'R,5'R,7a'S)-5'-((1S,2S,4S)-4-hydroxy-2-(2-hydroxyethyl)-1-methylcyclohexyl)-7a'-methyloctahydrospiro[[1,3]dioxolane-2,1'-inden]-4'-yl acetate (Compound No. 86, 2.01 g, 3.8 mmol), TBDPSCl (1.2 mL, 4.6 mmol) and imidazole (388 mg, 5.7 mmol) in DMF (8 mL) under argon at room temperature was stirred for 2 h. The reaction was quenched with water (50 mL), extracted with Et$_2$O (3×75 mL), washed successively with water (2×50 mL) and brine (50 mL), dried (Na$_2$SO$_4$) and concentrated. The residue was purified using chromatography on silica gel (5% to 10% EtOAc/hexanes) to afford impure (3a'R,4'R,5'R,7a'S)-5'-((1S,2S,4S)-2-(2-((tert-butyldiphenylsilyl)oxy)ethyl)-4-hydroxy-1-methylcyclohexyl)-7a'-methyloctahydrospiro[[1,3]dioxolane-2,1'-inden]-4'-yl acetate (Compound No. 87, 2.93 g) as a white foam.

B. A mixture of (3a'R,4'R,5'R,7a'S)-5'-((1S,2S,4S)-2-(2-((tert-butyldiphenylsilyl)oxy)ethyl)-4-hydroxy-1-methylcyclohexyl)-7a'-methyloctahydrospiro[[1,3]dioxolane-2,1'-inden]-4'-yl acetate (Compound No. 87, 2.91 g) in 80% AcOH (150 mL) and THF (50 mL) at 40° C. was stirred for 3.75 h. The reaction was concentrated and azeotroped from toluene (2×75 mL). The residue was purified by chromatography on silica gel (3:2 hexanes:EtOAc) to afford (3aR,4R,5R,7aS)-5-((1S,2S,4S)-2-(2-((tert-butyldiphenylsilyl)oxy)ethyl)-4-hydroxy-1-methylcyclohexyl)-7a-methyl-1-oxooctahydro-1H-inden-4-yl acetate (Compound No. 88, 1.87 g, 81% over 2 steps) as a white foam.

C. To a suspension of Ph$_3$PMeBr (2.77 g, 7.75 mmol) in THF (50 mL) under argon at 0° C. was added KO$^t$Bu (870 mg, 7.75 mmol). After 30 min a solution of (3aR,4R,5R,7aS)-5-((1S,2S,4S)-2-(2-((tert-butyldiphenylsilyl)oxy)ethyl)-4-hydroxy-1-methylcyclohexyl)-7a-methyl-1-oxooctahydro-1H-inden-4-yl acetate (Compound No. 88, 1.89 g, 3.1 mmol) in THF (25 mL) was added via cannula and the mixture was stirred at room temperature for 24 h. The reaction was quenched with brine (80 mL), extracted with EtOAc (3×75 mL), dried (Na$_2$SO$_4$) and concentrated. The residue was purified by chromatography on silica gel (2:1 hexanes:EtOAc) to afford (3aR,4R,5R,7aS)-5-((1S,2S,4S)-2-(2-((tert-butyldiphenylsilyl)oxy)ethyl)-4-hydroxy-1-methylcyclohexyl)-7a-methyl-1-methyleneoctahydro-1H-inden-4-yl acetate (Compound No. 89, 1.60 g, 85%) as a white foam.

D. A mixture of (3aR,4R,5R,7aS)-5-((1S,2S,4S)-2-(2-((tert-butyldiphenylsilyl)oxy)ethyl)-4-hydroxy-1-methylcyclohexyl)-7a-methyl-1-methyleneoctahydro-1H-inden-4-yl acetate (Compound No. 89, 1.60 g, 2.65 mmol), Ac$_2$O (0.5 mL, 5.3 mmol) and DMAP (32 mg, 0.26 mmol) in pyridine (50 mL) under argon at 0° C. was stirred and warmed to room temperature over 2.5 h. Water (50 mL) and EtOAc (250 mL) were added and separated. The organic layer was washed with brine (3×50 mL), dried (Na$_2$SO$_4$) and concentrated. The material was azeotroped from toluene (2×50 mL) to afford (3aR,4R,5R,7aS)-5-((1S,2S,4S)-4-acetoxy-2-(2-((tert-butyldiphenylsilyl)oxy)ethyl)-1-methylcyclohexyl)-7a-methyl-1-methyleneoctahydro-1H-inden-4-yl acetate (Compound No. 90, 1.84 g) as a solid white foam.

E. A mixture of (3aR,4R,5R,7aS)-5-((1S,2S,4S)-4-acetoxy-2-(2-((tert-butyldiphenylsilyl)oxy)ethyl)-1-methylcyclohexyl)-7a-methyl-1-methyleneoctahydro-1H-inden-4-yl acetate (Compound No. 90, 1.84 g) and TBAF (4 mL of a 1 M solution in THF, 4 mmol) in THF (60 mL) under argon at room temperature was stirred for 2.5 h. A solution of saturated NaHCO$_3$ solution (50 mL) was added and the mixture was extracted with EtOAc (3×50 mL), washed with brine (50 mL), dried (Na$_2$SO$_4$) and concentrated. The residue was purified by chromatography on silica gel (2:1 hexanes:EtOAc) to afford (3aR,4R,5R,7aS)-5-((1S,2S,4S)-4-acetoxy-2-(2-hydroxyethyl)-1-methylcyclohexyl)-7a-methyl-1-methyleneoctahydro-1H-inden-4-yl acetate (Compound No. 91, 0.99 g, 92% over 2 steps) as a white foam.

F. A mixture of (3aR,4R,5R,7aS)-5-((1S,2S,4S)-4-acetoxy-2-(2-hydroxyethyl)-1-methylcyclohexyl)-7a-methyl-1-methyleneoctahydro-1H-inden-4-yl acetate (Compound No. 91, 100 mg, 0.25 mmol) and IBX (210 mg, 0.75 mmol) in MeCN (5 mL) under argon was stirred at 65° C. for 75 min. The mixture was cooled to room temperature, filtered through Celite and concentrated to afford (3aR,4R,5R,7aS)-5-((1S,2R,4S)-4-acetoxy-1-methyl-2-(2-oxoethyl)cyclohexyl)-7a-methyl-1-methyleneoctahydro-1H-inden-4-yl acetate (Compound No. 92, 125 mg) as a white foam.

G. A mixture of (3aR,4R,5R,7aS)-5-((1S,2R,4S)-4-acetoxy-1-methyl-2-(2-oxoethyl)cyclohexyl)-7a-methyl-1-methyleneoctahydro-1H-inden-4-yl acetate (Compound No. 92, 58 mg, 0.14 mmol) and morpholine (33 µL, 0.35 mmol) in THF (5 mL) under argon at room temperature was allowed to stir for 5 min. To the resultant mixture was added NaBH(OAc)$_3$ (75 mg, 0.35 mmol) and the mixture was stirred for 21 h. The reaction was quenched with saturated NaHCO$_3$ solution (10 mL), extracted with EtOAc (3×10 mL), dried (Na$_2$SO$_4$) and concentrated. The residue was purified by radial chromatography (2:1 EtOAc:hexanes) to afford (3aR,4R,5R,7aS)-5-((1S,2S,4S)-4-acetoxy-1-methyl-2-(2-morpholinoethyl)cyclohexyl)-7a-methyl-1-methyleneoctahydro-1H-inden-4-yl acetate (Compound No. 93, 25 mg, 40%) as a colourless oil.

H. A mixture of (3aR,4R,5R,7aS)-5-((1S,2S,4S)-4-acetoxy-1-methyl-2-(2-morpholinoethyl)cyclohexyl)-7a-methyl-1-methyleneoctahydro-1H-inden-4-yl acetate (Compound No. 93, 25 mg, 0.05 mmol) and NaOMe (0.1 mL of a 5.4 M solution in MeOH, 54 mmol) in MeOH (2 mL) under argon at room temperature was stirred for 17 h. The reaction was quenched with saturated NaHCO$_3$ solution (10 mL), extracted successively with CH$_2$Cl$_2$ (2×15 mL) and EtOAc (2×15 mL), dried (Na$_2$SO$_4$) and concentrated to afford (3aR,4R,5R,7aS)-5-((1S,2S,4S)-4-hydroxy-1-methyl-2-(2-morpholinoethyl)cyclohexyl)-7a-methyl-1-methyleneoctahydro-1H-inden-4-yl acetate (Compound No. 94, 23 mg) as a white foam.

I. A mixture of (3aR,4R,5R,7aS)-5-((1S,2S,4S)-4-hydroxy-1-methyl-2-(2-morpholinoethyl)cyclohexyl)-7a-methyl-1-methyleneoctahydro-1H-inden-4-yl acetate (Compound No. 94, 23 mg) and LiAlH$_4$ (0.2 mL of a 2 M solution in THF, 0.4 mmol) in THF (8 mL) under argon at 0° C. was stirred and allowed to warm to room temperature over 17 h. The mixture was cooled to 0° C. and powdered Na$_2$SO$_4$.10H$_2$O (excess) was added in portions. The cooling bath was removed and the mixture was stirred for 20 min before being filtered and concentrated. The residue was purified using chromatography on silica gel (0% to 2% to 4% to 6% to 8% to 10% MeOH/EtOAc) to afford (3aR,4R,5R,7aS)-5-((1S,2S,4S)-4-hydroxy-1-methyl-2-(2-morpholinoethyl)cyclohexyl)-7a-methyl-1-methyleneoctahydro-1H-inden-4-ol (Compound No. 95, 14 mg, 70% over 2 steps) as a colourless oil.

J. A mixture of (3aR,4R,5R,7aS)-5-((1S,2S,4S)-4-hydroxy-1-methyl-2-(2-morpholinoethyl)cyclohexyl)-7a-methyl-1-methyleneoctahydro-1H-inden-4-ol (Compound No. 95, 14 mg, 0.04 mmol) and AcOH (20 µL) in MeOH (5 mL) at room temperature was stirred for 10 min before being concentrate. The residue was taken up in CH$_2$Cl$_2$:hexanes (1:1, 10 mL) and concentrated to afford (3aR,4R,5R,7aS)-5-((1S,2S,4S)-4-hydroxy-1-methyl-2-(2-morpholinoethyl)cyclohexyl)-7a-methyl-1-methyleneoctahydro-1H-inden-4-ol (Compound No. 96, 16 mg, 93%) as a white solid. $^1$H NMR (300 MHz, CDCl$_3$) δ4.64 (s, 1H), 4.61 (s, 1H), 3.75 (m, 4H), 3.68 (m, 1H), 3.49 (m, 1H), 2.58 (m, 4H), 2.49-2.21 (m, 3H), 2.02 (s, 3H), 1.86-1.16 (m, 18H), 1.12 (s, 3H), 0.77 (s, 3H); $^{13}$C NMR (75 MHz, CDCl$_3$) δ160.9, 101.5, 72.5, 70.7, 66.4, 57.5, 56.6, 53.5, 52.4, 45.7, 38.5, 37.7, 36.1, 35.4, 31.3, 31.0, 29.5, 25.1, 23.9, 22.9, 21.3, 18.7; MS m/z: 392.4 [M+H]$^+$ free base.

Example 46

Synthesis of (1S,3S,4R)-3-(aminomethyl)-4-((3aS,4R,5S,7aS)-4-(aminomethyl)-7a-methyl-1-methyleneoctahydro-1H-inden-5-yl)-4-methylcyclohexanol (Compound No. 99)

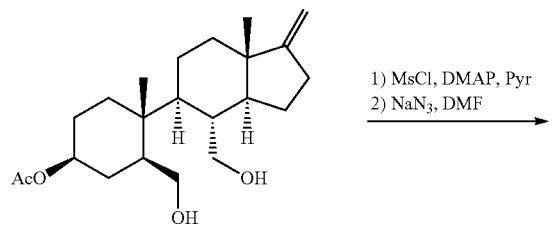

43

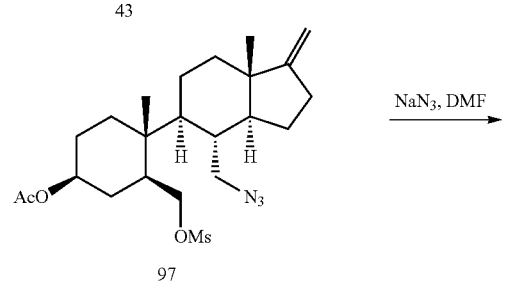

97

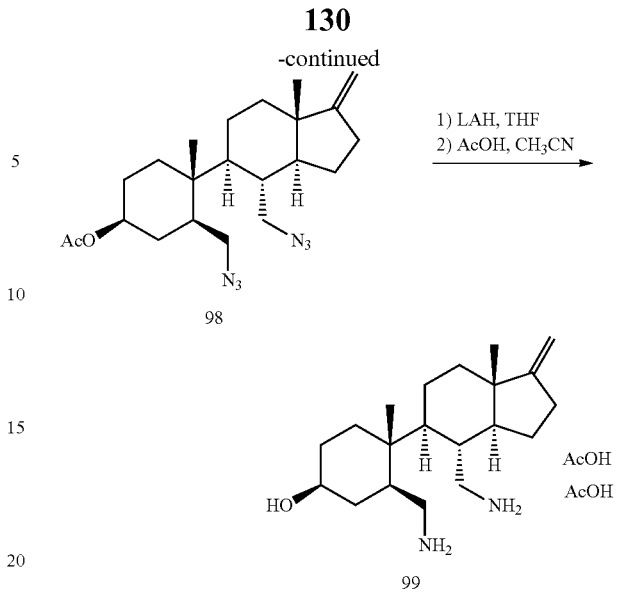

A. To a solution of (1S,3S,4R)-3-(hydroxymethyl)-4-((3aS,4R,5S,7aS)-4-(hydroxymethyl)-7a-methyl-1-methyleneoctahydro-1H-inden-5-yl)-4-methylcyclohexyl acetate (Compound No. 43, 519 mg, 1.43 mmol) and DMAP (catalytic amount) in pyridine (2.8 mL) under argon at 0° C. was added MsCl (0.66 mL, 8.5 mmol). The mixture was stirred for 17.5 h at room temperature, then cooled to 0° C. The reaction was quenched with saturated NaHCO$_3$ solution (15 mL), extracted with EtOAc (3×15 mL), washed with brine (3×15 mL), dried (MgSO$_4$) and concentrated to afford a brown oil. To a solution of the oil in DMF (10 mL) under argon was added NaN$_3$ (557 mg, 8.57 mmol) and the mixture was heated to 60° C. for 19 h. The mixture was cooled to room temperature and diluted with water (50 mL) and EtOAc (50 mL), washed with brine (2×50 mL), dried (MgSO$_4$) and concentrated. The residue was purified using chromatography on silica gel (hexanes:EtOAc, 4:1) to afford (1S,3S,4R)-4-((3aS,4R,5S,7aS)-4-(azidomethyl)-7a-methyl-1-methyleneoctahydro-1H-inden-5-yl)-4-methyl-3-(((methylsulfonyl)oxy)methyl)cyclohexyl acetate (Compound No. 97, 393 mg, 63%) as a colourless oil.

B. To a solution of (1S,3S,4R)-4-((3aS,4R,5S,7aS)-4-(azidomethyl)-7a-methyl-1-methyleneoctahydro-1H-inden-5-yl)-4-methyl-3-(((methylsulfonyl)oxy)methyl)cyclohexyl acetate (Compound No. 97, 133 mg, 0.284 mmol) in DMF (2 mL) under argon was added NaN$_3$ (232 mg, 3.57 mmol) and the mixture was heated to 100° C. for 24 h. The yellow suspension was cooled to room temperature, diluted with water (50 mL) and EtOAc (50 mL), washed with brine (2×50 mL), dried (MgSO$_4$), and concentrated. The residue was purified using chromatography on silica gel (hexanes:EtOAc, 19:1 to 9:1) to afford (1S,3S,4R)-3-(azidomethyl)-4-((3aS,4R,5S,7aS)-4-(azidomethyl)-7a-methyl-1-methyleneoctahydro-1H-inden-5-yl)-4-methylcyclohexyl acetate (Compound No. 98, 110 mg, 94%) as a colourless oil.

C. To a solution of (1S,3S,4R)-3-(azidomethyl)-4-((3aS,4R,5S,7aS)-4-(azidomethyl)-7a-methyl-1-methyleneoctahydro-1H-inden-5-yl)-4-methylcyclohexyl acetate (Compound No. 98, 650 mg, 1.57 mmol) in THF (30 mL) under argon at 0° C. was added LiAlH$_4$ (2 M in THF, 5.4 mL, 11 mmol) and the mixture was stirred for 23 h at room temperature. The reaction mixture was cooled to 0° C. and quenched with water (0.42 mL), 2 M NaOH (0.42 mL, 0.84 mmol), followed by water (1.23 mL). The suspension was stirred for 5 min, filtered, and washed with THF (120 mL). The filtrate was concentrated to afford a white solid. The solid was dissolved in MeOH (25 mL) and filtered through Celite to remove excess aluminum salts. The filtrate was concentrated and the residue was dissolved in acetic acid (1 mL), stirred 20 min and concentrated. The residue was dissolved in MeOH (4 mL) and MeCN (25 mL) was added. The mixture was stirred then was added MeCN (75 mL). The mixture was cooled to 0° C. and stirred until the product crashed out of solution. The suspension was filtered to afford (1S,3S,4R)-3-(aminomethyl)-4-((3aS,4R,5S,7aS)-4-(aminomethyl)-7a-methyl-1-methyleneoctahydro-1H-inden-5-yl)-4-methylcyclohexanol (Compound No. 99, 353 mg, 51%). $^1$H NMR (CD$_3$OD): δ4.59 (s, 2H), 3.47-3.38 (m, 1H), 2.97 (d, J=13.8 Hz, 2H), 2.53-2.44 (m, 2H), 2.27-2.19 (m, 1H), 1.96-1.20 (m, 23H), 1.06 (s, 3H), 0.76 (s, 3H). $^{13}$C NMR (CD$_3$OD): δ179.0, 160.5, 101.1, 68.9, 49.8, 43.8, 43.6, 41.2, 39.4, 39.3, 37.5, 36.3, 35.4, 33.3, 30.4, 28.8, 24.3, 23.1, 22.8, 20.3, 17.3, 12.9. MS m/z: 321.3.

Example 47

Synthesis of (3aR,4R,5R,7aS)-5-((1S,2S,4S)-4-hydroxy-1-methyl-2-(2-(4-methylpiperazin-1-yl)ethyl)cyclohexyl)-7a-methyl-1-methyleneoctahydro-1H-inden-4-ol (Compound No. 103)

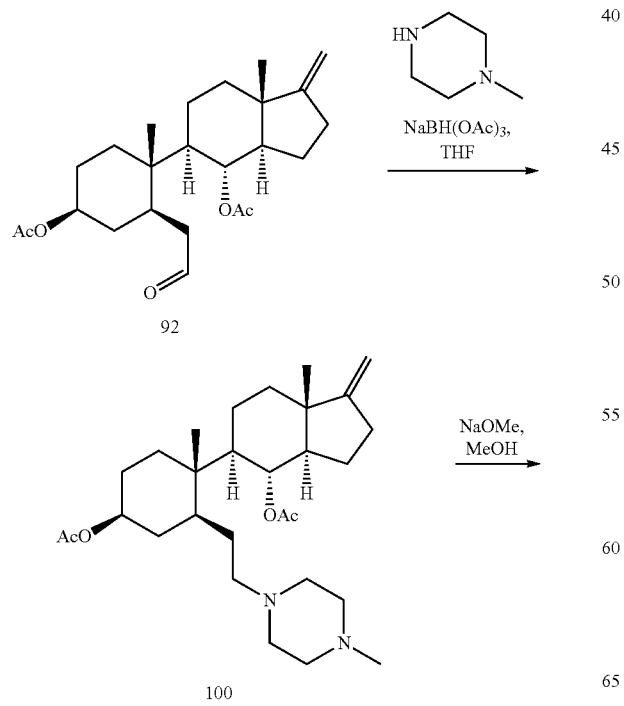

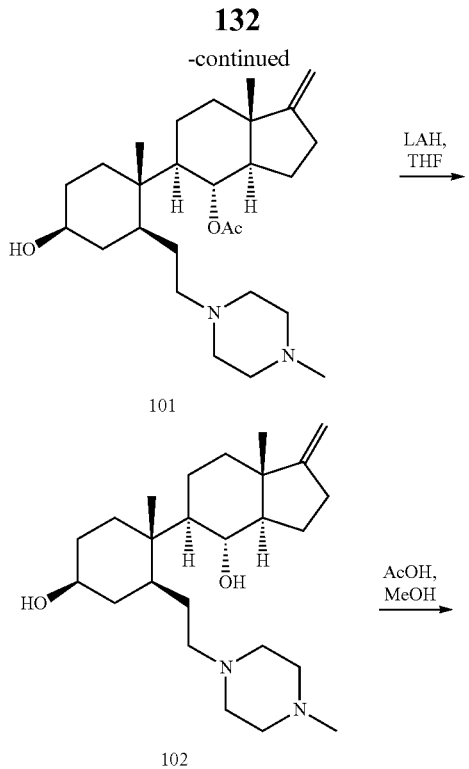

A. A mixture of (3aR,4R,5R,7aS)-5-((1S,2R,4S)-4-acetoxy-1-methyl-2-(2-oxoethyl)cyclohexyl)-7a-methyl-1-methyleneoctahydro-1H-inden-4-yl acetate (Compound No. 92, 60 mg, 0.15 mmol) and 1-methyl-piperazine (42 µL, 0.37 mmol) in THF (5 mL) under argon at room temperature was allowed to stir for 5 min. To the resultant mixture was added NaBH(OAc)$_3$ (75 mg, 0.35 mmol) and the mixture was stirred for 21 h. The reaction was quenched with saturated NaHCO$_3$ solution (10 mL), extracted with EtOAc (3×10 mL), dried (Na$_2$SO$_4$) and concentrated. The residue was purified using chromatography on silica gel (4:1 EtOAc:MeOH) to afford (3aR,4R,5R,7aS)-5-((1S,2S,4S)-4-acetoxy-1-methyl-2-(2-(4-methylpiperazin-1-yl)ethyl)cyclohexyl)-7a-methyl-1-methyleneoctahydro-1H-inden-4-yl acetate (Compound No. 100, 28 mg, 40%) as a colourless oil.

B. A mixture of (3aR,4R,5R,7aS)-5-((1S,2S,4S)-4-acetoxy-1-methyl-2-(2-(4-methylpiperazin-1-yl)ethyl)cyclohexyl)-7a-methyl-1-methyleneoctahydro-1H-inden-4-yl acetate (Compound No. 100, 28 mg, 0.05 mmol) and NaOMe (0.1 mL of a 5.4 M solution in MeOH, 54 mmol) in MeOH (2 mL) under argon at room temperature was stirred for 17 h. The reaction was quenched with saturated NaHCO$_3$ solution (10 mL), extracted successively with CH$_2$Cl$_2$ (2×15 mL) and EtOAc (2×15 mL), dried (Na₂SO₄) and concentrated to afford (3aR,4R,5R,7aS)-5-((1S,2S,4S)-4-hydroxy-1-methyl-2-(2-(4-methylpiperazin-1-yl)ethyl)cyclohexyl)-7a-methyl-1-methyleneoctahydro-1H-inden-4-yl acetate (Compound No. 101, 22 mg) as a white foam.

C. A mixture of (3aR,4R,5R,7aS)-5-((1S,2S,4S)-4-hydroxy-1-methyl-2-(2-(4-methylpiperazin-1-yl)ethyl)cyclohexyl)-7a-methyl-1-methyleneoctahydro-1H-inden-4-yl acetate (Compound No. 101, 22 mg) and LAH (0.2 mL of a 2 M solution in THF, 0.4 mmol) in THF (4 mL) under argon at 0° C. was stirred and allowed to warm to room temperature over 17 h. The mixture was cooled to 0° C. and powdered Na₂SO₄·10H₂O (excess) was added in portions. The cooling bath was removed and the mixture was stirred for 20 min before being filtered and concentrated. The residue was purified using chromatography on silica gel (0% to 25% to 50% to 50%+1% NH₄OH MeOH:EtOAc) to afford (3aR,4R,5R,7aS)-5-((1S,2S,4S)-4-hydroxy-1-methyl-2-(2-(4-methylpiperazin-1-yl)ethyl)cyclohexyl)-7a-methyl-1-methyleneoctahydro-1H-inden-4-ol (Compound No. 102, 18 mg, 91% over 2 steps) as a colourless oil.

D. A mixture of (3aR,4R,5R,7aS)-5-((1S,2S,4S)-4-hydroxy-1-methyl-2-(2-(4-methylpiperazin-1-yl)ethyl)cyclohexyl)-7a-methyl-1-methyleneoctahydro-1H-inden-4-ol (Compound No. 102, 18 mg, 0.04 mmol) and AcOH (40 µL) in MeOH (5 mL) at room temperature was stirred for 10 min then was concentrated. The residue was taken up in CH₂Cl₂: Hexanes (1:1, 10 mL) and concentrated to afford (3aR,4R,5R,7aS)-5-((1S,2S,4S)-4-hydroxy-1-methyl-2-(2-(4-methylpiperazin-1-yl)ethyl)cyclohexyl)-7a-methyl-1-methyleneoctahydro-1H-inden-4-ol (Compound No. 103, 20 mg, 95%) as an off-white solid. ¹H NMR (300 MHz, CDCl₃) δ 6.01 (br s, 1H), 4.63 (s, 1H), 4.60 (s, 1H), 3.66 (m, 1H), 3.44 (m, 1H), 2.70 (m, 8H), 2.48 (m, 3H), 2.38 (s, 2H), 2.23 (m, 1H), 2.00 (s, 3H), 1.95-1.16 (m, 18H), 1.11 (s, 3H), 0.76 (s, 3H); ¹³C NMR (75 MHz, CDCl₃) δ 160.9, 101.4, 72.4, 70.6, 57.0, 56.6, 54.3, 52.6, 52.4, 45.6, 45.4, 38.4, 37.6, 36.1, 35.4, 31.3, 31.0, 29.4, 25.7, 23.9, 22.8, 21.3, 18.7; MS m/z: 405.4 [M+H]⁺ free base.

Example 48

Synthesis of (3aR,4R,5R,7aS)-5-((1S,2S,4S)-2-(2-(1H-1,2,4-triazol-1-yl)ethyl)-4-hydroxy-1-methylcyclohexyl)-7a-methyl-1-methyleneoctahydro-1H-inden-4-ol (Compound No. 108)

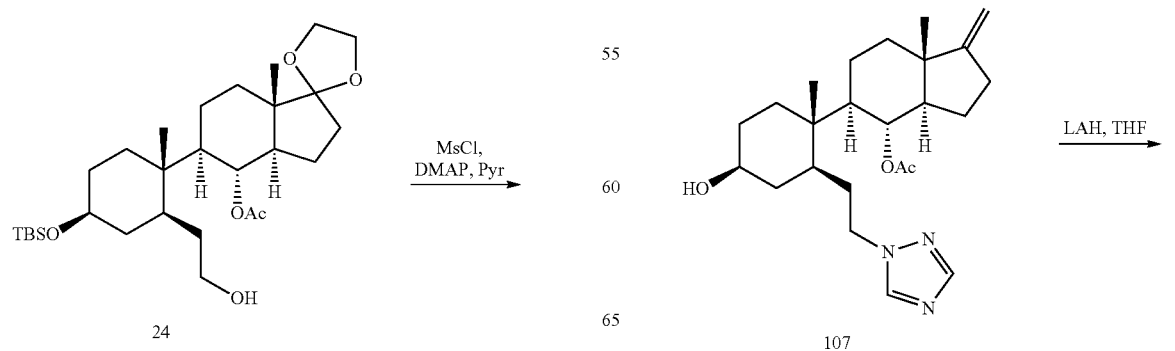

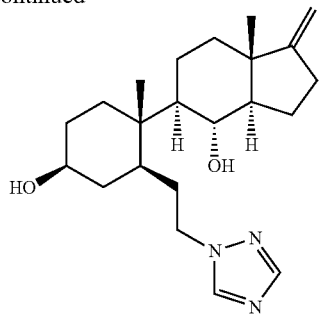

108

A. A solution of (3a'R,4'R,5'R,7a'S)-5'-((1S,2S,4S)-4-((tert-butyldimethylsilyl)oxy)-2-(2-hydroxyethyl)-1-methylcyclohexyl)-7a'-methyloctahydrospiro[[1,3]dioxolane-2,1'-inden]-4'-yl acetate (Compound No. 24, 389 mg, 0.74 mmol), MsCl (0.18 mL, 2.2 mmol) and DMAP (catalytic amount) in pyridine (4 mL) was stirred at room temperature under nitrogen for 30 min. The solution was cooled in ice, quenched with saturated NaHCO₃ solution (5 mL) for 20 min, diluted with EtOAc (100 mL), washed with brine (2×15 mL), dried (MgSO₄) and concentrated. The residue was purified using chromatography on silica gel (30% EtOAc/hexanes) to afford (3a'R,4'R,5'R,7a'S)-5'-((1S,2S,4S)-4-((tert-butyldimethylsilyl)oxy)-1-methyl-2-(2-((methylsulfonyl)oxy)ethyl)cyclohexyl)-7a'-methyloctahydrospiro[[1,3]dioxolane-2, 1'-inden]-4'-yl acetate (Compound No. 104, 423 mg, 95%) as a white foam.

B. To a solution of 1,2,4-triazole (465 mg, 6.60 mmol) in DMF (5 mL) at 0° C. under nitrogen was added NaH (264 mg, 6.60 mmol). After 1 h, added (3a'R,4'R,5'R,7a'S)-5'-((1S,2S,4S)-4-((tert-butyldimethylsilyl)oxy)-1-methyl-2-(2-((methylsulfonyl)oxy)ethyl)cyclohexyl)-7a'-methyloctahydrospiro[[1,3]dioxolane-2,1'-inden]-4'-yl acetate (Compound No. 104, 359 mg, 0.60 mmol). After 18 h, the solution was cooled in ice, quenched with saturated NaHCO₃ solution (5 mL), diluted with Et₂O (100 mL), washed with brine (3×15 mL), dried (MgSO₄) and concentrated. The residue was purified using chromatography on silica gel (50% then 65% EtOAc/hexanes) to afford (3a'R, 4'R,5'R,7a'S)-5'-((1S,2S,4S)-2-(2-(1H-1,2,4-triazol-1-yl) ethyl)-4-((tert-butyldimethylsilyl)oxy)-1-methylcyclohexyl)-7a'-methyloctahydrospiro[[1,3]dioxolane-2,1'-inden]-4'-yl acetate (Compound No. 105, 0.31 g, 91%) as a white solid.

C. A solution of (3a'R,4'R,5'R,7a'S)-5'-((1S,2S,4S)-2-(2-(1H-1,2,4-triazol-1-yl)ethyl)-4-((tert-butyldimethylsilyl) oxy)-1-methylcyclohexyl)-7a'-methyloctahydrospiro[[1,3] dioxolane-2,1'-inden]-4'-yl acetate (Compound No. 105, 0.31 g, 0.54 mmol) in acetic acid (40 mL) and water (10 mL) was stirred at room temperature for 3 d then was concentrated. The residue was 3 times concentrated from toluene (20 mL) then concentrated from CH₂Cl₂/hexanes to afford (3aR,4R,5R,7aS)-5-((1S,2S,4S)-2-(2-(1H-1,2,4-triazol-1-yl)ethyl)-4-hydroxy-1-methylcyclohexyl)-7a-methyl-1-oxooctahydro-1H-inden-4-yl acetate (Compound No. 106, 0.25 g, 100%) as a white foam.

D. A solution of methyl triphenylphosphonium bromide (970 mg, 2.7 mmol) and KOʳBu (310 mg, 2.7 mmol) in THF (4 mL) was stirred at room temperature under nitrogen for 1.5 h then added a suspension of (3aR,4R,5R,7aS)-5-((1S, 2S,4S)-2-(2-(1H-1,2,4-triazol-1-yl)ethyl)-4-hydroxy-1-methylcyclohexyl)-7a-methyl-1-oxooctahydro-1H-inden-4-yl acetate (Compound No. 106, 0.22 g, 0.54 mmol) in THF (7 mL) and CH₂Cl₂ (1 mL). After 45 min, the reaction flask was fitted with a reflux condenser and the solution was heated at 50° C. for 18 h. The solution was cooled to room temperature, diluted with saturated NaHCO₃ solution (5 mL) then EtOAc (100 mL), washed with brine (3×15 mL), dried (MgSO₄) and concentrated. The residue was purified using chromatography on silica gel (5% then 10% MeOH/EtOAc) to afford (3aR,4R,5R,7aS)-5-((1S,2S,4S)-2-(2-(1H-1,2,4-triazol-1-yl)ethyl)-4-hydroxy-1-methylcyclohexyl)-7a-methyl-1-methyleneoctahydro-1H-inden-4-yl acetate (Compound No. 107, 373 mg) as an impure white solid.

E. To a solution of (3aR,4R,5R,7aS)-5-((1S,2S,4S)-2-(2-(1H-1,2,4-triazol-1-yl)ethyl)-4-hydroxy-1-methylcyclohexyl)-7a-methyl-1-methyleneoctahydro-1H-inden-4-yl acetate (Compound No. 107, 220 mg, 0.54 mmol) in THF (5 mL) at 0° C. under nitrogen was added LiAH (0.54 mL of a 2 M solution in THF, 1.1 mmol). After 18 h, the solution was cooled in ice, diluted with Et₂O (10 mL) then had added to it Na₂SO₄.10H₂O (354 mg). After 1 h, the solution was filtered through Celite, eluted with EtOAc and concentrated. The residue was purified using chromatography on silica gel (EtOAc then 5% MeOH/EtOAc) to afford (3aR,4R,5R,7aS)-5-((1S,2S,4S)-2-(2-(1H-1,2,4-triazol-1-yl)ethyl)-4-hydroxy-1-methylcyclohexyl)-7a-methyl-1-methyleneoctahydro-1H-inden-4-ol (Compound No. 108, 70 mg, 35%) as a white solid. ¹H NMR (CDCl₃): δ8.05 (s, 1H), 7.95 (s, 1H), 4.62 (m, 2H), 4.28 (m, 1H), 4.15 (m, 1H), 3.62 (m, 1H), 3.55 (m, 1H), 2.55 (m, 1H), 2.25 (m, 1H), 2.00 (m, 2H), 1.85 (m, 2H), 0.95-1.70 (13H), 1.15 (s, 3H), 0.75 (s, 3H). ES-MS m/z 374 ([M+1]⁺).

Example 49

Synthesis of (3aR,4R,5R,7aS)-5-((1S,2S,4S)-2-(2-(1H-imidazol-1-yl)ethyl)-4-hydroxy-1-methylcyclohexyl)-7a-methyl-1-methyleneoctahydro-1H-inden-4-ol (Compound No. 119)

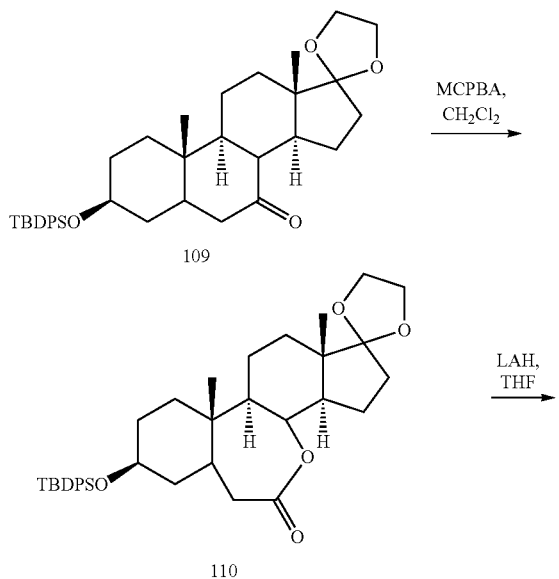

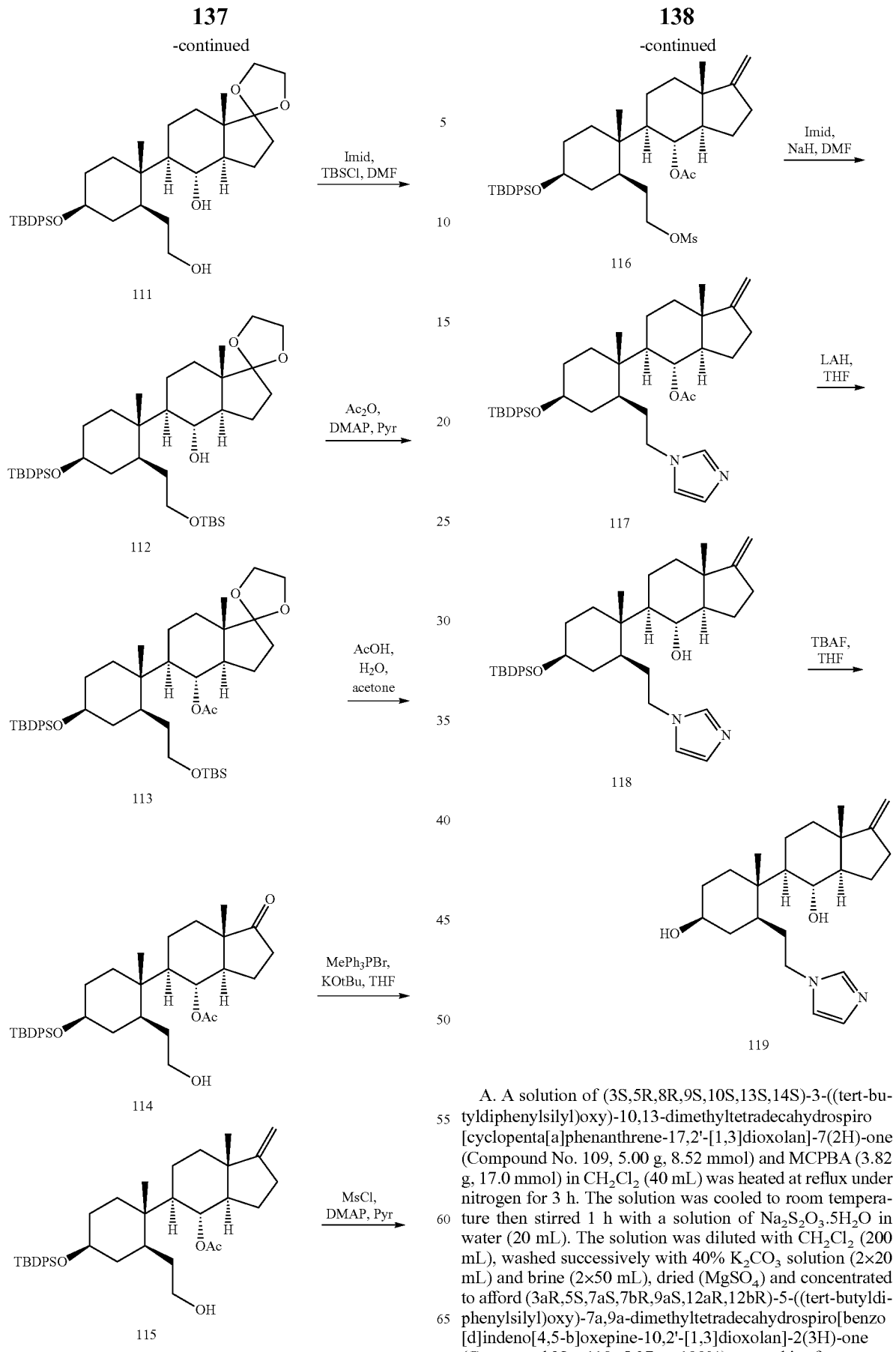

A. A solution of (3S,5R,8R,9S,10S,13S,14S)-3-((tert-butyldiphenylsilyl)oxy)-10,13-dimethyltetradecahydrospiro[cyclopenta[a]phenanthrene-17,2'-[1,3]dioxolan]-7(2H)-one (Compound No. 109, 5.00 g, 8.52 mmol) and MCPBA (3.82 g, 17.0 mmol) in $CH_2Cl_2$ (40 mL) was heated at reflux under nitrogen for 3 h. The solution was cooled to room temperature then stirred 1 h with a solution of $Na_2S_2O_3 \cdot 5H_2O$ in water (20 mL). The solution was diluted with $CH_2Cl_2$ (200 mL), washed successively with 40% $K_2CO_3$ solution (2×20 mL) and brine (2×50 mL), dried ($MgSO_4$) and concentrated to afford (3aR,5S,7aS,7bR,9aS,12aR,12bR)-5-((tert-butyldiphenylsilyl)oxy)-7a,9a-dimethyltetradecahydrospiro[benzo[d]indeno[4,5-b]oxepine-10,2'-[1,3]dioxolan]-2(3H)-one (Compound No. 110, 5.37 g, 100%) as a white foam.

B. A solution of (3aR,5S,7aS,7bR,9aS,12aR,12bR)-5-((tert-butyldiphenylsilyl)oxy)-7a,9a-dimethyltetradecahydrospiro[benzo[d]indeno[4,5-b]oxepine-10,2'-[1,3]dioxolan]-2(3H)-one (Compound No. 110, 5.14 g, 8.52 mmol), LAH (4.3 mL of a 2 M solution in THF, 8.6 mmol) in THF at 0° C. under nitrogen was stirred for 6 h. The solution was cooled in ice then added Na$_2$SO$_4$.10H$_2$O and stirred 16 h. The solution was filtered through Celite, eluted with EtOAc and concentrated. The residue was purified using chromatography on silica gel (50% EtOAc/hexanes) to afford (3a'R,4'R,5'R,7a'S)-5'-((1S,2S,4S)-4-((tert-butyldiphenylsilyl)oxy)-2-(2-hydroxyethyl)-1-methylcyclohexyl)-7a'-methyloctahydrospiro[[1,3]dioxolane-2,1'-inden]-4'-ol (Compound No. 111, 4.10 g, 79%) as a white solid.

C. A solution of (3a'R,4'R,5'R,7a'S)-5'-((1S,2S,4S)-4-((tert-butyldiphenylsilyl)oxy)-2-(2-hydroxyethyl)-1-methylcyclohexyl)-7a'-methyloctahydrospiro[[1,3]dioxolane-2,1'-inden]-4'-ol (Compound No. 111, 3.80 g, 6.26 mmol), imidazole (1.27 g, 18.8 mmol) and TBSCl (1.04 g, 6.89 mmol) in DMF (30 mL) at 0° C. under nitrogen was stirred for 1 h. The solution was diluted with Et$_2$O (150 mL), washed with brine (3×30 mL), dried (MgSO$_4$) and concentrated to afford (3a'R,4'R,5'R,7a'S)-5'-((1S,2S,4S)-2-(2-((tert-butyldimethylsilyl)oxy)ethyl)-4-((tert-butyldiphenylsilyl)oxy)-1-methylcyclohexyl)-7a'-methyloctahydrospiro[[1,3]dioxolane-2,1'-inden]-4'-ol (Compound No. 112, 4.54 g, 100%) as a white foam.

D. A solution of (3a'R,4'R,5'R,7a'S)-5'-((1S,2S,4S)-2-(2-((tert-butyldimethylsilyl)oxy)ethyl)-4-((tert-butyldiphenylsilyl)oxy)-1-methylcyclohexyl)-7a'-methyloctahydrospiro[[1,3]dioxolane-2,1'-inden]-4'-ol (Compound No. 112, 4.51 g, 6.26 mmol), acetic anhydride (1.8 mL, 18.8 mmol) and DMAP (73 mg, 0.6 mmol) in pyridine (30 mL) was stirred at room temperature under nitrogen for 3 h, then at 50° C. for 1 h. The solution was cooled in ice then added saturated NaHCO$_3$ solution (25 mL) and stirred at room temperature for 30 min. The solution was diluted with EtOAc (200 mL), washed with brine (3×30 mL), dried (MgSO$_4$) and concentrated. The residue was purified using chromatography on silica gel (10% then 15% EtOAc/hexanes) to afford (3a'R,4'R,5'R,7a'S)-5'-((1S,2S,4S)-2-(2-((tert-butyldimethylsilyl)oxy)ethyl)-4-((tert-butyldiphenylsilyl)oxy)-1-methylcyclohexyl)-7a'-methyloctahydrospiro[[1,3]dioxolane-2,1'-inden]-4'-yl acetate (Compound No. 113, 4.19 g, 88%) as a white foam.

E. A solution of (3a'R,4'R,5'R,7a'S)-5'-((1S,2S,4S)-2-(2-((tert-butyldimethylsilyl)oxy)ethyl)-4-((tert-butyldiphenylsilyl)oxy)-1-methylcyclohexyl)-7a'-methyloctahydrospiro[[1,3]dioxolane-2,1'-inden]-4'-yl acetate (Compound No. 113, 4.19 g, 5.49 mmol) in acetic acid (24 mL), water (6 mL) and acetone (40 mL) was stirred at room temperature for 4 days then at 80° C. for 5 h. The solution was cooled to room temperature, concentrated then concentrated 3 times from toluene (30 mL). The residue was purified using chromatography on silica gel (35% then 40% EtOAc/hexanes) to afford (3aR,4R,5R,7aS)-5-((1S,2S,4S)-4-((tert-butyldiphenylsilyl)oxy)-2-(2-hydroxyethyl)-1-methylcyclohexyl)-7a-methyl-1-oxooctahydro-1H-inden-4-yl acetate (Compound No. 114, 3.06 g, 92%) as a white foam.

F. A solution of methyl triphenylphosphonium bromide (6.03 g, 16.9 mmol) and KO$^t$Bu (1.93 g, 16.9 mmol) in THF (40 mL) was stirred at room temperature under nitrogen for 1 h then added (3aR,4R,5R,7aS)-5-((1S,2S,4S)-4-((tert-butyldiphenylsilyl)oxy)-2-(2-hydroxyethyl)-1-methylcyclohexyl)-7a-methyl-1-oxooctahydro-1H-inden-4-yl acetate (Compound No. 114, 3.06 g, 5.06 mmol) in THF (10 mL). After 18 h, added saturated NaHCO$_3$ solution (15 mL), diluted with EtOAc (200 mL), washed with brine (3×30 mL), dried (MgSO$_4$) and concentrated. The residue was purified using chromatography on silica gel (20% EtOAc/hexanes with 1% CH$_2$Cl$_2$) to afford (3aR,4R,5R,7aS)-5-((1S,2S,4S)-4-((tert-butyldiphenylsilyl)oxy)-2-(2-hydroxyethyl)-1-methylcyclohexyl)-7a-methyl-1-methyleneoctahydro-1H-inden-4-yl acetate (Compound No. 115, 2.78 g) as a white foam.

G. A solution of (3aR,4R,5R,7aS)-5-((1S,2S,4S)-4-((tert-butyldiphenylsilyl)oxy)-2-(2-hydroxyethyl)-1-methylcyclohexyl)-7a-methyl-1-methyleneoctahydro-1H-inden-4-yl acetate (Compound No. 115, 1.00 g, 1.66 mmol) and MsCl (0.39 mL, 4.98 mmol) in pyridine (8.5 mL) under nitrogen was stirred at 0° C. for 10 min then at room temperature for 80 min. The solution was cooled in ice, quenched with saturated NaHCO$_3$ solution (6 mL) for 20 min, diluted with EtOAc (200 mL), washed with brine (3×30 mL), dried (MgSO$_4$) and concentrated. The residue was concentrated 3 times from toluene (30 mL) to afford (3aR,4R,5R,7aS)-5-((1S,2S,4S)-4-((tert-butyldiphenylsilyl)oxy)-1-methyl-2-(2-((methylsulfonyl)oxy)ethyl)cyclohexyl)-7a-methyl-1-methyleneoctahydro-1H-inden-4-yl acetate (Compound No. 116, 1.14 g, 100%) as a white foam.

H. To a solution of imidazole (306 mg, 4.4 mmol) in DMF (5 mL) at 0° C. under nitrogen was added NaH (176 mg, 4.4 mmol). After 45 min, added (3aR,4R,5R,7aS)-5-((1S,2S,4S)-4-((tert-butyldiphenylsilyl)oxy)-1-methyl-2-(2-((methylsulfonyl)oxy)ethyl)cyclohexyl)-7a-methyl-1-methyleneoctahydro-1H-inden-4-yl acetate (Compound No. 116, 300 mg, 0.44 mmol). After 3 days, the solution was cooled in ice, quenched with saturated NaHCO$_3$ solution (5 mL), diluted with Et$_2$O, washed with brine, dried (MgSO$_4$) and concentrated. The crude white foam (3aR,4R,5R,7aS)-5-((1S,2S,4S)-2-(2-(1H-imidazol-1-yl)ethyl)-4-((tert-butyldiphenylsilyl)oxy)-1-methylcyclohexyl)-7a-methyl-1-methyleneoctahydro-1H-inden-4-yl acetate (Compound No. 117, 0.36 g) was used directly in the next step.

I. A solution of (3aR,4R,5R,7aS)-5-((1S,2S,4S)-2-(2-(1H-imidazol-1-yl)ethyl)-4-((tert-butyldiphenylsilyl)oxy)-1-methylcyclohexyl)-7a-methyl-1-methyleneoctahydro-1H-inden-4-yl acetate (Compound No. 117, 288 mg, 0.44 mmol) and LAH (0.66 mL of a 2 M solution in THF, 1.32 mmol) in THF (5 mL) was stirred at 60° C. under nitrogen for 2 h. The solution was cooled in ice, diluted with Et$_2$O (15 mL), quenched with Na$_2$SO$_4$.10H$_2$O for 1.5 h then filtered through Celite, eluted with EtOAc and concentrated. The crude white solid (3aR,4R,5R,7aS)-5-((1S,2S,4S)-2-(2-(1H-imidazol-1-yl)ethyl)-4-((tert-butyldiphenylsilyl)oxy)-1-methylcyclohexyl)-7a-methyl-1-methyleneoctahydro-1H-inden-4-ol (Compound No. 118, 318 mg) was used directly in the next step.

J. To a solution of (3aR,4R,5R,7aS)-5-((1S,2S,4S)-2-(2-(1H-imidazol-1-yl)ethyl)-4-((tert-butyldiphenylsilyl)oxy)-1-methylcyclohexyl)-7a-methyl-1-methyleneoctahydro-1H-inden-4-ol (Compound No. 118, 269 mg, 0.44 mmol) and TBAF (0.85 mL of a 1 M solution in THF, 0.88 mmol) in THF was stirred at room temperature under nitrogen for 16 h. The solution was concentrated and the residue purified using chromatography on silica gel (5% then 10% MeOH/EtOAc) to afford (3aR,4R,5R,7aS)-5-((1S,2S,4S)-2-(2-(1H-imidazol-1-yl)ethyl)-4-hydroxy-1-methylcyclohexyl)-7a-methyl-1-methyleneoctahydro-1H-inden-4-ol (Compound No. 119, 142 mg, 86% over 3 steps) as a white solid. $^1$H NMR (CDCl$_3$): δ7.45 (s, 1H), 7.05 (s, 1H), 6.88 (s, 1H), 4.62 (2H), 4.05 (m, 1H), 3.85 (m, 1H), 3.60 (m, 1H), 3.53 (m, 1H), 2.55 (m, 1H), 2.25 (m, 1H), 1.0-2.0 (16H), 1.15 (s, 3H), 0.80 (m, 1H), 0.75 (s, 3H). ES-MS m/z 373 ([M+1]$^+$).

Example 50

Synthesis of (3aR,4R,5R,7aS)-5-((1S,2S,4S)-2-(2-(1H-pyrazol-1-yl)ethyl)-4-hydroxy-1-methylcyclohexyl)-7a-methyl-1-methyleneoctahydro-1H-inden-4-ol (Compound No. 122)

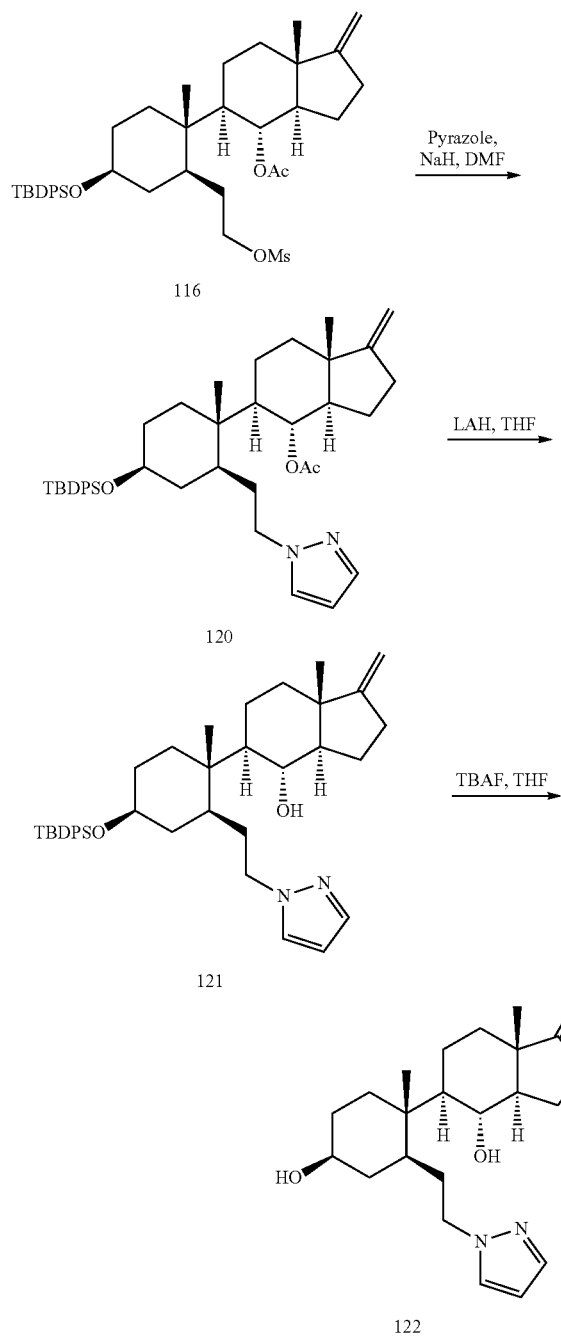

A. To a solution of pyrazole (300 mg, 4.4 mmol) in DMF (5 mL) at 0° C. under nitrogen was added NaH (176 mg, 4.4 mmol). After 45 min, (3aR,4R,5R,7aS)-5-((1S,2S,4S)-4-((tert-butyldiphenylsilyl)oxy)-1-methyl-2-(2-((methylsulfonyl)oxy)ethyl)cyclohexyl)-7a-methyl-1-methyleneoctahydro-1H-inden-4-yl acetate (Compound No. 116, 300 mg, 0.44 mmol) was added. After 1 day, the solution was cooled in ice, quenched with saturated NaHCO₃ solution (5 mL), diluted with EtOAc (100 mL), washed with brine, dried (MgSO₄) and concentrated to give (3aR,4R,5R,7aS)-5-((1S,2S,4S)-2-(2-(1H-pyrazol-1-yl)ethyl)-4-((tert-butyldiphenylsilyl)oxy)-1-methylcyclohexyl)-7a-methyl-1-methyleneoctahydro-1H-inden-4-yl acetate (Compound No. 120).

B. A solution of (3aR,4R,5R,7aS)-5-((1S,2S,4S)-2-(2-(1H-pyrazol-1-yl)ethyl)-4-((tert-butyldiphenylsilyl)oxy)-1-methylcyclohexyl)-7a-methyl-1-methyleneoctahydro-1H-inden-4-yl acetate (Compound No. 120, 288 mg, 0.44 mmol) and LAH (0.66 mL of a 2 M solution in THF, 1.32 mmol) in THF (5 mL) was stirred at 60° C. under nitrogen for 1 h. The solution was cooled in ice, diluted with Et₂O (15 mL), quenched with Na₂SO₄·10H₂O for 1 h then filtered through Celite, eluted with EtOAc (200 mL) and concentrated to give (3aR,4R,5R,7aS)-5-((1S,2S,4S)-2-(2-(1H-pyrazol-1-yl)ethyl)-4-((tert-butyldiphenylsilyl)oxy)-1-methylcyclohexyl)-7a-methyl-1-methyleneoctahydro-1H-inden-4-ol (Compound No. 121).

C. To a solution of (3aR,4R,5R,7aS)-5-((1S,2S,4S)-2-(2-(1H-pyrazol-1-yl)ethyl)-4-((tert-butyldiphenylsilyl)oxy)-1-methylcyclohexyl)-7a-methyl-1-methyleneoctahydro-1H-inden-4-ol (Compound No. 121, 269 mg, 0.44 mmol) and TBAF (0.88 mL of a 1 M solution in THF, 0.88 mmol) in THF at 6° C. was stirred under nitrogen for 3 h. The solution was concentrated and the residue purified using chromatography on silica gel (80% EtOAc/hexanes) to afford (3aR,4R,5R,7aS)-5-((1S,2S,4S)-2-(2-(1H-pyrazol-1-yl)ethyl)-4-hydroxy-1-methylcyclohexyl)-7a-methyl-1-methyleneoctahydro-1H-inden-4-ol (Compound No. 122, 144 mg, 88% over 3 steps) as a white foam. ¹H NMR (CDCl₃): δ7.50 (s, 1H), 7.38 (s, 1H), 6.25 (s, 1H), 4.62 (2H), 4.25 (m, 1H), 4.05 (m, 1H), 3.58 (2H), 2.54 (m, 1H), 2.25 (m, 1H), 2.00 (2H), 1.82 (2H), 1.0-1.7 (12H), 1.15 (s, 3H), 0.90 (m, 1H), 0.75 (s, 3H). ES-MS m/z 373 ([M+1]⁺).

Example 51

Synthesis of (3aR,4R,5R,7aS)-5-((1S,2S,4S)-2-(2-(1H-pyrrol-1-yl)ethyl)-4-hydroxy-1-methylcyclohexyl)-7a-methyl-1-methyleneoctahydro-1H-inden-4-ol (Compound No 123)

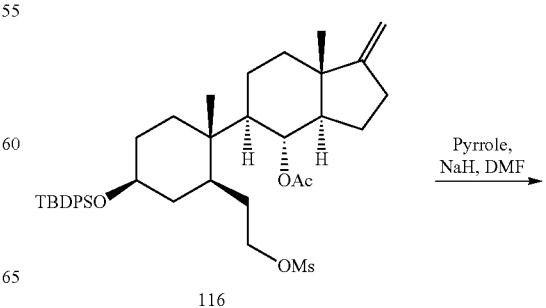

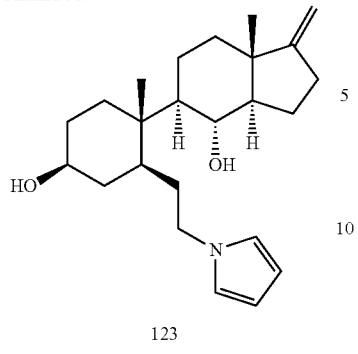

123

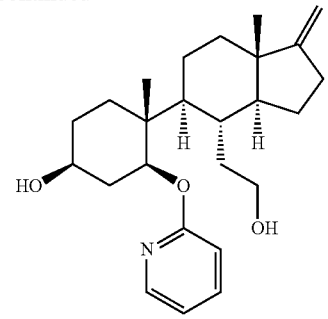

125

To a solution of pyrrole (0.31 mL, 4.4 mmol) in DMF (5 mL) at 0° C. under nitrogen was added NaH (176 mg, 4.4 mmol). After 45 min, (3aR,4R,5R,7aS)-5-((1S,2S,4S)-4-((tert-butyldiphenylsilyl)oxy)-1-methyl-2-(2-((methylsulfonyl)oxy)ethyl)cyclohexyl)-7a-methyl-1-methyleneoctahydro-1H-inden-4-yl acetate (Compound No. 116, 300 mg, 0.44 mmol) was added. After 3 days, the solution was cooled in ice, quenched with saturated NaHCO$_3$ solution (5 mL), diluted with Et$_2$O (100 mL), washed with brine, dried (MgSO$_4$) and concentrated. The residue was purified using chromatography on silica gel (50% then 60% EtOAc/hexanes) to afford (3aR,4R,5R,7aS)-5-((1S,2S,4S)-2-(2-(1H-pyrrol-1-yl)ethyl)-4-hydroxy-1-methylcyclohexyl)-7a-methyl-1-methyleneoctahydro-1H-inden-4-ol (Compound No. 123, 116 mg, 71%) as an off-white foam. $^1$H NMR (CDCl$_3$): δ6.62 (m, 2H), 6.15 (m, 2H), 4.62 (2H), 4.00 (m, 1H), 3.98 (m, 1H), 3.58 (2H), 2.54 (m, 1H), 2.25 (m, 1H), 1.90 (4H), 0.9-1.6 (17H), 1.15 (s, 3H), 0.75 (s, 3H). ES-MS m/z 430 ([M+OAc]$^+$).

Example 52

Synthesis of (1S,3S,4R)-4-((3aS,4S,5S,7aS)-4-(2-hydroxyethyl)-7a-methyl-1-methyleneoctahydro-1H-inden-5-yl)-4-methyl-3-(pyridin-2-yloxy)cyclohexanol (Compound No. 125)

A mixture of (1S,3S,4R)-4-((3aS,4S,5S,7aS)-4-(2-hydroxyethyl)-7a-methyl-1-methyleneoctahydro-1H-inden-5-yl)-4-methylcyclohexane-1,3-diyl diacetate (Compound No. 124, 200 mg, 0.5 mmol), 2-bromo-pyridine (0.14 mL, 1.5 mmol) and NaH (60 mg of a 60% solution, 1.5 mmol) in DMF (5 mL) under argon at 40° C. was stirred overnight. The resultant mixture was cooled to room temperature and partitioned between saturated NaHCO$_3$ solution (5 mL) and Et$_2$O (100 mL). The organic layer was washed successively with water (5×10 mL) and brine (10 mL), dried (Na$_2$SO$_4$) and concentrated. A solution of the residue and NaOMe (1 mL of 5.4 M solution in MeOH, 5.4 mmol) in MeOH (5 mL) was stirred at room temperature for 3 d. Water (10 mL) was added and the MeOH was removed by distillation. The resultant mixture was extracted with EtOAc (3×15 mL), dried (Na$_2$SO$_4$) and concentrated. The residue was purified using chromatography on silica gel (EtOAc) to afford (1S,3S,4R)-4-((3aS,4S,5S,7aS)-4-(2-hydroxyethyl)-7a-methyl-1-methyleneoctahydro-1H-inden-5-yl)-4-methyl-3-(pyridin-2-yloxy)cyclohexanol (Compound No. 125, 21 mg, 10%) as a white solid. $^1$H NMR (300 MHz, CDCl$_3$) δ8.10 (m, 1H), 7.57 (m, 1H), 6.86 (m, 1H), 6.72 (d, J=8.3, 1H), 5.69 (br s, 1H), 4.59 (d, J=11.5, 2H), 3.90 (m, 1H), 3.84-3.59 (m, 2H), 2.51-2.24 (m, 3H), 1.96 (m, 2H), 1.89-1.18 (m, 15H), 1.18 (s, 3H), 0.70 (s, 3H); $^{13}$C NMR (75 MHz, CDCl$_3$) δ163.1, 161.5, 146.8, 139.2, 117.0, 112.0, 101.2, 74.5, 67.6, 59.6, 53.1, 43.9, 40.0, 36.1, 35.9, 34.9, 30.1, 29.2, 25.2, 23.8, 19.8, 18.1; MS m/z: 400.4 [M+H]$^+$.

Example 53

Synthesis of (1S,3S,4R)-4-((3aS,4R,5S,7aS)-4-(hydroxymethyl)-7a-methyl-1-methyleneoctahydro-1H-inden-5-yl)-4-methyl-3-((pyridin-2-yloxy)methyl)cyclohexanol (Compound No. 130)

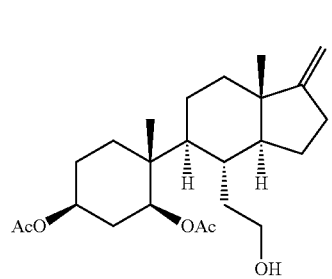

124

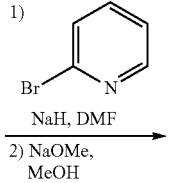

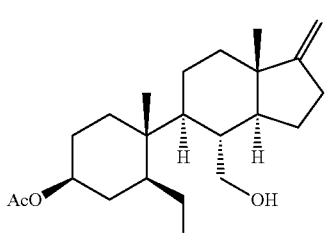

43

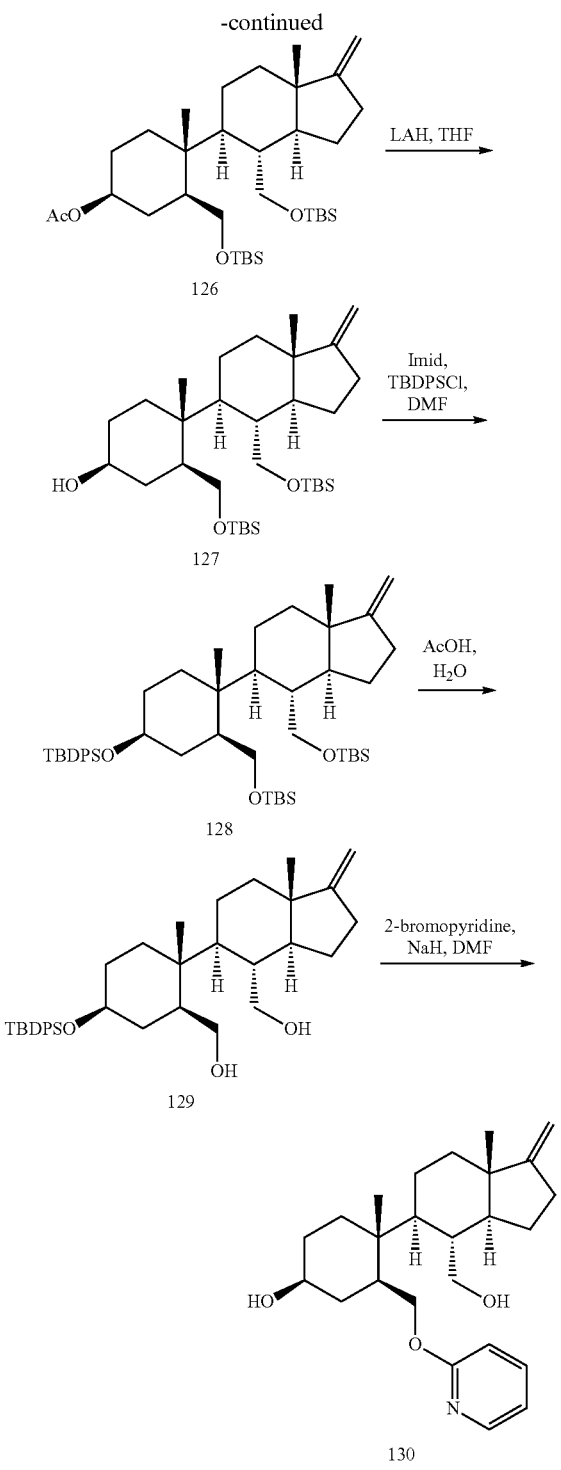

A. To a solution of (1S,3S,4R)-3-(hydroxymethyl)-4-((3aS,4R,5S,7aS)-4-(hydroxymethyl)-7a-methyl-1-methyleneoctahydro-1H-inden-5-yl)-4-methylcyclohexyl acetate (Compound No. 43, 1.00 g, 2.74 mmol), imidazole (1.12 g, 16.4 mmol) and TBSCl (1.24 g, 8.23 mmol) in DMF (14 mL) under argon was stirred at room temperature for 18 h. The solution was cooled in ice, quenched with saturated NaHCO$_3$ solution (5 mL), diluted with Et$_2$O (100 mL), wash with brine (3×15 mL), dried (MgSO$_4$) and concentrated to give (1S,3S,4R)-3-(((tert-butyldimethylsilyl)oxy)methyl)-4-((3aS,4R,5S,7aS)-4-(((tert-butyldimethylsilyl)oxy)methyl)-7a-methyl-1-methyleneoctahydro-1H-inden-5-yl)-4-methylcyclohexyl acetate (Compound No. 126).

B. To a solution of (1S,3S,4R)-3-(((tert-butyldimethylsilyl)oxy)methyl)-4-((3aS,4R,5S,7aS)-4-(((tert-butyldimethylsilyl)oxy)methyl)-7a-methyl-1-methyleneoctahydro-1H-inden-5-yl)-4-methylcyclohexyl acetate (Compound No. 126, 1.63 g, 2.74 mmol) in THF (12 mL) at 0° C. under argon was added LAH (2.7 mL of a 2 M solution in THF, 5.4 mmol). After 1 h, added Et$_2$O (20 mL) and Na$_2$SO$_4$.10H$_2$O (1.74 g) then stirred 45 min. The solution was filtered through Celite, eluted with EtOAc and concentrated to give (1S,3S,4R)-3-(((tert-butyldimethylsilyl)oxy)methyl)-4-((3aS,4R,5S,7aS)-4-(((tert-butyldimethylsilyl)oxy)methyl)-7a-methyl-1-methyleneoctahydro-1H-inden-5-yl)-4-methylcyclohexanol (Compound No. 127).

C. A solution of (1S,3S,4R)-3-(((tert-butyldimethylsilyl)oxy)methyl)-4-((3aS,4R,5S,7aS)-4-(((tert-butyldimethylsilyl)oxy)methyl)-7a-methyl-1-methyleneoctahydro-1H-inden-5-yl)-4-methylcyclohexanol (Compound No. 127, 1.51 g, 2.74 mmol), imidazole (560 mg, 8.22 mmol) and TBDPSCl (1.10 mL, 4.11 mmol) in DMF (14 mL) under argon was stirred at room temperature for 4 d. The solution was diluted in Et$_2$O (150 mL), washed successively with saturated NaHCO$_3$ solution (10 mL) and brine (3×15 mL), dried (MgSO$_4$) and concentrated to give tert-butyl(((1S,3S,4R)-3-(((tert-butyldimethylsilyl)oxy)methyl)-4-((3aS,4R,5S,7aS)-4-(((tert-butyldimethylsilyl)oxy)methyl)-7a-methyl-1-methyleneoctahydro-1H-inden-5-yl)-4-methylcyclohexyl)oxy)diphenylsilane (Compound No. 128).

D. A solution of tert-butyl(((1S,3S,4R)-3-(((tert-butyldimethylsilyl)oxy)methyl)-4-((3aS,4R,5S,7aS)-4-(((tert-butyldimethylsilyl)oxy)methyl)-7a-methyl-1-methyleneoctahydro-1H-inden-5-yl)-4-methylcyclohexyl)oxy)diphenylsilane (Compound No. 128, 2.16 g, 2.74 mmol) in acetic acid (80 mL), water (20 mL), THF (50 mL) and acetone (50 mL) was heated at 40° C. for 1 day then at 50° C. for 1 day then at 60° C. for 1 day. The solution was concentrated and the residue was 3 times taken up in toluene (30 mL) and concentrated. The residue was purified using chromatography on silica gel (5% EtOAc and 5% CH$_2$Cl$_2$ in hexanes) to afford ((1S,2R,5S)-5-((tert-butyldiphenylsilyl)oxy)-2-((3aS,4R,5S,7aS)-4-(hydroxymethyl)-7a-methyl-1-methyleneoctahydro-1H-inden-5-yl)-2-methylcyclohexyl)methanol (Compound No. 129, 664 mg, 36%) as a white foam.

E. To a solution of ((1S,2R,5S)-5-(((tert-butyldiphenylsilyl)oxy)-2-((3aS,4R,5S,7aS)-4-(hydroxymethyl)-7a-methyl-1-methyleneoctahydro-1H-inden-5-yl)-2-methylcyclohexyl)methanol (Compound No. 129, 100 mg, 0.18 mmol) and 2-bromopyridine (0.085 mL, 0.89 mmol) in DMF (2 mL) at room temperature under nitrogen was added NaH (36 mg of a 60% solution in mineral oil, 0.89 mmol). The solution was heated at 40° C. for 3 h, cooled in ice, quenched with saturated NaHCO$_3$ solution (3 mL), diluted with Et$_2$O (100 mL), washed with brine (3×15 mL), dried (MgSO$_4$) and concentrated. The residue was purified using chromatography on silica gel (10% then 20% then 30% EtOAc/hexanes) to afford 17 mg of a 2 component mixture. The material was taken up in THF (2 mL) and TBAF (0.5 mL of a 1 M solution in THF, 0.5 mmol) and stirred at room temperature for 3 days then at 55° C. for 3 days. The solution was concentrated and the residue was purified using chromatography on silica gel (50% EtOAc/hexanes) to afford (1S,3S,4R)-4-((3aS,4R,5S,7aS)-4-(hydroxymethyl)-7a-methyl-1-methyleneoctahydro-1H-inden-5-yl)-4-methyl-3-((pyridin-2-yloxy)methyl)cyclohexanol (Compound No.

130, 9 mg, 12%) as a white solid. $^1$H NMR (CDCl$_3$): δ8.15 (m, 1H), 7.57 (m, 1H), 6.85 (m, 1H), 6.72 (m, 1H), 4.62 (2H), 4.38 (m, 1H), 4.00 (m, 1H), 3.97 (m, 1H), 3.70 (m, 1H), 3.60 (m, 1H), 2.50 (m, 1H), 2.30 (m, 1H), 2.20 (2H), 1.2-2.0 (13H), 1.30 (s, 3H), 0.85 (m, 1H), 0.80 (s, 3H). ES-MS m/z 400 ([M+1]$^+$)

Example 54

Synthesis of (3aR,4R,5R,7aS)-5-((1S,2S,4S)-4-hydroxy-1-methyl-2-(2-(pyrimidin-2-yloxy)ethyl)cyclohexyl)-7a-methyl-1-methyleneoctahydro-1H-inden-4-ol (Compound No. 133)

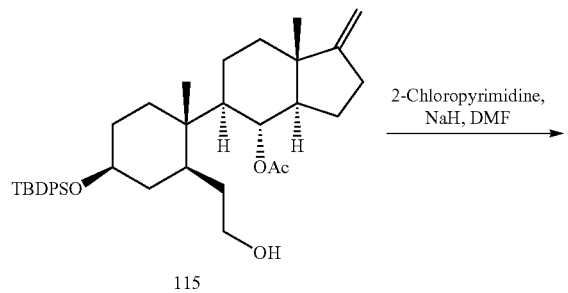

115

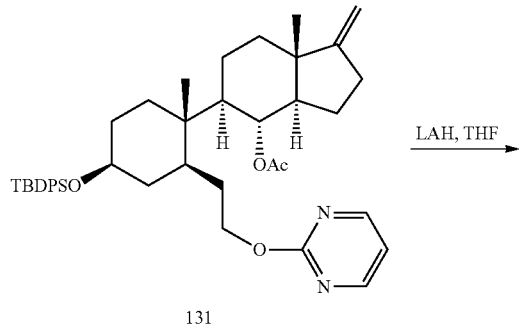

131

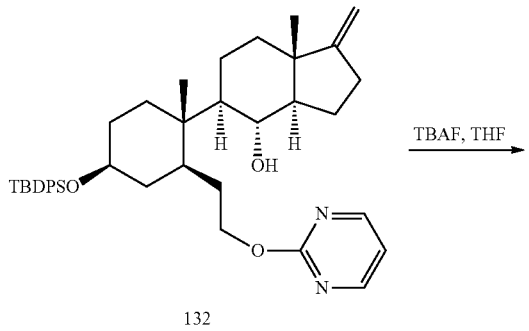

132

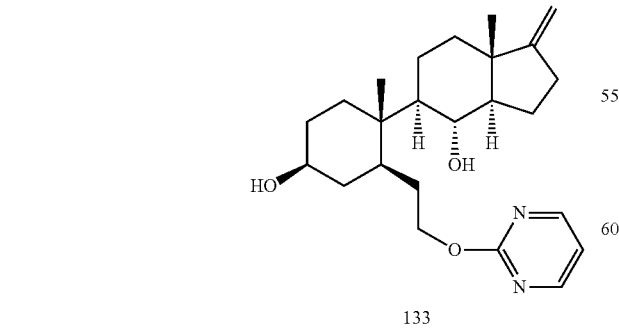

133

A. To a solution of (3aR,4R,5R,7aS)-5-((1S,2S,4S)-4-((tert-butyldiphenylsilyl)oxy)-2-(2-hydroxyethyl)-1-methylcyclohexyl)-7a-methyl-1-methyleneoctahydro-1H-inden-4-yl acetate (Compound No. 115, 300 mg, 0.50 mmol) and 2-chloropyrimidine (170 mg, 1.5 mmol) in DMF (5 mL) at room temperature under nitrogen was added NaH (60 mg of a 60% solution in mineral oil, 1.5 mmol). The solution was heated at 40° C. for 5 h, cooled in ice, quenched with saturated NaHCO$_3$ solution (3 mL), diluted with Et$_2$O (100 mL), washed with brine (3×15 mL), dried (MgSO$_4$) and concentrated to give (3aR,4R,5R,7aS)-5-((1S,2S,4S)-4-((tert-butyldiphenylsilyl)oxy)-1-methyl-2-(2-(pyrimidin-2-yloxy)ethyl)cyclohexyl)-7a-methyl-1-methyleneoctahydro-1H-inden-4-yl acetate (Compound No. 131).

B. A solution of (3aR,4R,5R,7aS)-5-((1S,2S,4S)-4-((tert-butyldiphenylsilyl)oxy)-1-methyl-2-(2-(pyrimidin-2-yloxy)ethyl)cyclohexyl)-7a-methyl-1-methyleneoctahydro-1H-inden-4-yl acetate (Compound No. 131, 339 mg, 0.50 mmol) and LAH (0.50 mL of a 2 M solution in THF, 1.0 mmol) in THF (5 mL) was stirred at 60° C. under nitrogen for 1 h. The solution was cooled in ice, quenched with Na$_2$SO$_4$.10H$_2$O (0.32 g) for 1 h then filtered through paper, eluted with EtOAc and concentrated to give (3aR,4R,5R,7aS)-5-((1S,2S,4S)-4-((tert-butyldiphenylsilyl)oxy)-1-methyl-2-(2-(pyrimidin-2-yloxy)ethyl)cyclohexyl)-7a-methyl-1-methyleneoctahydro-1H-inden-4-ol (Compound No. 132).

C. To a solution of (3aR,4R,5R,7aS)-5-((1S,2S,4S)-4-((tert-butyldiphenylsilyl)oxy)-1-methyl-2-(2-(pyrimidin-2-yloxy)ethyl)cyclohexyl)-7a-methyl-1-methyleneoctahydro-1H-inden-4-ol (Compound No. 132, 318 mg, 0.50 mmol) and TBAF (1.5 mL of a 1 M solution in THF, 1.5 mmol) in THF (5 mL) was stirred at room temperature under nitrogen for 3 d. The solution was concentrated and the residue purified using chromatography on silica gel (50% then 65% then 80% EtOAc/hexanes) to afford (3aR,4R,5R,7aS)-5-((1S,2S,4S)-4-hydroxy-1-methyl-2-(2-(pyrimidin-2-yloxy)ethyl)cyclohexyl)-7a-methyl-1-methyleneoctahydro-1H-inden-4-ol (Compound No. 133, 41 mg, 20%) as a white solid. $^1$H NMR (CDCl$_3$): δ8.50 (m, 2H), 6.95 (m, 1H), 4.62 (2H), 4.50 (m, 1H), 4.35 (m, 1H), 3.72 (m, 1H), 3.55 (m, 1H), 2.55 (m, 1H), 2.25 (m, 1H), 0.85-2.05 (17H), 1.20 (s, 3H), 0.80 (s, 3H). ES-MS m/z 401 ([M+1]$^+$).

Example 55

Synthesis of (3aR,4R,5R,7aS)-5-((1S,2S,4S)-4-hydroxy-1-methyl-2-(2-(pyrazin-2-yloxy)ethyl)cyclohexyl)-7a-methyl-1-methyleneoctahydro-1H-inden-4-ol (Compound No. 136)

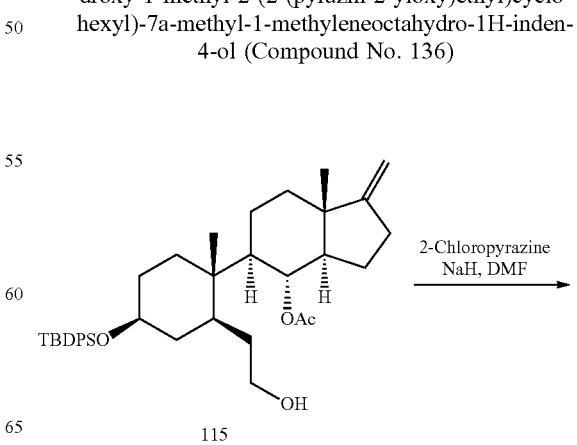

115

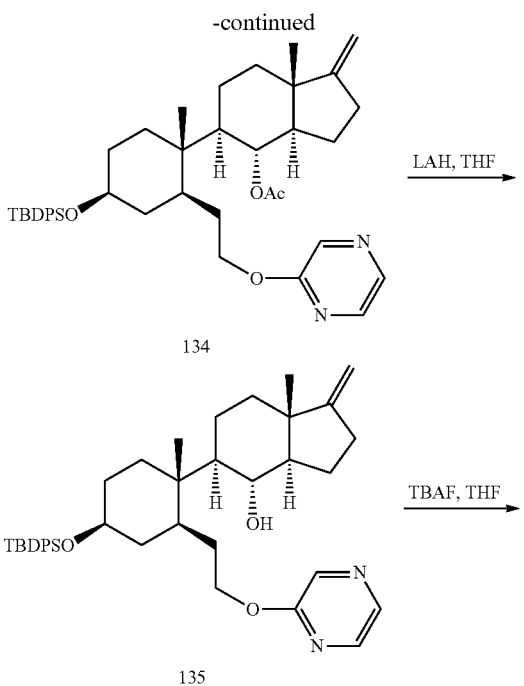

A. To a solution of (3aR,4R,5R,7aS)-5-((1S,2S,4S)-4-((tert-butyldiphenylsilyl)oxy)-2-(2-hydroxyethyl)-1-methylcyclohexyl)-7a-methyl-1-methyleneoctahydro-1H-inden-4-yl acetate (Compound No. 115, 300 mg, 0.50 mmol) and 2-chloropyrazine (0.13 mL, 1.5 mmol) in DMF (5 mL) at room temperature under nitrogen was added NaH (60 mg of a 60% solution in mineral oil, 1.5 mmol). The solution was heated at 40° C. for 5 h, cooled in ice, quenched with saturated NaHCO₃ solution (3 mL), diluted with Et₂O (100 mL), washed with brine (3×15 mL), dried (MgSO₄) and concentrated to give (3aR,4R,5R,7aS)-5-((1S,2S,4S)-4-((tert-butyldiphenylsilyl)oxy)-1-methyl-2-(2-(pyrazin-2-yloxy)ethyl)cyclohexyl)-7a-methyl-1-methyleneoctahydro-1H-inden-4-yl acetate (Compound No. 134).

B. A solution of (3aR,4R,5R,7aS)-5-((1S,2S,4S)-4-((tert-butyldiphenylsilyl)oxy)-1-methyl-2-(2-(pyrazin-2-yloxy)ethyl)cyclohexyl)-7a-methyl-1-methyleneoctahydro-1H-inden-4-yl acetate (Compound No. 134, 339 mg, 0.50 mmol) and LAH (0.50 mL of a 2 M solution in THF, 1.0 mmol) in THF (5 mL) was stirred at 60° C. under nitrogen for 1 h. The solution was cooled in ice, quenched with Na₂SO₄.10H₂O (0.32 g) for 1 h then filtered through paper, eluted with EtOAc and concentrated to give (3aR,4R,5R,7aS)-5-((1S,2S,4S)-4-((tert-butyldiphenylsilyl)oxy)-1-methyl-2-(2-(pyrazin-2-yloxy)ethyl)cyclohexyl)-7a-methyl-1-methyleneoctahydro-1H-inden-4-ol (Compound No. 135).

C. To a solution of (3aR,4R,5R,7aS)-5-((1S,2S,4S)-4-((tert-butyldiphenylsilyl)oxy)-1-methyl-2-(2-(pyrazin-2-yloxy)ethyl)cyclohexyl)-7a-methyl-1-methyleneoctahydro-1H-inden-4-ol (Compound No. 135, 318 mg, 0.50 mmol) and TBAF (1.5 mL of a 1 M solution in THF, 1.5 mmol) in THF (5 mL) was stirred at room temperature under nitrogen for 3 d then was heated at 55° C. for 4 h. The solution was concentrated and the residue purified using chromatography on silica gel (50% then 70% EtOAc/hexanes) to afford (3aR,4R,5R,7aS)-5-((1S,2S,4S)-4-hydroxy-1-methyl-2-(2-(pyrazin-2-yloxy)ethyl)cyclohexyl)-7a-methyl-1-methyleneoctahydro-1H-inden-4-ol (Compound No. 136, 81 mg, 40%) as a white solid. ¹H NMR (CDCl₃): δ8.20 (s, 1H), 8.12 (m, 1H), 8.07 (m, 1H), 4.62 (2H), 4.40 (m, 1H), 4.33 (m, 1H), 3.72 (m, 1H), 3.54 (m, 1H), 2.55 (m, 1H), 2.25 (m, 1H), 1.82 (2H), 0.95-2.00 (15H), 1.20 (s, 3H), 0.80 (s, 3H). ES-MS m/z 401 ([M+1]⁺).

Example 56

Synthesis of (3aR,4R,5R,7aS)-5-((1S,2S,4S)-4-hydroxy-1-methyl-2-(2-(pyridin-2-yloxy)ethyl)cyclohexyl)-7a-methyl-1-methyleneoctahydro-1H-inden-4-ol (Compound No. 138)

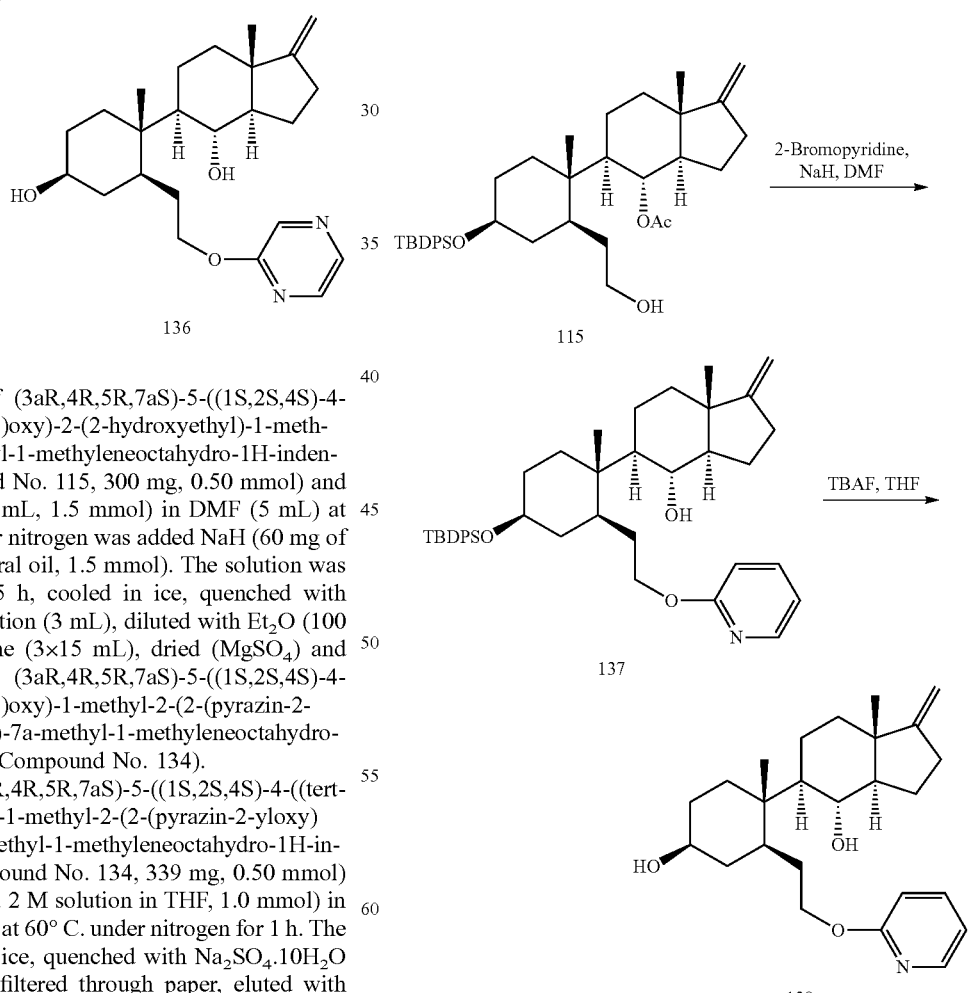

A. To a solution of (3aR,4R,5R,7aS)-5-((1S,2S,4S)-4-((tert-butyldiphenylsilyl)oxy)-2-(2-hydroxyethyl)-1-methylcyclohexyl)-7a-methyl-1-methyleneoctahydro-1H-inden-4-yl acetate (Compound No. 115, 300 mg, 0.50 mmol) and 2-bromopyridine (0.14 mL, 1.5 mmol) in DMF (5 mL) at room temperature under nitrogen was added NaH (60 mg of a 60% solution in mineral oil, 1.5 mmol). The solution was heated at 40° C. for 16 h, cooled in ice, quenched with saturated NaHCO$_3$ solution (5 mL), diluted with Et$_2$O (100 mL), washed with brine (3×15 mL), dried (MgSO$_4$) and concentrated. The residue was purified using chromatography on silica gel (10% EtOAc/hexanes) to afford (3aR,4R,5R,7aS)-5-((1S,2S,4S)-4-((tert-butyldiphenylsilyl)oxy)-1-methyl-2-(2-(pyridin-2-yloxy)ethyl)cyclohexyl)-7a-methyl-1-methyleneoctahydro-1H-inden-4-ol (Compound No. 137, 64 mg, 20%) as a white foam.

B. To a solution of (3aR,4R,5R,7aS)-5-((1S,2S,4S)-4-((tert-butyldiphenylsilyl)oxy)-1-methyl-2-(2-(pyridin-2-yloxy)ethyl)cyclohexyl)-7a-methyl-1-methyleneoctahydro-1H-inden-4-ol (Compound No. 137, 61 mg, 0.10 mmol) and TBAF (0.30 mL of a 1 M solution in THF, 0.30 mmol) in THF was stirred at room temperature under nitrogen for 16 h then was heated at 60° C. for 2 h. More TBAF (0.30 mL, 0.30 mmol) was added and the solution was heated at 60° C. for 7 h. The solution was concentrated and the residue purified using chromatography on silica gel (50% EtOAc/hexanes) to afford (3aR,4R,5R,7aS)-5-((1S,2S,4S)-4-hydroxy-1-methyl-2-(2-(pyridin-2-yloxy)ethyl)cyclohexyl)-7a-methyl-1-methyleneoctahydro-1H-inden-4-ol (Compound No. 138, 37 mg, 97%) as a white solid. $^1$H NMR (CDCl$_3$): δ8.18 (m, 1H), 7.59 (m, 1H), 6.85 (m, 1H), 6.70 (m, 1H), 4.62 (2H), 4.39 (m, 1H), 4.27 (m, 1H), 3.72 (m, 1H), 3.54 (m, 1H), 2.55 (m, 1H), 2.25 (m, 1H), 1.82 (2H), 0.95-2.05 (15H), 1.20 (s, 3H), 0.80 (s, 3H). ES-MS m/z 400 ([M+1]$^+$).

Example 57

Synthesis of (1S,3S,4R)-4-((3aS,6S,7R,7aS)-7-(aminomethyl)-3,3a-dimethyl-3a,4,5,6,7,7a-hexahydro-1H-inden-6-yl)-3-(hydroxymethyl)-4-methylcyclohexanol (Compound No. 139)

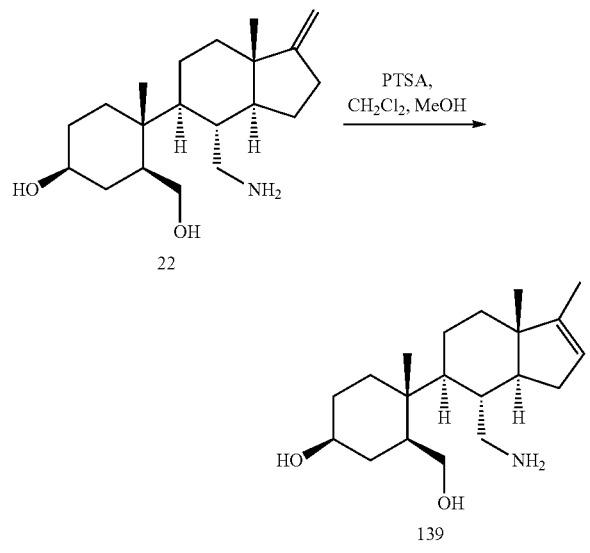

To a solution of (1S,3S,4R)-4-((3aS,4R,5S,7aS)-4-(aminomethyl)-7a-methyl-1-methyleneoctahydro-1H-inden-5-yl)-3-(hydroxymethyl)-4-methylcyclohexanol (Compound No. 22, 523 mg, 1.63 mmol) in 5% MeOH/CH$_2$Cl$_2$ (16 mL) was added PTSA H$_2$O (371 mg, 1.95 mmol) then stirred at room temperature for 8 d. The solution was diluted with 5% MeOH/CH$_2$Cl$_2$ (10 mL) and washed with 1 N NaOH (aq) (10 mL). The aqueous phase was extracted with 5% MeOH/CH$_2$Cl$_2$ (4×10 mL), and the combined organic layers were dried (MgSO$_4$) and concentrated. The residue was purified by chromatography on silica gel (100:10:1 CH$_2$Cl$_2$/MeOH/NH$_4$OH) to afford (1S,3S,4R)-4-((3aS,6S,7R,7aS)-7-(aminomethyl)-3,3a-dimethyl-3a,4,5,6,7,7a-hexahydro-1H-inden-6-yl)-3-(hydroxymethyl)-4-methylcyclohexanol (Compound No. 139, 40 mg, 8%) as a colourless foam. $^1$H NMR (CD$_3$OD): δ5.29 (m, 1H), 3.74 (dd, J=11, 2.4 Hz, 1H), 3.45 (m, 1H), 3.14 (m, 1H), 3.07 (dd, J=14, 2.7 Hz, 1H), 2.74 (m, 1H), 2.14 (m, 1H), 1.21-1.93 (m, 18H), 1.09 (s, 3H), 0.78 (s, 3H); $^{13}$C NMR (CD$_3$OD): δ 152.4, 123.3, 71.1, 62.9, 54.3, 47.0, 45.5, 44.4, 43.5, 38.7, 38.3, 35.9, 35.2, 32.4, 32.1, 24.2, 21.6, 15.3, 12.5. ES-MS m/z 322 ([M+1]$^+$).

Example 58

Synthesis of N-(((3aR,6S,7R,7aS)-6-((1R,2S,4S)-4-hydroxy-2-(hydroxymethyl)-1-methylcyclohexyl)-3a-methyl-3a,4,5,6,7,7a-hexahydro-1H-inden-7-yl)methyl)pentanamide (Compound No. 143)

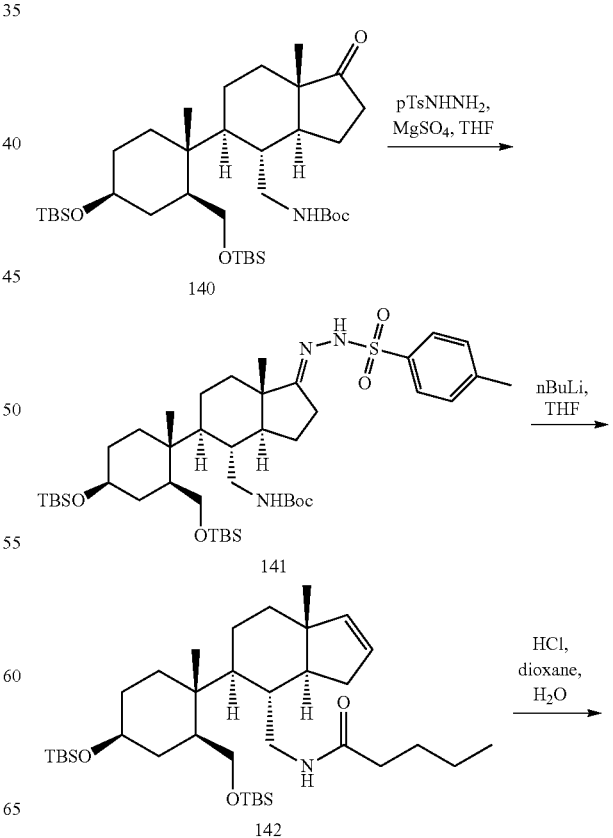

-continued

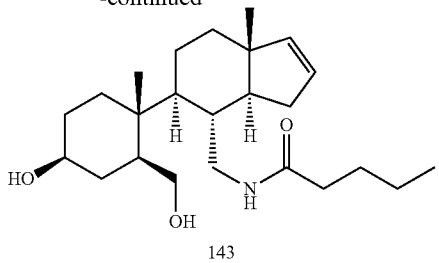

143

A. To a solution of tert-butyl ((((3aS,4R,5S,7aS)-5-((1R,2S,4S)-4-((tert-butyldimethylsilyl)oxy)-2-(((tert-butyldimethylsilyl)oxy)methyl)-1-methylcyclohexyl)-7a-methyl-1-oxooctahydro-1H-inden-4-yl)methyl)carbamate (Compound No. 140, 706 mg, 1.08 mmol) in THF (4.3 mL) was added MgSO$_4$ (326 mg, 2.71 mmol) and p-toluenesulfonyl hydrazide (302 mg, 1.62 mmol), and the mixture was stirred at room temperature under argon. After 21 h, the mixture was heated to reflux for 4 h then filtered and concentrated. The residue was purified by chromatography on silica gel (15:85-40:60 EtOAc/hexanes) to tert-butyl ((((3aS,4R,5S,7aS,E)-5-((1R,2S,4S)-4-((tert-butyldimethylsilyl)oxy)-2-(((tert-butyldimethylsilyl)oxy)methyl)-1-methylcyclohexyl)-7a-methyl-1-(2-tosylhydrazono)octahydro-1H-inden-4-yl)methyl)carbamate (Compound No. 141, 715 mg, 81%) as a colourless foam.

B. To a solution of tert-butyl ((((3aS,4R,5S,7aS, E)-5-((1R,2S,4S)-4-((tert-butyldimethylsilyl)oxy)-2-(((tert-butyldimethylsilyl)oxy)methyl)-1-methylcyclohexyl)-7a-methyl-1-(2-tosylhydrazono)octahydro-1H-inden-4-yl)methyl) carbamate (Compound No. 141, 710 mg, 0.865 mmol) in THF (8.7 mL) was added n-butyllithium (4.80 mL of a 1.8 M solution in hexanes, 8.64 mmol) at room temperature under argon. After stirring for 15 min, the mixture was cooled to 00° C. and saturated aqueous NH$_4$Cl (15 mL) was added followed by EtOAc (15 mL). The organic layer was washed with brine (10 mL) then dried (MgSO$_4$) and concentrated. The residue was purified by chromatography on silica gel (5:95 EtOAc/CH$_2$Cl$_2$) to give N-(((3aR,6S,7R,7aS)-6-((1R,2S,4S)-4-((tert-butyldimethylsilyl)oxy)-2-(((tert-butyldimethylsilyl)oxy)methyl)-1-methylcyclohexyl)-3a-methyl-3a,4,5,6,7,7a-hexahydro-1H-inden-7-yl)methyl)pentanamide (Compound No. 142, 164 mg, 31%) as a light yellow foam.

C. To a solution of N-(((3aR,6S,7R,7aS)-6-((1R,2S,4S)-4-((tert-butyldimethylsilyl)oxy)-2-(((tert-butyldimethylsilyl)oxy)methyl)-1-methylcyclohexyl)-3a-methyl-3a,4,5,6,7,7a-hexahydro-1H-inden-7-yl)methyl)pentanamide (Compound No. 142, 164 mg, 0.264 mmol) in 1,4-dioxane (2 mL) was added 4 M HCl in dioxane (2 mL) followed by H$_2$O (0.5 mL). The mixture was stirred at room temperature for 2 h then cooled to 0° C. and 1 N NaOH (aq) (10 mL) was added. The mixture was extracted with 10% MeOH/CH$_2$Cl$_2$ (2×10 mL) and CH$_2$Cl$_2$ (3×10 mL), and the combined extracts were dried (MgSO$_4$) and concentrated. The residue was purified by chromatography on silica gel (10:90 MeOH/CH$_2$Cl$_2$) to afford N-(((3aR,6S,7R,7aS)-6-((1R,2S,4S)-4-hydroxy-2-(hydroxymethyl)-1-methylcyclohexyl)-3a-methyl-3a,4,5,6,7,7a-hexahydro-1H-inden-7-yl)methyl)pentanamide (Compound No. 143, 91 mg, 88%) as a colourless foam. $^1$H NMR (CDCl$_3$): δ5.85 (m, 1H), 5.70 (m, 1H), 5.36 (m, 1H), 3.74 (dd, J=11, 2.7 Hz, 1H), 3.58 (m, 1H), 3.49 (m, 2H), 3.30 (m, 1H), 1.26-2.21 (m, 25H), 1.01 (s, 3H), 0.92 (t, J=7.4 Hz, 3H), 0.79 (s, 3H); $^{13}$C NMR (CDCl$_3$): δ173.6, 143.6, 129.1, 69.9, 62.6, 53.7, 46.5, 45.3, 43.0, 42.0, 37.3, 36.6, 36.4, 35.2, 34.3, 32.9, 31.1, 29.8, 28.0, 23.5, 22.5, 21.2, 16.8, 13.9. ES-MS m/z 392 ([M+1]$^+$).

Example 59

Synthesis of (1S,3S,4R)-4-((3aS,4S,5S,7aR)-4-(aminomethyl)-1-ethyl-7a-methyloctahydro-1H-inden-5-yl)-3-(hydroxymethyl)-4-methylcyclohexanol (Compound No. 145)

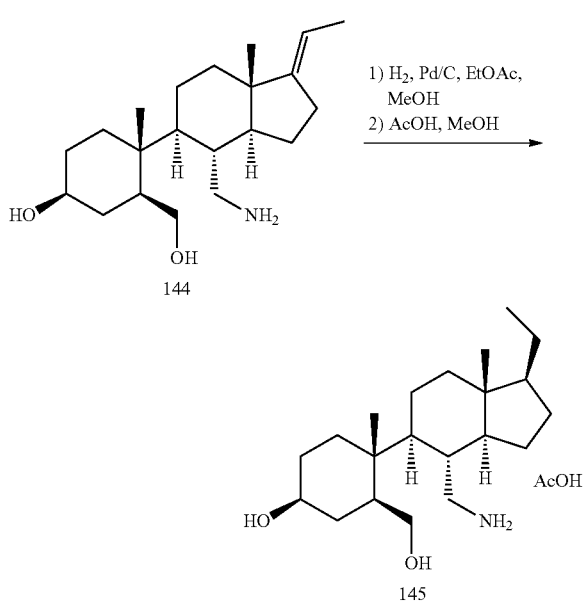

A suspension of (1S,3S,4R)-4-((3aS,4R,5S,7aS,E)-4-(aminomethyl)-1-ethylidene-7a-methyloctahydro-1H-inden-5-yl)-3-(hydroxymethyl)-4-methylcyclohexanol (Compound No. 144, 0.86 g, 2.6 mmol) and 10% Pd/C (86 mg) in EtOAc (55 mL) and MeOH (3 mL) under H$_2$ (balloon) at room temperature was stirred for 3 days. The resultant mixture was filtered through Celite and concentrated. The residue was dissolved in MeOH (20 mL) and AcOH (0.8 mL, 13 mmol) was added. After stirring for 15 min, the mixture was concentrated, reconstituted in MeCN (15 mL) and reconcentrated. The residue was dissolved in MeOH (2 mL) and MeCN (50 mL) was added in a single portion. The mixture was stirred for 20 min at room temperature and the solid was collected by filtration to afford (1S,3S,4R)-4-((1S,3aS,4S,5S,7aR)-4-(aminomethyl)-1-ethyl-7a-methyloctahydro-1H-inden-5-yl)-3-(hydroxymethyl)-4-methylcyclohexanol as the acetate salt (Compound No. 145, 434 mg, 42%) as a white solid. $^1$H NMR (300 MHz, CD$_3$OD) δ3.70 (d, J=8.3, 1H), 3.45 (m, 1H), 3.13 (t, J=10.2, 1H), 2.97 (d, J=11.8, 1H), 2.13 (m, 1H), 1.90 (s, 3H), 1.87-1.74 (m, 11H) 1.64-1.15 (m, 14H), 1.07 (s, 3H), 0.90 (t, J=7.3, 3H), 0.64 (s, 3H); $^{13}$C NMR (75 MHz, CD$_3$OD) δ70.9, 62.6, 54.4, 52.2, 45.5, 44.6, 43.0, 42.6, 38.9, 38.1, 37.4, 35.1, 31.9, 31.8, 28.8, 25.8, 24.2, 24.1, 23.8, 21.8, 13.6, 12.5; MS m/z: 338.1 [M+H]$^+$ free base.

Example 60

Synthesis of (1S,3S,4R)-3-(hydroxymethyl)-4-methyl-4-((3aS,4R,5S,7aS)-7a-methyl-1-methylene-4-((pyridin-2-ylmethoxy)methyl)octahydro-1H-inden-5-yl)cyclohexanol (Compound No. 154)

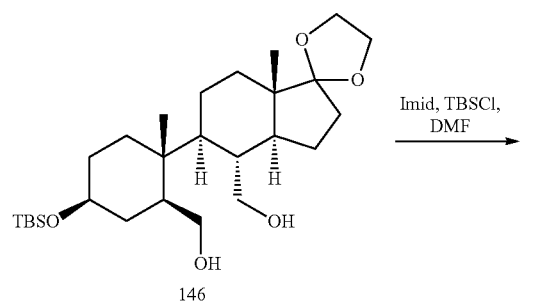
146

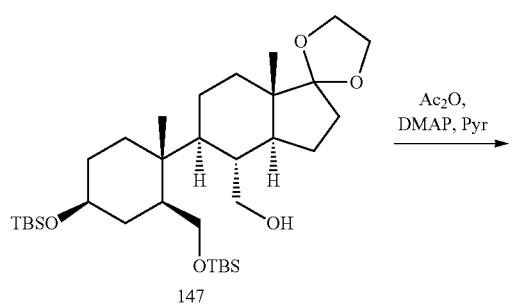
147

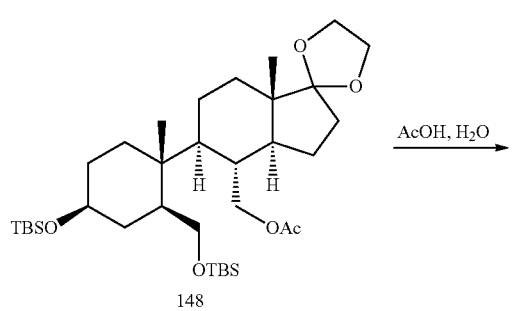
148

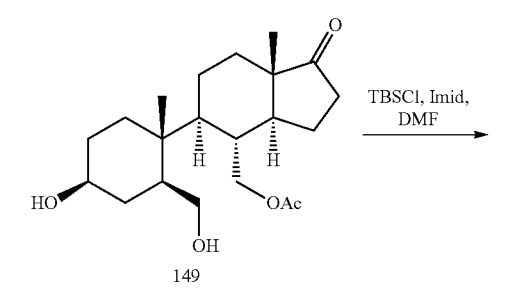
149

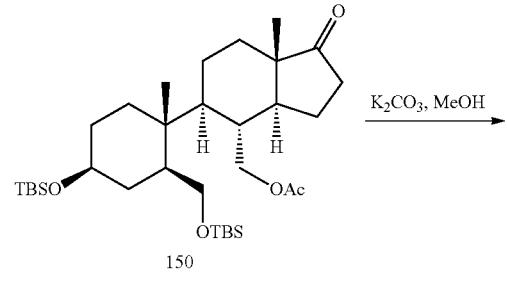
150

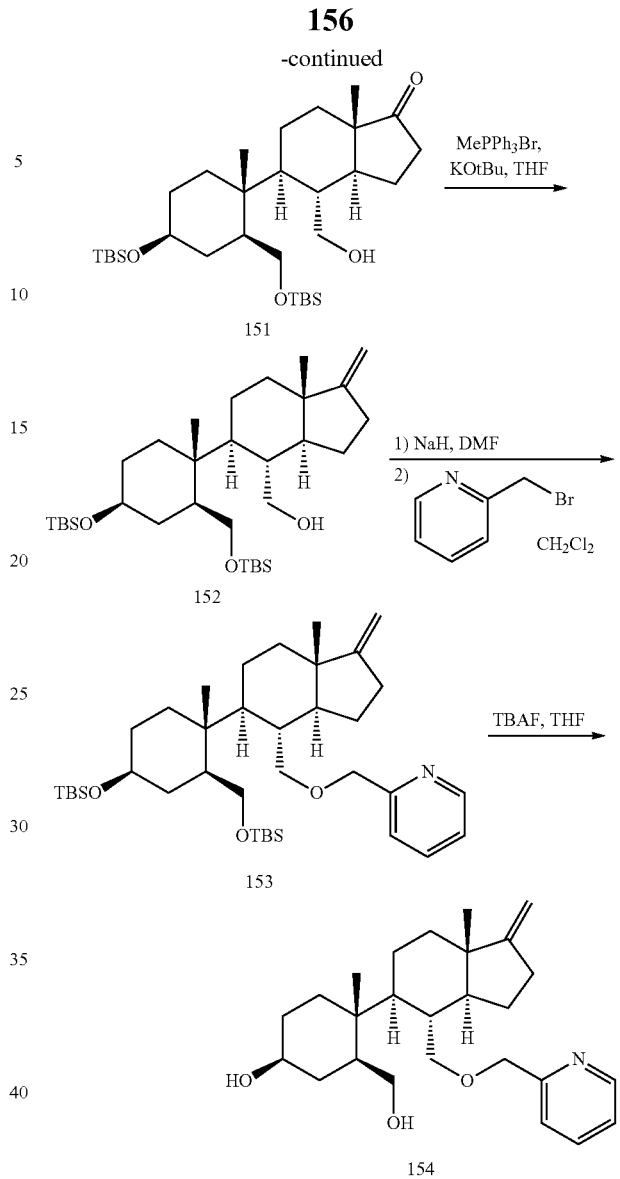

A. To a solution of (((1S,2R,5S)-5-((tert-butyldimethylsilyl)oxy)-2-((3a'S,4'R,5'S,7a'S)-4'-(hydroxymethyl)-7a'-methyloctahydrospiro[[1,3]dioxolane-2,1'-inden]-5'-yl)-2-methylcyclohexyl)methanol (Compound No. 146, 4.75 g, 9.84 mmol) and imidazole (804 mg, 11.8 mmol) in DMF (20 mL) at 0° C. was added TBSCl (1.56 g, 10.4 mmol), and the solution was stirred at room temperature under argon for 19 h. The mixture was diluted with EtOAc (100 mL) and washed with $H_2O$ (2×25 mL) and brine (6×20 mL) then dried ($MgSO_4$) and concentrated. The residue was purified by chromatography on silica gel (20:80 EtOAc/hexanes) to give ((3a'S,4'R,5'S,7a'S)-5'-((1R,2S,4S)-4-((tert-butyldimethylsilyl)oxy)-2-(((tert-butyldimethylsilyl)oxy)methyl)-1-methylcyclohexyl)-7a'-methyloctahydrospiro[[1,3]dioxolane-2,1'-inden]-4'-yl)methanol (Compound No. 147, 5.41 g, 92%) as a colourless foam.

B. To a solution of ((3a'S,4'R,5'S,7a'S)-5'-((1R,2S,4S)-4-((tert-butyldimethylsilyl)oxy)-2-(((tert-butyldimethylsilyl)oxy)methyl)-1-methylcyclohexyl)-7a'-methyloctahydrospiro[[1,3]dioxolane-2,1'-inden]-4'-yl)methanol (Compound No. 147, 5.41 g, 9.06 mmol) and DMAP (110 mg, 0.900 mmol) in pyridine (45 mL) at 0° C. under argon was added Ac₂O (2.53 g, 24.8 mmol) then stirred at room temperature for 24 h. The mixture was concentrated, and azeotropic removal of remaining pyridine was carried out with toluene (3×50 mL). The pale foam ((3a'S,4'R,5'S,7a'S)-5'-((1R,2S,4S)-4-((tert-butyldimethylsilyl)oxy)-2-(((tert-butyldimethylsilyl)oxy)methyl)-1-methylcyclohexyl)-7a'-methyloctahydrospiro[[1,3]dioxolane-2,1'-inden]-4'-yl) methyl acetate (Compound No. 148, 5.92 g) that was obtained was used in the next step without further purification.

C. A suspension of ((3a'S,4'R,5'S,7a'S)-5'-((1R,2S,4S)-4-((tert-butyldimethylsilyl)oxy)-2-(((tert-butyldimethylsilyl)oxy)methyl)-1-methylcyclohexyl)-7a'-methyloctahydrospiro[[1,3]dioxolane-2,1'-inden]-4'-yl)methyl acetate (Compound No. 148, 5.92 g) in 80% acetic acid (aq) (90 mL) was stirred at room temperature for 19 h then heated to 40° C. for 2 h. The mixture was concentrated, and azeotropic removal of remaining acetic acid and H₂O was carried out with toluene (3×50 mL). The residue was partially purified by chromatography on silica gel (3:97 MeOH/EtOAc) to give a colourless foam (3.28 g). The foam (3.28 g) was dissolved in EtOAc (75 mL) and washed with H₂O (20 mL) and brine (5×20 mL) then dried (MgSO₄) and concentrated to give ((3aS,4R,5S,7aS)-5-((1R,2S,4S)-4-hydroxy-2-(hydroxymethyl)-1-methylcyclohexyl)-7a-methyl-1-oxooctahydro-1H-inden-4-yl)methyl acetate (Compound No. 149, 3.08 g, 93% over 2 steps) as a colourless foam.

D. To a solution of ((3aS,4R,5S,7aS)-5-((1R,2S,4S)-4-hydroxy-2-(hydroxymethyl)-1-methylcyclohexyl)-7a-methyl-1-oxooctahydro-1H-inden-4-yl)methyl acetate (Compound No. 149, 3.06 g, 8.35 mmol) and imidazole (1.31 g, 19.2 mmol) in DMF (34 mL) at 0° C. was added TBSCl (2.64 g, 17.5 mmol), and the mixture was stirred at room temperature for 3 d. The mixture was diluted with EtOAc (150 mL) and washed with H₂O (2×40 mL) and brine (6×30 mL) then dried (MgSO₄) and concentrated. The colourless solid ((3aS,4R,5S,7aS)-5-((1R,2S,4S)-4-((tert-butyldimethylsilyl)oxy)-2-(((tert-butyldimethylsilyl)oxy)methyl)-1-methylcyclohexyl)-7a-methyl-1-oxooctahydro-1H-inden-4-yl)methyl acetate (Compound No. 150, 4.50 g) that was obtained was used in the next step without further purification.

E. A suspension of ((3aS,4R,5S,7aS)-5-((1R,2S,4S)-4-((tert-butyldimethylsilyl)oxy)-2-(((tert-butyldimethylsilyl)oxy)methyl)-1-methylcyclohexyl)-7a-methyl-1-oxooctahydro-1H-inden-4-yl)methyl acetate (Compound No. 150, 4.50 g) and potassium carbonate (2.1 g, 15 mmol) in MeOH (76 mL) was heated to 50° C. for 18 h. The mixture was concentrated, and the residue was partitioned between CH₂Cl₂ (100 mL), H₂O (100 mL) and brine (50 mL). The aqueous phase was extracted with CH₂Cl₂ (2×50 mL), and the combined organic layers were dried (MgSO₄) and concentrated to give (3aS,4R,5S,7aS)-5-((1R,2S,4S)-4-((tert-butyldimethylsilyl)oxy)-2-(((tert-butyldimethylsilyl)oxy)methyl)-1-methylcyclohexyl)-4-(hydroxymethyl)-7a-methyloctahydro-1H-inden-1-one (Compound No. 151, 4.21 g) as a pale foam.

F. Potassium tert-butoxide (2.54 g, 22.6 mmol) was added to a suspension of methyltriphenylphosphonium bromide (8.10 g, 22.7 mmol) in THF (38 mL) at 0° C. under argon and stirred at 0° C. for 1 h. A solution of (3aS,4R,5S,7aS)-5-((1R,2S,4S)-4-((tert-butyldimethylsilyl)oxy)-2-(((tert-butyldimethylsilyl)oxy)methyl)-1-methylcyclohexyl)-4-(hydroxymethyl)-7a-methyloctahydro-1H-inden-1-one (Compound No. 151, 4.21 g) in THF (20 mL) was added then heated to reflux for 1.5 h. The mixture was stirred at room temperature overnight then cooled to 0° C. and brine (20 mL) was added followed by EtOAc (30 mL). The aqueous phase was extracted with EtOAc (2×20 mL), and the combined organic layers were dried (MgSO₄) and concentrated. The residue was stirred in 20:80 EtOAc/hexanes (160 mL) for 2.25 h then filtered and concentrated. The residue was purified by chromatography on silica gel (10:90 EtOAc/hexanes) to give ((3aS,4R,5S,7aS)-5-((1R,2S,4S)-4-((tert-butyldimethylsilyl)oxy)-2-(((tert-butyldimethylsilyl)oxy)methyl)-1-methylcyclohexyl)-7a-methyl-1-methyleneoctahydro-1H-inden-4-yl)methanol (Compound No. 152, 3.85 g, 84% over 3 steps) as a colourless foam.

G. A solution of 2-(bromomethyl)pyridine in CH₂Cl₂ was freshly prepared as follows. 2-(Bromomethyl)pyridine hydrobromide (452 mg, 1.79 mmol) was partitioned between CH₂Cl₂ (20 mL) and saturated aqueous NaHCO₃ (15 mL). The aqueous phase was extracted with CH₂Cl₂ (2×10 mL), and the combined organic layers were dried (MgSO₄) and concentrated to approximately 0.3 mL. To a suspension of NaH (18 mg of a 60% solution, 0.45 mmol) in DMF (0.9 mL) at 0° C. under argon was added ((3aS,4R,5S,7aS)-5-((1R,2S,4S)-4-((tert-butyldimethylsilyl)oxy)-2-(((tert-butyldimethylsilyl)oxy)methyl)-1-methylcyclohexyl)-7a-methyl-1-methyleneoctahydro-1H-inden-4-yl)methanol (Compound No. 152, 101 mg, 0.183 mmol) and stirred at room temperature for 0.5 h. The freshly prepared 2-(bromomethyl)pyridine solution (0.1 mL, ca. 0.6 mmol) was added to the above mixture and stirred at room temperature for 18 h. The mixture was diluted with EtOAc (40 mL) and washed with brine (6×10 mL) then dried (MgSO₄) and concentrated. The residue was purified by chromatography on silica gel (10:90 EtOAc/hexanes) to give 2-(((((3aS,4R,5S,7aS)-5-((1R,2S,4S)-4-((tert-butyldimethylsilyl)oxy)-2-(((tert-butyldimethylsilyl)oxy)methyl)-1-methylcyclohexyl)-7a-methyl-1-methyleneoctahydro-1H-inden-4-yl)methoxy)methyl)pyridine (Compound No. 153, 64 mg, 54%) as a colourless film.

H. TBAF (0.40 mL of a 1 M solution in THF, 0.40 mmol) was added to a solution of 2-(((((3aS,4R,5S,7aS)-5-((1R,2S,4S)-4-((tert-butyldimethylsilyl)oxy)-2-(((tert-butyldimethylsilyl)oxy)methyl)-1-methylcyclohexyl)-7a-methyl-1-methyleneoctahydro-1H-inden-4-yl)methoxy)methyl)pyridine (Compound No. 153, 64 mg, 0.10 mmol) in THF (2.0 mL) and heated to 50° C. for 21 h. The solution was concentrated, and the residue was purified by chromatography on silica gel (2:98-5:95 MeOH/EtOAc) to give (1S,3S,4R)-3-(hydroxymethyl)-4-methyl-4-((3aS,4R,5S,7aS)-7a-methyl-1-methylene-4-((pyridin-2-ylmethoxy)methyl)octahydro-1H-inden-5-yl)cyclohexanol (Compound No. 154, 38 mg, 93%) as colourless crystals. ¹H NMR (CDCl₃): δ8.52 (d, J=4.5 Hz, 1H), 7.69 (m, 1H), 7.42 (d, J=7.5 Hz, 1H), 7.18 (m, 1H), 4.63 (br s, 2H), 4.55 (d, J=13 Hz, 1H), 4.47 (d, J=13 Hz, 1H), 3.77 (m, 2H), 3.58 (br s, 1H), 3.49 (m, 1H), 3.30 (br s, 1H), 2.47 (m, 1H), 2.13-2.29 (m, 2H), 1.21-1.82 (m, 15H), 1.03 (s, 3H), 0.77 (s, 3H). ES-MS m/z 414 ([M+1]⁺).

Example 61

Synthesis of (2S,3aS,4R,5S,7aS)-4-(aminomethyl)-5-((1R,2S,4S)-4-hydroxy-2-(hydroxymethyl)-1-methylcyclohexyl)-7a-methyl-1-methyleneoctahydro-1H-inden-2-ol (Compound No. 162)

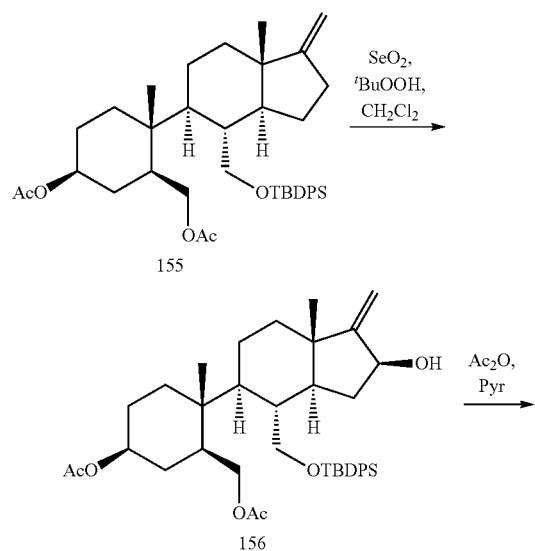

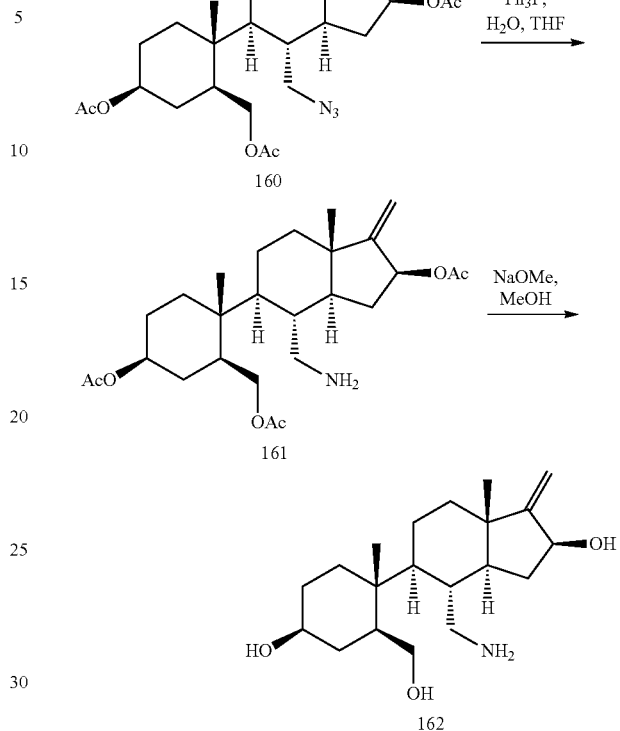

A. To a solution of $SeO_2$ (70 mg, 0.62 mmol) and tert-butyl hydroperoxide (0.34 mL of a 70% solution in water, 2.5 mmol) in $CH_2Cl_2$ (3 mL) was added ((1S,2R,5S)-5-acetoxy-2-((3aS,4R,5S,7aS)-4-(((tert-butyldiphenylsilyl)oxy)methyl)-7a-methyl-1-methyleneoctahydro-1H-inden-5-yl)-2-methylcyclohexyl)methyl acetate (Compound No. 155, 800 mg, 1.2 mmol) in $CH_2Cl_2$ (4 mL). After 5 hours the solution was diluted with EtOAc (75 mL), washed successively with 10% NaOH solution (2×20 mL) and brine (3×15 mL), dried ($MgSO_4$) and concentrated. The residue was purified using chromatography on silica gel (25% EtOAc/hexanes) to afford ((1S,2R,5S)-5-acetoxy-2-((2S,3aS,4R,5S,7aS)-4-(((tert-butyldiphenylsilyl)oxy)methyl)-2-hydroxy-7a-methyl-1-methyleneoctahydro-1H-inden-5-yl)-2-methylcyclohexyl)methyl acetate (Compound No. 156, 452 mg, 55%) as a white foam.

B. To a solution of ((1S,2R,5S)-5-acetoxy-2-((2S,3aS,4R,5S,7aS)-4-(((tert-butyldiphenylsilyl)oxy)methyl)-2-hydroxy-7a-methyl-1-methyleneoctahydro-1H-inden-5-yl)-2-methylcyclohexyl)methyl acetate (Compound No. 156, 146 mg, 0.22 mmol) in pyridine (5 mL) at 0° C. under argon was added $Ac_2O$ (0.06 mL, 0.66 mmol). After 2 hours DMAP (catalytic amount) was added then after another 2 hours the reaction was quenched by addition of saturated $NaHCO_3$ solution (3 mL). After 15 minutes the solution was diluted with EtOAc (75 mL), washed with brine (3×15 mL), dried ($MgSO_4$) and concentrated to afford ((1S,2R,5S)-5-acetoxy-2-((2S,3aS,4R,5S,7aS)-2-acetoxy-4-(((tert-butyldiphenylsilyl)oxy)methyl)-7a-methyl-1-methyleneoctahydro-1H-inden-5-yl)-2-methylcyclohexyl)methyl acetate (Compound No. 157, 160 mg, 100%) as a white foam.

C. A solution of ((1S,2R,5S)-5-acetoxy-2-((2S,3aS,4R,5S,7aS)-2-acetoxy-4-(((tert-butyldiphenylsilyl)oxy)

methyl)-7a-methyl-1-methyleneoctahydro-1H-inden-5-yl)-2-methylcyclohexyl)methyl acetate (Compound No. 157, 155 mg, 0.22 mmol) and TBAF (0.70 mL of a 1M solution in THF, 0.70 mmol) in THF (10 mL) was heated at reflux under argon for 2 hours. The mixture was concentrated and the residue was purified using chromatography on silica gel (30% then 50% EtOAc/hexanes) to afford ((1S,2R,5S)-5-acetoxy-2-((2S,3aS,4R,5S,7aS)-2-acetoxy-4-(hydroxymethyl)-7a-methyl-1-methyleneoctahydro-1H-inden-5-yl)-2-methylcyclohexyl)methyl acetate (Compound No. 158, 66 mg, 66%) as a white foam.

D. To a solution of ((1S,2R,5S)-5-acetoxy-2-((2S,3aS,4R,5S,7aS)-2-acetoxy-4-(hydroxymethyl)-7a-methyl-1-methyleneoctahydro-1H-inden-5-yl)-2-methylcyclohexyl)methyl acetate (Compound No. 158, 66 mg, 0.14 mmol) in pyridine (3 mL) and $CH_2Cl_2$ (3 mL) at 0° C. under argon was added MsCl (0.03 mL, 0.43 mmol). After 2.5 hours the solution was cooled in ice then added saturated $NaHCO_3$ solution (3 mL) and stirred 1 hour. The mixture was diluted with EtOAc (40 mL), washed with brine (3×8 mL), dried ($MgSO_4$) and concentrated to afford ((1S,2R,5S)-5-acetoxy-2-((2S,3aS,4R,5S,7aS)-2-acetoxy-7a-methyl-1-methylene-4-(((methylsulfonyl)oxy)methyl)octahydro-1H-inden-5-yl)-2-methylcyclohexyl)methyl acetate (Compound No. 159, 79 mg, 100%) as a film.

E. A solution of ((1S,2R,5S)-5-acetoxy-2-((2S,3aS,4R,5S,7aS)-2-acetoxy-7a-methyl-1-methylene-4-(((methylsulfonyl)oxy)methyl)octahydro-1H-inden-5-yl)-2-methylcyclohexyl)methyl acetate (Compound No. 159, 77 mg, 0.14 mmol) and $NaN_3$ (27 mg, 0.42 mmol) in DMF (5 mL) at 60° C. was stirred under argon for 16 hours. The mixture was diluted with $Et_2O$ (40 mL), washed with brine (3×8 mL), dried ($MgSO_4$) and concentrated to afford ((1S,2R,5S)-5-acetoxy-2-((2S,3aS,4R,5S,7aS)-2-acetoxy-4-(azidomethyl)-7a-methyl-1-methyleneoctahydro-1H-inden-5-yl)-2-methylcyclohexyl)methyl acetate (Compound No. 160, 70 mg, 100%) as a film.

F. A solution of ((1S,2R,5S)-5-acetoxy-2-((2S,3aS,4R,5S,7aS)-2-acetoxy-4-(azidomethyl)-7a-methyl-1-methyleneoctahydro-1H-inden-5-yl)-2-methylcyclohexyl)methyl acetate (Compound No. 160, 69 mg, 0.14 mmol), triphenylphosphine (185 mg, 0.70 mmol) and water (0.01 mL, 0.7 mmol) in THF (5 mL) was stirred at room temperature for 2 days. The mixture was concentrated and the residue was purified using chromatography on silica gel (5% MeOH/$CH_2Cl_2$ then 10% MeOH/$CH_2Cl_2$ with 2% $NH_4OH$) to afford ((1S,2R,5S)-5-acetoxy-2-((2S,3aS,4R,5S,7aS)-2-acetoxy-4-(aminomethyl)-7a-methyl-1-methyleneoctahydro-1H-inden-5-yl)-2-methylcyclohexyl)methyl acetate (Compound No. 161, 35 mg, 54%) as a film.

G. A solution of ((1S,2R,5S)-5-acetoxy-2-((2S,3aS,4R,5S,7aS)-2-acetoxy-4-(aminomethyl)-7a-methyl-1-methyleneoctahydro-1H-inden-5-yl)-2-methylcyclohexyl)methyl acetate (Compound No. 161, 35 mg, 0.075 mmol) and NaOMe (0.21 mL of a 25% solution in MeOH) in MeOH (5 mL) was stirred at room temperature for 18 hours. The mixture was purified using chromatography on silica gel (5% MeOH/EtOAc then 10% MeOH/EtOAc with 2% $NH_4OH$ then 20% MeOH/EtOAc with 4% $NH_4OH$) to afford (2S,3aS,4R,5S,7aS)-4-(aminomethyl)-5-((1R,2S,4S)-4-hydroxy-2-(hydroxymethyl)-1-methylcyclohexyl)-7a-methyl-1-methyleneoctahydro-1H-inden-2-ol (Compound No. 162, 24 mg, 99%) as a film. $^1$H NMR ($CD_3OD$): δ5.05 (1H), 4.85 (1H), 4.62 (m, 1H), 3.72 (m, 1H), 3.45 (m, 1H), 3.12 (2H), 2.75 (m, 1H), 2.15 (m, 1H), 1.9-1.2 (15H), 1.10 (s, 3H), 0.82 (s, 3H). ES-MS m/z 338 ([M+1]$^+$)

Example 62

Synthesis of ((1S,2R,5S)-5-amino-2-((3aS,4R,5S,7aS)-4-(hydroxymethyl)-7a-methyl-1-methyleneoctahydro-1H-inden-5-yl)-2-methylcyclohexyl)methanol (Compound No. 167)

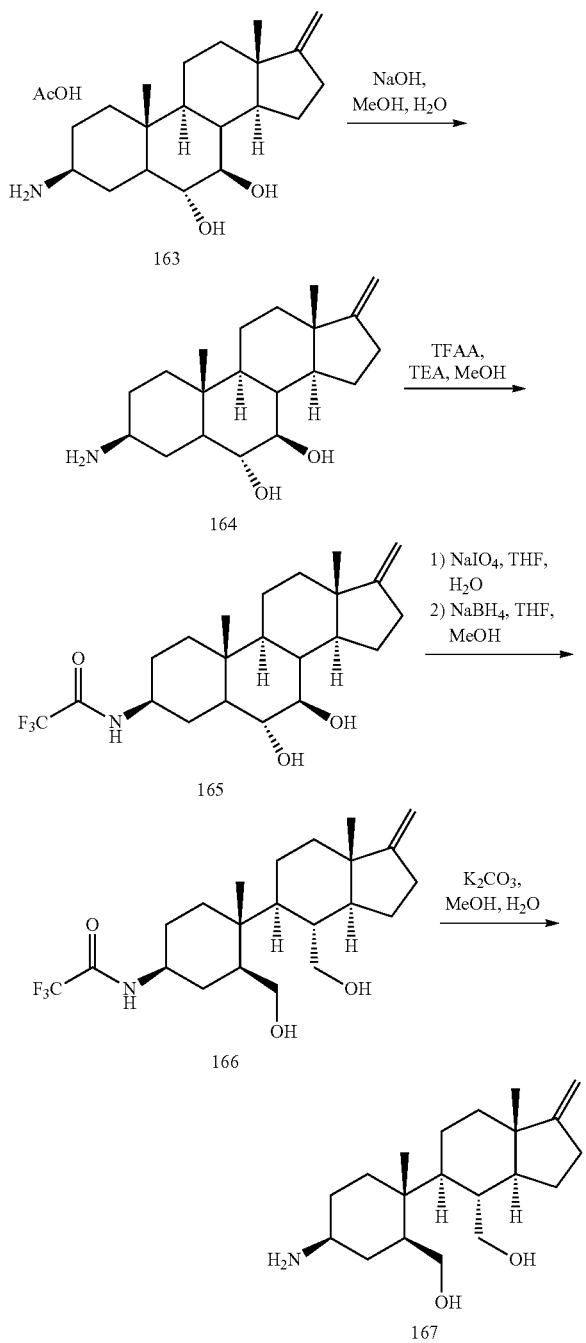

A. To a solution of (3S,5S,6R,7R,8R,9S,10R,13S,14S)-3-amino-10,13-dimethyl-17-methylenehexadecahydro-1H-cyclopenta[a]phenanthrene-6,7-diol acetate (Compound No.

163, 3.86 g, 10.2 mmol) in 1:1 MeOH/H₂O (16 mL) was added 1 N NaOH (aq) (20 mL, 20 mmol), giving a colourless precipitate that was collected by filtration and washed with H₂O. The precipitate was dissolved in MeOH and concentrated followed by azeotropic removal of remaining H₂O using toluene (30 mL). The colourless solid (3S,5S,6R,7R,8R,9S,10R,13S,14S)-3-amino-10,13-dimethyl-17-methylenehexadecahydro-1H-cyclopenta[a]phenanthrene-6,7-diol (Compound No. 164, 3.30 g) that was obtained was used in the next step without further purification.

B. To a solution of (3S,5S,6R,7R,8R,9S,10R,13S,14S)-3-amino-10,13-dimethyl-17-methylenehexadecahydro-1H-cyclopenta[a]phenanthrene-6,7-diol (Compound No. 164, 3.30 g) and Et₃N (3.55 mL, 25.5 mmol) in MeOH (10 mL) at 0° C. under argon was added trifluoroacetic anhydride (1.98 mL, 14.2 mmol) dropwise, and the solution was stirred at room temperature for 15 h. More Et₃N (1.8 mL, 13 mmol) was added and the mixture was cooled to 0° C. Trifluoroacetic anhydride (1.98 mL, 14.2 mmol) was added dropwise and stirred at room temperature for 2.5 h then concentrated. The residue was dissolved in EtOAc (100 mL) and washed with saturated aqueous NaHCO₃ (50 mL then 3×20 mL) and brine (15 mL) then dried (MgSO₄) and concentrated to give N-((3S,5S,6R,7R,8R,9S,10R,13S,14S)-6,7-dihydroxy-10,13-dimethyl-17-methylenehexadecahydro-1H-cyclopenta[a]phenanthren-3-yl)-2,2,2-trifluoroacetamide (Compound No. 165, 3.09 g) as a pale foam.

C. A suspension of sodium periodate (3.18 g, 14.9 mmol) in H₂O (7.4 mL) was added to a solution of N-((3S,5S,6R,7R,8R,9S,10R,13S,14S)-6,7-dihydroxy-10,13-dimethyl-17-methylenehexadecahydro-1H-cyclopenta[a]phenanthren-3-yl)-2,2,2-trifluoroacetamide (Compound No. 165, 3.09 g) in THF (74 mL), and the mixture was stirred at room temperature for 1.5 h. The mixture was concentrated, and the residue was partitioned between CH₂Cl₂ (40 mL) and H₂O (30 mL). The aqueous phase was extracted with CH₂Cl₂ (15 mL), and the combined organic layers were dried (MgSO₄) and concentrated. The resulting colourless foam (3.09 g) was dissolved in 1:1 THF/MeOH (74 mL) and cooled to 0° C. under argon. NaBH₄ (0.56 g, 15 mmol) was added, and the mixture was stirred at 0° C. for 30 min then at room temperature for 3 h. Acetone (5 mL) was added and the mixture was concentrated. The residue was dissolved in EtOAc (100 mL) and washed with brine (2×25 mL) then dried (MgSO₄) and concentrated. The residue was purified by chromatography on silica gel (60:40 EtOAc/hexanes) to give 2,2,2-trifluoro-N-((1S,3S,4R)-3-(hydroxymethyl)-4-((3aS,4R,5S,7aS)-4-(hydroxymethyl)-7a-methyl-1-methyleneoctahydro-1H-inden-5-yl)-4-methylcyclohexyl)acetamide (Compound No. 166, 2.40 g, 56% over 4 steps) as a colourless solid.

D. To a solution of 2,2,2-trifluoro-N-((1S,3S,4R)-3-(hydroxymethyl)-4-((3aS,4R,5S,7aS)-4-(hydroxymethyl)-7a-methyl-1-methyleneoctahydro-1H-inden-5-yl)-4-methylcyclohexyl)acetamide (Compound No. 166, 654 mg, 1.57 mmol) in 9:1 MeOH/H₂O (31 mL) was added potassium carbonate (4.3 g, 31 mmol) and heated to 65° C. for 22 h. The mixture was filtered and concentrated, and 1 N NaOH (aq) (3 mL) and H₂O (10 mL) were added to the residue. The mixture was stirred and a colourless solid was collected by filtration and washed with H₂O. The solid was dissolved in MeOH and concentrated to give ((1S,2R,5S)-5-amino-2-((3aS,4R,5S,7aS)-4-(hydroxymethyl)-7a-methyl-1-methyleneoctahydro-1H-inden-5-yl)-2-methylcyclohexyl)methanol (Compound No. 167, 405 mg, 80%) as a colourless solid. ¹H NMR (CD₃OD): δ4.62 (s, 2H), 3.93 (m, 1H), 3.73 (m, 1H), 3.64 (m, 1H), 3.11 (m, 1H), 2.53 (m, 2H), 2.26 (m, 1H), 2.06 (m, 1H), 1.10-1.94 (m, 18H), 0.80 (s, 3H). ES-MS m/z 322 ([M+1]⁺).

Example 63

Synthesis of (1S,3S,4R)-3-(hydroxymethyl)-4-((3aS,4R,5S,7aS)-4-(hydroxymethyl)-7a-methyl-1-methylene-3a,4,5,6,7,7a-hexahydro-1H-inden-5-yl)-4-methylcyclohexanol (Compound No. 171)

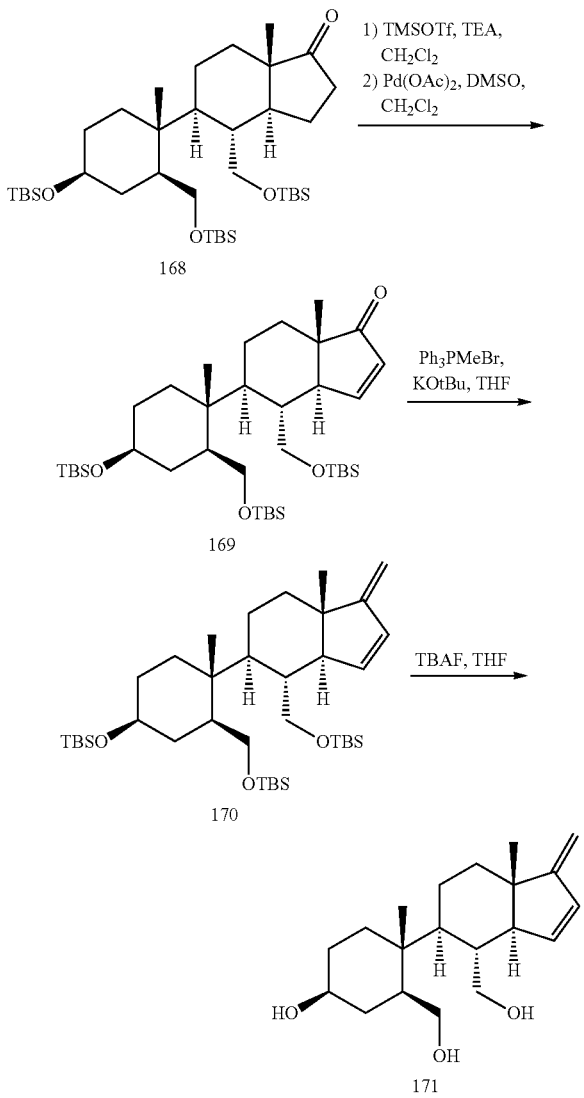

A. A mixture of (3aS,4R,5S,7aS)-5-((1R,2S,4S)-4-((tert-butyldimethylsilyl)oxy)-2-(((tert-butyldimethylsilyl)oxy)methyl)-1-methylcyclohexyl)-4-(((tert-butyldimethylsilyl)oxy)methyl)-7a-methyloctahydro-1H-inden-1-one (Compound No. 168, 1.28 g, 1.9 mmol), TMSOTf (1.4 mL, 7.7 mmol) and TEA (1.6 mL, 11.5 mmol) in CH₂Cl₂ (50 mL) under argon at 0° C. was stirred for 90 min. The reaction was quenched with saturated NaHCO₃ solution (50 mL), extracted with CH₂Cl₂ (2×25 mL), dried (Na₂SO₄) and concentrated. The residue was dissolved in DMSO (30 mL) and CH₂Cl₂ (20 mL) under argon at room temperature. To this mixture was added Pd(OAc)$_2$ (426 mg, 1.9 mmol) and the resultant mixture was stirred for 18 h. Dilution with Et$_2$O (200 mL) was followed by washing with water (3×50 mL). The aqueous washes were the back extracted with Et$_2$O (3×75 mL). The combined organic layers were dried (Na$_2$SO$_4$) and concentrated. The residue was purified using chromatography on silica gel (9:1 hexanes:EtOAc) to afford (3aS,4R,5S,7aS)-5-((1R,2S,4S)-4-((tert-butyldimethylsilyl)oxy)-2-(((tert-butyldimethylsilyl)oxy)methyl)-1-methylcyclohexyl)-4-(((tert-butyldimethylsilyl)oxy)methyl)-7a-methyl-3a,4,5,6,7,7a-hexahydro-1H-inden-1-one (Compound No. 169, 1.09 g, 86% over 2 steps).

B. To a suspension of Ph$_3$PMeBr (3.64 g, 1.02 mmol) in THF (60 mL) under argon at 0° C. was added KOtBu (1.14 g, 10.2 mmol). After 30 min a solution of (3aS,4R,5S,7aS)-5-((1R,2S,4S)-4-((tert-butyldimethylsilyl)oxy)-2-(((tert-butyldimethylsilyl)oxy)methyl)-1-methylcyclohexyl)-4-(((tert-butyldimethylsilyl)oxy)methyl)-7a-methyl-3a,4,5,6,7,7a-hexahydro-1H-inden-1-one (Compound No. 169, 0.68 g, 1.0 mmol) in THF (30 mL) was added via cannula and the mixture was stirred at room temperature for 2.5 h. The reaction was diluted with EtOAc (200 mL), washed successively with saturated NaHCO$_3$ solution (2×50 mL) and brine (50 mL), dried (Na$_2$SO$_4$) and concentrated. The residue was purified by chromatography on silica gel (0% to 5% to 10% EtOAc/hexanes) to afford tert-butyl(((3aS,4R,5S,7aS)-5-((1R,2S,4S)-4-((tert-butyldimethylsilyl)oxy)-2-(((tert-butyldimethylsilyl)oxy)methyl)-1-methylcyclohexyl)-7a-methyl-1-methylene-3a,4,5,6,7,7a-hexahydro-1H-inden-4-yl)methoxy)dimethylsilane (Compound No. 170, 119 mg, 18%) as a colourless oil.

C. A mixture of tert-butyl(((3aS,4R,5S,7aS)-5-((1R,2S,4S)-4-((tert-butyldimethylsilyl)oxy)-2-(((tert-butyldimethylsilyl)oxy)methyl)-1-methylcyclohexyl)-7a-methyl-1-methylene-3a,4,5,6,7,7a-hexahydro-1H-inden-4-yl)methoxy)dimethylsilane (Compound No. 170, 119 mg, 0.18 mmol) and TBAF (1.8 mL of a 1 M solution in THF, 1.8 mmol) in THF (10 mL) under argon at room temperature was stirred for 24 h. TBAF (0.9 mL, 0.9 mmol) was added and the mixture was stirred for 5 h. The solution was diluted with EtOAc (100 mL), washed successively with saturated NaHCO$_3$ solution (2×25 mL) and brine (25 mL), dried (Na$_2$SO$_4$) and concentrated. The residue was purified using chromatography on silica gel (0% to 2% to 5% to 10% MeOH/CH$_2$Cl$_2$) to afford (1S,3S,4R)-3-(hydroxymethyl)-4-((3aS,4R,5S,7aS)-4-(hydroxymethyl)-7a-methyl-1-methylene-3a,4,5,6,7,7a-hexahydro-1H-inden-5-yl)-4-methylcyclohexanol (Compound No. 171, 36 mg, 63%) as a thick colourless oil. $^1$H NMR (300 MHz, CD$_3$OD) δ6.28 (d, J=5.8, 1H), 6.10 (m, 1H), 4.74 (s, 1H), 4.60 (s, 1H), 3.97 (d, J=9.4, 1H), 3.86 (d, J=11.1, 1H), 3.73 (d, J=8.8, 1H), 3.45 (m, 1H), 3.13 (m, 1H), 2.51 (m, 1H), 2.15 (m, 1H), 1.83 (m, 7H), 1.58-1.20 (m, 7H), 1.12 (s, 3H), 0.98 (s, 3H). $^{13}$C NMR (75 MHz, CD$_3$OD) δ164.5, 138.2, 133.5, 100.8, 71.2, 63.2, 62.9, 58.1, 46.4, 44.6, 38.3, 35.2, 34.7, 32.1, 24.3, 22.6, 21.7; MS m/z: 379.1 [M+acetate]$^-$.

Example 64

Synthesis of (1S,3S,4R)-3-(hydroxymethyl)-4-((4R,5S)-4-(hydroxymethyl)-1,1-dimethyl-4,5,6,7-tetrahydro-1H-inden-5-yl)-4-methylcyclohexanol (Compound No. 172)

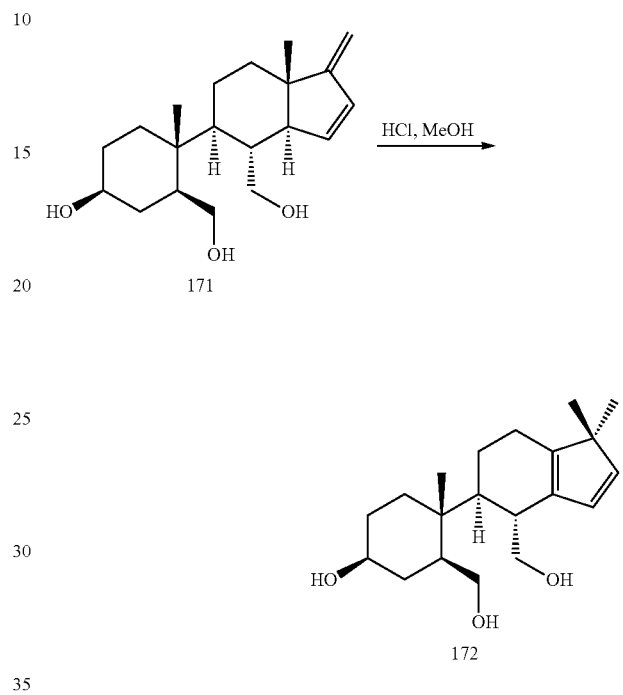

A mixture of (1S,3S,4R)-3-(hydroxymethyl)-4-((3aS,4R,5S,7aS)-4-(hydroxymethyl)-7a-methyl-1-methylene-3a,4,5,6,7,7a-hexahydro-1H-inden-5-yl)-4-methylcyclohexanol (Compound No. 171, 17 mg, 0.05 mmol) and concentrated HCl (2 mL) in MeOH (4 mL) at 40° C. was stirred for 20 h. The resultant mixture was cooled to room temperature, concentrated and taken up in EtOAc (25 mL). This mixture was washed successively with saturated NaHCO$_3$ solution (3×5 mL) and brine (5 mL), dried (Na$_2$SO$_4$) and concentrated. The residue was purified using chromatography on silica gel (0% to 5% to 10% MeOH/CH$_2$Cl$_2$) to afford (1S,3S,4R)-3-(hydroxymethyl)-4-((4R,5S)-4-(hydroxymethyl)-1,1-dimethyl-4,5,6,7-tetrahydro-1H-inden-5-yl)-4-methylcyclohexanol (Compound No. 172, 14 mg, 82%) as a thick colourless oil. $^1$H NMR (300 MHz, CD$_3$OD) δ5.15 (s, 1H), 5.10 (d, J=6.7, 1H), 3.71 (d, J=10.6, 1H), 3.64 (t, J=7.7, 1H), 3.49 (m, 1H), 3.17 (t, J=10.0, 1H), 3.04 (m, 1H), 2.18 (m, 3H), 1.88-1.14 (m, 10H), 1.67 (s, 3H), 1.08 (s, 3H), 0.87 (s, 3H); $^{13}$C NMR (75 MHz, CD$_3$OD) δ156.1, 122.3, 89.5, 73.4, 71.4, 62.8, 50.9, 48.3, 43.1, 41.3, 41.1, 38.7, 35.3, 34.2, 31.8, 30.9, 27.8, 19.3, 18.5, 12.2; MS m/z: 379.3 [M+acetate]$^-$.

Example 65
Synthesis of (2R,4R,5S)-5-((1R,2S,4S)-4-hydroxy-2-(hydroxymethyl)-1-methylcyclohexyl)-4-(hydroxymethyl)-1,1-dimethyl-2,3,4,5,6,7-hexahydro-1H-inden-2-ol (Compound No. 184)
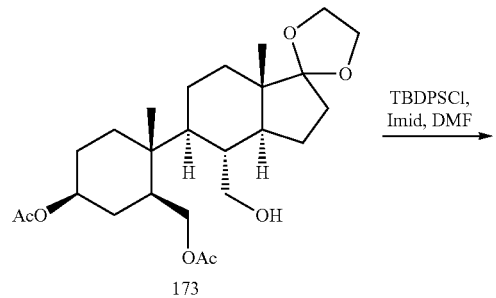
173
→ TBDPSCl, Imid, DMF
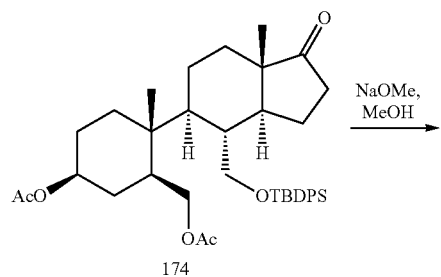
174
→ NaOMe, MeOH
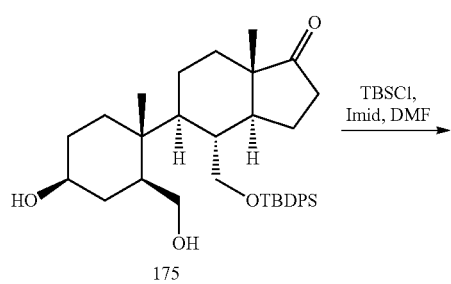
175
→ TBSCl, Imid, DMF
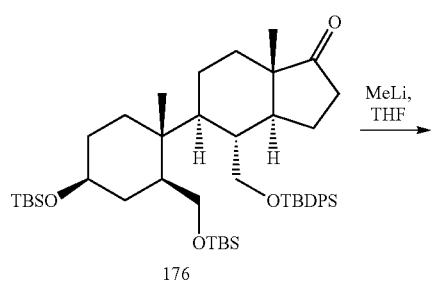
176
→ MeLi, THF
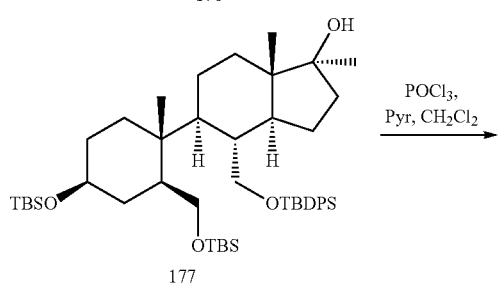
177
→ POCl$_3$, Pyr, CH$_2$Cl$_2$
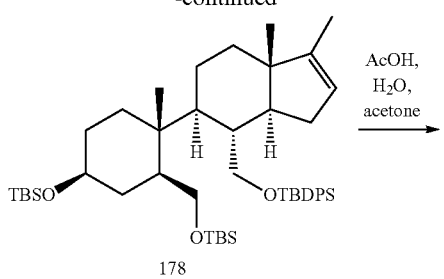
178
→ AcOH, H$_2$O, acetone
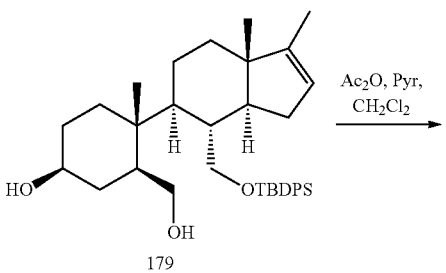
179
→ Ac$_2$O, Pyr, CH$_2$Cl$_2$
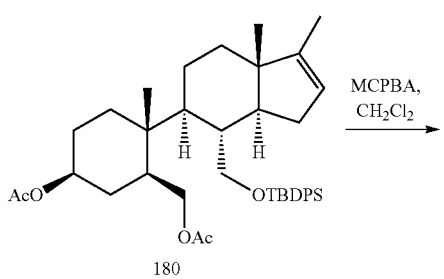
180
→ MCPBA, CH$_2$Cl$_2$
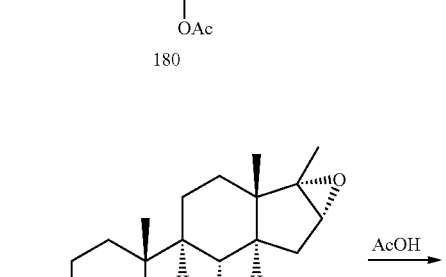
181
→ AcOH
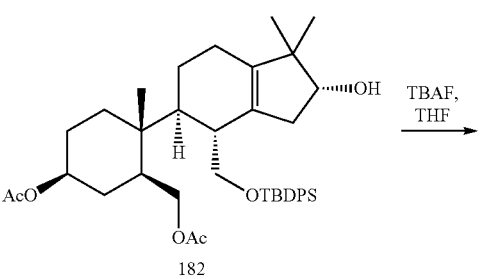
182
→ TBAF, THF
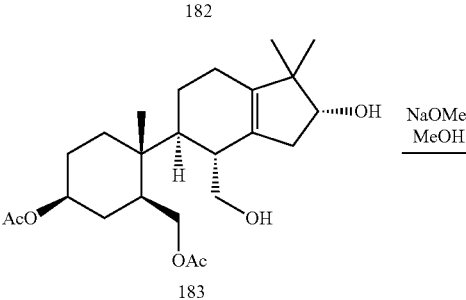
183
→ NaOMe, MeOH -continued

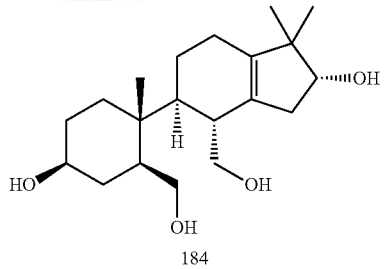

184

A. A solution of ((1S,2R,5S)-5-acetoxy-2-((3a'S,4'R,5'S,7a'S)-4'-(hydroxymethyl)-7a'-methyloctahydrospiro[[1,3]dioxolane-2,1'-inden]-5'-yl)-2-methylcyclohexyl)methyl acetate (Compound No. 173, 5.51 g, 12.2 mmol), TBDPSCl (4.7 mL, 18.6 mmol) and imidazole (2.5 g, 36.6 mmol) in DMF (40 mL) was stirred at room temperature under nitrogen for 21 hours. The mixture was poured into cold water (80 mL), extracted with Et₂O (350 mL), washed with brine (40 mL), dried (MgSO₄) and concentrated. The residue was taken up in AcOH (80 mL) and water (20 mL) and heated at 40° C. for 2 hours, stood at room temperature overnight then heated at 40° C. for 2 hours. The mixture was concentrated and the residue was taken up in EtOAc (350 mL), washed successively with saturated NaHCO₃ solution (3×50 mL) and brine (3×30 mL), dried (MgSO₄) and concentrated. The residue was purified using chromatography on silica gel (20% EtOAc/hexanes) to afford ((1S,2R,5S)-5-acetoxy-2-((3aS,4R,5S,7aS)-4-(((tert-butyldiphenylsilyl)oxy)methyl)-7a-methyl-1-oxooctahydro-1H-inden-5-yl)-2-methylcyclohexyl)methyl acetate (Compound No. 174, 4.86 g, 61%) as a white foam.

B. A solution of ((1S,2R,5S)-5-acetoxy-2-((3aS,4R,5S,7aS)-4-(((tert-butyldiphenylsilyl)oxy)methyl)-7a-methyl-1-oxooctahydro-1H-inden-5-yl)-2-methylcyclohexyl)methyl acetate (Compound No. 174, 3.47 g, 5.36 mmol) and NaOMe (7.9 mL of a 5.4M solution in MeOH) in MeOH (30 mL) was stirred at room temperature for 2 days. The solution was cooled in ice then was added AcOH (2.5 mL). The mixture was concentrated and the residue was taken up in EtOAc (200 mL) and water (20 mL). The EtOAc layer was washed with brine (3×15 mL), dried (MgSO₄) and concentrated to afford (3aS,4R,5S,7aS)-4-(((tert-butyldiphenylsilyl)oxy)methyl)-5-((1R,2S,4S)-4-hydroxy-2-(hydroxymethyl)-1-methylcyclohexyl)-7a-methyloctahydro-1H-inden-1-one (Compound No. 175, 3.55 g) of a white solid.

C. A solution of (3aS,4R,5S,7aS)-4-(((tert-butyldiphenylsilyl)oxy)methyl)-5-((1R,2S,4S)-4-hydroxy-2-(hydroxymethyl)-1-methylcyclohexyl)-7a-methyloctahydro-1H-inden-1-one (Compound No. 175, 3.02 g, 5.36 mmol), TBSCl (1.94 g, 12.9 mmol) and imidazole (1.75 g, 25.7 mmol) in DMF was stirred at room temperature under nitrogen for 1.5 hours. The mixture was diluted with Et₂O (300 mL), washed successively with water (40 mL) and brine (2×40 mL), dried (MgSO₄) and concentrated. The residue was purified using chromatography on silica gel (5% then 10% EtOAc/hexanes) to afford (3aS,4R,5S,7aS)-5-((1R,2S,4S)-4-((tert-butyldimethylsilyl)oxy)-2-(((tert-butyldimethylsilyl)oxy)methyl)-1-methylcyclohexyl)-4-(((tert-butyldiphenylsilyl)oxy)methyl)-7a-methyloctahydro-1H-inden-1-one (Compound No. 176, 3.75 g, 88%) as a white foam.

D. To a solution of (3aS,4R,5S,7aS)-5-((1R,2S,4S)-4-((tert-butyldimethylsilyl)oxy)-2-(((tert-butyldimethylsilyl)oxy)methyl)-1-methylcyclohexyl)-4-(((tert-butyldiphenylsilyl)oxy)methyl)-7a-methyloctahydro-1H-inden-1-one (Compound No. 176, 3.65 g, 4.61 mmol) in THF (20 mL) at −78° C. under nitrogen was added MeLi (12.6 mL of a 1.1M solution in Et₂O, 13.8 mmol). After 1 hour the reaction temperature was increased to 0° C. for 4 hours then was added saturated NaHCO₃ solution (10 mL). The mixture was diluted with EtOAc (350 mL), washed with brine (3×30 mL), dried (MgSO₄) and concentrated. The residue was purified using chromatography on silica gel (5% then 15% EtOAc/hexanes) to afford (1S,3aS,4R,5S,7aS)-5-((1R,2S,4S)-4-((tert-butyldimethylsilyl)oxy)-2-(((tert-butyldimethylsilyl)oxy)methyl)-1-methylcyclohexyl)-4-(((tert-butyldiphenylsilyl)oxy)methyl)-1,7a-dimethyloctahydro-1H-inden-1-ol (Compound No. 177, 2.54 g, 68%) as a white foam.

E. To a solution of (1S,3aS,4R,5S,7aS)-5-((1R,2S,4S)-4-((tert-butyldimethylsilyl)oxy)-2-(((tert-butyldimethylsilyl)oxy)methyl)-1-methylcyclohexyl)-4-(((tert-butyldiphenylsilyl)oxy)methyl)-1,7a-dimethyloctahydro-1H-inden-1-ol (Compound No. 177, 2.54 g, 3.14 mmol) in pyridine (5 mL) and CH₂Cl₂ (25 mL) at 0° C. under nitrogen was added POCl₃ (0.88 mL, 9.4 mmol). After 24 hours, the solution was cooled in ice then added saturated NaHCO₃ solution (15 mL) and EtOAc (350 mL). The EtOAc layer was washed with brine (2×30 mL), dried (MgSO₄) and concentrated to afford tert-butyl(((3aS,6S,7R,7aS)-6-((1R,2S,4S)-4-((tert-butyldimethylsilyl)oxy)-2-(((tert-butyldimethylsilyl)oxy)methyl)-1-methylcyclohexyl)-3,3a-dimethyl-3a,4,5,6,7,7a-hexahydro-1H-inden-7-yl)methoxy)diphenylsilane (Compound No. 178, 2.49 g) as a white foam.

F. A solution of tert-butyl(((3aS,6S,7R,7aS)-6-((1R,2S,4S)-4-((tert-butyldimethylsilyl)oxy)-2-(((tert-butyldimethylsilyl)oxy)methyl)-1-methylcyclohexyl)-3,3a-dimethyl-3a,4,5,6,7,7a-hexahydro-1H-inden-7-yl)methoxy)diphenylsilane (Compound No. 178, 2.48 g, 3.14 mmol) in AcOH (80 mL), water (20 mL) and acetone (200 mL) was stirred at room temperature for 3 days. The mixture was concentrated and the residue was purified using chromatography on silica gel (50% then 70% EtOAc/hexanes) to afford (1S,3S,4R)-4-((3aS,6S,7R,7aS)-7-(((tert-butyldiphenylsilyl)oxy)methyl)-3,3a-dimethyl-3a,4,5,6,7,7a-hexahydro-1H-inden-6-yl)-3-(hydroxymethyl)-4-methylcyclohexanol (Compound No. 179, 1.52 g) of a white solid.

G. To a solution of (1S,3S,4R)-4-((3aS,6S,7R,7aS)-7-(((tert-butyldiphenylsilyl)oxy)methyl)-3,3a-dimethyl-3a,4,5,6,7,7a-hexahydro-1H-inden-6-yl)-3-(hydroxymethyl)-4-methylcyclohexanol (Compound No. 179, 1.52 g, 2.71 mmol) in pyridine (5 mL) and CH₂Cl₂ (25 mL) at 0° C. under nitrogen was added Ac₂O (1.5 mL, 16.3 mmol). After 16 hours, the reaction was fitted with a reflux condenser and was heated in a 50° C. oil bath for 7 hours then was allowed to continue at room temperature overnight. The solution was cooled in ice then added saturated NaHCO₃ solution (5 mL). After 10 minutes, the solution was diluted with EtOAc (200 mL), washed with brine (3×30 mL), dried (MgSO₄) and concentrated. The residue was purified using chromatography on silica gel (10% EtOAc/hexanes) to afford ((1S,2R,5S)-5-acetoxy-2-((3aS,6S,7R,7aS)-7-(((tert-butyldiphenylsilyl)oxy)methyl)-3,3a-dimethyl-3a,4,5,6,7,7a-hexahydro-1H-inden-6-yl)-2-methylcyclohexyl)methyl acetate (Compound No. 180, 1.52 g) as a white foam.

H. A solution of ((1S,2R,5S)-5-acetoxy-2-((3aS,6S,7R,7aS)-7-(((tert-butyldiphenylsilyl)oxy)methyl)-3,3a-dimethyl-3a,4,5,6,7,7a-hexahydro-1H-inden-6-yl)-2-methylcyclohexyl)methyl acetate (Compound No. 180, 1.52 g, 2.36 mmol) and MCPBA (1.53 g, 7.09 mmol) in CH₂Cl₂ (20 mL) at 0° C. under nitrogen was stirred 1.5 hours then was quenched with a 10% Na₂SO₃ solution (20 mL). After 10 minutes, the solution was diluted with EtOAc (200 mL), washed successively with saturated NaHCO$_3$ solution (3×30 mL) and brine (3×30 mL), dried (MgSO$_4$) and concentrated. The residue was purified using chromatography on silica gel (15% then 20% EtOAc/hexanes) to afford ((1S,2R,5S)-5-acetoxy-2-((1 aS, 1 bS,4S,5R,5aS,6aR)-5-(((tert-butyldiphenylsilyl)oxy)methyl)-1a,1b-dimethyloctahydro-1aH-indeno[1,2-b]oxiren-4-yl)-2-methylcyclohexyl)methyl acetate (Compound No. 181, 1.14 g) as a white foam.

I. A solution of ((1S,2R,5S)-5-acetoxy-2-((1 aS, 1 bS,4S, 5R,5aS,6aR)-5-(((tert-butyldiphenylsilyl)oxy)methyl)-1a, 1 b-dimethyloctahydro-1aH-indeno[1,2-b]oxiren-4-yl)-2-methylcyclohexyl)methyl acetate (Compound No. 181, 616 mg, 0.932 mmol) and AcOH (20 mL) was stirred at room temperature for 24 hours then was concentrated. The residue was purified using chromatography on silica gel (25% then 30% EtOAc/hexanes) to afford ((1S,2R,5S)-5-acetoxy-2-((2R,4R,5S)-4-(((tert-butyldiphenylsilyl)oxy)methyl)-2-hydroxy-1,1-dimethyl-2,3,4,5,6,7-hexahydro-1H-inden-5-yl)-2-methylcyclohexyl)methyl acetate (Compound No. 182, 171 mg) as a white foam.

J. A solution of ((1S,2R,5S)-5-acetoxy-2-((2R,4R,5S)-4-(((tert-butyldiphenylsilyl)oxy)methyl)-2-hydroxy-1,1-dimethyl-2,3,4,5,6,7-hexahydro-1H-inden-5-yl)-2-methylcyclohexyl)methyl acetate (Compound No. 182, 117 mg, 0.18 mmol) and TBAF (1 mL of a 1M solution in THF, 1 mmol) in THF (5 mL) was stirred at room temperature under nitrogen for 16 hours then was concentrated. The residue was purified using chromatography on silica gel (70% then 80% EtOAc/hexanes) to afford ((1S,2R,5S)-5-acetoxy-2-((2R,4R,5S)-2-hydroxy-4-(hydroxymethyl)-1,1-dimethyl-2,3,4,5,6,7-hexahydro-1H-inden-5-yl)-2-methylcyclohexyl) methyl acetate (Compound No. 183, 83 mg) as a white foam.

K. A solution of ((1S,2R,5S)-5-acetoxy-2-((2R,4R,5S)-2-hydroxy-4-(hydroxymethyl)-1,1-dimethyl-2,3,4,5,6,7-hexahydro-1H-inden-5-yl)-2-methylcyclohexyl)methyl acetate (Compound No. 183, 83 mg, 0.20 mmol) and NaOMe (0.4 mL of a 5.4M solution in MeOH, 2 mmol) in MeOH (3 mL) was stirred at room temperature for 1 hour then added AcOH (1 mL) and concentrated. The residue was purified using chromatography on silica gel (5% MeOH/EtOAc) to afford (2R,4R,5S)-5-((1R,2S,4S)-4-hydroxy-2-(hydroxymethyl)-1-methylcyclohexyl)-4-(hydroxymethyl)-1,1-dimethyl-2,3, 4,5,6,7-hexahydro-1H-inden-2-ol (Compound No. 184, 64 mg, 97%) as a film. $^1$H NMR (CD$_3$OD): δ3.80 (2H), 3.60 (m, 1H), 3.45 (m, 1H), 3.30 (m, 1H), 3.20 (m, 1H), 2.35 (2H), 2.25-1.75 (7H), 1.65 (2H), 1.25 (4H), 0.90 (6H), 0.85 (s, 3H). ES-MS m/z 339 ([M+1]$^+$)

Example 66

Synthesis of (1S,3S,4R)-4-((3aS,4R,5S,7aS)-4-(benzyloxymethyl)-7a-methyl-1-methyleneoctahydro-1H-inden-5-yl)-3-(hydroxymethyl)-4-methylcyclohexanol (Compound No. 186)

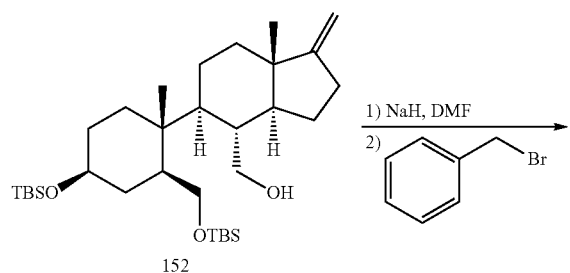

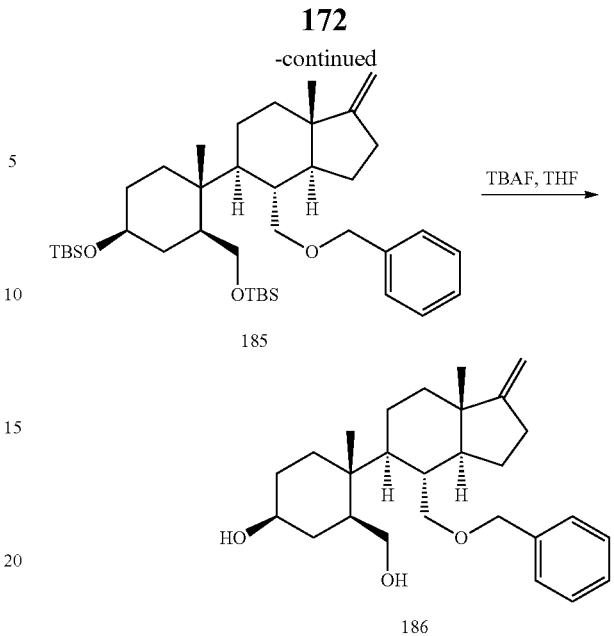

A. To a suspension of NaH (24 mg of a 60% solution, 0.60 mmol) in DMF (1.2 mL) at 0° C. under argon was added ((3aS,4R,5S,7aS)-5-((1R,2S,4S)-4-((tert-butyldimethylsilyl)oxy)-2-(((tert-butyldimethylsilyl)oxy)methyl)-1-methylcyclohexyl)-7a-methyl-1-methyleneoctahydro-1H-inden-4-yl)methanol (Compound No. 152, 133 mg, 0.241 mmol) and stirred at room temperature for 0.5 h. A solution of benzyl bromide (103 mg, 0.602 mmol) in DMF (1.2 mL) was added and stirred at room temperature for 4 h. The mixture was diluted with EtOAc (40 mL) and washed with H$_2$O (10 mL) and brine (6×10 mL) then dried (MgSO$_4$) and concentrated. The residue was purified by chromatography on silica gel (2:98 EtOAc/hexanes) to give (((1S,3S,4R)-4-((3aS,4R,5S, 7aS)-4-((benzyloxy)methyl)-7a-methyl-1-methyleneoctahydro-1H-inden-5-yl)-3-(((tert-butyldimethylsilyl)oxy) methyl)-4-methylcyclohexyl)oxy)(tert-butyl)dimethylsilane (Compound No. 185, 142 mg, 92%) as a colourless oil.

B. TBAF (0.89 mL of a 1 M solution in THF, 0.89 mmol) was added to a solution of (((1S,3S,4R)-4-((3aS,4R,5S,7aS)-4-((benzyloxy)methyl)-7a-methyl-1-methyleneoctahydro-1H-inden-5-yl)-3-(((tert-butyldimethylsilyl)oxy)methyl)-4-methylcyclohexyl)oxy)(tert-butyl)dimethylsilane (Compound No. 185, 142 mg, 0.221 mmol) in THF (4.4 mL) and heated to 50° C. for 17.5 h. The solution was concentrated, and the residue was purified by chromatography on silica gel (80:20 EtOAc/hexanes) to give (1S,3S,4R)-4-((3aS,4R,5S,7aS)-4-(benzyloxymethyl)-7a-methyl-1-methyleneoctahydro-1H-inden-5-yl)-3-(hydroxymethyl)-4-methylcyclohexanol (Compound No. 186, 74 mg, 81%) as a colourless solid. $^1$H NMR (CDCl$_3$): δ7.31 (m, 5H), 4.62 (m, 2H), 4.43 (d, J=11 Hz, 1H), 4.34 (d, J=12 Hz, 1H), 3.71 (m, 2H), 3.58 (br s, 1H), 3.38 (m, 1H), 3.30 (br s, 1H), 2.46 (m, 1H), 2.13-2.29 (m, 2H), 1.25-1.80 (m, 15H), 1.03 (s, 3H), 0.76 (s, 3H). ES-MS m/z 395 ([M−17]+).

Example 67

Synthesis of (1S,3S,4R)-4-((3aS,4R,5S,7aS)-4-((3,5-dimethoxybenzyloxy)methyl)-7a-methyl-1-methyleneoctahydro-1H-inden-5-yl)-3-(hydroxymethyl)-4-methylcyclohexanol (Compound No. 188)

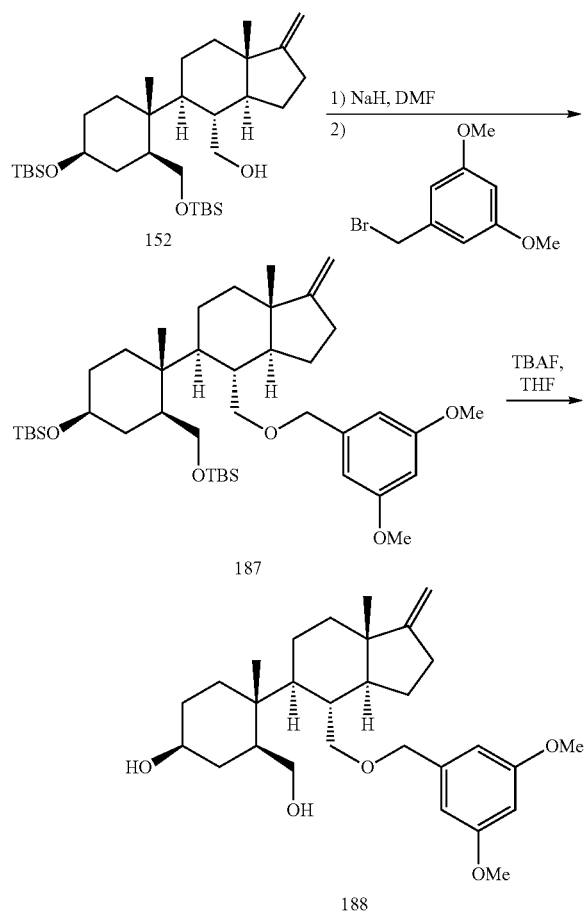

A. To a suspension of NaH (18 mg of a 60% solution, 0.45 mmol) in DMF (0.9 mL) at 0° C. under argon was added ((3aS,4R,5S,7aS)-5-((1R,2S,4S)-4-((tert-butyldimethylsilyl)oxy)-2-(((tert-butyldimethylsilyl)oxy)methyl)-1-methylcyclohexyl)-7a-methyl-1-methyleneoctahydro-1H-inden-4-yl)methanol (Compound No. 152, 99 mg, 0.18 mmol) and stirred at room temperature for 0.5 h. A solution of 3,5-dimethoxybenzyl bromide (104 mg, 0.450 mmol) in DMF (0.9 mL) was added and stirred at room temperature for 16.5 h. The mixture was diluted with EtOAc (40 mL) and washed with brine (6×10 mL) then dried (MgSO$_4$) and concentrated. The residue was purified by chromatography on silica gel (2:98 EtOAc/hexanes) to give tert-butyl(((1S,2R,5S)-5-((tert-butyldimethylsilyl)oxy)-2-((3aS,4R,5S,7aS)-4-(((3,5-dimethoxybenzyl)oxy)methyl)-7a-methyl-1-methyleneoctahydro-1H-inden-5-yl)-2-methylcyclohexyl)methoxy)dimethylsilane (Compound No. 187, 87 mg, 69%) as a colourless oil.

B. TBAF (0.50 mL of a 1 M solution in THF, 0.50 mmol) was added to a solution of tert-butyl(((1S,2R,5S)-5-((tert-butyldimethylsilyl)oxy)-2-((3aS,4R,5S,7aS)-4-(((3,5-dimethoxybenzyl)oxy)methyl)-7a-methyl-1-methyleneocta-hydro-1H-inden-5-yl)-2-methylcyclohexyl)methoxy)dimethylsilane (Compound No. 187, 87 mg, 0.12 mmol) in THF (2.5 mL) and heated to 50° C. for 16 h. The solution was concentrated, and the residue was purified by chromatography on silica gel (90:10 EtOAc/hexanes) to give (1S,3S,4R)-4-((3aS,4R,5S,7aS)-4-((3,5-dimethoxybenzyloxy)methyl)-7a-methyl-1-methyleneoctahydro-1H-inden-5-yl)-3-(hydroxymethyl)-4-methylcyclohexanol (Compound No. 188, 50 mg, 85%) as a colourless solid. $^1$H NMR (CDCl$_3$): δ6.47 (s, 2H), 6.38 (s, 1H), 4.62 (m, 2H), 4.39 (d, J=12 Hz, 1H), 4.27 (d, J=12 Hz, 1H), 3.66-3.78 (m, 8H), 3.58 (br s, 1H), 3.39 (m, 1H), 3.30 (br s, 1H), 2.46 (m, 1H), 2.13-2.27 (m, 2H), 1.20-1.80 (m, 15H), 1.04 (s, 3H), 0.76 (s, 3H). ES-MS m/z 473 ([M+1]$^+$).

Example 68

Synthesis of N-(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)nicotinamide (Compound No. 191)

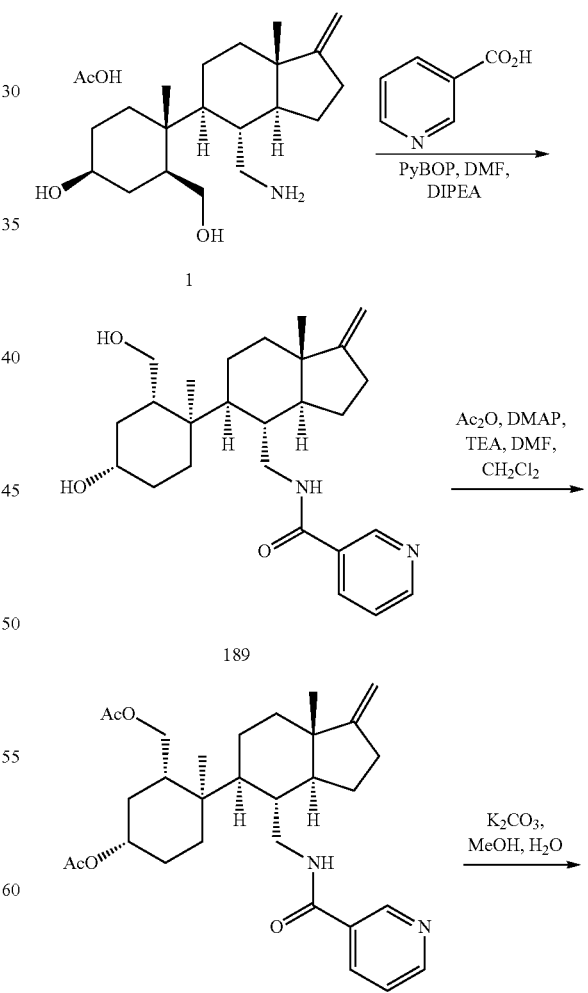

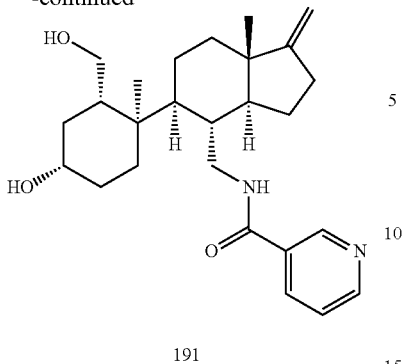

191

A. To a solution of nicotinic acid (34 mg, 0.28 mmol) in DMF (2 mL) was added PyBOP (158 mg, 0.30 mmol). After 10 min (1S,3S,4R)-4-((3aS,4R,5S,7aS)-4-(aminomethyl)-7a-methyl-1-methyleneoctahydro-1H-inden-5-yl)-3-(hydroxymethyl)-4-methylcyclohexanol acetate (Compound No. 1, 101 mg, 0.26 mmol) was added and DIPEA (0.16 mL, 0.92 mmol). After overnight, the mixture was diluted with EtOAc (50 mL) and brine (15 mL) and stirred 1 h. The EtOAc layer was separated and washed successively with brine (3×10 mL) and water (10 mL), dried (NaS$_2$O$_4$) and concentrated. The residue was purified using chromatography on silica gel (4% then 10% then 15% MeOH/CH$_2$Cl$_2$) to afford N-(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)nicotinamide (Compound No. 189, 105 mg) as an impure off-white solid.

B. A solution of N-(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)nicotinamide (Compound No. 189, 105 mg), triethylamine (150 µL, 1.08 mmol), acetic anhydride (70 µL, 0.74 mmol) and DMAP (2 mg) in DMF (1 mL) and CH$_2$Cl$_2$ (4 mL) was stirred at room temperature for 5 h. The mixture was diluted with EtOAc (25 mL), washed successively with brine (4×10 mL) and water (10 mL), dried (Na$_2$SO$_4$) and concentrated. The residue was purified using chromatography on silica gel (3% then 5% MeOH/CH$_2$Cl$_2$) to afford ((1S,2R,5S)-5-acetoxy-2-methyl-2-((3aS,4R,5S,7aS)-7a-methyl-1-methylene-4-(nicotinamidomethyl)octahydro-1H-inden-5-yl)cyclohexyl)methyl acetate (Compound No. 190, 90 mg) as an oil.

C. A solution of ((1S,2R,5S)-5-acetoxy-2-methyl-2-((3aS,4R,5S,7aS)-7a-methyl-1-methylene-4-(nicotinamidomethyl)octahydro-1H-inden-5-yl)cyclohexyl)methyl acetate (Compound No. 190, 70 mg, 0.14 mmol) and K$_2$CO$_3$ (375 mg) in MeOH (4.5 mL) and water (0.5 mL) was stirred at room temperature for 2 d. The mixture was concentrated and the residue was taken up in 10% MeOH/CH$_2$Cl$_2$ (40 mL) and water (20 mL). The layers were separated and the aqueous layer was extracted with CH$_2$Cl$_2$ (2×15 mL). The organic layers were combined, dried (Na$_2$SO$_4$) and concentrated. The residue was purified using chromatography on silica gel (4% then 10% MeOH/CH$_2$Cl$_2$) to afford N-(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)nicotinamide (Compound No. 191, 61 mg) as a white solid. $^1$H NMR (CDCl$_3$): δ8.90 (m, 1H), 8.72 (m, 1H), 8.08 (m, 1H), 7.40 (m, 1H), 6.14 (m, 1H), 4.62 (2H), 3.70 (3H), 3.60 (m, 1H), 3.25 (m, 1H), 2.50 (m, 1H), 2.25 (m, 1H), 2.15 (m, 1H), 1.2-2.0 (15H), 1.03 (s, 3H), 0.82 (s, 3H). ES-MS m/z 427 ([M+1]$^+$)

Example 69

Synthesis of N-(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)isonicotinamide (Compound No. 192)

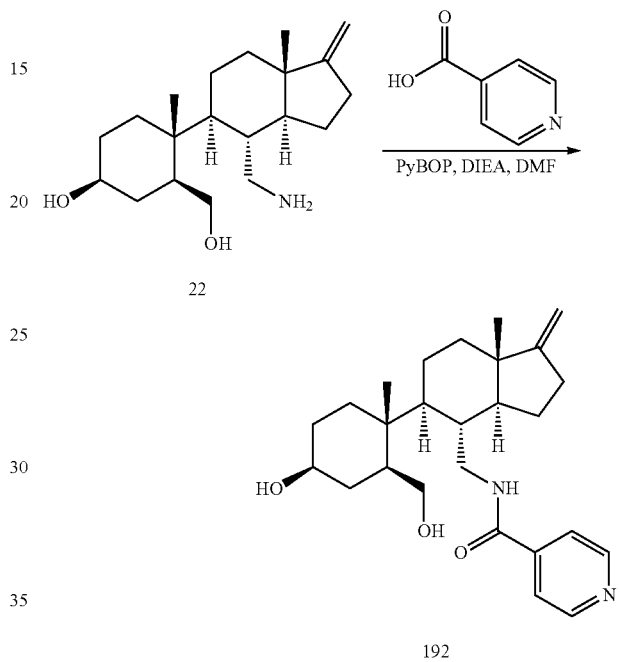

A mixture of (1S,3S,4R)-4-((3aS,4R,5S,7aS)-4-(aminomethyl)-7a-methyl-1-methyleneoctahydro-1H-inden-5-yl)-3-(hydroxymethyl)-4-methylcyclohexanol (Compound No. 22, 100 mg, 0.310 mmol), PyBop (210 mg, 0.400 mmol), isonicotinic acid (50 mg, 0.40 mmol) and DIEA (0.81 mL, 0.81 mmol) in DMF (3.0 mL) at room temperature under argon was stirred for 24 h. The mixture was diluted with EtOAc (20 mL), washed with NaHCO$_3$ solution (2×10 mL) and saturated NaCl solution (2×10 mL) and concentrated. The residue was purified by chromatography on silica gel (9% MeOH/CH$_2$Cl$_2$) to afford N-(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)isonicotinamide (Compound No. 192, 83 mg, 62%) as a white solid. $^1$H NMR (300 MHz, CD$_3$OD): δ8.65 (d, J=6 Hz, 2H), 7.67 (d, J=6 Hz, 2H), 4.64 (s, 2H), 3.7 (m, 1H), 3.63 (s, 2H), 3.47 (m, 1H), 2.48 (m, 1H), 2.15 (m, 2H), 1.85 (m, 9H), 1.69 (m, 3H), 1.48 (m, 6H), 1.28 (m, 3H), 1.04 (s, 3H), 0.83 (s, 3H); $^{13}$C NMR (75 MHz, CD$_3$OD): δ168.8, 162.4, 150.7, 144.4, 123.1, 101.9, 71.1, 62.9, 52.7, 47.5, 45.0, 44.8, 44.0, 41.0, 38.1, 38.0, 36.9, 35.2, 32.1, 30.1, 26.1, 24.4, 21.7, 18.7; MS m/z: 427.2 [M+H]$^+$.

Example 70

Synthesis of N-(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)pyrazine-2-carboxamide (Compound No. 193)

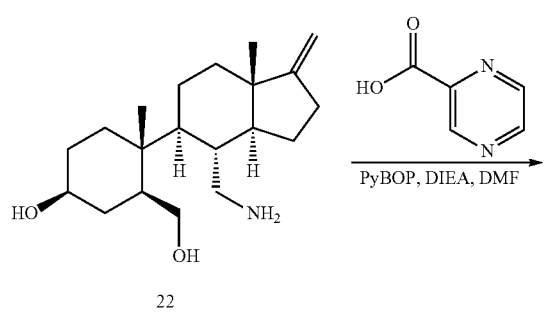

Example 71

Synthesis of N-(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)picolinamide (Compound No. 194)

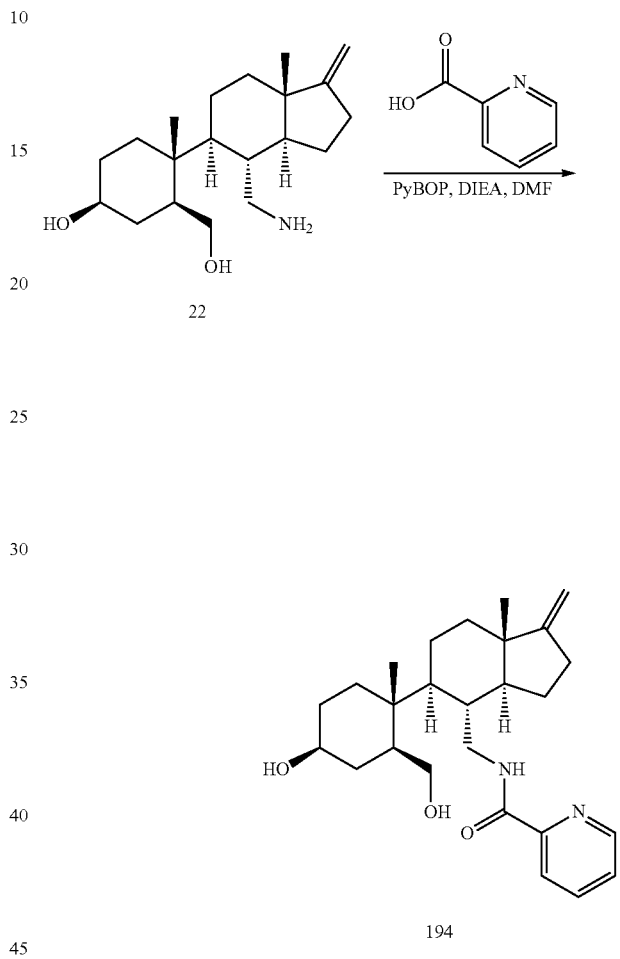

A mixture of (1S,3S,4R)-4-((3aS,4R,5S,7aS)-4-(aminomethyl)-7a-methyl-1-methyleneoctahydro-1H-inden-5-yl)-3-(hydroxymethyl)-4-methylcyclohexanol (Compound No. 22, 100 mg, 0.310 mmol), PyBop (210 mg, 0.400 mmol), 2-pyrazinecarboxylic acid (50 mg, 0.40 mmol) and DIEA (0.81 mL, 0.81 mmol) in DMF (3.0 mL) at room temperature under argon was stirred for 24 h. The mixture was diluted with EtOAc (20 mL), washed with NaHCO$_3$ solution (2×10 mL) and saturated NaCl solution (2×10 mL) and concentrated. The residue was purified by chromatography on silica gel (9% MeOH/CH$_2$Cl$_2$) to afford N-(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)pyrazine-2-carboxamide (Compound No. 193, 118 mg, 89%) as a white solid. $^1$H NMR (300 MHz, CD$_3$OD): δ9.23 (s, 1H), 8.80 (m, 1H), 8.68 (m, 1H), 4.62 (s, 2H), 3.71 (m, 2H), 3.60 (m, 1H), 3.46 (m, 1H), 3.12 (m, 1H), 2.48 (m, 1H), 2.18 (m, 2H), 1.87 (m, 5H), 1.68 (m, 1H), 1.45 (m, 5H), 1.26 (m, 4H), 1.06 (s, 3H), 0.85 (s, 3H); MS m/z: 425.9 [M+H]$^+$.

A mixture of (1S,3S,4R)-4-((3aS,4R,5S,7aS)-4-(aminomethyl)-7a-methyl-1-methyleneoctahydro-1H-inden-5-yl)-3-(hydroxymethyl)-4-methylcyclohexanol (Compound No. 22 100 mg, 0.310 mmol), PyBop (130 mg, 0.400 mmol), picolinic acid (50 mg, 0.40 mmol) and DIEA (0.81 mL, 0.81 mmol) in DMF (3.0 mL) at room temperature under argon was stirred for 24 h. The mixture was diluted with EtOAc (20 mL), washed with NaHCO$_3$ solution (2×10 mL) and saturated NaCl solution (2×10 mL) and concentrated. The residue was purified by chromatography on silica gel (9% MeOH/CH$_2$Cl$_2$) to afford N-(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)picolinamide (Compound No. 194, 121 mg, 84%) as a white solid. $^1$H NMR (300 MHz, CD$_3$OD) δ8.63 (m, 1H), 8.10 (m, 1H), 7.97 (m, 1H), 7.56 (m, 1H), 4.62 (s, 2H), 3.71 (m, 2H), 3.66 (m, 1H), 3.46 (m, 1H), 3.13 (m, 1H), 2.48 (m, 1H), 2.17 (m, 2H), 1.87 (m, 5H), 1.67 (m, 1H), 1.45 (m, 5H), 1.28 (m, 4H), 1.06 (s, 3H), 0.85 (m, 3H); MS m/z: 426.9 [M+H]$^+$.

Example 72

Synthesis of N-(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)benzo[d][1,3]dioxole-5-carboxamide (Compound No. 195)

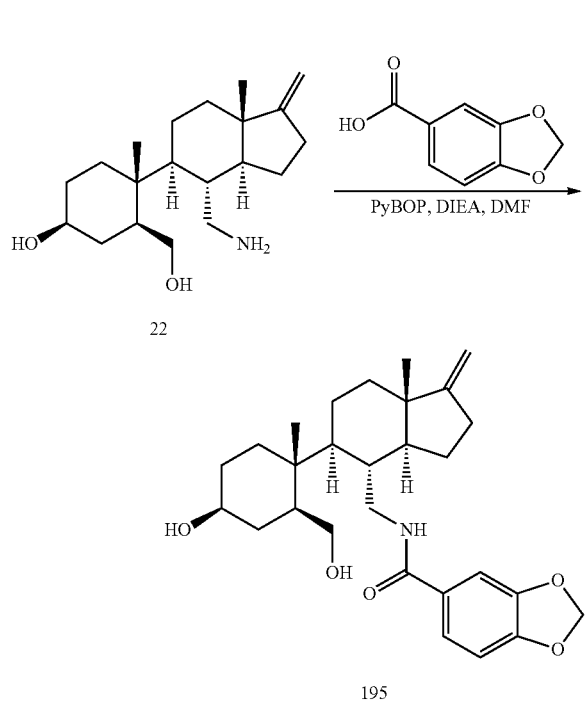

To a mixture of (1S,3S,4R)-4-((3aS,4R,5S,7aS)-4-(aminomethyl)-7a-methyl-1-methyleneoctahydro-1H-inden-5-yl)-3-(hydroxymethyl)-4-methylcyclohexanol (Compound No. 22, 100 mg, 0.310 mmol), PyBop (210 mg, 0.400 mmol), piperonylic acid (67 mg, 0.40 mmol) under argon were added DIEA (0.81 mL, 0.81 mmol) and DMF (3.0 mL). After 24 h EtOAc (20 mL) was added to the solution, and the resulting mixture was washed successively with NaHCO$_3$ (2×10 mL) and brine (2×10 mL) and concentrated. The residue was purified using chromatography on silica gel (0 to 10% MeOH/CH$_2$Cl$_2$) to afford N-(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)benzo[d][1,3]dioxole-5-carboxamide (Compound No. 195, 156 mg, 68%) as a white solid. $^1$H NMR (300 MHz, CD$_3$OD) δ7.33 (m, 1H), 7.24 (m, 1H), 6.87 (m, 1H), 6.01 (s, 2H), 4.64 (s, 2H), 3.73 (m, 1H), 3.58 (m, 2H), 3.47 (m, 1H), 2.48 (m, 1H), 2.20 (m, 2H), 1.85 (m, 5H), 1.68 (m, 1H), 1.50 (m, 5H), 1.37 (m, 2H), 1.29 (m, 2H), 1.03 (s, 3H), 0.84 (s, 3H); $^{13}$C NMR (75 MHz, CD$_3$OD) δ170.1, 162.5, 151.8, 149.2, 129.9, 123.3, 108.8, 103.1, 101.8, 71.0, 62.8, 52.9, 45.0, 44.8, 43.9, 38.1, 36.9, 35.2, 32.1, 30.2, 27.4, 27.3, 26.1, 24.4, 21.7, 18.8; MS m/z: 468.1 [M+H]$^+$.

Example 73

Synthesis of N-(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)-4-methoxybenzamide (Compound No. 196)

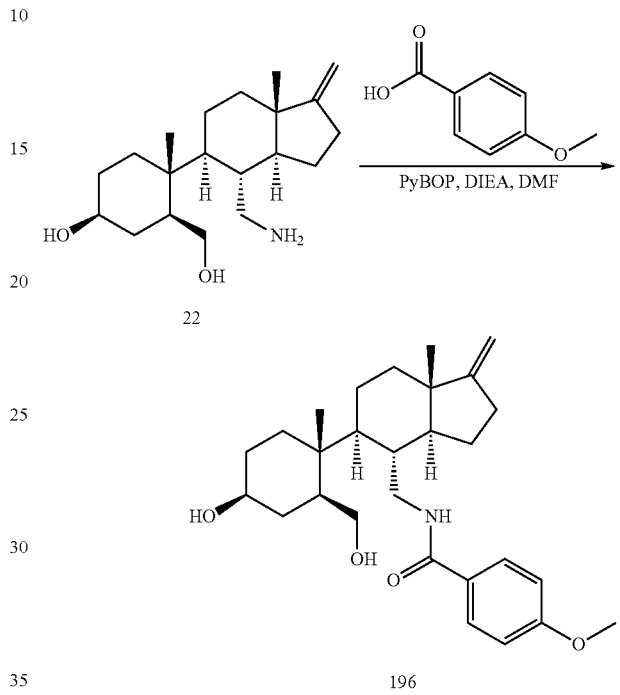

To a mixture of (1S,3S,4R)-4-((3aS,4R,5S,7aS)-4-(aminomethyl)-7a-methyl-1-methyleneoctahydro-1H-inden-5-yl)-3-(hydroxymethyl)-4-methylcyclohexanol (Compound No. 22, 100 mg, 0.310 mmol), PyBop (210 mg, 0.400 mmol), 4-methoxybenzoic acid (61 mg, 0.40 mmol) under argon were added DIEA (0.81 mL, 0.81 mmol) and DMF (3.0 mL) and the solution was stirred for 24 h. The solution was diluted with EtOAc (20 mL), washed with saturated NaHCO$_3$ solution (2×10 mL) and brine (2×10 mL) and concentrated. The residue was purified using chromatography on silica gel (0% to 10% MeOH/CH$_2$Cl$_2$) to afford N-(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)-4-methoxybenzamide (Compound No. 196, 125 mg, 65%) as a white solid. $^1$H NMR (300 MHz, CD$_3$OD) δ7.73 (d, J=9.3 Hz, 2H), 6.97 (d, J=8.7 Hz, 2H), 4.63 (s, 2H), 3.74 (m, 1H), 3.58 (m, 2H), 3.46 (m 1H), 3.13 (m, 1H), 2.48 (m, 1H), 2.19 (m, 2H), 1.85 (m, 5H), 1.68 (m, 1H), 1.47 (m, 5H), 1.29 (m, 5H), 1.04 (s, 3H), 0.84 (m, 3H); $^{13}$C NMR (75 MHz, CD$_3$OD) δ170.6, 163.9, 162.6, 130.2, 128.1, 114.7, 101.8, 71.1, 62.9, 55.9, 52.9, 47.6, 45.0, 44.8, 43.7, 38.2, 38.1, 37.0, 35.2, 32.1, 30.2, 26.1, 24.4, 21.7, 18.7; MS m/z: 454.1 [M–H]$^-$.

Example 74

Synthesis of 4-fluoro-N-(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)benzamide (Compound No. 197)

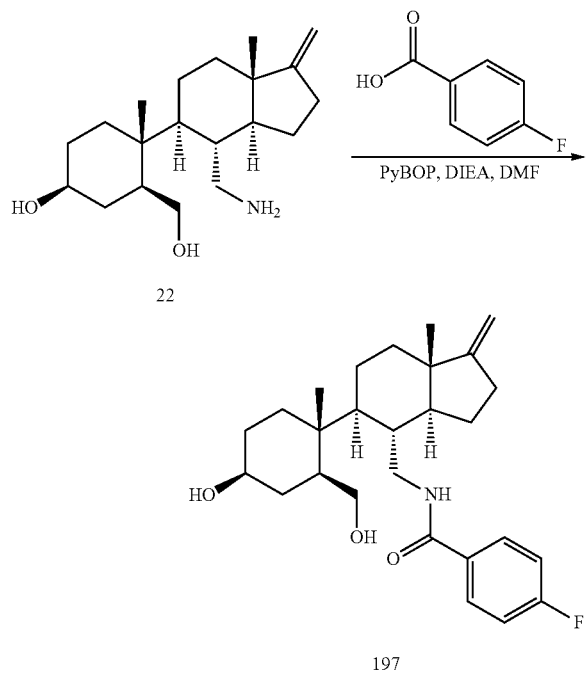 [SMILES: C=C1CC[C@H]2[C@H](CN)[C@@H]([C@@]3(C)CC[C@H](O)C[C@@H]3CO)CC[C@]12C ; O=C(O)c1ccc(F)cc1 ; C=C1CC[C@H]2[C@H](CNC(=O)c3ccc(F)cc3)[C@@H]([C@@]3(C)CC[C@H](O)C[C@@H]3CO)CC[C@]12C]

To a mixture of (1S,3S,4R)-4-((3aS,4R,5S,7aS)-4-(aminomethyl)-7a-methyl-1-methyleneoctahydro-1H-inden-5-yl)-3-(hydroxymethyl)-4-methylcyclohexanol (Compound No. 22, 100 mg, 0.310 mmol), PyBop (210 mg, 0.400 mmol), 4-fluorobenzoic acid (56 mg, 0.40 mmol) under argon were added DIEA (0.81 mL, 0.81 mmol) and DMF (3.0 mL) and the solution was stirred 24 h. The solution was diluted with EtOAc (20 mL), washed successively with saturated NaHCO$_3$ solution (2×10 mL) and brine (2×10 mL) and then was concentrated. The residue was purified using chromatography on silica gel (0% to 10% MeOH/CH$_2$Cl$_2$) to afford 4-fluoro-N-(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)benzamide (Compound No. 197, 91 mg, 66%) as a white solid. $^1$H NMR (300 MHz, CD$_3$OD) δ7.80 (m, 2H), 7.18 (m, 2H), 4.64 (s, 2H), 3.72 (m, 1H), 3.60 (m, 2H), 3.46 (m, 1H), 3.14 (m, 1H), 2.48 (m, 1H), 2.19 (m, 2H), 1.83 (m, 5H), 1.68 (m, 1H), 1.46 (m, 5H), 1.28 (m, 4H), 1.04 (s, 3H), 0.85 (s, 3H); $^{13}$C NMR (75 MHz, CD$_3$OD) δ170.0, 167.7, 102.5, 132.4, 131.0, 116.4, 101.8, 71.1, 62.8, 55.9, 52.8, 47.5, 45.0, 43.9, 38.1, 36.9, 35.2, 32.1, 30.1, 27.4, 27.3, 26.1, 24.4, 21.7, 18.7; MS m/z: 442.1 [M−H]$^−$.

Example 75

Synthesis of N-(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)-4-(trifluoromethyl)benzamide (Compound No. 198)

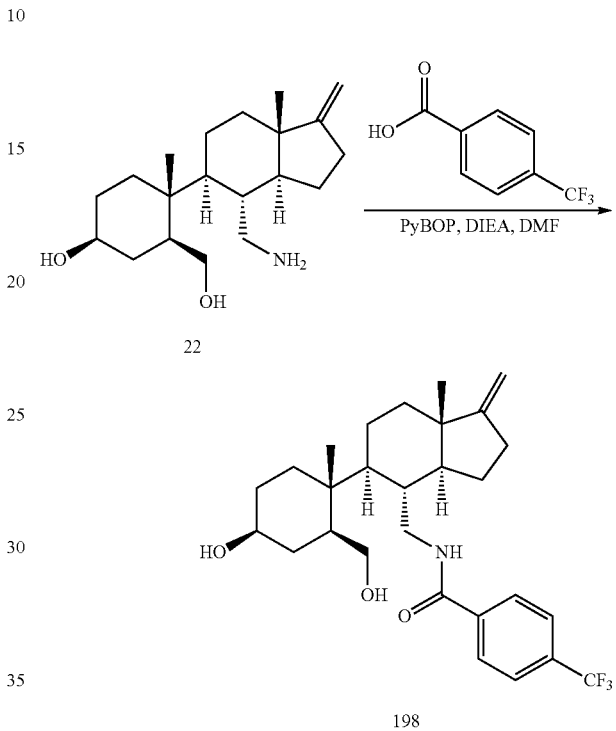

To a mixture of (1S,3S,4R)-4-((3aS,4R,5S,7aS)-4-(aminomethyl)-7a-methyl-1-methyleneoctahydro-1H-inden-5-yl)-3-(hydroxymethyl)-4-methylcyclohexanol (Compound No. 22, 100 mg, 0.310 mmol), PyBop (210 mg, 0.400 mmol), 4-trifluoromethylbenzoic acid (77 mg, 0.40 mmol) under argon were added DIEA (0.81 mL, 0.81 mmol) and DMF (3.0 mL). The solution was stirred for 24 h then was diluted with EtOAc (20 mL), washed successively with saturated NaHCO$_3$ solution (2×10 mL) and brine (2×10 mL) and concentrated. The residue was purified using chromatography on silica gel (0% to 10% MeOH/CH$_2$Cl$_2$) to afford N-(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)-4-(trifluoromethyl)benzamide (Compound No. 198, 105 mg, 68%) as a white solid. $^1$H NMR (300 MHz, CD$_3$OD) δ 7.89 (d, J=8.0 Hz, 2H), 7.76 (d, J=8.0 Hz, 2H), 4.64 (s, 2H), 3.72 (m, 1H), 3.63 (m, 2H), 3.47 (m, 1H), 3.13 (m, 1H), 2.50 (m, 1H), 2.20 (m, 2H), 1.86 (m, 5H), 1.69 (m, 1H), 1.49 (m, 5H), 1.28 (m, 4H), 1.05 (s, 3H), 0.85 (s, 3H); $^{13}$C NMR (75 MHz, CD$_3$OD) δ169.9, 162.5, 139.9, 134.0, 129.2, 126.4, 119.0, 101.8, 71.1, 62.8, 52.8, 47.4, 45.0, 44.8, 43.9, 38.1, 38.9, 35.2, 30.2, 26.1, 24.4, 21.7, 18.7; MS m/z: 492.1 [M−H]$^−$.

Example 76

Synthesis of N-(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)-4-methylbenzamide (Compound No. 199)

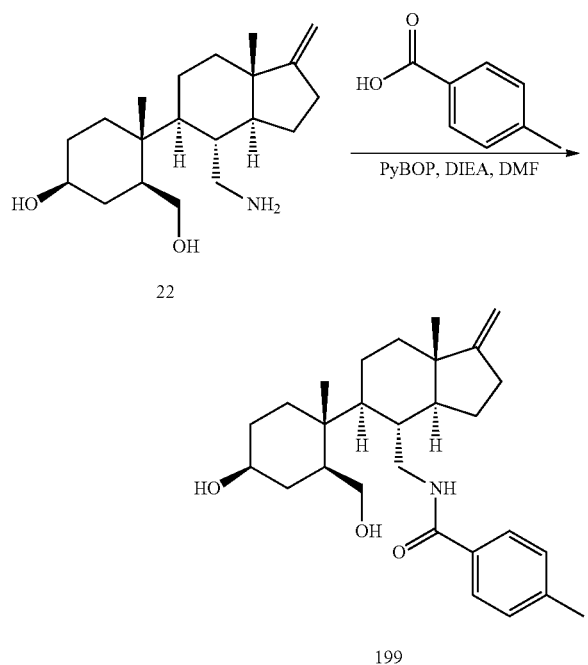

Example 77

Synthesis of N-(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)-2-methylbenzamide (Compound No. 200)

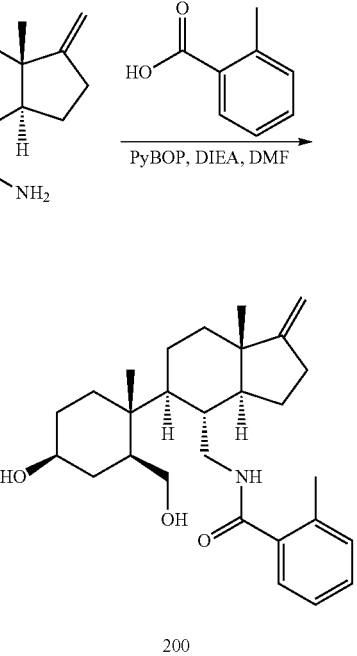

To a mixture of (1S,3S,4R)-4-((3aS,4R,5S,7aS)-4-(aminomethyl)-7a-methyl-1-methyleneoctahydro-1H-inden-5-yl)-3-(hydroxymethyl)-4-methylcyclohexanol (Compound No. 22, 100 mg, 0.310 mmol), PyBop (210 mg, 0.400 mmol), p-toluic acid (55 mg, 0.40 mmol) under argon were added DIEA (0.81 mL, 0.81 mmol) and DMF (3.0 mL). The solution was stirred for 24 then was diluted with EtOAc (20 mL), washed successively with saturated NaHCO$_3$ solution (2×10 mL) and brine (2×10 mL) and concentrated. The residue was purified using chromatography on silica gel (0% to 10% MeOH/EtOAc) to afford N-(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)-4-methylbenzamide (Compound No. 199, 115 mg, 85%) as a white solid. $^1$H NMR (300 MHz, CD$_3$OD) δ7.65 (d, J=8.2 Hz, 2H), 7.26 (d, J=7.6 Hz, 2H), 4.63 (s, 2H), 3.73 (m, 1H), 3.60 (m, 2H), 3.46 (m, 1H), 2.48 (m, 1H), 2.18 (m, 2H), 1.85 (m, 5H), 1.70 (m, 1H), 1.49 (m, 5H), 1.29 (m, 4H), 1.05 (s, 3H), 0.84 (s, 3H); $^{13}$C NMR (75 MHz, CD$_3$OD) δ171.1, 162.5, 143.1, 133.2, 130.1, 128.4, 101.9, 71.1, 62.9, 52.9, 47.6, 47.4, 45.0, 44.8, 43.7, 38.1, 37.0, 35.2, 32.1, 30.2, 27.3, 26.1, 24.4, 21.7, 21.4, 18.8; MS m/z: 438.2 [M+H]$^+$.

To a mixture of (1S,3S,4R)-4-((3aS,4R,5S,7aS)-4-(aminomethyl)-7a-methyl-1-methyleneoctahydro-1H-inden-5-yl)-3-(hydroxymethyl)-4-methylcyclohexanol (Compound No. 22, 100 mg, 0.310 mmol), PyBop (210 mg, 0.400 mmol), o-toluic acid (55 mg, 0.40 mmol) under argon were added DIEA (0.81 mL, 0.81 mmol) and DMF (3.0 mL). The solution was stirred for 24 h then was diluted with EtOAc (20 mL), washed successively with saturated NaHCO$_3$ solution (2×10 mL) and brine (2×10 mL) then was concentrated. The residue was purified using chromatography on silica gel (0% to 10% MeOH/EtOAc) to afford N-(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)-2-methylbenzamide (Compound No. 200, 111 mg, 81%) as a white solid. $^1$H NMR (300 MHz, CD$_3$OD) δ7.30 (m, 1H), 7.23 (m, 3H), 4.63 (s, 2H), 3.69 (m, 1H), 3.61 (m, 2H), 3.45 (m, 1H), 3.10 (m, 1H), 2.52 (m, 1H), 2.21 (m, 2H), 1.83 (m, 5H), 1.66 (m, 1H), 1.47 (m, 5H), 1.29 (m, 4H), 1.07 (s, 3H), 0.85 (s, 3H); $^{13}$C NMR (75 MHz, CDCl$_3$) δ 173.8, 162.5, 138.4, 136.3, 131.5, 130.6, 128.0, 126.6, 101.9, 71.1, 62.8, 52.1, 46.5, 44.9, 44.7, 43.2, 38.1, 37.6, 36.9, 35.1, 32.1, 31.8, 30.1, 25.9, 24.3, 21.3, 21.4, 19.7, 18.7; MS m/z: 438.2 [M−H]$^−$.

Example 78

Synthesis of N-(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)-1H-pyrrole-2-carboxamide (Compound No. 201)

Example 79

Synthesis of N-(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)-3-methylbenzamide (Compound No. 202)

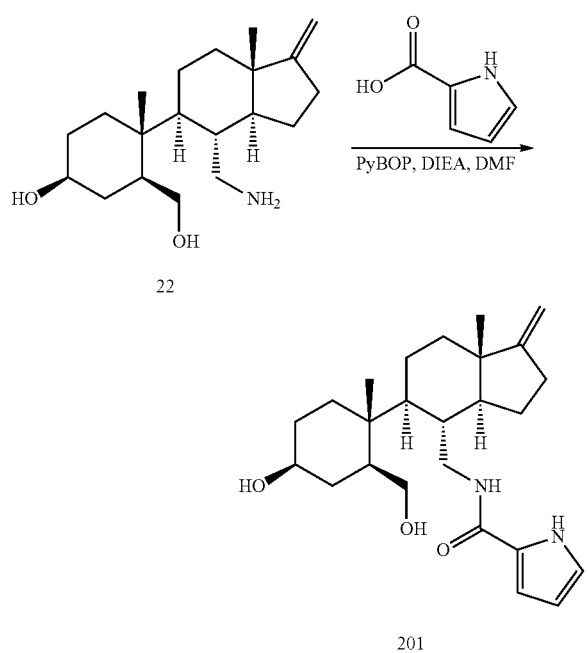

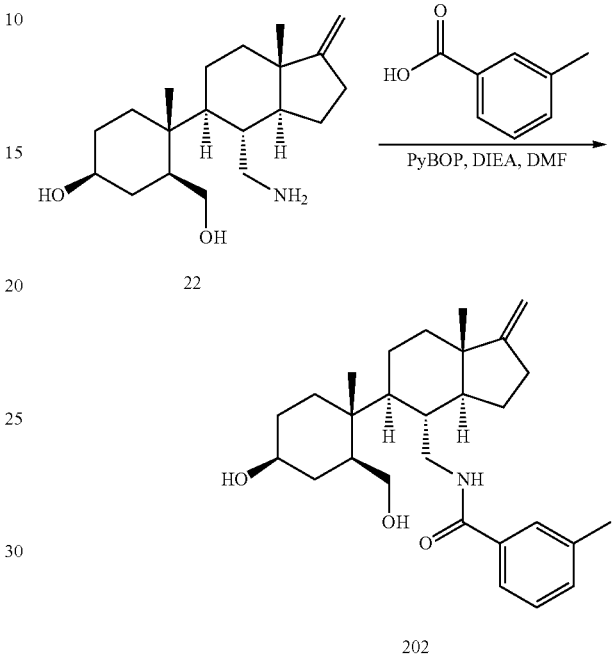

To a mixture of (1S,3S,4R)-4-((3aS,4R,5S,7aS)-4-(aminomethyl)-7a-methyl-1-methyleneoctahydro-1H-inden-5-yl)-3-(hydroxymethyl)-4-methylcyclohexanol (Compound No. 22, 100 mg, 0.310 mmol), PyBop (210 mg, 0.400 mmol), 2-pyrrolecarboxylic acid (45 mg, 0.40 mmol) under argon were added DIEA (0.81 mL, 0.81 mmol) and DMF (3.0 mL). The solution was stirred for 24 h then was diluted with EtOAc (20 mL), washed successively with saturated NaHCO$_3$ solution (2×10 mL) and brine (2×10 mL) then was concentrated. The residue was purified using chromatography on silica gel (0% to 10% MeOH/EtOAc) to afford N-(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)-1H-pyrrole-2-carboxamide (Compound No. 201, 69 mg, 54%) as a white solid. $^1$H NMR (300 MHz, CD$_3$OD) δ6.88 (m, 2H), 6.16 (m, 1H), 4.64 (s, 2H), 3.73 (m, 1H), 3.57 (m, 2H), 3.47 (m, 1H), 3.13 (m, 1H), 2.48 (m, 1H), 2.21 (m, 2H), 1.86 (m, 5H), 1.67 (m, 1H), 1.47 (m, 5H), 1.31 (m, 4H), 1.03 (s, 3H), 0.84 (s, 3H); $^{13}$C NMR (75 MHz, CD$_3$OD) δ162.9, 161.4, 125.6, 121.8, 111.2, 109.0, 100.6, 69.9, 61.7, 51.6, 46.3, 43.8, 43.6, 41.8, 36.9, 36.9, 35.8, 34.0, 30.9, 28.9, 24.8, 23.2, 20.5, 17.5; MS m/z: 412.9 [M−H]$^-$.

To a mixture of (1S,3S,4R)-4-((3aS,4R,5S,7aS)-4-(aminomethyl)-7a-methyl-1-methyleneoctahydro-1H-inden-5-yl)-3-(hydroxymethyl)-4-methylcyclohexanol (Compound No. 22, 100 mg, 0.310 mmol), PyBop (210 mg, 0.400 mmol), m-toluic acid (55 mg, 0.40 mmol) under argon were added DIEA (0.81 mL, 0.81 mmol) and DMF (3.0 mL). The solution was stirred for 24 h then was diluted with EtOAc (20 mL), washed successively with saturated NaHCO$_3$ solution (2×10 mL) and brine (2×10 mL) then was concentrated. The residue was purified using chromatography on silica gel (0% to 10% MeOH/EtOAc) to afford N-(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)-3-methylbenzamide (Compound No. 202, 99 mg, 73%) as a white solid. $^1$H NMR (300 MHz, CD$_3$OD) δ7.67 (s, 1H), 7.53 (m, 1H), 7.34 (m, 2H), 4.64 (s, 2H), 3.73 (m, 1H), 3.60 (m, 2H), 3.46 (m, 1H), 3.13 (m, 1H), 2.47 (m, 1H), 2.20 (m, 2H), 1.87 (m, 5H), 1.69 (m, 1H), 1.49 (m, 5H), 1.30 (m, 4H), 1.05 (s, 3H), 0.84 (s, 3H); $^{13}$C NMR (75 MHz, CD$_3$OD) δ108.2, 161.0, 138.7, 134.8, 132.4, 128.6, 127.7, 123.7, 101.6, 69.9, 62.6, 51.8, 50.6, 46.6, 43.9, 43.3, 41.7, 37.1, 36.9, 35.9, 34.2, 31.1, 29.1, 24.9, 23.5, 21.5, 21.3, 18.4; MS m/z: 438.1 [M−H]$^-$.

Example 80

Synthesis of N-(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)furan-2-carboxamide (Compound No. 203)

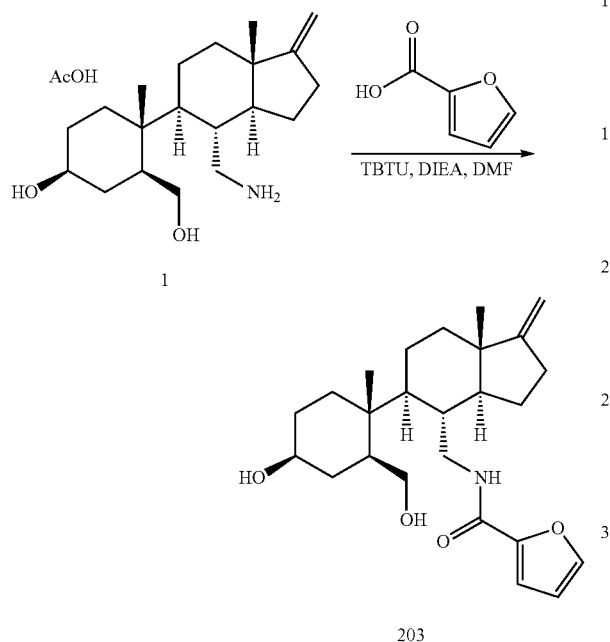

To a solution of (1S,3S,4R)-4-((3aS,4R,5S,7aS)-4-(aminomethyl)-7a-methyl-1-methyleneoctahydro-1H-inden-5-yl)-3-(hydroxymethyl)-4-methylcyclohexanol acetate (Compound No. 1, 111 mg, 0.291 mmol), O-(benzotriazol-1-yl)-N,N,N',N'-tetramethyluronium tetrafluoroborate (103 mg, 0.321 mmol), and 2-furoic acid (36 mg, 0.32 mmol) in DMF (1.5 mL) was added N,N-diisopropylethylamine (0.12 mL, 0.69 mmol), and the solution was stirred at room temperature for 28 h. The mixture was concentrated, and the residue was partitioned between EtOAc (35 mL) and saturated aqueous NaHCO₃ (10 mL). The organic layer was washed with brine (5×10 mL) then dried (MgSO₄) and concentrated. The residue was purified by chromatography on silica gel (7:93 MeOH/CH₂Cl₂) to give N-(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)furan-2-carboxamide (Compound No. 203, 39 mg, 32%) as a colourless solid. $^1$H NMR (CD$_3$OD): δ7.66 (s, 1H), 7.39 (br s, 1H), 7.12 (d, J=3.3 Hz, 1H), 6.58 (m, 1H), 4.63 (s, 2H), 3.70 (m, 2H), 3.43-3.56 (m, 2H), 3.13 (m, 1H), 2.49 (m, 1H), 2.13-2.29 (m, 2H), 1.20-1.88 (m, 15H), 1.05 (s, 3H), 0.84 (s, 3H). ES-MS m/z 416 ([M+1]⁺).

Example 81

Synthesis of N-(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)cyclopropanecarboxamide (Compound No. 204)

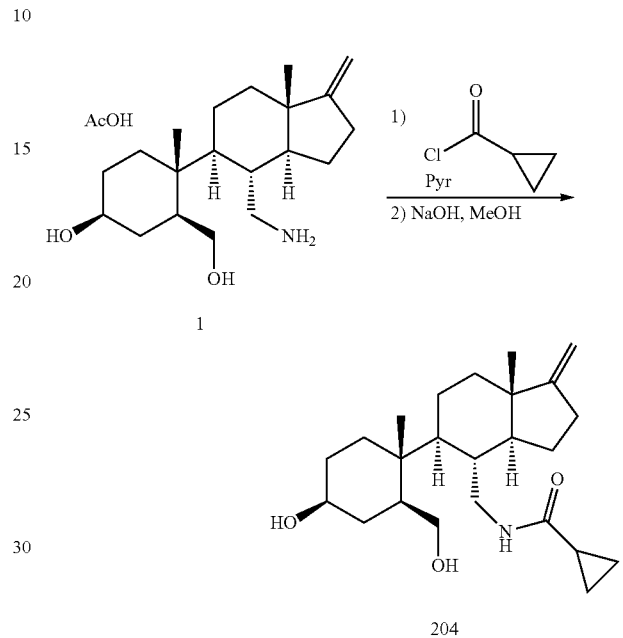

To a suspension of (1S,3S,4R)-4-((3aS,4R,5S,7aS)-4-(aminomethyl)-7a-methyl-1-methyleneoctahydro-1H-inden-5-yl)-3-(hydroxymethyl)-4-methylcyclohexanol acetate (Compound No. 1, 98 mg, 0.26 mmol) in pyridine (2.6 mL) was added cyclopropanecarbonyl chloride (0.071 mL, 0.78 mmol), and the mixture was stirred at room temperature under argon for 17 h then concentrated. Azeotropic removal of remaining pyridine was carried out with toluene (2×4 mL). The residue was dissolved in MeOH (2.6 mL), and 10N NaOH (aq) (0.26 mL, 2.6 mmol) was added then heated to reflux for 45 min. The mixture was concentrated, and the residue was partitioned between EtOAc (25 mL) and H₂O (10 mL). The organic layer was washed with brine (10 mL) then dried (MgSO₄) and concentrated. The residue was purified by chromatography on silica gel (7:93 MeOH/CH₂Cl₂) to give N-(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)cyclopropanecarboxamide (Compound No. 204, 72 mg, 72%) as a colourless solid. $^1$H NMR (CD$_3$OD): δ7.72 (br s, 1H), 4.64 (s, 2H), 3.73 (m, 1H), 3.47 (m, 2H), 3.33 (m, 1H), 3.14 (m, 1H), 2.50 (m, 1H), 2.13-2.30 (m, 2H), 1.20-1.90 (m, 16H), 0.99 (s, 3H), 0.70-0.83 (m, 7H). ES-MS m/z 390 ([M+1]⁺).

Example 82

Synthesis of N-(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)cyclohexanecarboxamide (Compound No. 205)

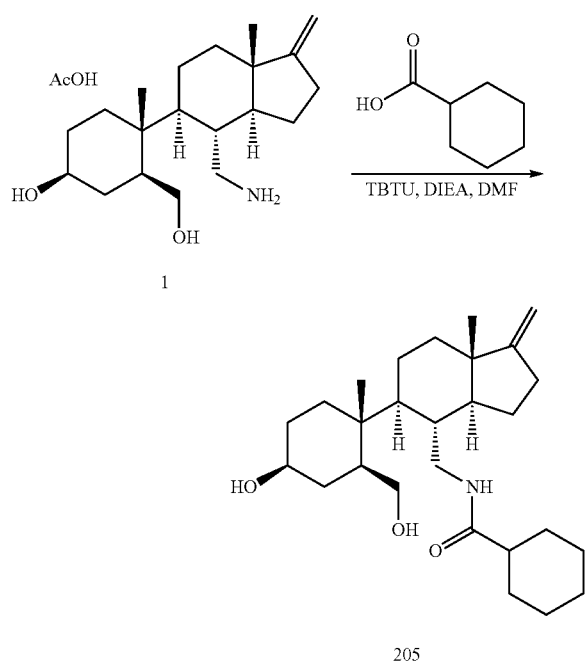

To a solution of (1S,3S,4R)-4-((3aS,4R,5S,7aS)-4-(aminomethyl)-7a-methyl-1-methyleneoctahydro-1H-inden-5-yl)-3-(hydroxymethyl)-4-methylcyclohexanol acetate (Compound No. 1, 103 mg, 0.270 mmol), O-(benzotriazol-1-yl)-N,N,N',N'-tetramethyluronium tetrafluoroborate (95 mg, 0.30 mmol), and cyclohexanecarboxylic acid (0.067 mL, 0.54 mmol) in DMF (1.3 mL) was added N,N-diisopropylethylamine (0.11 mL, 0.63 mmol), and the solution was stirred at room temperature for 3 d. The mixture was concentrated, and the residue was partitioned between EtOAc (35 mL), H₂O (5 mL) and saturated aqueous NaHCO₃ (10 mL). The organic layer was washed with brine (5×10 mL) then dried (MgSO₄) and concentrated. The residue was purified by chromatography on silica gel (6:94 MeOH/CH₂Cl₂) to give N-(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)cyclohexanecarboxamide (Compound No. 205, 44 mg, 38%) as a colourless solid. ¹H NMR (CD₃OD): δ7.41 (br s, 1H), 4.64 (s, 2H), 3.72 (m, 1H), 3.31-3.45 (m, 3H), 3.13 (m, 1H), 2.49 (m, 1H), 2.13-2.39 (m, 3H), 1.20-1.86 (m, 25H), 0.98 (s, 3H), 0.82 (s, 3H). ES-MS m/z 432 ([M+1]⁺).

Example 83

Synthesis of 1-ethyl-3-(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)urea (Compound No. 206)

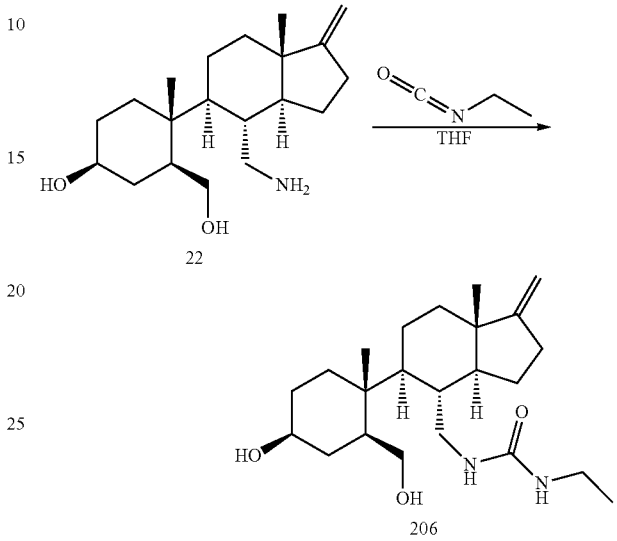

To a solution of (1S,3S,4R)-4-((3aS,4R,5S,7aS)-4-(aminomethyl)-7a-methyl-1-methyleneoctahydro-1H-inden-5-yl)-3-(hydroxymethyl)-4-methylcyclohexanol (Compound No. 22, 49 mg, 0.15 mmol) in THF (3.0 mL) at 0° C. under argon was added ethyl isocyanate (0.024 mL, 0.31 mmol), and the solution was stirred at room temperature for 17 h then concentrated. The residue was purified by chromatography on silica gel (100:10:2 CH₂Cl₂/MeOH/NH₄OH) to give 1-ethyl-3-(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)urea (Compound No. 206, 52 mg, 87%) as a colourless solid. ¹H NMR (CD₃OD): δ5.93 (br s, 1H), 5.67 (br s, 1H), 4.63 (s, 2H), 3.70 (m, 1H), 3.25-3.45 (m, 3H), 3.13 (m, 3H), 2.50 (m, 1H), 2.13-2.26 (m, 2H), 1.21-1.87 (m, 15H), 1.08 (t, J=7.2 Hz, 3H), 1.02 (s, 3H), 0.82 (s, 3H). ES-MS m/z 393 ([M+1]⁺).

Example 84

Synthesis of 1-(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)-3-methylthiourea (Compound No. 207)

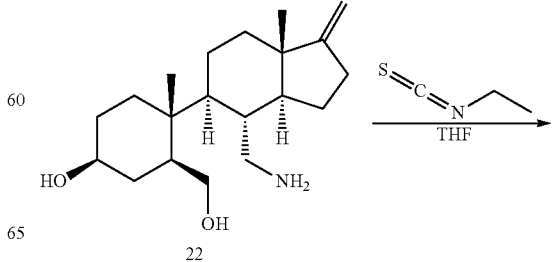

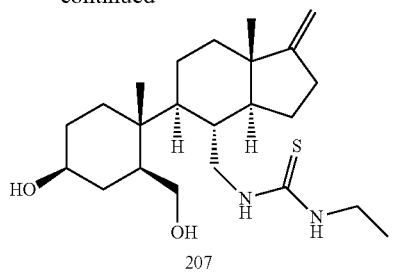
207

To a solution of (1S,3S,4R)-4-((3aS,4R,5S,7aS)-4-(aminomethyl)-7a-methyl-1-methyleneoctahydro-1H-inden-5-yl)-3-(hydroxymethyl)-4-methylcyclohexanol (Compound No. 22, 50 mg, 0.16 mmol) in THF (3.1 mL) at 0° C. under argon was added methyl isothiocyanate (23 mg, 0.31 mmol), and the solution was stirred at room temperature for 17 h then concentrated. The residue was purified by chromatography on silica gel (100:10:2 $CH_2Cl_2$/MeOH/$NH_4$OH) to give 1-(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)-3-methylthiourea (Compound No. 207, 50 mg, 82%) as a colourless solid. $^1$H NMR (CD$_3$OD): δ6.82 (br s, 1H), 4.64 (s, 2H), 3.46-3.72 (m, 4H), 3.13 (m, 1H), 2.98 (s, 3H), 2.50 (m, 1H), 2.13-2.29 (m, 2H), 1.20-1.88 (m, 15H), 0.97 (s, 3H), 0.83 (s, 3H). ES-MS m/z 395 ([M+1]$^+$).

Example 85

Synthesis of 2,2,2-trifluoro-N-(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)acetamide (Compound No. 208)

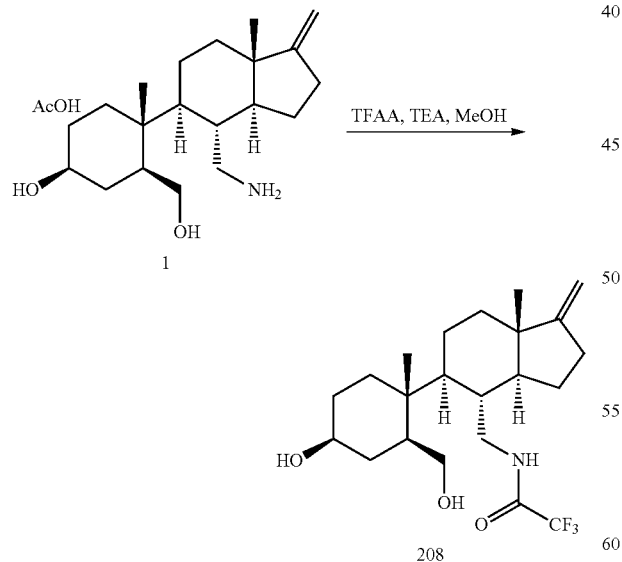

To a suspension of (1S,3S,4R)-4-((3aS,4R,5S,7aS)-4-(aminomethyl)-7a-methyl-1-methyleneoctahydro-1H-inden-5-yl)-3-(hydroxymethyl)-4-methylcyclohexanol acetate (Compound No. 1, 2.31 g, 6.05 mmol) in MeOH (6.1 mL) was added Et$_3$N (2.53 mL, 18.2 mmol), and the mixture was cooled to 0° C. under argon. Trifluoroacetic anhydride (1.18 mL, 8.49 mmol) was added dropwise, and the solution was stirred at room temperature for 2.2 h then concentrated. The residue was dissolved in EtOAc (60 mL) and washed with H$_2$O (20 mL) followed by saturated aqueous NaHCO$_3$ (5×20 mL) and brine (15 mL). The organic layer was dried (MgSO$_4$) and concentrated, and a portion of the residue (306 mg of 2.47 g) was purified by chromatography on silica gel (5:95 MeOH/CH$_2$Cl$_2$) to give 2,2,2-trifluoro-N-(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)acetamide (Compound No. 208, 303 mg, 97%) as colourless crystals. $^1$H NMR (CD$_3$OD): δ4.65 (s, 2H), 3.71 (m, 1H), 3.57 (m, 1H), 3.46 (m, 2H), 3.12 (m, 1H), 2.51 (m, 1H), 2.13-2.30 (m, 2H), 1.20-1.90 (m, 15H), 1.00 (s, 3H), 0.82 (s, 3H). ES-MS m/z 416 ([M−1]$^−$).

Example 86

Synthesis of 2-((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)acetonitrile (Compound No. 210)

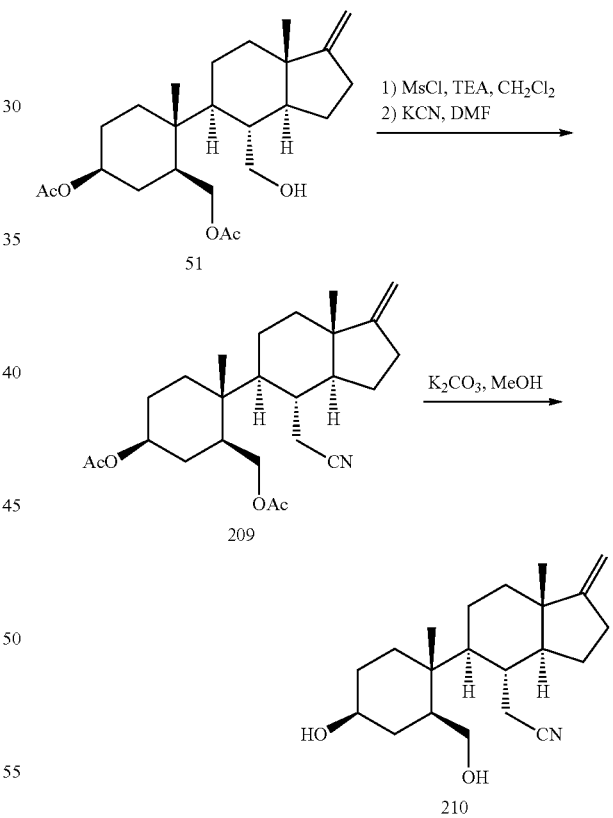

A. To a solution of ((1S,2R,5S)-5-acetoxy-2-((3aS,4R,5S,7aS)-4-(hydroxymethyl)-7a-methyl-1-methyleneoctahydro-1H-inden-5-yl)-2-methylcyclohexyl)methyl acetate (Compound No. 51, 660 mg, 1.62 mmol) and Et$_3$N (0.29 mL, 2.1 mmol) in CH$_2$Cl$_2$ (16 mL) at 0° C. under argon was added MsCl (0.14 mL, 1.8 mmol), and the solution was stirred at room temperature for 1 h. The solution was washed with saturated aqueous NaHCO$_3$ (15 mL), and the aqueous layer was extracted with CH$_2$Cl$_2$ (2×10 mL). The combined organic layers were dried (MgSO$_4$) and concentrated. Azeotropic removal of impurities was carried out with toluene (3×30 mL), and the resulting yellow solid (1.08 g) was dissolved in DMF (5.4 mL). KCN (317 mg, 4.87 mmol) was added, and the mixture was heated to 80° C. under argon for 18 h. The mixture was partitioned between EtOAc (60 mL) and H$_2$O (10 mL), and the organic layer was washed with brine (5×20 mL) then dried (MgSO$_4$) and concentrated. The residue was purified by chromatography on silica gel (1:99-5:95 EtOAc/CH$_2$Cl$_2$) to give ((1S,2R,5S)-5-acetoxy-2-((3aS,4R,5S,7aS)-4-(cyanomethyl)-7a-methyl-1-methyleneoctahydro-1H-inden-5-yl)-2-methylcyclohexyl)methyl acetate (Compound No. 209, 534 mg, 79% over 2 steps) as a colourless solid.

B. To a suspension of ((1S,2R,5S)-5-acetoxy-2-((3aS,4R,5S,7aS)-4-(cyanomethyl)-7a-methyl-1-methyleneoctahydro-1H-inden-5-yl)-2-methylcyclohexyl)methyl acetate (Compound No. 209, 534 mg, 1.28 mmol) in MeOH (25 mL) was added potassium carbonate (710 mg, 5.14 mmol) and heated to 40° C. for 1 h. The mixture was concentrated, and the residue was partially purified by chromatography on silica gel (5:95 MeOH/CH$_2$Cl$_2$) to give a colourless solid (458 mg). The solid (458 mg) was partitioned between 1:9 MeOH/CH$_2$Cl$_2$ (40 mL) and H$_2$O (10 mL), and the aqueous layer was extracted with 1:9 MeOH/CH$_2$Cl$_2$ (10 mL). The combined organic layers were dried (MgSO$_4$) and concentrated to give 2-((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)acetonitrile (Compound No. 210, 448 mg) as a colourless solid. $^1$H NMR (CD$_3$OD): δ4.67 (s, 2H), 3.69 (m, 1H), 3.46 (m, 1H), 3.14 (m, 1H), 2.88 (dd, J=18, 3.5 Hz, 1H), 2.55 (m, 2H), 2.31 (m, 1H), 2.16 (m, 1H), 1.86 (m, 6H), 1.21-1.58 (m, 9H), 1.12 (s, 3H), 0.83 (s, 3H). ES-MS m/z 390 ([M−1+60]$^-$).

Example 87

Synthesis of (1S,3S,4R)-3-(hydroxymethyl)-4-((3aS,4R,5S,7aS)-4-((methoxyamino)methyl)-7a-methyl-1-methyleneoctahydro-1H-inden-5-yl)-4-methylcyclohexanol (Compound No. 214)

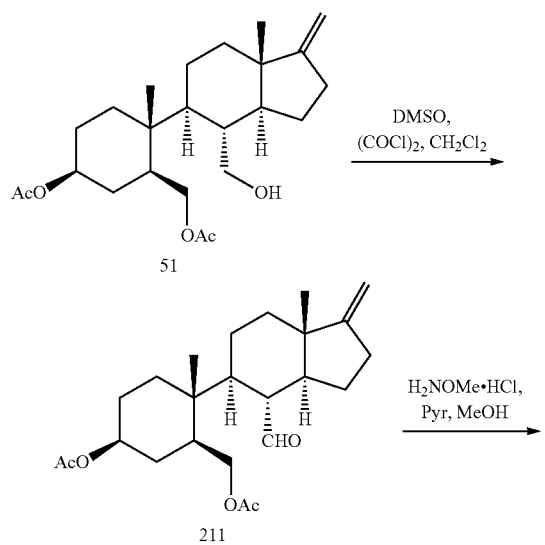

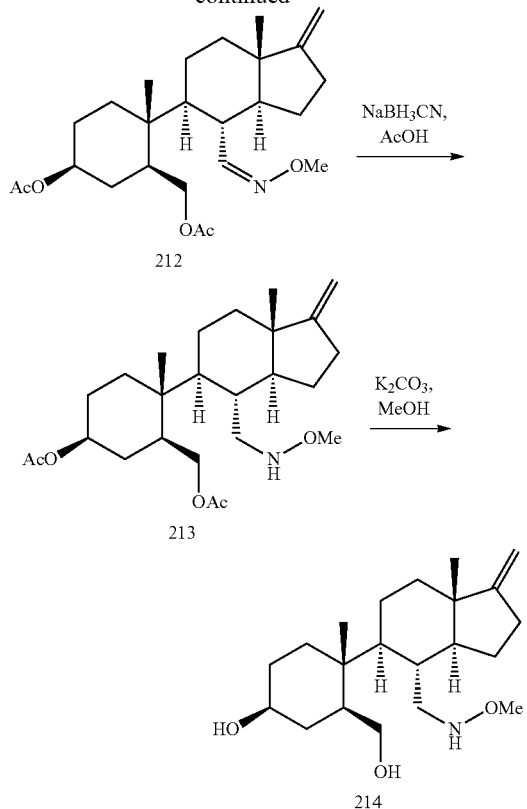

A. DMSO (0.078 mL, 1.1 mmol) was added dropwise to a solution of oxalyl chloride (0.048 mL, 0.55 mmol) in CH$_2$Cl$_2$ (1.6 mL) at −78° C. under argon then stirred at −78° C. for 15 min. A solution of ((1S,2R,5S)-5-acetoxy-2-((3aS,4R,5S,7aS)-4-(hydroxymethyl)-7a-methyl-1-methyleneoctahydro-1H-inden-5-yl)-2-methylcyclohexyl)methyl acetate (Compound No. 51, 149 mg, 0.366 mmol) in CH$_2$Cl$_2$ (0.8 mL) was added dropwise and stirred at −78° C. for 1.25 h then Et$_3$N (0.26 mL, 1.9 mmol) was added. The mixture was stirred at −78° C. for 0.5 h then at room temperature for 1.25 h, and H$_2$O (10 mL) was added followed by EtOAc (40 mL). The organic layer was washed with saturated aqueous NaHCO$_3$ (20 mL) and brine (5×20 mL) then dried (MgSO$_4$) and concentrated to give ((1S,2R,5S)-5-acetoxy-2-((3aS,4R,5S,7aS)-4-formyl-7a-methyl-1-methyleneoctahydro-1H-inden-5-yl)-2-methylcyclohexyl)methyl acetate (Compound No. 211, 191 mg) as a yellow oil.

B. To a solution of ((1S,2R,5S)-5-acetoxy-2-((3aS,4R,5S,7aS)-4-formyl-7a-methyl-1-methyleneoctahydro-1H-inden-5-yl)-2-methylcyclohexyl)methyl acetate (Compound No. 211, 191 mg) in 10:1 MeOH/pyridine (7.7 mL) was added methoxylamine hydrochloride (153 mg, 1.83 mmol), and the mixture was stirred at room temperature under argon for 3 d. The mixture was concentrated followed by azeotropic removal of remaining pyridine with toluene (2×20 mL). The residue was purified by chromatography on silica gel (20:80 EtOAc/hexanes) to give ((1S,2R,5S)-5-acetoxy-2-((3aS,4R,5S,7aS)-4-((Z)-(methoxyimino)methyl)-7a-methyl-1-methyleneoctahydro-1H-inden-5-yl)-2-methylcyclohexyl)methyl acetate (Compound No. 212, 85 mg, 53% over 2 steps) as a colourless film.

C. Sodium cyanoborohydride (49 mg, 0.78 mmol) was added to a solution of ((1S,2R,5S)-5-acetoxy-2-((3aS,4R, 5S,7aS)-4-((Z)-(methoxyimino)methyl)-7a-methyl-1-methyleneoctahydro-1H-inden-5-yl)-2-methylcyclohexyl)methyl acetate (Compound No. 212, 85 mg, 0.20 mmol) in acetic acid (3.9 mL) and stirred at room temperature for 18 h. More sodium cyanoborohydride (70 mg, 1.1 mmol) was added portionwise over 20 min and stirred at room temperature for 5 h. The mixture was concentrated followed by azeotropic removal of remaining acetic acid with toluene (20 mL). The mixture was filtered through silica gel (30:70 EtOAc/hexanes), and the residue was purified by chromatography on silica gel (15:85 EtOAc/hexanes) to give ((1S,2R,5S)-5-acetoxy-2-((3aS,4R,5S,7aS)-4-((methoxyamino)methyl)-7a-methyl-1-methyleneoctahydro-1H-inden-5-yl)-2-methylcyclohexyl)methyl acetate (Compound No. 213, 18 mg, 21%) as a colourless film.

D. To a solution of ((1S,2R,5S)-5-acetoxy-2-((3aS,4R,5S,7aS)-4-((methoxyamino)methyl)-7a-methyl-1-methyleneoctahydro-1H-inden-5-yl)-2-methylcyclohexyl)methyl acetate (Compound No. 213, 18 mg, 0.041 mmol) in MeOH (2.1 mL) was added potassium carbonate (23 mg, 0.17 mmol) and heated to 40° C. for 1.5 h. The mixture was concentrated, and the residue was purified by chromatography on silica gel (5:95 MeOH/CH$_2$Cl$_2$) to give (1S,3S,4R)-3-(hydroxymethyl)-4-((3aS,4R,5S,7aS)-4-((methoxyamino)methyl)-7a-methyl-1-methyleneoctahydro-1H-inden-5-yl)-4-methylcyclohexanol (Compound No. 214, 13 mg, 87%) as a colourless solid. $^1$H NMR (CD$_3$OD): δ4.62 (s, 2H), 3.69 (m, 1H), 3.48 (m, 4H), 3.02-3.20 (m, 3H), 2.49 (m, 1H), 2.12-2.28 (m, 2H), 1.14-1.92 (m, 18H), 0.79 (s, 3H). ES-MS m/z 352 ([M+1]$^+$).

Example 88

Synthesis of N-(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)cyanamide (Compound No. 215)

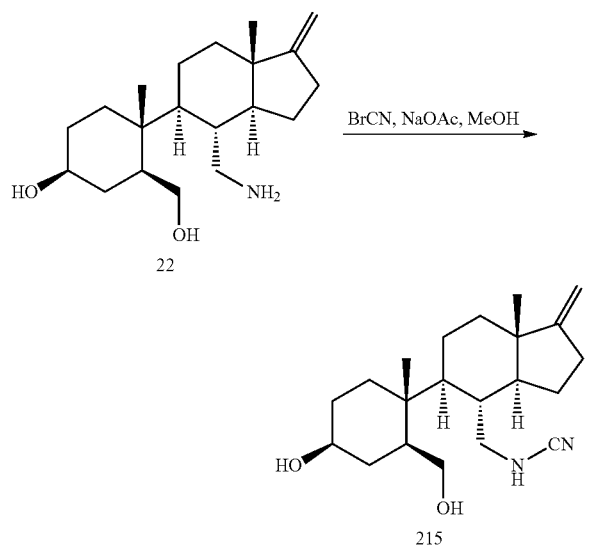

A solution of (1S,3S,4R)-4-((3aS,4R,5S,7aS)-4-(aminomethyl)-7a-methyl-1-methyleneoctahydro-1H-inden-5-yl)-3-(hydroxymethyl)-4-methylcyclohexanol (Compound No. 22, 96 mg, 0.30 mmol) in MeOH (3.0 mL) was cooled to 0° C. under argon and sodium acetate (73 mg, 0.89 mmol) was added followed by cyanogen bromide (41 mg, 0.39 mmol). The mixture was stirred at 0° C. for 20 min then at room temperature for 18 h. The mixture was concentrated, and the residue was purified by chromatography on silica gel (8:92 MeOH/CH$_2$Cl$_2$) to give N-(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)cyanamide (Compound No. 215, 102 mg, 99%) as a colourless solid. $^1$H NMR (CD$_3$OD): δ4.65 (s, 2H), 3.70 (m, 1H), 3.48 (m, 2H), 3.22 (m, 1H), 3.13 (m, 1H), 2.51 (m, 1H), 2.14-2.35 (m, 2H), 1.21-1.86 (m, 15H), 1.09 (s, 3H), 0.82 (s, 3H). ES-MS m/z 345 ([M−1]$^−$).

Example 89

Synthesis of 2-((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)acetamide (Compound No. 216)

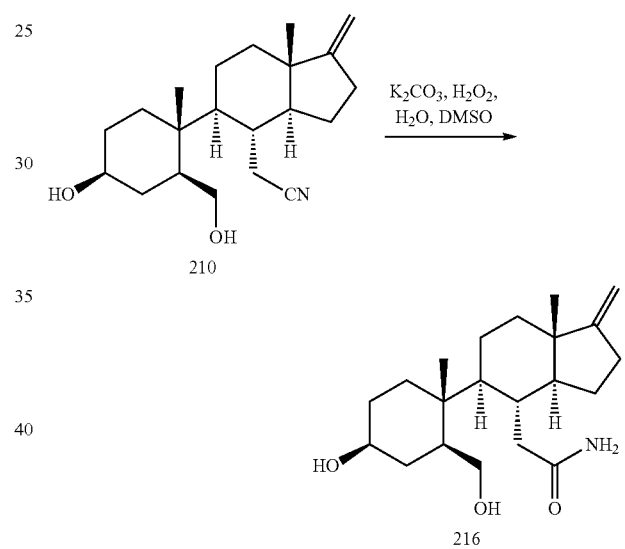

Potassium carbonate (53 mg, 0.38 mmol) was added to a solution of (1S,3S,4R)-4-((3aS,4R,5S,7aS)-4-(aminomethyl)-7a-methyl-1-methyleneoctahydro-1H-inden-5-yl)-3-(hydroxymethyl)-4-methylcyclohexanol (Compound No. 210, 255 mg, 0.769 mmol) in DMSO (7.7 mL) and stirred at room temperature while hydrogen peroxide (0.67 mL of a 50% solution in water, 12 mmol) was added dropwise. The mixture was stirred at room temperature for 19.5 h then cooled to 0° C. and ice-H$_2$O (10 mL) was added. The mixture was extracted with EtOAc (2×25 mL), and the combined organic layers were washed with brine (5×10 mL) then dried (MgSO$_4$) and concentrated. The residue was purified by chromatography on silica gel (100:10:2 EtOAc/MeOH/NH$_4$OH) to give 2-((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)acetamide (Compound No. 216, 183 mg, 68%) as a colourless solid. $^1$H NMR (CD$_3$OD): δ4.61 (s, 2H), 3.69 (m, 1H), 3.45 (m, 1H), 3.10 (m, 1H), 2.65 (m, 1H), 2.46 (m, 1H), 2.05-2.34 (m, 4H), 1.19-1.85 (m, 14H), 1.05 (s, 3H), 0.81 (s, 3H). ES-MS m/z 350 ([M+1]$^+$).

Example 90

Synthesis of 1-benzyl-3-(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)urea (Compound No. 217)

Example 91

Synthesis of 1-(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)-3-phenylurea (Compound No. 218)

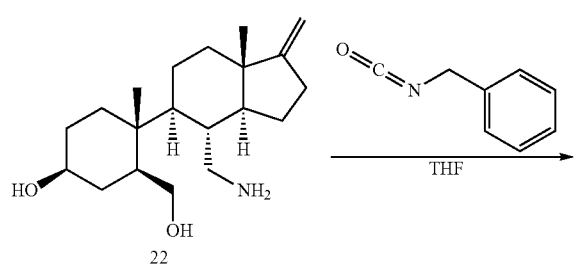

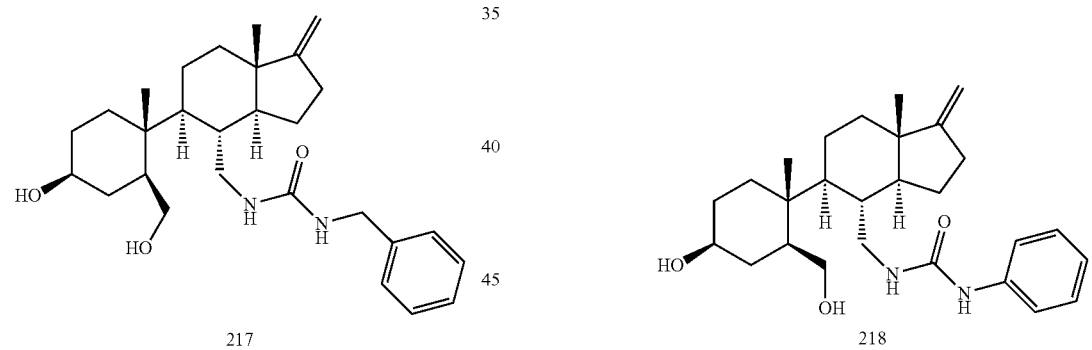

To a suspension of (1S,3S,4R)-4-((3aS,4R,5S,7aS)-4-(aminomethyl)-7a-methyl-1-methyleneoctahydro-1H-inden-5-yl)-3-(hydroxymethyl)-4-methylcyclohexanol (Compound No. 22, 56 mg, 0.17 mmol) in THF (3.5 mL) under argon was added benzyl isocyanate (0.043 mL, 0.35 mmol), and the solution was stirred at room temperature for 22 h then concentrated. The residue was purified by chromatography on silica gel (8:92 MeOH/CH$_2$Cl$_2$) to give 1-benzyl-3-(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)urea (Compound No. 217, 50 mg, 63%) as a colourless solid. $^1$H NMR (CD$_3$OD): δ7.27 (m, 5H), 6.40 (br s, 1H), 5.77 (br s, 1H), 4.63 (s, 2H), 4.30 (m, 2H), 3.69 (m, 1H), 3.31-3.46 (m, 3H), 3.12 (m, 1H), 2.49 (m, 1H), 2.13-2.25 (m, 2H), 1.20-1.86 (m, 15H), 1.02 (s, 3H), 0.82 (s, 3H). ES-MS m/z 455 ([M+1]$^+$).

To a suspension of (1S,3S,4R)-4-((3aS,4R,5S,7aS)-4-(aminomethyl)-7a-methyl-1-methyleneoctahydro-1H-inden-5-yl)-3-(hydroxymethyl)-4-methylcyclohexanol (Compound No. 22, 59 mg, 0.18 mmol) in THF (3.7 mL) at 00° C. under argon was added phenyl isocyanate (0.040 mL, 0.37 mmol), and the solution was stirred at room temperature for 22 h then concentrated. The residue was purified by chromatography on silica gel (100:8:1 CH$_2$Cl$_2$/MeOH/NH$_4$OH) to give 1-(((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methyl)-3-phenylurea (Compound No. 218, 19 mg, 23%) as a colourless solid. $^1$H NMR (CD$_3$OD): δ8.24 (s, 1H), 7.33 (d, J=7.8 Hz, 2H), 7.23 (m, 2H), 6.95 (t, J=7.4 Hz, 1H), 5.97 (br s, 1H), 4.64 (s, 2H), 3.72 (m, 1H), 3.31-3.53 (m, 3H), 3.15 (m, 1H), 2.51 (m, 1H), 2.14-2.28 (m, 2H), 1.22-1.89 (m, 15H), 1.07 (s, 3H), 0.84 (s, 3H). ES-MS m/z 441 ([M+1]$^+$).

Example 92

Synthesis of N-(2-((3aS,4S,5S,7aS)-5-((1R,2S,4S)-2,4-dihydroxy-1-methylcyclohexyl)-7a-methyl-1-methyleneoctahydro-1H-inden-4-yl)ethyl)benzo[d][1,3]dioxole-5-carboxamide (Compound No. 219)

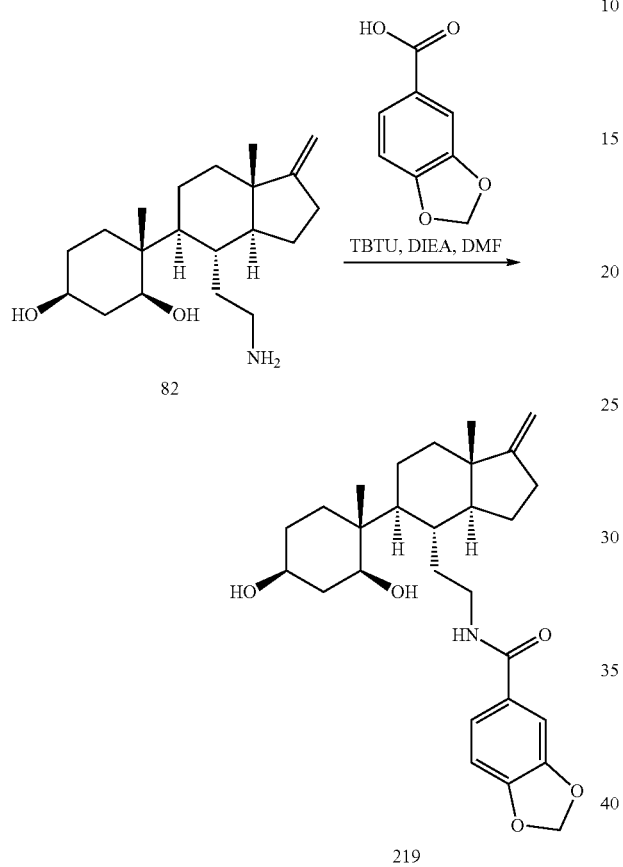

Example 93

Synthesis of 3-((1S,2S,5S)-5-hydroxy-2-((3aR,4R,5R,7aS)-4-hydroxy-7a-methyl-1-methyleneoctahydro-1H-inden-5-yl)-2-methylcyclohexyl)propanenitrile (Compound No. 221)

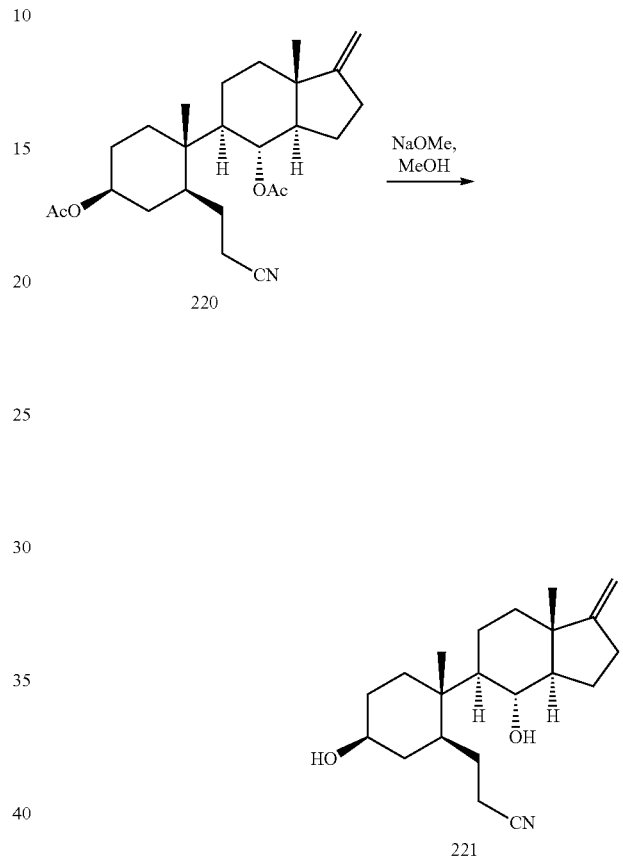

A mixture of (1S,3S,4R)-4-((3aS,4S,5S,7aS)-4-(2-aminoethyl)-7a-methyl-1-methyleneoctahydro-1H-inden-5-yl)-4-methylcyclohexane-1,3-diol (Compound No. 82, 40 mg, 0.12 mmol), TBTU (55 mg, 0.17 mmol), DIEA (49 µL, 0.27 mmol) and piperonylic acid (25 mg, 0.15 mmol) in DMF (3 mL) under argon at room temperature was stirred for 2 d. The mixture was diluted with EtOAc (30 mL), washed successively with water (5×3 mL) and brine (2×3 mL), dried (Na$_2$SO$_4$) and concentrated. The residue was purified using chromatography on silica gel (EtOAc) to afford N-(2-((3aS,4S,5S,7aS)-5-((1R,2S,4S)-2,4-dihydroxy-1-methylcyclohexyl)-7a-methyl-1-methyleneoctahydro-1H-inden-4-yl)ethyl)benzo[d][1,3]dioxole-5-carboxamide (Compound No. 219, 41 mg, 73%) as a white solid. $^1$H NMR (300 MHz, CD$_3$OD) δ7.38 (d, J=8.1, 1H), 7.29 (s, 1H), 6.86 (d, J=8.2, 1H), 6.02 (s, 2H), 4.62 (s, 2H), 3.81 (m, 1H), 3.51 (s, 1H), 3.42 (s, 2H), 2.81 (s, 1H), 2.49 (m, 1H), 2.29 (m, 1H), 2.12-1.23 (m, 18H), 1.20 (s, 3H), 0.80 (s, 3H); $^{13}$C NMR (75 MHz, CD$_3$OD) δ169.4, 162.9, 151.8, 149.3, 129.8, 123.2, 108.8, 108.4, 103.1, 101.6, 72.2, 69.6, 53.9, 46.7, 44.8, 41.4, 40.3, 37.3, 37.0, 32.0, 31.4, 30.1, 29.1, 26.1, 24.7, 19.7, 18.6; MS m/z: 470.3 [M+H]$^+$.

A solution of (3aR,4R,5R,7aS)-5-((1S,2S,4S)-4-acetoxy-2-(2-cyanoethyl)-1-methylcyclohexyl)-7a-methyl-1-methyleneoctahydro-1H-inden-4-yl acetate (Compound No. 220, 49 mg, 0.12 mmol) and NaOMe (0.22 mL of a 5.4 M solution in MeOH, 1.2 mmol) in MeOH (5 mL) was stirred at room temperature overnight then was quenched with AcOH (0.5 mL) and concentrated. The residue was purified using chromatography on silica gel (50% EtOAc/hexanes) to afford 42 mg of a white foam for which 1H NMR indicated only 1 of the acetates had been hydrolysed. A solution of the white foam (42 mg) and NaOMe (0.20 mL, 1.1 mmol) in MeOH at 60° C. under nitrogen was stirred for 6 days then was quenched with AcOH (1 mL) and concentrated. The residue was purified using chromatography on silica gel (50% then 80% EtOAc/hexanes) to afford 3-((1S,2S,5S)-5-hydroxy-2-((3aR,4R,5R,7aS)-4-hydroxy-7a-methyl-1-methyleneoctahydro-1H-inden-5-yl)-2-methylcyclohexyl)propanenitrile (Compound No. 221, 36 mg, 92%) as a white solid. $^1$H NMR (300 MHz, CD$_3$OD) δ4.62 (2H), 3.75 (m, 1H), 3.55 (m, 1H), 2.55 (m, 1H), 2.42 (m, 1H), 2.30 (2H), 1.95-1.20 (16H), 1.15 (s, 3H), 0.88 (m, 1H), 0.80 (s, 3H). MS m/z: 390 [M+AcO]$^+$.

Example 94

Synthesis of 3-((1S,2S,5S)-5-hydroxy-2-((3aR,4R,5R,7aS)-4-hydroxy-7a-methyl-1-methyleneoctahydro-1H-inden-5-yl)-2-methylcyclohexyl)propanamide (Compound No. 230)

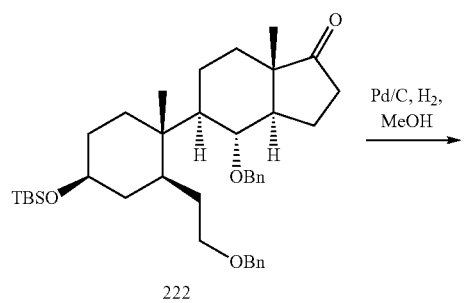
222

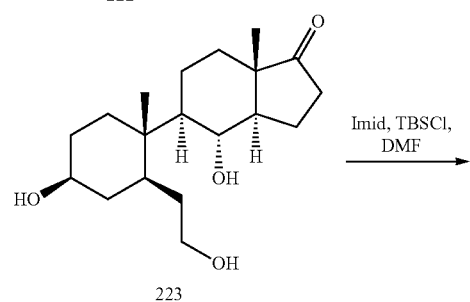
223

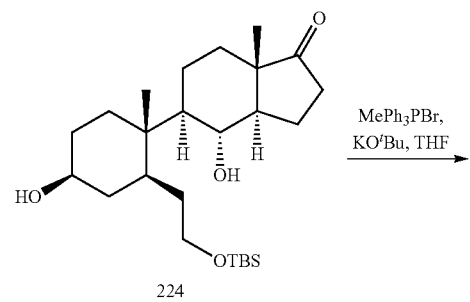
224

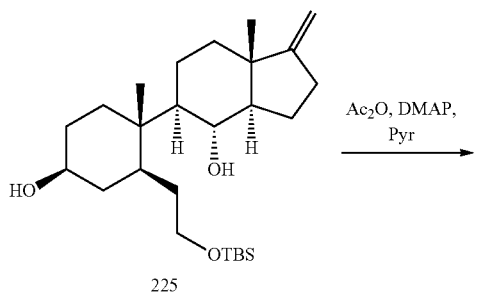
225

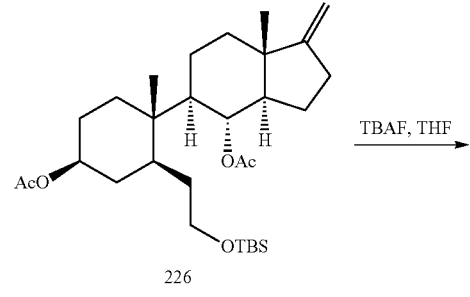
226

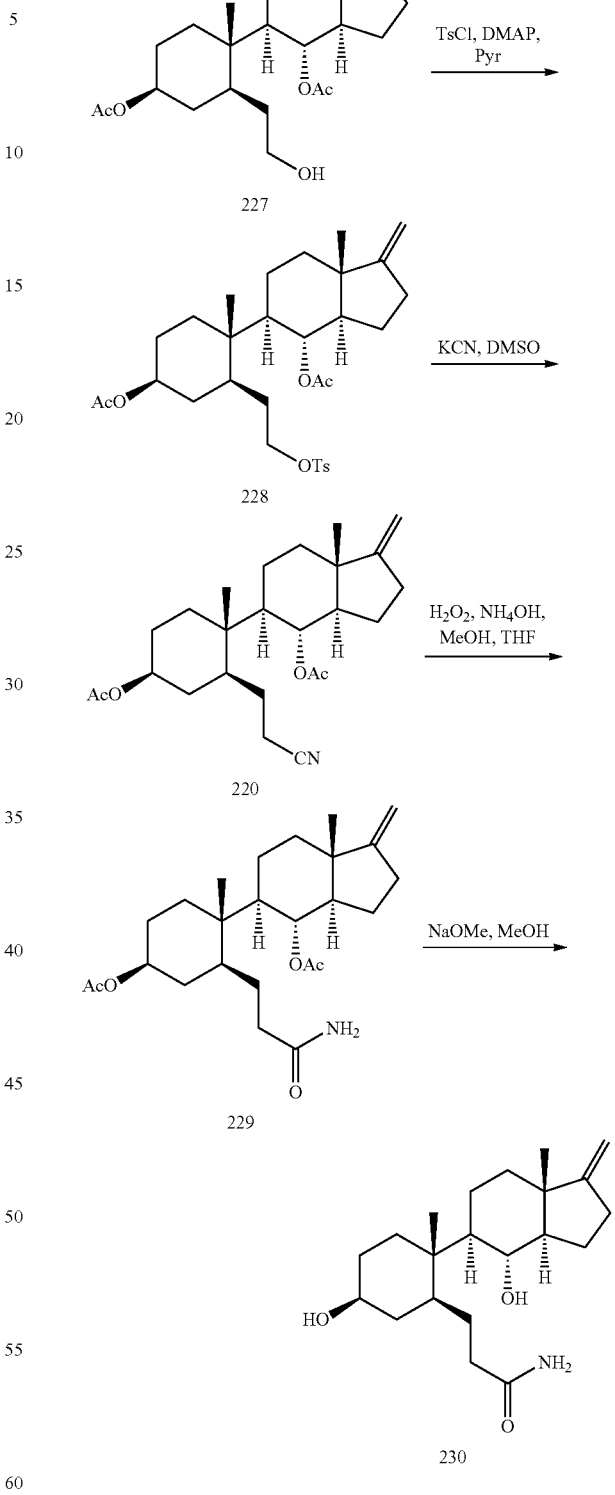

A. A solution of (3aR,4R,5R,7aS)-4-(benzyloxy)-5-((1S,2S,4S)-2-(2-(benzyloxy)ethyl)-4-((tert-butyldimethylsilyl)oxy)-1-methylcyclohexyl)-7a-methyloctahydro-1H-inden-1-one (Compound No. 222, 3.00 g, 4.85 mmol) and Pd (52 mg of a 10% solution on carbon, 0.05 mmol) in MeOH (90 mL) under 35 psi hydrogen was agitated for 18 h. The solution was filtered through Celite, eluted with EtOAc and concentrated to afford (3aR,4R,5R,7aS)-4-hydroxy-5-((1S,2S,4S)-4-hydroxy-2-(2-hydroxyethyl)-1-methylcyclohexyl)-7a-methyloctahydro-1H-inden-1-one (Compound No. 223, 1.88 g, >100%) as a white foam.

B. A solution of (3aR,4R,5R,7aS)-4-hydroxy-5-((1S,2S,4S)-4-hydroxy-2-(2-hydroxyethyl)-1-methylcyclohexyl)-7a-methyloctahydro-1H-inden-1-one (Compound No. 223, 1.6 g, 4.9 mmol), imidazole (0.74 g, 11 mmol) and TBSCl (0.82 g, 5.4 mmol) in DMF (25 mL) under nitrogen was stirred at 0° C. for 40 min then at room temperature for 4 h. The solution was poured into water (75 mL), extracted with $Et_2O$ (200 mL), washed with brine (40 mL), dried ($MgSO_4$) and concentrated. The residue was purified using chromatography on silica gel (50% then 70% EtOAc/hexanes) to afford (3aR,4R,5R,7aS)-5-((1S,2S,4S)-2-(2-((tert-butyldimethylsilyl)oxy)ethyl)-4-hydroxy-1-methylcyclohexyl)-4-hydroxy-7a-methyloctahydro-1H-inden-1-one (Compound No. 224, 1.33 g, 61%) as a white foam.

C. A solution of methyl triphenylphosphonium bromide (7.33 g, 20.5 mmol) and KO$^t$Bu (2.33 g, 20.2 mmol) in THF (20 mL) was stirred at room temperature under nitrogen for 2 h then added (3aR,4R,5R,7aS)-5-((1S,2S,4S)-2-(2-((tert-butyldimethylsilyl)oxy)ethyl)-4-hydroxy-1-methylcyclohexyl)-4-hydroxy-7a-methyloctahydro-1H-inden-1-one (Compound No. 224, 1.45 g, 3.31 mmol) in THF (10 mL). The reaction flask was fitted with a condenser and the solution was heated at reflux for 2 h. The solution was quenched with saturated $NaHCO_3$ solution (10 mL), diluted with EtOAc (200 mL), washed with brine (3×30 mL), dried ($MgSO_4$) and concentrated. The residue was purified using chromatography on silica gel (50% EtOAc/hexanes with 1% $CH_2Cl_2$) to afford (3aR,4R,5R,7aS)-5-((1S,2S,4S)-2-(2-((tert-butyldimethylsilyl)oxy)ethyl)-4-hydroxy-1-methylcyclohexyl)-7a-methyl-1-methyleneoctahydro-1H-inden-4-ol (Compound No. 225, 1.25 g, 87%) as a white solid.

D. A solution of (3aR,4R,5R,7aS)-5-((1S,2S,4S)-2-(2-((tert-butyldimethylsilyl)oxy)ethyl)-4-hydroxy-1-methylcyclohexyl)-7a-methyl-1-methyleneoctahydro-1H-inden-4-ol (Compound No. 225, 1.25 g, 2.87 mmol), acetic anhydride (1.10 mL, 11.5 mmol) and DMAP (35 mg, 0.29 mmol) in pyridine (15 mL) initially at 0° C. under nitrogen was stirred for 1 d. The solution was cooled in ice, quenched with saturated $NaHCO_3$ solution (10 mL) for 15 min, diluted with EtOAc (200 mL), washed with brine (3×30 mL), dried ($MgSO_4$) and concentrated to give (3aR,4R,5R,7aS)-5-((1S,2S,4S)-4-acetoxy-2-(2-((tert-butyldimethylsilyl)oxy)ethyl)-1-methylcyclohexyl)-7a-methyl-1-methyleneoctahydro-1H-inden-4-yl acetate (Compound No. 226).

E. A solution of (3aR,4R,5R,7aS)-5-((1S,2S,4S)-4-acetoxy-2-(2-((tert-butyldimethylsilyl)oxy)ethyl)-1-methylcyclohexyl)-7a-methyl-1-methyleneoctahydro-1H-inden-4-yl acetate (Compound No. 226, 1.49 g, 2.87 mmol) and TBAF (5.7 mL of a 1 M solution in THF, 5.7 mmol) in THF (14 mL) at 50° C. under nitrogen was stirred 1.5 h then was concentrated. The residue was purified using chromatography on silica gel (30% EtOAc/hexanes with 1% $CH_2Cl_2$) to afford (3aR,4R,5R,7aS)-5-((1S,2S,4S)-4-acetoxy-2-(2-hydroxyethyl)-1-methylcyclohexyl)-7a-methyl-1-methyleneoctahydro-1H-inden-4-yl acetate (Compound No. 227, 1.137 g, 97%) as a white foam.

F. A solution of (3aR,4R,5R,7aS)-5-((1S,2S,4S)-4-acetoxy-2-(2-hydroxyethyl)-1-methylcyclohexyl)-7a-methyl-1-methyleneoctahydro-1H-inden-4-yl acetate (Compound No. 227, 200 mg, 0.492 mmol), DMAP (6 mg, 0.05 mmol) and TsCl (281 mg, 1.48 mmol) in pyridine (2.5 mL) was maintained at 0° C. under nitrogen for 3.5 h. The solution was quenched with saturated $NaHCO_3$ solution (10 mL) for 25 min, diluted with EtOAc (100 mL), washed with brine (3×15 mL), dried ($MgSO_4$) and concentrated to give (3aR,4R,5R,7aS)-5-((1S,2S,4S)-4-acetoxy-1-methyl-2-(2-(tosyloxy)ethyl)cyclohexyl)-7a-methyl-1-methyleneoctahydro-1H-inden-4-yl acetate (Compound No. 228).

G. A solution of (3aR,4R,5R,7aS)-5-((1S,2S,4S)-4-acetoxy-1-methyl-2-(2-(tosyloxy)ethyl)cyclohexyl)-7a-methyl-1-methyleneoctahydro-1H-inden-4-yl acetate (Compound No. 228, 276 mg, 0.492 mmol) and KCN (100 mg, 1.48 mmol) in DMSO (2.5 mL) under nitrogen was heated at 60° C. for 2 h then at 80° C. for 3.5 h. The room temperature solution was poured into water (20 mL), extracted with $Et_2O$ (75 mL), washed with brine (20 mL), dried ($MgSO_4$) and concentrated. The residue was purified using chromatography on silica gel (25% EtOAc/hexanes) to afford (3aR,4R,5R,7aS)-5-((1S,2S,4S)-4-acetoxy-2-(2-cyanoethyl)-1-methylcyclohexyl)-7a-methyl-1-methyleneoctahydro-1H-inden-4-yl acetate (Compound No. 220, 161 mg, 78%) as a white foam.

H. A solution of (3aR,4R,5R,7aS)-5-((1S,2S,4S)-4-acetoxy-2-(2-cyanoethyl)-1-methylcyclohexyl)-7a-methyl-1-methyleneoctahydro-1H-inden-4-yl acetate (Compound No. 220, 161 mg, 0.39 mmol) and $H_2O_2$ (0.20 mL of a 50% solution in water, 3.9 mmol) in $NH_4OH$ (2 mL), MeOH (2 mL) and THF (1 mL) was stirred at room temperature for 1 d. The solution was concentrated to give (3aR,4R,5R,7aS)-5-((1S,2S,4S)-4-acetoxy-2-(3-amino-3-oxopropyl)-1-methylcyclohexyl)-7a-methyl-1-methyleneoctahydro-1H-inden-4-yl acetate (Compound No. 229) as a white solid.

I. A solution of (3aR,4R,5R,7aS)-5-((1S,2S,4S)-4-acetoxy-2-(3-amino-3-oxopropyl)-1-methylcyclohexyl)-7a-methyl-1-methyleneoctahydro-1H-inden-4-yl acetate (Compound No. 229, 168 mg, 0.39 mmol) and NaOMe (0.7 mL of a 5.4 M solution in MeOH, 3.9 mmol) in MeOH (10 mL) at 60° C. under nitrogen was stirred for 4 d. The solution was cooled in ice, quenched with acetic acid (1 mL) and concentrated. The residue was purified using chromatography on silica gel (5% MeOH/EtOAc) to afford 3-((1S,2S,5S)-5-hydroxy-2-((3aR,4R,5R,7aS)-4-hydroxy-7a-methyl-1-methyleneoctahydro-1H-inden-5-yl)-2-methylcyclohexyl)propanamide (Compound No. 230, 58 mg, 43%) as a white solid. $^1$H NMR ($CD_3OD$): δ4.62 (2H), 3.62 (m, 1H), 3.42 (m, 1H), 2.52 (m, 1H), 2.28 (m, 2H), 2.09 (m, 1H), 1.2-2.0 (16H), 1.18 (s, 3H), 0.90 (m, 1H), 0.78 (s, 3H). ES-MS m/z 350 ([M+1]$^+$).

Example 95

Synthesis of N-(((1S,2S,5S)-5-hydroxy-2-((3aR,4R,5R,7aS)-4-hydroxy-7a-methyl-1-methyleneoctahydro-1H-inden-5-yl)-2-methylcyclohexyl)methyl)benzo[d][1,3]dioxole-5-carboxamide (Compound No. 235)

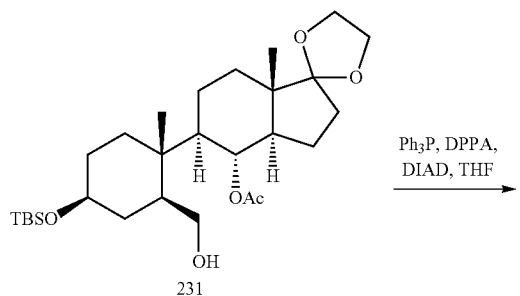

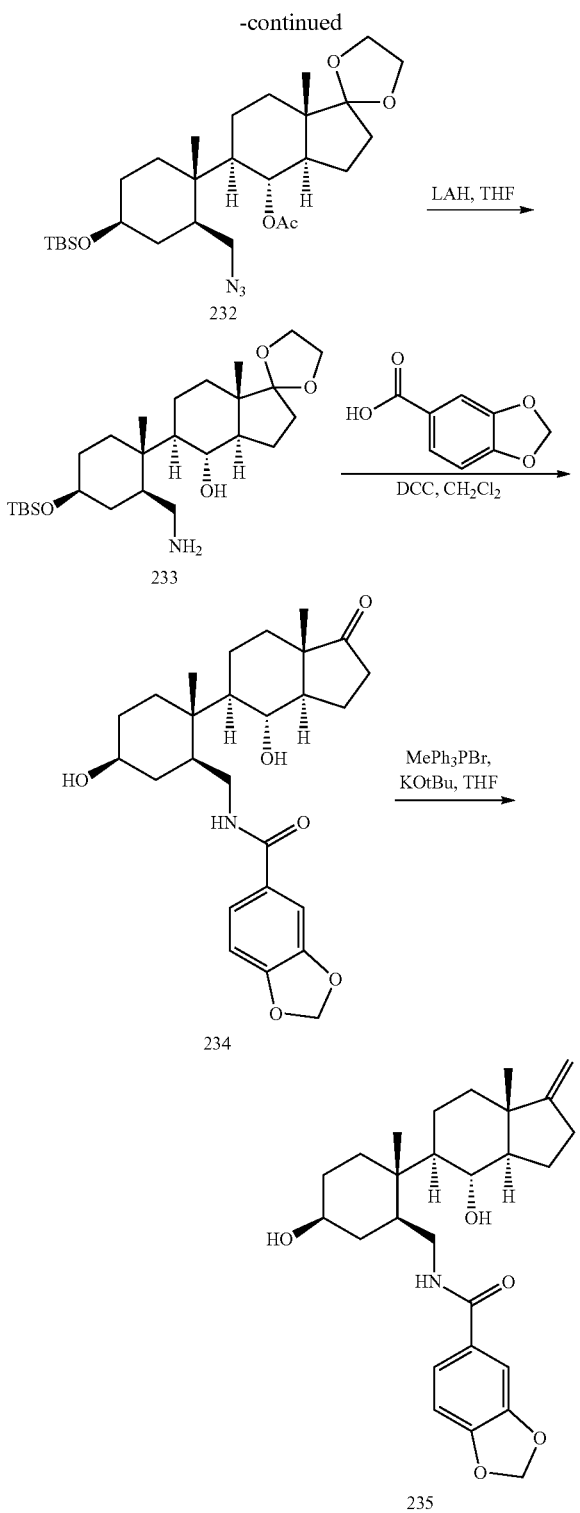

(100 mL), washed with brine (3×15 mL), dried (MgSO$_4$) and concentrated. The residue was purified using chromatography on silica gel (10% then 20% then 40% EtOAc/hexanes) to afford (4'R,7a'S)-5'-((1S,2S,4S)-2-(azidomethyl)-4-((tert-butyldimethylsilyl)oxy)-1-methylcyclohexyl)-7a'-methyloctahydrospiro[[1,3]dioxolane-2,1'-inden]-4'-yl acetate (Compound No. 232, 220 mg, 70%) as a white foam.

B. A solution of (4'R,7a'S)-5'-((1S,2S,4S)-2-(azidomethyl)-4-((tert-butyldimethylsilyl)oxy)-1-methylcyclohexyl)-7a'-methyloctahydrospiro[[1,3]dioxolane-2,1'-inden]-4'-yl acetate (Compound No. 232, 220 mg, 0.41 mmol) and LAH (0.62 mL of a 2 M solution in THF, 1.2 mmol) in THF (6 mL) at 60° C. under nitrogen was stirred 1 h. The solution was cooled in ice, diluted with Et$_2$O (20 mL), quenched with Na$_2$SO$_4$.10H$_2$O (0.4 g) for 2 h, filtered through Celite, eluted with EtOAc and concentrated to give (4'R,7a'S)-5'-((1S,2S,4S)-2-(aminomethyl)-4-((tert-butyldimethylsilyl)oxy)-1-methylcyclohexyl)-7a'-methyloctahydrospiro[[1,3]dioxolane-2,1'-inden]-4'-ol (Compound No. 233, 170 mg) as a white foam.

C. A solution of (4'R,7a'S)-5'-((1S,2S,4S)-2-(aminomethyl)-4-((tert-butyldimethylsilyl)oxy)-1-methylcyclohexyl)-7a'-methyloctahydrospiro[[1,3]dioxolane-2,1'-inden]-4'-ol (Compound No. 233, 170 mg, 0.36 mmol), piperonylic acid (72 mg, 0.44 mmol) and DCC (90 mg, 0.44 mmol) in CH$_2$Cl$_2$ at room temperature under nitrogen was stirred for 18 h. More DCC (45 mg, 0.22 mmol) was added and the reaction was allowed to continue for 24 h. The solution was filtered through a plug of silica gel, eluted with EtOAc and concentrated. The residue was purified using chromatography on silica gel (20% then 50% EtOAc/hexanes) to afford 76 mg of a white solid. This material was taken up in acetic acid (16 mL) and water (4 mL) and stirred at room temperature for 4 d then was concentrated. The residue was 3 times taken up in toluene (20 mL) and concentrated. The resulting white solid was purified using chromatography on silica gel (80% then 100% EtOAc/hexanes) to afford N-(((1S,2S,5S)-5-hydroxy-2-((4R,7aS)-4-hydroxy-7a-methyl-1-oxooctahydro-1H-inden-5-yl)-2-methylcyclohexyl)methyl)benzo[d][1,3]dioxole-5-carboxamide (Compound No. 234, 40 mg, 24%) as a white solid.

D. A solution of methyl triphenylphosphonium bromide (312 mg, 0.87 mmol) and KO$^t$Bu (100 mg, 0.87 mmol) in THF (3 mL) was stirred at room temperature under nitrogen for 1 h then was added N-(((1S,2S,5S)-5-hydroxy-2-((4R,7aS)-4-hydroxy-7a-methyl-1-oxooctahydro-1H-inden-5-yl)-2-methylcyclohexyl)methyl)benzo[d][1,3]dioxole-5-carboxamide (Compound No. 234, 40 mg, 0.087 mmol) in THF (3 mL). After 25 h, the solution was quenched with saturated NaHCO$_3$ solution (3 mL), diluted with EtOAc (100 mL), washed with brine (3×15 mL), dried (MgSO$_4$) and concentrated. The residue was purified using chromatography on silica gel (50% then 80% EtOAc/hexanes) to afford N-(((1S,2S,5S)-5-hydroxy-2-((3aR,4R,5R,7aS)-4-hydroxy-7a-methyl-1-methyleneoctahydro-1H-inden-5-yl)-2-methylcyclohexyl)methyl)benzo[d][1,3]dioxole-5-carboxamide (Compound No. 235, 26 mg, 65%) as a white solid. $^1$H NMR (CDCl$_3$): δ 7.30 (m, 1H), 6.82 (m, 1H), 6.05 (m, 1H), 6.02 (s, 2H), 4.65 (2H), 3.75 (m, 1H), 3.63 (m, 1H), 3.58 (m, 1H), 3.00 (m, 1H), 2.55 (m, 1H), 2.30 (m, 1H), 2.09 (m, 1H), 1.25-2.15 (13H), 1.22 (s, 3H), 1.15 (m, 1H), 0.80 (s, 3H). ES-MS m/z 456 ([M+1]$^+$)

A. A solution of (4'R,7a'S)-5'-((1S,2S,4S)-4-((tert-butyldimethylsilyl)oxy)-2-(hydroxymethyl)-1-methylcyclohexyl)-7a'-methyloctahydrospiro[[1,3]dioxolane-2,1'-inden]-4'-yl acetate (Compound No. 231, 300 mg, 0.587 mmol), triphenylphosphine (339 mg, 1.29 mmol), diphenylphosphoryl azide (0.28 mL, 1.29 mmol) and DIAD (0.25 mL, 1.29 mmol) in THF (6 mL) initially at 0° C. under nitrogen was stirred 18 h. The solution was made basic with saturated NaHCO$_3$ solution (3 mL), diluted with EtOAc

Example 96

Synthesis of 3-((1R,2S,5S)-5-hydroxy-2-((3aR,4R,5R,7aS)-4-hydroxy-7a-methyl-1-methyleneoctahydro-1H-inden-5-yl)-2-methylcyclohexyl)propanoic acid (Compound No. 236)

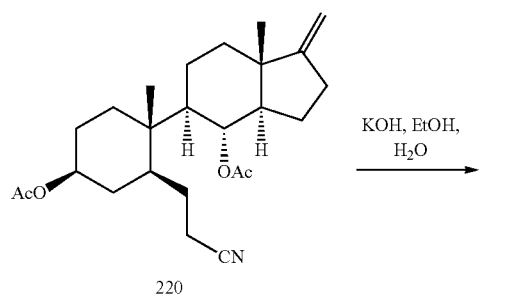

Example 97

Synthesis of (3aS,4R,5S,7aS)-5-((1R,2R,4S)-4-hydroxy-2-(hydroxymethyl)-1-methylcyclohexyl)-7a-methyl-1-methyleneoctahydro-1H-indene-4-carboxylic acid (Compound No. 239)

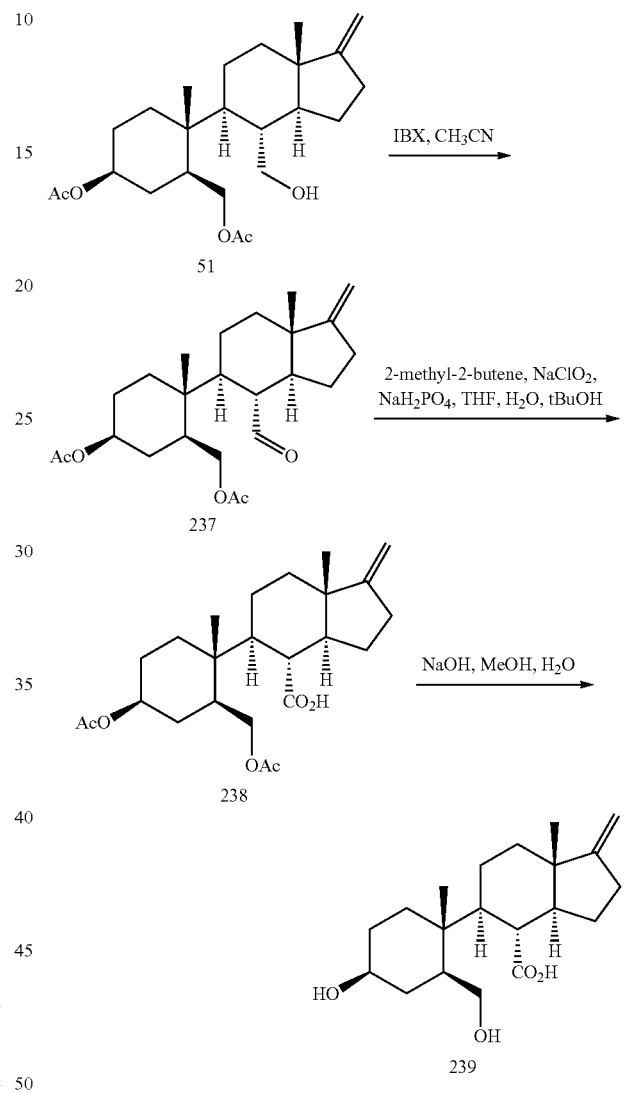

A solution of (3aR,4R,5R,7aS)-5-((1S,2S,4S)-4-acetoxy-2-(2-cyanoethyl)-1-methylcyclohexyl)-7a-methyl-1-methyleneoctahydro-1H-inden-4-yl acetate (Compound No. 220, 100 mg, 0.24 mmol) and KOH (95 mg, 1.7 mmol) in EtOH (5 mL) was heated in an 80° C. oil bath. Water (1 mL and 4 mL) was added after 18 hours and 32 hours, respectively. After a total of 6 days the solution was cooled in ice then added AcOH (1 mL) and concentrated. The residue was taken up in water (40 mL), extracted with $CH_2Cl_2$ (5×15 mL), dried ($MgSO_4$) and concentrated. The residue was purified using chromatography on silica gel (1%, then 2%, then 5% then 100% MeOH/EtOAc) to afford 3-((1R,2S,5S)-5-hydroxy-2-((3aR,4R,5R,7aS)-4-hydroxy-7a-methyl-1-methyleneoctahydro-1H-inden-5-yl)-2-methylcyclohexyl) propanoic acid (Compound No. 236, 44 mg, 52%) as a white solid. $^1$H NMR ($CD_3OD$): δ4.62 (2H), 3.60 (m, 1H), 3.40 (m, 1H), 2.50 (m, 1H), 2.25 (2H), 2.03 (m, 1H), 1.90 (2H), 2.85-1.60 (5H), 1.55-1.20 (9H), 1.18 (s, 3H), 0.90 (1H), 0.78 (s, 3H). ES-MS m/z 349 ([M−1]⁻)

A. A mixture of ((1S,2R,5S)-5-acetoxy-2-((3aS,4R,5S,7aS)-4-(hydroxymethyl)-7a-methyl-1-methyleneoctahydro-1H-inden-5-yl)-2-methylcyclohexyl)methyl acetate (Compound No. 51, 305 mg, 0.75 mmol) and IBX (540 mg, 1.93 mmol) in MeCN (7.5 mL) under argon at 65° C. was stirred for 22 h. The resultant mixture was cooled to room temperature, filtered through Celite and concentrated. The residue was purified using chromatography on silica gel (3:7 EtOAc:hexanes) to afford impure ((1S,2R,5S)-5-acetoxy-2-((3aS,4R,5S,7aS)-4-formyl-7a-methyl-1-methyleneoctahydro-1H-inden-5-yl)-2-methylcyclohexyl)methyl acetate (Compound No. 237, 85 mg) which was carried on with no further purification.

B. A mixture of ((1S,2R,5S)-5-acetoxy-2-((3aS,4R,5S,7aS)-4-formyl-7a-methyl-1-methyleneoctahydro-1H-inden-5-yl)-2-methylcyclohexyl)methyl acetate (Compound No.

237, 85 mg), NaH$_2$PO$_4$.H$_2$O (174 mg, 1.26 mmol), NaClO$_2$ (57 mg, 0.63 mmol), 2-methyl-2-butene (2 mL) in THF (2 mL), $^t$BuOH (2 mL) and H$_2$O (0.5 mL) at room temperature was stirred for 24 h. Additional NaH$_2$PO$_4$.H$_2$O (87 mg, 0.63 mmol), NaClO$_2$ (29 mg, 0.32 mmol) and 2-methyl-2-butene (1 mL) were added and the mixture was stirred for an additional 24 h. The mixture was diluted with EtOAc (30 mL), washed successively with water (3×10 mL) and brine (10 mL), dried (Na$_2$SO$_4$) and concentrated. The residue was purified using chromatography on silica gel (4:1 to 3:2 hexanes:EtOAc then MeOH) to afford impure (3aS,4R,5S,7aS)-5-((1R,2R,4S)-4-acetoxy-2-(acetoxymethyl)-1-methylcyclohexyl)-7a-methyl-1-methyleneoctahydro-1H-indene-4-carboxylic acid (Compound No. 238, 50 mg) which was carried on with no further purification.

C. A mixture of (3aS,4R,5S,7aS)-5-((1R,2R,4S)-4-acetoxy-2-(acetoxymethyl)-1-methylcyclohexyl)-7a-methyl-1-methyleneoctahydro-1H-indene-4-carboxylic acid (Compound No. 238, 50 mg) and 2 M NaOH (1 mL, 1 mmol) in MeOH (3 mL) at room temperature was stirred for 19 h. The mixture was concentrated and reconstituted in water (10 mL) and AcOH (0.5 mL). This mixture was extracted successively with EtOAc (2×20 mL) and CH$_2$Cl$_2$ (20 mL), dried (Na$_2$SO$_4$) and concentrated. The residue was purified using chromatography on silica gel (9:1 CH$_2$Cl$_2$:MeOH then MeOH) to afford (3aS,4R,5S,7aS)-5-((1R,2R,4S)-4-hydroxy-2-(hydroxymethyl)-1-methylcyclohexyl)-7a-methyl-1-methyleneoctahydro-1H-indene-4-carboxylic acid (Compound No. 239, 33 mg, 13% over 3 steps) as a white solid. $^1$H NMR (300 MHz, CD$_3$OD) δ4.64 (s, 2H), 3.76 (d, J=10.9, 1H), 3.44 (m, 1H), 3.11 (m, 1H), 2.44 (m, 1H), 2.29 (m, 3H), 2.02-1.07 (m, 14H), 0.99 (s, 3H), 0.79 (s, 3H); $^{13}$C NMR (75 MHz, CD$_3$OD) δ186.1, 162.3, 102.0, 71.4, 62.7, 53.2, 48.3, 47.0, 44.1, 43.7, 38.8, 36.7, 35.0, 31.9, 31.4, 30.0, 26.2, 22.4, 19.7, 18.4; MS m/z: 335.1 [M−H]$^−$.

Example 98

His-hSHIP1 Activity of Representative Compounds

Test compounds are dissolved in 95% ethanol to form stock solutions. Before screening, the stock solutions are diluted with Phosphatase Assay Buffer (20 mM Tris-HCL, 10 mM MgCl$_2$ pH 7.5, 0.02% Tween 20) to form working assay solutions that contain 10% ethanol. The assay is carried out on 96-well microtiter plates using a modified procedure of that reported by Ong et al., *Blood* 110, 1942-1949, 2007 and Yang et al., *Org Lett* 7, 1073-1076, 2005, both of which references are incorporated herein by reference in their entirety.

Data were generated by one of two variant methods. Test compounds are screened by one of two approaches described as follows. In the first approach, each reaction contains 5 μL of His-hSHIP1 enzyme (5-20 ng), 10 μL of the substrate, 1,3,4,5-inositol tetrakisphosphate (IP4; 50 μM final), 5 μL of Phosphatase Assay Buffer, and 5 L of test compound at various concentrations in 10% ethanol (0-300 μM final). Control blanks are also prepared by replacing His-hSHIP1 enzyme, IP4, or test compounds with Phosphatase Assay Buffer. After adding the reaction components in a 96-well microtiter plate on ice, the reaction is mixed by briefly shaking the plate vigorously. The reaction is then incubated at 37° C. for 15 min with gentle shaking followed by addition of 100 μL of Biomol Green Reagent (BIOMOL, PA, USA) to terminate the reaction. The free phosphate released from IP4 by His-hSHIP1 binds to the Biomol Green Reagent, which turns the dye to green color. After incubating the mixture for 20 min at room temperature for color development, the absorbance is read with SpectraMax Plus 96-well plate reader (Molecular Devices, Sunnyvale, Calif., USA) at a wavelength of 650 nm.

In the second approach, a master mix is prepared that contains 50 μL of His-hSHIP1 enzyme (0.4-1.6 ng/μL final), 25 μL of the substrate, IP4 (25 or 250 μM final), and 50 μL of test compound in 3.3% ethanol (100 μL final). Control blanks are also prepared by replacing His-hSHIP1 enzyme, IP4, or test compounds with Phosphate Assay Buffer. A reference compound that has been shown to activate SHIP1 is also included. Each reaction component is preincubated at 37° C. for 30 min before adding to a 96-well microtiter plate. The master mix is then incubated at 37° C. At time 0, 20, and 30 min, 25 μL of the master mix is removed and transferred to a new 96-well microtiter plate, to which 100 μL of Biomol Green Reagent is added to stop the reaction. After incubating the mixture for 20 min at room temperature for color development, the absorbance is read with SpectraMax Plus 96-well plate reader at a wavelength of 650 nm. Phosphate released is plotted against time to calculate the initial velocities (i.e., slope of the graph) at each IP4 concentration. The initial velocities are baseline corrected and the ratio of initial velocities (IP4$_{25}$/IP4$_{250}$) is calculated and used to rate the test compounds.

According to the above assay(s), the representative compounds listed in Table 2 below were found to modulate His-hSHIP1 enzyme at concentrations≤300 μM. The compound numbers in Table 2 correspond to the compound numbers in Table 1 above. Scoring of the compound is expressed as follows:

| Scoring | Approach 1 (% increase relative to background) | Approach 2 (Initial velocity Ratio) |
|---|---|---|
| +++ | x ≥ 65 | higher than reference or reference − 15% |
| ++ | 50 ≤ x < 65 | reference − 16% to reference − 30% |
| + | 0 < x < 50 | reference − 31% or lower |
| − | N/A | inhibitor |

Data generated by the first method is distinguished by an asterisk.

TABLE 2

| Cpd. No. | Scoring |
|---|---|
| 1 | ++ |
| 2 | + |
| 4 | + |
| 5 | +++ |
| 6 | ++ |
| 7 | + |
| 8 | + |
| 10 | − |
| 11 | + |
| 15 | ++ |
| 18 | + |
| 26 | ++ |
| 27 | + |
| 29 | + |
| 30 | ++ |
| 31 | − |
| 32 | +++ |
| 34 | + |
| 35 | ++ |
| 37 | ++ |
| 38 | ++ |
| 43 | ++ |
| 44 | ++ |

TABLE 2-continued

| Cpd. No. | Scoring |
|---|---|
| 45 | − |
| 46 | ++ |
| 47 | + |
| 48 | + |
| 50 | + |
| 52 | − |
| 56 | − |
| 57 | − |
| 59 | ++ |
| 61 | ++ |
| 63 | ++* |
| 65 | ++ |
| 66 | + |
| 67 | ++ |
| 69 | + |
| 91 | + |
| 93 | ++ |

Example 99

Activity of Representative Compounds on Akt Phosphorylation in Lymphocytes

Phosphorylation of AKT has been shown to be modulated by SHIP1 (Helgason et al., *J Exp Med* 191, 781-794, 2000). Molt-4 (PTEN-/SHIP1+) cells are starved in serum free RPMI for overnight. In a 15 mL conical tube, 2-3 million serum starved cells (1 million cells per mL) are treated with various concentrations of test compound (0.1, 1, or 10 µM final in 0.1% DMSO) for 30 min at 37° C. followed by stimulation with 100 ng/mL of IGF-1 for 1 hour at 37° C. After stimulation, cells are washed once with ice-cold DPBS and lysed with Lysis Buffer (20 mM Tris-HCl, pH 7.5, 140 mM NaCl, 1% NP-40, Complete Mini Protease Inhibitor Cocktail, 10 mM NaF, 1 mM $Na_3VO_4$, 1 mM β-glycerolphosphate) on ice for 30 min with vortexing every 10 min. Samples are then centrifuged at 13,000 rpm for 20 min, and supernatants are collected as total cell lysate samples. Protein concentration is determined using bicinchonic acid assay, and about 15 µg of total protein from each sample is loaded and separated on a 4-12% Tris-Glycine gel. After SDS-PAGE, proteins are transferred from the gel to a nitrocellulose membrane. The membrane is blocked in 5% BSA in PBS containing 0.1% Tween-20 (PBS-T) for 1 hour at room temperature before probing with primary antibodies for overnight at 4° C. The following antibodies are used: mouse anti-SHIP1 (1:500 dilution; Santa Cruz, Calif., USA), rabbit anti-phospho-Akt (Ser473) (1:1000 dilution; Cell Signaling Technologies, MA, USA), rabbit anti-Akt (1:1000; Cell Signaling Technologies, MA, USA), and rabbit anti-actin (1:2000; Cell Signaling Technologies, MA, USA). The membrane is then incubated with goat anti-rabbit or anti-mouse secondary antibodies (1:3000) for 1 hour at room temperature. Target proteins on the membrane are detected with ECL solution and exposed on a film.

According to the above assay, the representative compounds listed in Table 3 below were found to inhibit Akt phosphorylation at ≤30 µM in Molt-4 (SHIP1+). The compound numbers in Table 3 correspond to the compound numbers in Table 1. Scoring in Table 3 is expressed as follows: +(inhibits Akt phosphorylation at 30 µM); −(no effect on Akt phosphorylation at 30 µM).

TABLE 3

| Cpd. No. | Molt-4 (SHIP+) |
|---|---|
| 1 | + |
| 3 | + |
| 11 | + |
| 18 | + |
| 20 | + |
| 21 | + |
| 22 | + |
| 23 | + |
| 24 | + |
| 25 | + |
| 27 | − |
| 29 | + |
| 32 | + |
| 34 | + |
| 46 | + |
| 48 | + |
| 50 | + |
| 57 | + |
| 81 | + |
| 82 | + |
| 83 | + |
| 84 | + |
| 85 | + |
| 86 | + |
| 87 | + |
| 88 | + |
| 89 | + |
| 90 | + |
| 94 | + |
| 95 | + |
| 97 | + |
| 98 | + |

Example 100

Activity of Representative Compounds on Passive Cutaneous Anaphylaxis in Mice

The activity of representative compounds on passive cutaneous anaphylaxis in mice may be evaluated according to the procedures disclosed by Ovary, *J Immunol* 81, 355-357, 1958 and Halpern et al., *Br J Pharmacol Chemother* 20, 389-398, 1963, both of which are incorporated herein by reference in their entirety.

To induce a passive cutaneous anaphylaxis, mice undergo intradermal ear inoculation on their right ear with 25 ng in 20 µL of anti-DNP-IgE. The left ears are untreated and serve as negative controls. Twenty-four hours after inoculation, all mice are administered test compound by oral gavage (PO). Sixty minutes after oral administration, mice are given a tail vein injection of 2% Evan's Blue (0.2 m filtered, in 200 µL saline) followed by a second tail IV injection of 100 µg DNP-HSA (in 200 µL). Sixty minutes following the DNP-HAS injection, mice are euthanized using $CO_2$ inhalation. Subsequently, ear biopsies are performed by taking four millimeter punches from both ears, which will then undergo Evan's Blue extraction using formamide incubation in 96 well plates. Eighty µL of eluents are transferred to flat-bottom 96-well plates and absorbance read using Spectra-Max M5 spectrophotometer (Molecular Devices, Sunnyvale, Calif., USA) at 620 nm. Background readings from all samples are taken at 740 nm and subtracted from the 620 nm readings. Data are reported as OD.

Example 101

Activity of Representative Compounds on Carrageenan Paw Edema in Mice

The activity of representative compounds on carrageenan paw edema in mice may be evaluated according to the procedures disclosed by Winter et al., *Proc Soc Exp Biol Med* 111, 544-547, 1962 which is incorporated herein by reference in its entirety. To induce edema in the paw, test compounds are administered orally one hour before intraplantar injection of the right hind paw with carrageenan (50 μL of 1% suspension). Hind paw edema, as a measure of inflammation, is recorded using a plethysmometer (Ugo Basile, Italy) 4 hours after λ-carrageenan administration.

All of the U.S. patents, U.S. patent application publications, U.S. patent applications, foreign patents, foreign patent applications and non-patent publications referred to in this specification, including U.S. Provisional Patent Application 61/785,860, filed Mar. 14, 2013, are incorporated herein by reference in their entireties.

Although the foregoing invention has been described in some detail to facilitate understanding, it will be apparent that certain changes and modifications may be practiced within the scope of the appended claims. Accordingly, the described embodiments are to be considered as illustrative and not restrictive, and the invention is not to be limited to the details given herein, but may be modified within the scope and equivalents of the appended claims.

What is claimed is:

1. A compound of formula (I):

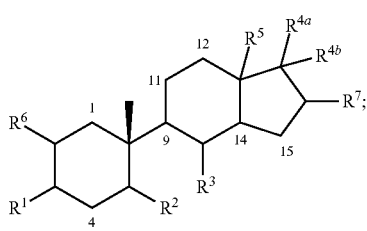

wherein:
C1, C4, C11 and C12 are each independently substituted with two hydrogens;
C9 is substituted with one hydrogen;
C14 is substituted with one hydrogen when $R^5$ is not a direct bond to C14;
C15 is substituted with two hydrogens when $R^7$ is not a direct bond to C15, and one hydrogen when $R^7$ is a direct bond to C15;
$R^1$ is —$R^8$—$OR^9$ or —$R^8$—$N(R^9)_2$;
$R^2$ is —$R^8$—$OR^9$, —$R^8$—CN, —$R^8$—C(O)$OR^9$, —$R^8$—C(O)N($R^9$)$_2$, —$R^8$—N($R^9$)$_2$, —$R^8$—N($R^9$)C(O)$R^9$, optionally substituted heterocyclylalkyl or optionally substituted heteroarylalkyl;
$R^{4a}$ and $R^{4b}$ together form methylene;
$R^3$ is —CH$_2$—N(H)CH$_2$-(2,2-difluorobenzodioxolyl), —CH$_2$—CH$_2$—N(4-methoxybenzyl)$_2$, —CH$_2$—CH$_2$—N(H)-(4-methoxy)benzyl, —CH$_2$—N(H)-(2-fluoro-4-methoxy)benzyl, —CH$_2$—N(H)-(2-fluoro-4-methyl)benzyl, —CH$_2$—N(H)-(2-methoxy-4-fluoro)benzyl, —CH$_2$—N(H)-(2-methyl-4-fluoro)benzyl, —CH$_2$—N(H)-(3,5-dimethoxy)benzyl, —CH$_2$—N(H)-(4-fluoro)benzyl, —CH$_2$—N(H)-(4-methoxy)benzyl, —CH$_2$—N(H)-(4-trifluoromethyl)benzyl, —CH$_2$—N(H)-(4-benzoyl)benzyl, —CH$_2$—N(H)CH$_2$-benzimidazolyl, —CH$_2$—CH$_2$—N(H)CH$_2$-benzodioxolyl or —CH$_2$—N(H)CH$_2$CH$_2$-(4-methoxy)phenyl;
$R^5$ is alkyl or $R^5$ is a direct bond to C14;
$R^6$ is hydrogen;
$R^7$ is hydrogen, —$R^8$—$OR^9$ or a direct bond to C15;
each $R^8$ is independently a direct bond or a straight or branched alkylene chain; and
each $R^9$ is independently hydrogen, alkyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl or optionally substituted heteroarylalkyl;

or a stereoisomer, enantiomer or tautomer thereof or mixtures thereof;

or a pharmaceutically acceptable salt or solvate thereof.

2. The compound of claim 1 wherein:
C1, C4, C11 and C12 are each independently substituted with two hydrogens;
C9 is substituted with one hydrogen;
C14 is substituted with one hydrogen;
C15 is substituted with two hydrogens;
$R^1$ is —$R^8$—$OR^9$;
$R^2$ is —$R^8$—$OR^9$;
$R^{4a}$ and $R^{4b}$ together form methylene;
$R^3$ is —CH$_2$—N(H)CH$_2$-(2,2-difluorobenzodioxolyl), —CH$_2$—CH$_2$—N(4-methoxybenzyl)$_2$, —CH$_2$—CH$_2$—N(H)-(4-methoxy)benzyl, —CH$_2$—N(H)-(2-fluoro-4-methoxy)benzyl, —CH$_2$—N(H)-(2-fluoro-4-methyl)benzyl, —CH$_2$—N(H)-(2-methoxy-4-fluoro)benzyl, —CH$_2$—N(H)-(2-methyl-4-fluoro)benzyl, —CH$_2$—N(H)-(3,5-dimethoxy)benzyl, —CH$_2$—N(H)-(4-fluoro)benzyl, —CH$_2$—N(H)-(4-methoxy)benzyl, —CH$_2$—N(H)-(4-trifluoromethyl)benzyl, —CH$_2$—N(H)-(4-benzoyl)benzyl, —CH$_2$—N(H)CH$_2$-benzimidazolyl, —CH$_2$—CH$_2$—N(H)CH$_2$-benzodioxolyl or —CH$_2$—N(H)CH$_2$CH$_2$-(4-methoxy)phenyl;
$R^5$ is alkyl;
$R^6$ is hydrogen;
$R^7$ is hydrogen;
each $R^8$ is independently a direct bond or a straight or branched alkylene chain; and
each $R^9$ is independently hydrogen, alkyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl or optionally substituted heteroarylalkyl.

3. The compound of claim 2 wherein:
C1, C4, C11 and C12 are each independently substituted with two hydrogens;
C9 is substituted with one hydrogen;
C14 is substituted with one hydrogen;
C15 is substituted with two hydrogens;
$R^1$ is —OH;
$R^2$ is —OH or —CH$_2$OH;
$R^{4a}$ and $R^{4b}$ together form methylene;
$R^3$ is —CH$_2$—N(H)CH$_2$-(2,2-difluorobenzodioxolyl), —CH$_2$—CH$_2$—N(4-methoxybenzyl)$_2$, —CH$_2$—CH$_2$—N(H)-(4-methoxy)benzyl, —CH$_2$—N(H)-(2-fluoro-4-methoxy)benzyl, —CH$_2$—N(H)-(2-fluoro-4-methyl)benzyl, —CH$_2$—N(H)-(2-methoxy-4-fluoro)benzyl, —CH$_2$—N(H)-(2-methyl-4-fluoro)benzyl, —CH$_2$—N(H)-(3,5-dimethoxy)benzyl, —CH$_2$—N(H)-(4-fluoro)benzyl, —CH$_2$—N(H)-(4-methoxy)benzyl, —CH$_2$—N(H)-(4-trifluoromethyl)benzyl, —CH$_2$—N(H)-(4-benzoyl)benzyl, —CH$_2$—N(H)CH$_2$-benzimidazolyl, —CH$_2$—CH$_2$—N(H)CH$_2$-benzodioxolyl or —CH$_2$—N(H)CH$_2$CH$_2$-(4-methoxy)phenyl;
$R^5$ is methyl;

$R^6$ is hydrogen; and
$R^7$ is hydrogen.

4. The compound of claim 3 selected from:

(4-((((3aS,4R,5S,7aS)-5-((1R,2S,4S)-4-hydroxy-2-(hydroxymethyl)-1-methylcyclohexyl)-7a-methyl-1-methyleneoctahydro-1H-inden-4-yl)methylamino)methyl)phenyl)(phenyl)methanone;

(1S,3S,4R)-4-((3aS,4R,5S,7aS)-4-((4-fluorobenzylamino)methyl)-7a-methyl-1-methyleneoctahydro-1H-inden-5-yl)-3-(hydroxymethyl)-4-methylcyclohexanol;

(1S,3S,4R)-3-(hydroxymethyl)-4-((3aS,4R,5S,7aS)-4-((4-methoxybenzylamino)methyl)-7a-methyl-1-methyleneoctahydro-1H-inden-5-yl)-4-methylcyclohexanol;

(1S,3S,4R)-3-(hydroxymethyl)-4-methyl-4-((3aS,4R,5S,7aS)-7a-methyl-1-methylene-4-((4-(trifluoromethyl)benzylamino)methyl)octahydro-1H-inden-5-yl)cyclohexanol;

(1S,3S,4R)-4-((3aS,4R,5S,7aS)-4-((3,5-dimethoxybenzylamino)methyl)-7a-methyl-1-methyleneoctahydro-1H-inden-5-yl)-3-(hydroxymethyl)-4-methylcyclohexanol;

(1S,3S,4R)-4-((3aS,4R,5S,7aS)-4-(((1H-benzo[d]imidazol-2-yl)methylamino)methyl)-7a-methyl-1-methyleneoctahydro-1H-inden-5-yl)-3-(hydroxymethyl)-4-methylcyclohexanol;

(1S,3S,4R)-4-((3aS,4R,5S,7aS)-4-(((2,2-difluorobenzo[d][1,3]dioxol-5-yl)methylamino)methyl)-7a-methyl-1-methyleneoctahydro-1H-inden-5-yl)-3-(hydroxymethyl)-4-methylcyclohexanol;

(1S,3S,4R)-4-((3aS,4R,5S,7aS)-4-((4-fluoro-2-methylbenzylamino)methyl)-7a-methyl-1-methyleneoctahydro-1H-inden-5-yl)-3-(hydroxymethyl)-4-methylcyclohexanol;

(1S,3S,4R)-4-((3aS,4R,5S,7aS)-4-((2-fluoro-4-methoxybenzylamino)methyl)-7a-methyl-1-methyleneoctahydro-1H-inden-5-yl)-3-(hydroxymethyl)-4-methylcyclohexanol;

(1S,3S,4R)-4-((3aS,4R,5S,7aS)-4-((4-fluoro-2-methoxybenzylamino)methyl)-7a-methyl-1-methyleneoctahydro-1H-inden-5-yl)-3-(hydroxymethyl)-4-methylcyclohexanol;

(1S,3S,4R)-4-((3aS,4R,5S,7aS)-4-((2-fluoro-4-methylbenzylamino)methyl)-7a-methyl-1-methyleneoctahydro-1H-inden-5-yl)-3-(hydroxymethyl)-4-methylcyclohexanol;

(1S,3S,4R)-4-((3aS,4S,5S,7aS)-4-(2-(bis(4-methoxybenzyl)amino)ethyl)-7a-methyl-1-methyleneoctahydro-1H-inden-5-yl)-4-methylcyclohexane-1,3-diol;

(1S,3S,4R)-4-((3aS,4S,5S,7aS)-4-(2-(4-methoxybenzylamino)ethyl)-7a-methyl-1-methyleneoctahydro-1H-inden-5-yl)-4-methylcyclohexane-1,3-diol;

(1S,3S,4R)-3-(hydroxymethyl)-4-((3aS,4R,5S,7aS)-4-((4-methoxyphenethylamino)methyl)-7a-methyl-1-methyleneoctahydro-1H-inden-5-yl)-4-methylcyclohexanol; and (1S,3S,4R)-4-((3aS,4S,5S,7aS)-4-(2-(benzo[d][1,3]dioxol-5-ylmethylamino)ethyl)-7a-methyl-1-methyleneoctahydro-1H-inden-5-yl)-4-methylcyclohexane-1,3-diol.

5. A composition comprising a compound of formula (I) as described in claim 1, or a stereoisomer, enantiomer or tautomer thereof or mixtures thereof; or a pharmaceutically acceptable salt or solvate thereof, and a pharmaceutically acceptable excipient.

6. A method for modulating SHIP1 comprising administering an effective amount of a compound of formula (I) as described in claim 1, or a stereoisomer, enantiomer or tautomer thereof or mixtures thereof; or a pharmaceutically acceptable salt or solvate thereof, to a mammal in need thereof.

7. A method for treating a disease, disorder or condition that would benefit from SHIP1 modulation comprising administering an effective amount of a compound of formula (I) as described in claim 1, or a stereoisomer, enantiomer or tautomer thereof or mixtures thereof; or a pharmaceutically acceptable salt or solvate thereof, to a mammal having said disease, disorder or condition, where the disease, disorder or condition is an autoimmune disease, disorder or condition, an inflammatory disease, disorder or condition, or a neoplastic or cell proliferative disease, disorder or condition.

* * * * *